(12) United States Patent
Chellappan et al.

(10) Patent No.: US 10,906,874 B2
(45) Date of Patent: Feb. 2, 2021

(54) YAP1 INHIBITORS THAT TARGET THE INTERACTION OF YAP1 WITH OCT4

(71) Applicant: H. LEE MOFFITT CANCER CENTER AND RESEARCH INSTITUTE, INC., Tampa, FL (US)

(72) Inventors: Srikumar Chellappan, Tampa, FL (US); Nicholas J. Lawrence, Tampa, FL (US); Sujeewa Ranatunga Mahanthe Mudiyanselage, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 16/334,087

(22) PCT Filed: Sep. 18, 2017

(86) PCT No.: PCT/US2017/052103
§ 371 (c)(1),
(2) Date: Mar. 18, 2019

(87) PCT Pub. No.: WO2018/053446
PCT Pub. Date: Mar. 22, 2018

(65) Prior Publication Data
US 2019/0375709 A1    Dec. 12, 2019

Related U.S. Application Data

(60) Provisional application No. 62/396,190, filed on Sep. 18, 2016, provisional application No. 62/396,383, filed on Sep. 19, 2016.

(51) Int. Cl.
| | | |
|---|---|---|
| *C07D 211/34* | (2006.01) | |
| *C07D 405/06* | (2006.01) | |
| *C07D 401/10* | (2006.01) | |
| *C07D 211/60* | (2006.01) | |
| *C07C 237/22* | (2006.01) | |
| *C07C 251/24* | (2006.01) | |
| *C07C 255/57* | (2006.01) | |
| *C07D 211/96* | (2006.01) | |
| *C07D 233/92* | (2006.01) | |
| *C07D 241/04* | (2006.01) | |
| *C07D 401/06* | (2006.01) | |
| *C07D 401/12* | (2006.01) | |
| *C07D 403/06* | (2006.01) | |
| *C07D 405/12* | (2006.01) | |
| *A61K 45/06* | (2006.01) | |

(52) U.S. Cl.
CPC .......... *C07D 211/60* (2013.01); *C07C 237/22* (2013.01); *C07C 251/24* (2013.01); *C07C 255/57* (2013.01); *C07D 211/34* (2013.01); *C07D 211/96* (2013.01); *C07D 233/92* (2013.01); *C07D 241/04* (2013.01); *C07D 401/06* (2013.01); *C07D 401/10* (2013.01); *C07D 401/12* (2013.01); *C07D 403/06* (2013.01); *C07D 405/06* (2013.01); *C07D 405/12* (2013.01); *A61K 45/06* (2013.01)

(58) Field of Classification Search
CPC .. C07D 211/34; C07D 405/06; C07D 401/12; C07D 211/96; C07D 401/10
USPC ................................................. 546/184, 192
See application file for complete search history.

(56) References Cited

U.S. PATENT DOCUMENTS

| | | | | |
|---|---|---|---|---|
| 6,147,083 A | * | 11/2000 | Russell | ................ C07D 211/14 514/278 |
| 2015/0157584 A1 | | 6/2015 | Guan et al. | |

FOREIGN PATENT DOCUMENTS

| | | |
|---|---|---|
| WO | 2000-043415 | 7/2000 |
| WO | 03/009847 A1 | 2/2003 |
| WO | 2005077914 A1 | 8/2005 |
| WO | 2011/097300 A1 | 8/2011 |
| WO | 2015-019325 | 2/2015 |
| WO | 2016/058547 A1 | 4/2016 |

OTHER PUBLICATIONS

International Preliminary Report on Patentability Opinion issued for International Application No. PCT/US2017/052103, dated Mar. 28, 2019, 10 pages.
International Search Report and the Written Opinion issued for International Application No. PCT/US2017/052103, dated Jan. 5, 2018, 15 pages.
Karpavichyus, K. I. et al., "Phenylalanine derivatives containing an acyl residue of the stereoisomeric N-[di (ethylenimino)(thio) phosphoryl]-4-aminocyclohexanecarboxylic acids", Russian Chemical Bulletin, 1978, vol. 27, No. 4, pp. 790-795.

(Continued)

*Primary Examiner* — Niloofar Rahmani
(74) *Attorney, Agent, or Firm* — Meunier Carlin & Curfman LLC

(57) ABSTRACT

Binding of the transcriptional co-activator, YAP1, to the transcription factor Oct4, induces Sox2, which is a transcription actor necessary for the self-renewal of stem-like cells from non-small cell lung cancer. The WW domain of YAP1 binds to the PPxY motif of Oct4 to induce Sox2. Delivering a peptide corresponding to the WAV domain could prevent the induction of Sox2 and stemness. Similarly, peptides and mimetics of the PPxY motif would be able to inhibit stemness. Disclosed are compounds that affect the Yap1:Oct4 interaction.

19 Claims, 39 Drawing Sheets

(56) References Cited

OTHER PUBLICATIONS

Chemical Abstract Compound, STN express, RN 754928-65-9 (Entered STN: Oct. 1, 2004).
Chemical Abstract Compounds, STN express, RN 1824945-77-8 (Entered STN: Dec. 8, 2015).
Chemical Abstract Compounds, STN express, RNs 1315859-64-3, 1315837-45-6 (Entered STN: Aug. 11, 2011).
Chemical Abstract Compounds, STN express, RN 1293634-04-4 (Entered STN: May 12, 2011).
Chemical Abstract Compounds, STN express, RN 1100267-42-2 (Entered STN: Feb. 3, 2009).
Chemical Abstract Compounds, STN express, RN 1100240-13-8 (Entered STN: Feb. 3, 2009).
Chemical Abstract Compounds, STN express, RN 931623-21-1 (Entered STN: Apr. 22, 2007).
Chemical Abstract Compounds, STN express, RN 924478-95-5 (Entered STN: Mar. 2, 2007).
Chemical Abstract Compounds, STN express, RN 852688-60-9 (Entered STN: Jun. 22, 2005).
Chemical Abstract Compounds, STN express, RN 851964-70-0 (Entered STN: Jun. 9, 2005).
Bora-Singhal et al. YAP 1 Regulates OCT 4 Activity and SOX 2 Expression to Facilitate Self-Renewal and Vascular Mimicry of Stem-Like Cells. Stem Cells. Jun. 2015;33(6):1705-18.
Demicheli R, et al. Recurrence dynamics does not depend on the recurrence site. Breast Cancer Res. 2008;10(5):R83.
Demicheli R, et al. Recurrence dynamics for non-small-cell lung cancer: effect of surgery on the development of metastases. J Thorac Oncol. 2012;7(4):723-30.
Giancotti FG. Mechanisms governing metastatic dormancy and reactivation. Cell. 2013;155(4):750-64.
Kanelis, Voula, Daniela Rotin, and Julie D. Forman-Kay. Solution structure of a Nedd4 WW domain—ENaC peptide complex. Nature Structural & Molecular Biology 8.5 (2001): 407.
Lau AN, et al. Tumor-propagating cells and Yap/Taz activity contribute to lung tumor progression and metastasis. Embo J. 2014;33(5):468-81.
Lee N, et al. Melanoma stem cells and metastasis: mimicking hematopoietic cell trafficking? Lab Invest. 2014;94(1):13-30.
Leeman KT, et al. Lung stem and progenitor cells in tissue homeostasis and disease. Curr Top Dev Biol. 2014;107:207-33.
Lundin A, et al. Lung cancer stem cells: progress and prospects. Cancer Lett. 2013;338(1):89-93.
Macias, Maria J., et al. Structure of the WW domain of a kinase-associated protein complexed with a proline-rich peptide Nature 382.6592 (1996): 646.
Mao B, et al. SIRT1 regulates YAP2-mediated cell proliferation and chemoresistance in hepatocellular carcinoma. Oncogene 33, 2013 1468-1474. Epub Apr. 2, 2013. doi: 10.1038/onc.2013.88.
Mizuno T, et al. YAP induces malignant mesothelioma cell proliferation by upregulating transcription of cell cycle-promoting genes. Oncogene. 2012;31(49):5117-22.
Morrison BJ, et al. Lung cancer-initiating cells: a novel target for cancer therapy. Target Oncol. 2013;8(3):159-72.
Patel P, et al. Cancer stem cells, tumor dormancy, and metastasis. Front Endocrinol (Lausanne). 2012; 3:125.
Peacock CD, et al. Cancer stem cells and the ontogeny of lung cancer. J Clin Oncol. 2008;26(17):2883-9.
Senthi S, et al. Patterns of disease recurrence after stereotactic ablative radiotherapy for early stage non-small-cell lung cancer: a retrospective analysis. Lancet Oncol. 2012;13(8):802-9.
Seve P, et al. Chemoresistance in non-small cell lung cancer. Curr Med Chem Anticancer Agents. 2005;5(1):73-88.
Siegel R, et al. Cancer statistics, 2013. CA Cancer J Clin. 2013;63(1):11-30.
Singh S, et al. Lung cancer stem cells: Molecular features and therapeutic targets. Mol Aspects Med. 2013, 50-60. Epub Sep. 11, 2013. doi: 10.1016/j.mam.2013.08.003.
Sureshbabu VV, Venkataramanarao R, Naik SA, Chennakrishnareddy G. Synthesis of tetrazole analogues of amino acids using Fmoc chemistry: isolation of amino free tetrazoles and their incorporation into peptides. Tetrahedron Letters. Sep. 24, 2007;48(39):7038-41.
Sutherland KD, et al. Multiple cells-of-origin of mutant K-Ras-induced mouse lung adenocarcinoma. Proc Natl Acad Sci U S A. 2014, 4952-4957. Epub Mar. 4, 2014.
Toyoizumi, et al. Combined therapy with chemotherapeutic agents and herpes simplex virus type IICP34.5 mutant (HSV-1716) in human non-small cell lung cancer. Human Gene Therapy, 1999, 10(18):17 3013.
Verdecia, Mark A., et al. Structural basis for phosphoserine-proline recognition by group IV WW domains. Nature Structural & Molecular Biology 7.8 (2000): 639.
Yu FX, et al. The Hippo pathway: regulators and regulations. Genes Dev. 2013;27(4):355-71.
Zhao B, et al. The Hippo pathway in organ size control, tissue regeneration and stem cell self-renewal. Nat Cell Biol. 2011;13(8):877-83.
International Search Report and the Written Opinion issued for International Application No. PCT/US2019/022337, dated Jun. 3, 2019.
PubChem CID 56813592 Create Date Mar. 8, 2013.
PubChem CID 81970138 Create Date Oct. 20, 2014.
The Extended European Search Report issued for Application No. 17851738, dated Feb. 26, 2020.
Patockiene L et al: Izvestiya Akademii Nauk SSSR, Seriya Khimicheskaya, Institut Organicheskoi Khimii Im. N. D. Zelinskogo Rossiiskoi Akademii, RU, vol. 6, Jan. 1, 1980 (Jan. 1, 1980), pp. 1426-1428, XP009518806, ISSN: 0002-3353 p. 1427; compounds I, II, III, IV.
Official Notification issued by the Eurasian Patent Office for Application No. 201990761, dated Mar. 12, 2020.
Allan Al, et al. Tumor dormancy and cancer stem cells: implications for the biology and treatment of breast cancer metastasis. Breast Dis. 2006;26:87-98.
Brugger W, et al. EGFR-TKI resistant non-small cell lung cancer (NSCLC): new developments and implications for future treatment. Lung Cancer. 2012;77(1):2-8.
Demko ZP, Sharpless KB. An expedient route to the tetrazole analogues of α-amino acids. Organic letters. Jul. 25, 2002;4(15):2525-7.
Gunn SJ, Baker A, Bertram RD, Warriner SL. A novel approach to the solid-phase synthesis of peptides with a tetrazole at the C-terminus. Synlett. Oct. 2007;2007(17):2643-6.
Hashmi et al. Gold catalysis: mild conditions for the synthesis of oxazoles from N-propargylcarboxamides and mechanistic aspects. Organic letters. Nov. 11, 2004;6(23):4391-4.
Koren A, et al. Lung cancer stem cells: a biological and clinical perspective. Cell Oncol (Dordr). 2013;36(4):265-75.
Lara PN, Jr., et al. Non-small-cell lung cancer progression after first-line chemotherapy. Curr Treat Options Oncol. 2002;3(1):53-8.
Nozaki S, Muramatsu I. Convenient synthesis of N-protected amino acid amides. Bulletin of the Chemical Society of Japan. Jul. 1988;61(7):2647-8.
Wang, Jing, et al. Lung cancer stem cells and implications for future therapeutics. Cell biochemistry and biophysics 69.3 (2014): 389-398.
Oku et al., Small molecules inhibiting the nuclear localization of YAP/TAZ for chemotherapeutics and chemosensitizers against breast cancers, FEBS Open Bio, vol. 5, 2015, 542-549.
Search Report and Written Opinion issued by Intellectual Property Office of Singapore in SG 11201902029X, dated Jul. 29, 2020.

\* cited by examiner

Set 1

*11 peptidomimetic analogs were synthesized and evaluated*

SR1-083

*in vitro:*
5 µM/10 µM= 72.6% / 80.8%
IC50= 5.3 µM
*in cell:* >75% (50 µM)

Log P : 3.9
CLogP : 4.7

---

Set 2

- SR1-083 was modified at N-terminal
- 13 analogs were synthesized and evaluated

SR1-117

*in vitro* at 10 µM= 57%
in cell= 70% (50 µM)

SR1-118

*in vitro* at 10 µM= 75%,
$IC_{50}$= 9.9 µM
in cell= 84% (50 µM)

SR1-119

*in vitro* at 10 µM= 90%
$IC_{50}$= 0.99 µM
in cell= 90% (50 µM)

Log P : 4.7
CLogP : 4.0

SR1-122

*in vitro* at 10 µM= 80%
$IC_{50}$= 2.2 µM
in cell= 82% (50 µM)

Treatment- H1650 cells treated with 20 and 50 µM compounds for 48h

Treatment- H1650 cells treated with 20 and 50 µM compounds for 48h

- *Cisplatin 5 μM - 7 days of Cisplatin treatment (Days 0, 4)*
- *Peptidomimetic compounds - 7 days treatment*
- *Combination - 7 days Cisplatin 5 μM treatment (Days 0, 4) - spheres collected, dissociated and re-plated at low density. Followed by 5 days peptidomimetic compound treatment*

YAP1 INHIBITORS THAT TARGET THE INTERACTION OF YAP1 WITH OCT4

CROSS REFERENCE TO RELATED APPLICATIONS

This application claims the benefit of priority to U.S. Provisional Applications 62/396,190, filed Sep. 18, 2016, and 62/396,383, filed Sep. 19, 2016, which are both incorporated by reference herein in their entirities.

BACKGROUND

Lung cancer is the leading cause of cancer related mortality in the United States (Siegel R, et al. Cancer statistics, 2013. *CA Cancer J Clin.* 2013; 63(1):11-30), with majority of this (85%) resulting from non-small cell lung cancer (NSCLC). Patients with early stage disease are treated by surgery, but about 30-60% will develop recurrent tumors, which result in mortality (Demicheli R, et al. Recurrence dynamics does not depend on the recurrence site. *Breast Cancer Res.* 2008; 10(5):R83; Demicheli R, et al. Recurrence dynamics for non-small-cell lung cancer: effect of surgery on the development of metastases. *J Thorac Oncol.* 2012; 7(4):723-30; Senthi S, et al. Patterns of disease recurrence after stereotactic ablative radiotherapy for early stage non-small-cell lung cancer: a retrospective analysis. *Lancet Oncol.* 2012; 13(8):802-9). Although chemotherapeutic agents like gemcitabine, platinum compounds and taxanes improve survival to a limited extent, overall survival rates remain low due to recurrence of more aggressive, drug resistant tumors (Seve P, et al. Chemoresistance in non-small cell lung cancer. *Curr Med Chem Anticancer Agents.* 2005; 5(1):73-88; Lara P N, Jr., et al. Non-small-cell lung cancer progression after first-line chemotherapy. *Curr Treat Options Oncol.* 2002; 3(1):53-8). Even patients harboring EGFR mutations who respond well to EGFR inhibitors like Erlotinib eventually develop resistance and succumb to the disease (Brugger W, et al. EGFR-TKI resistant non-small cell lung cancer (NSCLC): new developments and implications for future treatment. *Lung Cancer.* 2012; 77(1):2-8). It has been hypothesized that tumor initiating cells or cancer stem-like cells might contribute to the initiation, progression, metastasis and recurrence of tumors (Patel P, et al. Cancer stem cells, tumor dormancy, and metastasis. *Front Endocrinol (Lausanne).* 2012; 3:125; Allan A L, et al. Tumor dormancy and cancer stem cells: implications for the biology and treatment of breast cancer metastasis. *Breast Dis.* 2006; 26:87-98; Giancotti F G. Mechanisms governing metastatic dormancy and reactivation. *Cell.* 2013; 155(4): 750-64; Lee N, et al. Melanoma stem cells and metastasis: mimicking hematopoietic cell trafficking? *Lab Invest.* 2014; 94(1):13-30) and this idea is gaining significant traction in the lung cancer arena (Peacock C D, et al. Cancer stem cells and the ontogeny of lung cancer. *J Clin Oncol.* 2008; 26(17):2883-9; Singh S, et al. Lung cancer stem cells: Molecular features and therapeutic targets. *Mol Aspects Med.* 2013. Epub 2013 Sep. 11. doi: 10.1016/j.mam.2013.08.003; Koren A, et al. Lung cancer stem cells: a biological and clinical perspective. *Cell Oncol (Dordr).* 2013; 36(4):265-75; Lundin A, et al. Lung cancer stem cells: progress and prospects. *Cancer Lett.* 2013; 338(1):89-93; Morrison B J, et al. Lung cancer-initiating cells: a novel target for cancer therapy. *Target Oncol.* 2013; 8(3):159-72; Leeman K T, et al. Lung stem and progenitor cells in tissue homeostasis and disease. *Curr Top Dev Biol.* 2014; 107: 207-33; Sutherland K D, et al. Multiple cells-of-origin of mutant K-Ras-induced mouse lung adenocarcinoma. *Proc Natl Acad Sci USA.* 2014. Epub 2014/03/04; Wang J, et al. Lung Cancer Stem Cells and Implications for Future Therapeutics. *Cell Biochem Biophys.* 2014. Epub 2014/02/20. doi: 10.1007/s12013-014-9844-4; Lau A N, et al. Tumor-propagating cells and Yap/Taz activity contribute to lung tumor progression and metastasis. *Embo J.* 2014; 33(5):468-81). In this context, our studies have shown that the oncogenic component of the Hippo signaling pathway, YAP1, contributes to the self-renewal and vascular mimicry of stem-like cells.

The classic Hippo signaling cascade leads to the activation of the kinases Lats1/2 and Mst1/2, which phosphorylate YAP1 or its orthologue TAZ resulting in their cytoplasmic sequestration and/or degradation (Yu F X, et al. The Hippo pathway: regulators and regulations. *Genes Dev.* 2013; 27(4):355-71; Zhao B, et al. The Hippo pathway in organ size control, tissue regeneration and stem cell self-renewal. *Nat Cell Biol.* 2011; 13(8):877-83). Inactivation of the Hippo pathway leads to the activation and nuclear translocation of YAP1, where it associates mainly with TEAD family transcription factors, to promote cell proliferation (Mizuno T, et al. YAP induces malignant mesothelioma cell proliferation by upregulating transcription of cell cycle-promoting genes. *Oncogene.* 2012; 31(49):5117-22; Mao B, et al. SIRT1 regulates YAP2-mediated cell proliferation and chemoresistance in hepatocellular carcinoma. *Oncogene.* 2013. Epub 2013 Apr. 2. doi: 10.1038/onc.2013.88). YAP1 levels are elevated in multiple tumor types, and YAP1 has been found to contribute to the genesis and progression of multiple cancers including those of the pancreas and lung. YAP1 can physically interact with additional transcription factors to promote cell proliferation, angiogenesis and cancer metastasis. In this context, our studies had shown that YAP1 physically interacts with the Oct4 transcription factor to induce another embryonic stem cell transcription factor, Sox2. This interaction occurred through the WW domain of YAP1 and the PPxY motif of Oct4. We had found that disruption of the Oct4-YAP1 interaction could prevent the self-renewal of stem-like side-population cells from lung cancer cell lines, and could prevent vascular mimicry. What are thus needed are compositions and methods that disrupt the Oct4-YAP1 interaction, which will have anti-cancer effects, since such agents would prevent self-renewal, cell proliferation and potentially angiogenesis. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anti-cancer compounds. More specifically, the subject matter disclosed herein relates to inhibitors of YAP1.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

Peptidomimetic compounds and NCI hits eliminate H1650 cancer cells (stained in red) when co-cultured with cancer associated fibroblasts (CAFs, stained in green). Effect of the drugs was visualized 24 hrs or 48 hrs after treatment. CAFs confer resistance to drugs, and this experiment shows that the YAP1 inhibitors can work even when the survival signals from CAFs are present. Further, there was minimal impact of CAFs, which are relatively normal cells.

Figure 1:
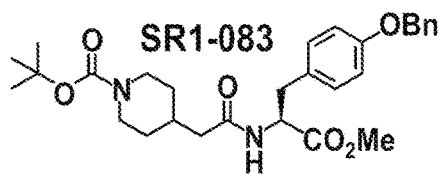
FIG. 1 is a schematic summary of peptidomimetic analogs.
Figure 1:
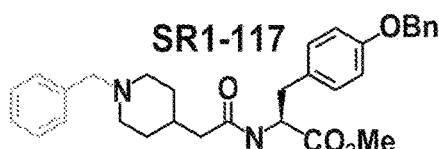
Figure 1:
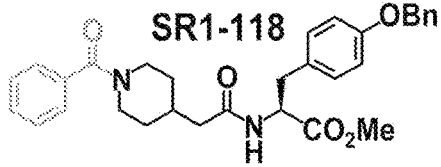
Figure 1:
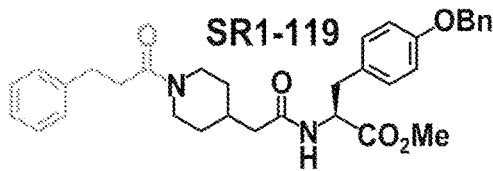
Figure 1:
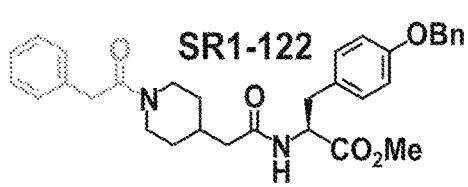
Figure 2:
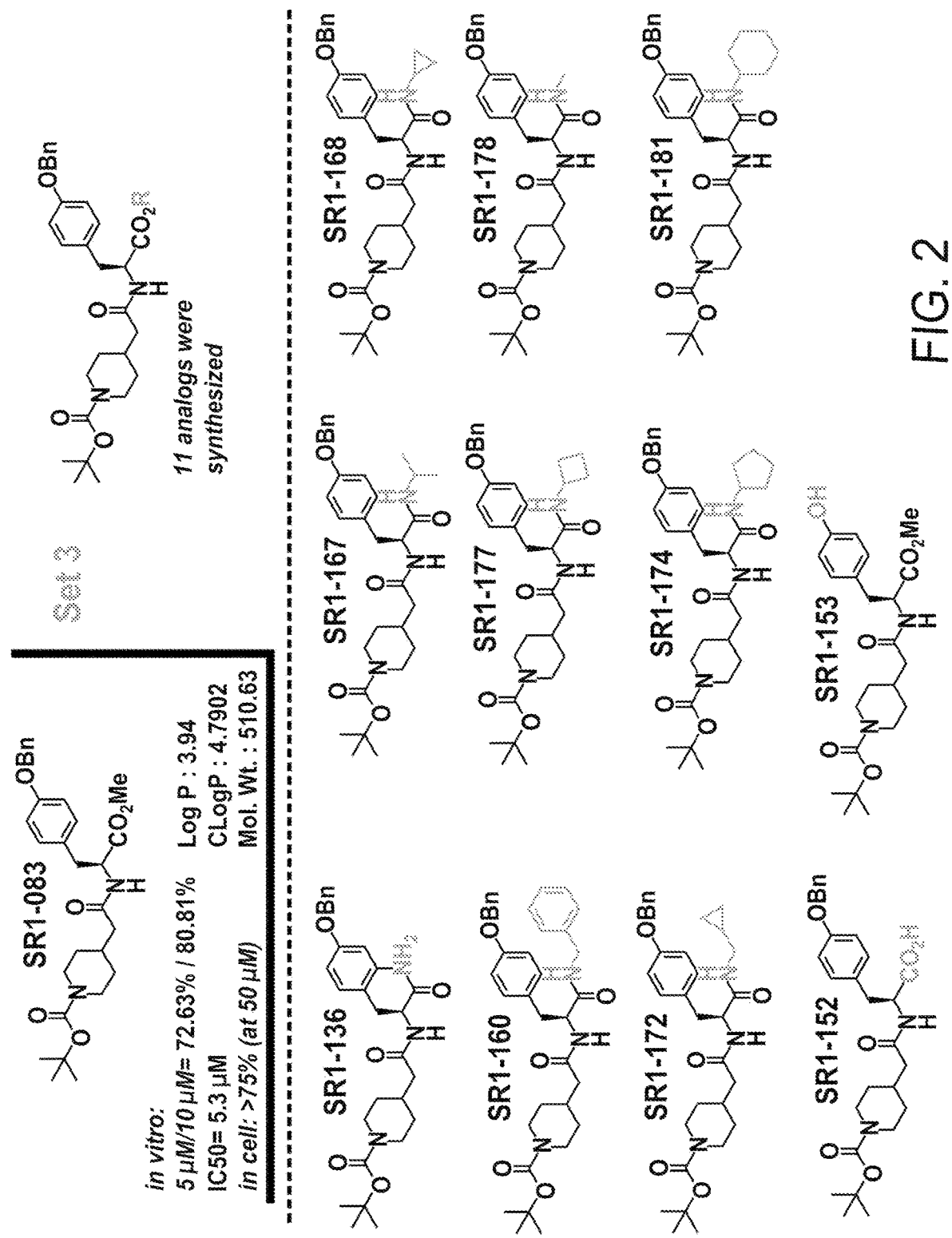
FIG. 2 is a schematic showing synthesis of C-terminal variants of SR1-083.
Figure 3:
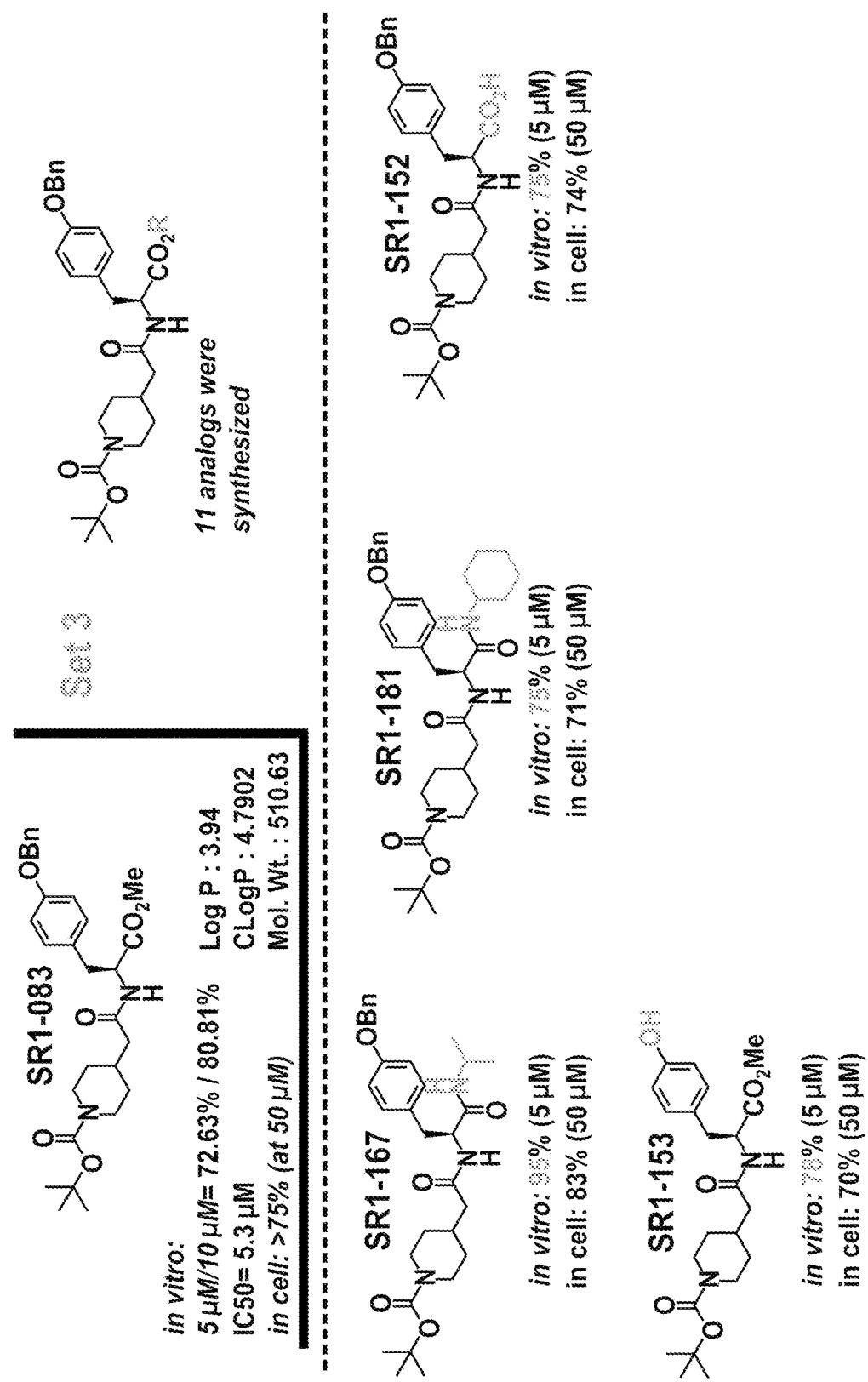
FIG. 3 is a schematic summary of potent C-terminal modified SR1-083 analogs.
Figure 4:
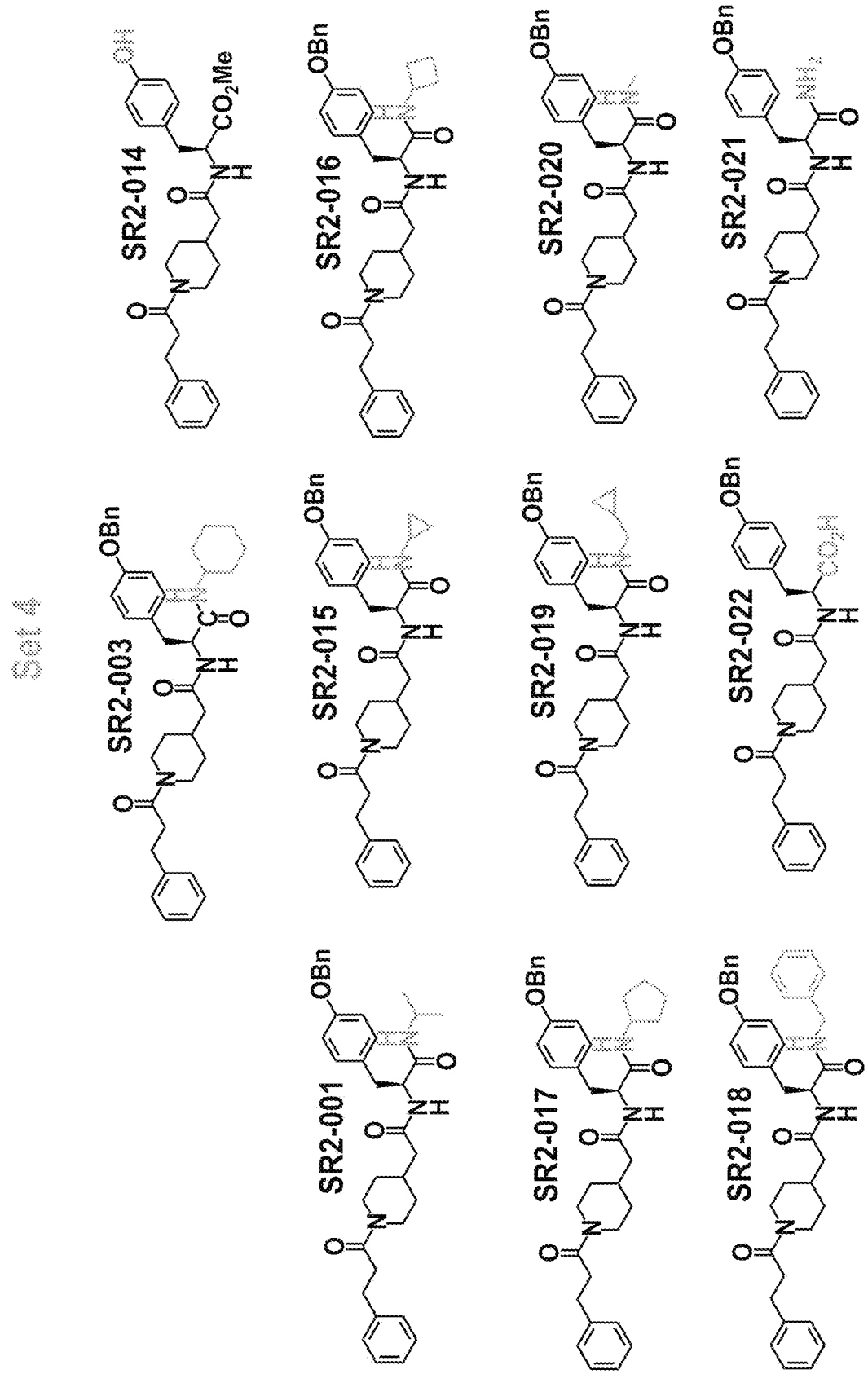
FIG. 4 is a schematic showing SR1-119 based C-terminal variants.
Figure 5:
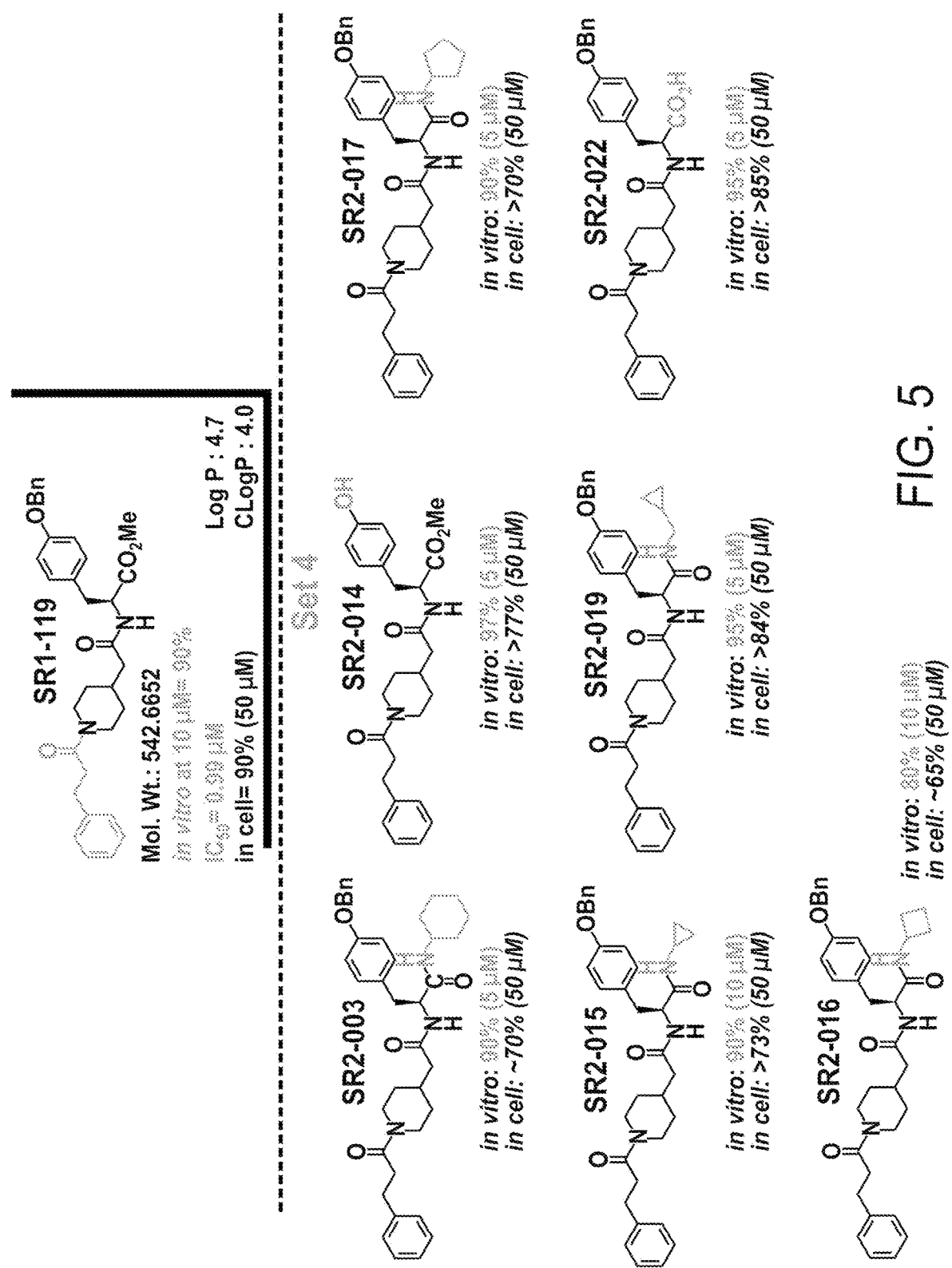
FIG. 5 is a schematic summary of potent C-terminal variants of SR1-119.
Figure 6:
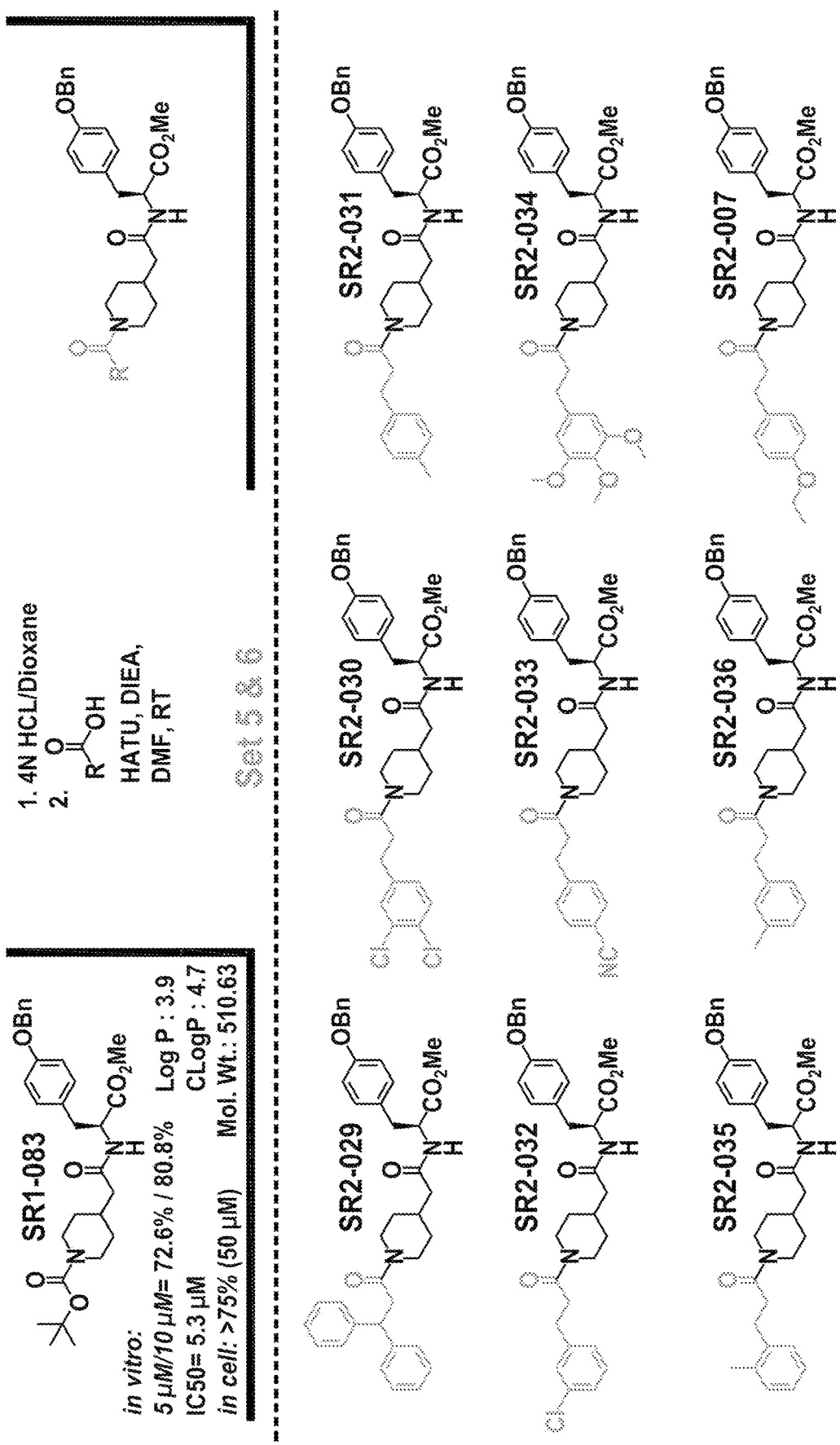
FIG. 6 is a schematic showing further N-terminal modified SR1-119 analogs (SR1-083-based series).
Figure 6:
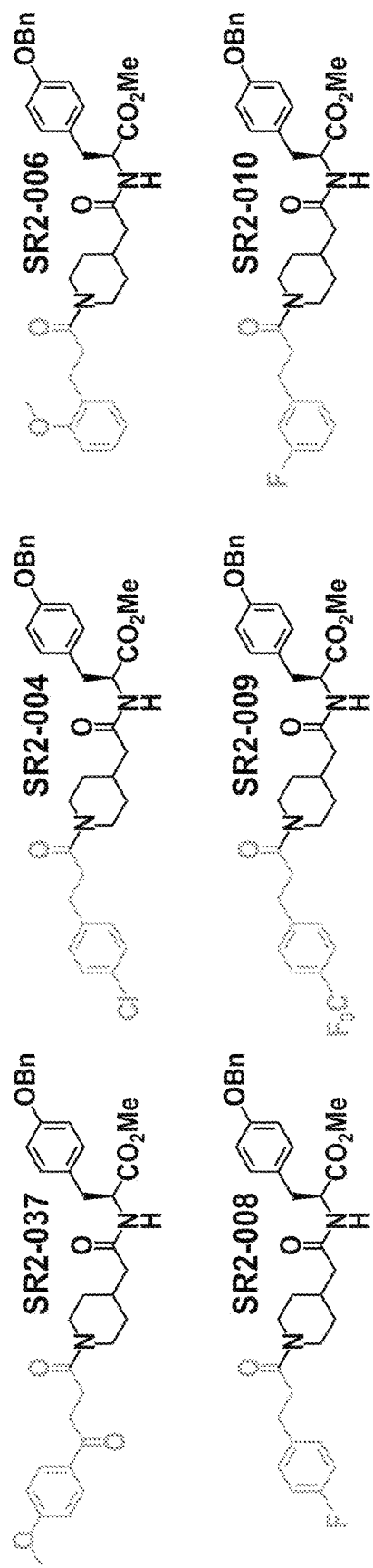
Figure 7:
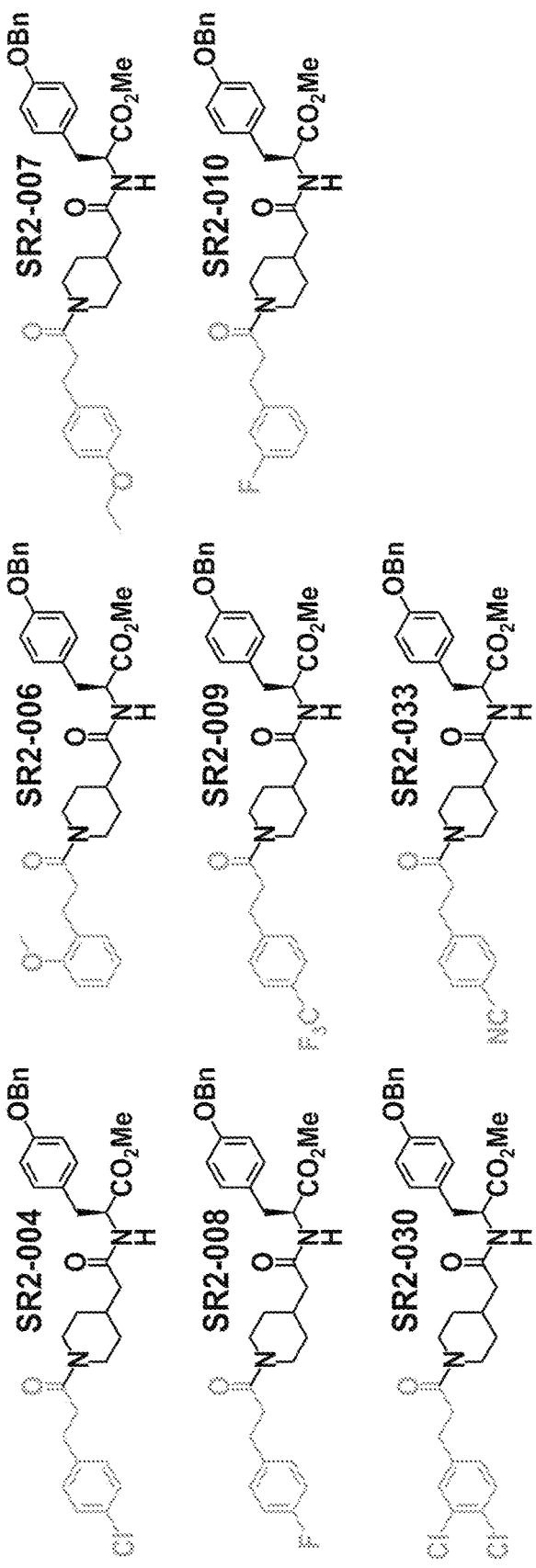
FIG. 7 is a schematic summary of potent N-terminal modified SR1-119 analogs (SR1-083 series).
Figure 8:
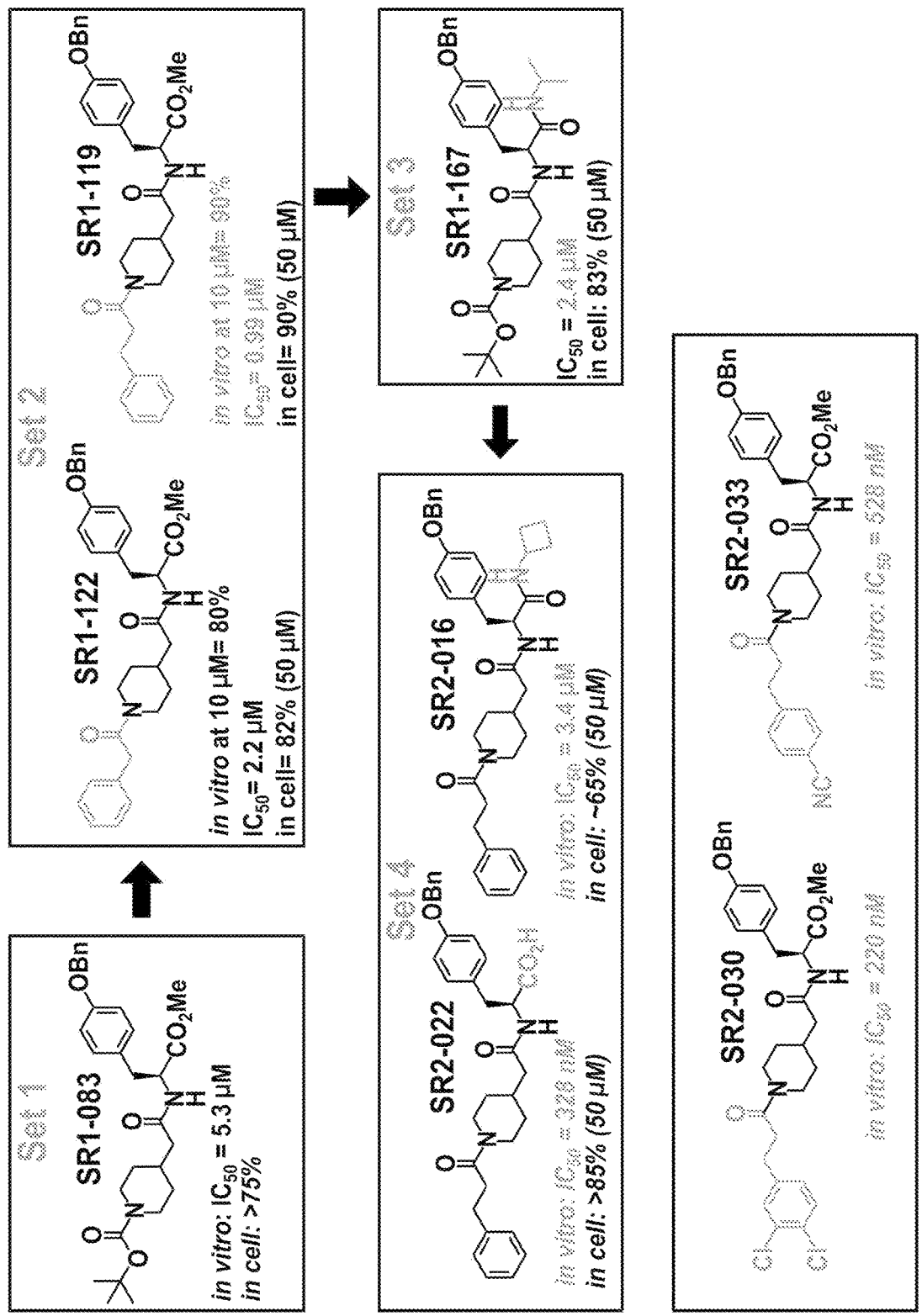
FIG. 8 is a schematic summary of potent analogs.
Figure 9:
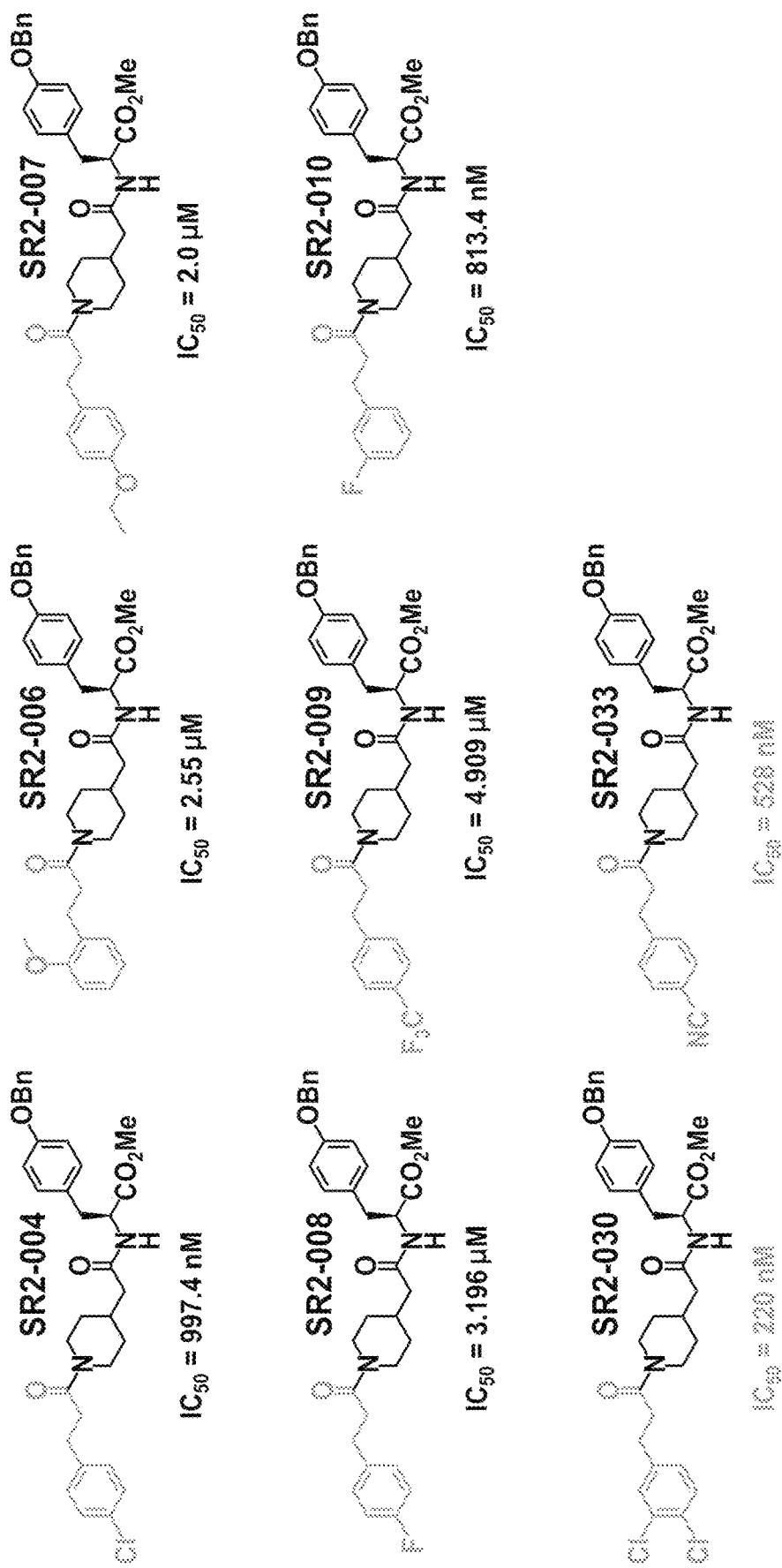
FIG. 9 is a schematic summary of potent analogs.
Figure 10:
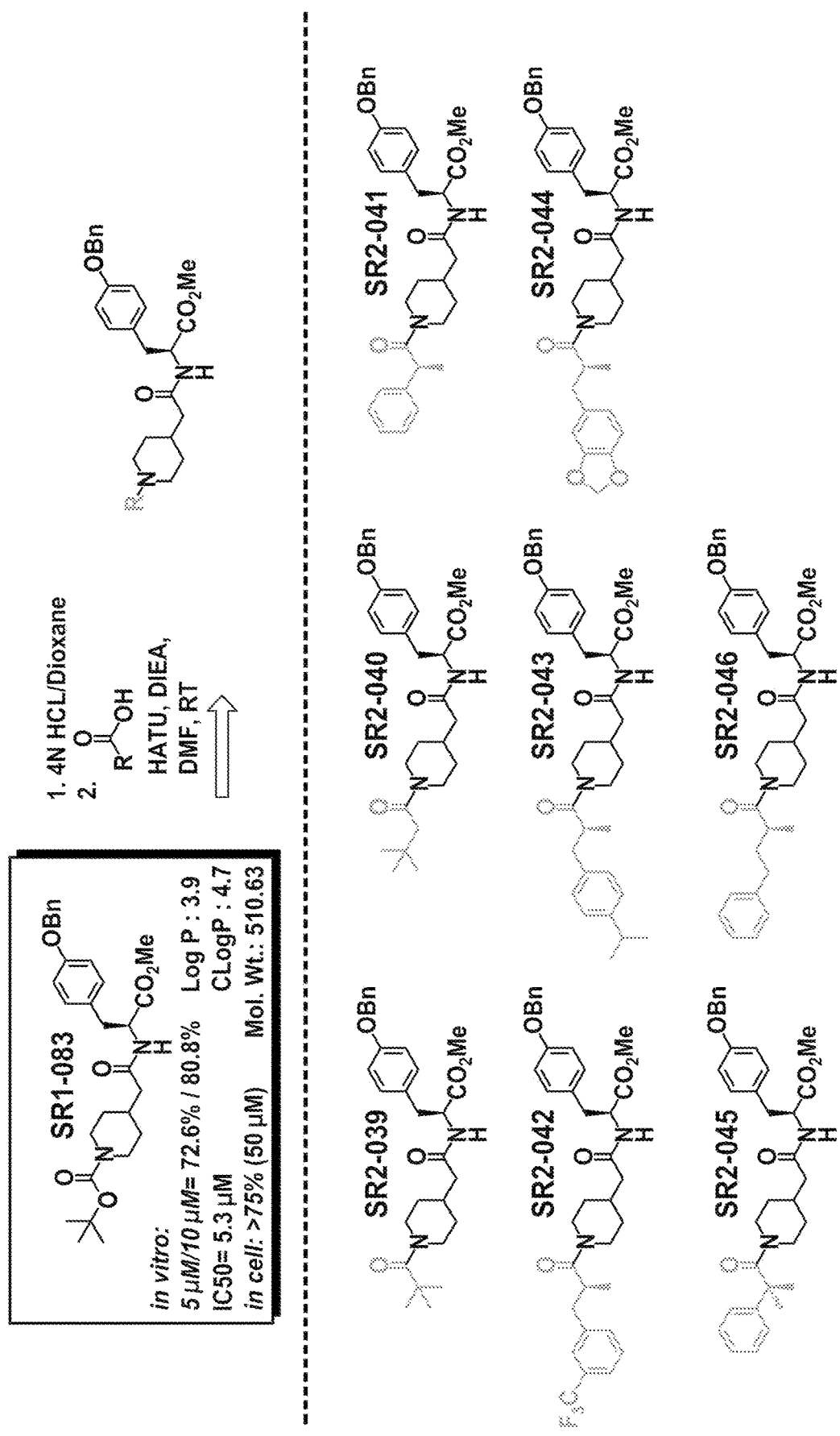
FIG. 10 is a schematic of a further synthesis of N-terminal variants of SR1-083 for SAR validation.
Figure 11:
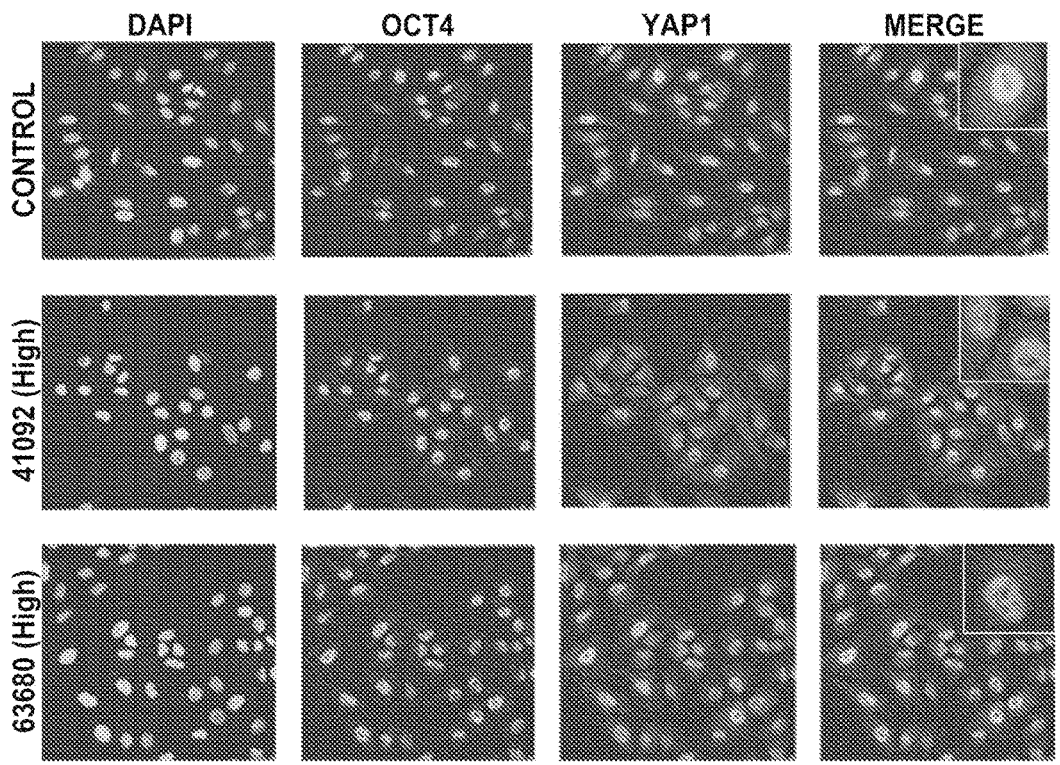
FIG. 11 is a group of cell micrographs showing disruption of YAP1 and Oct4 colocalization by high and medium priority NCI compounds. A double immunofluorescence experiments showing the co-localization of Oct4 and YAP1. Cells were treated with the indicated compounds for 48 hrs and double immunofluorescence experiment was conducted following protocols described in Bora-Singhal et al., *Stem Cells*, 2015, 33(6):1705-18. Co-localization of Oct4 and YAP1 is seen as yellow or orange color in the merged image. This is inhibited by initial NCI hits, as seen by the reduction in the yellow/orange color in co-localization experiment. The inset shows an enlarged nucleus.
Figure 12:
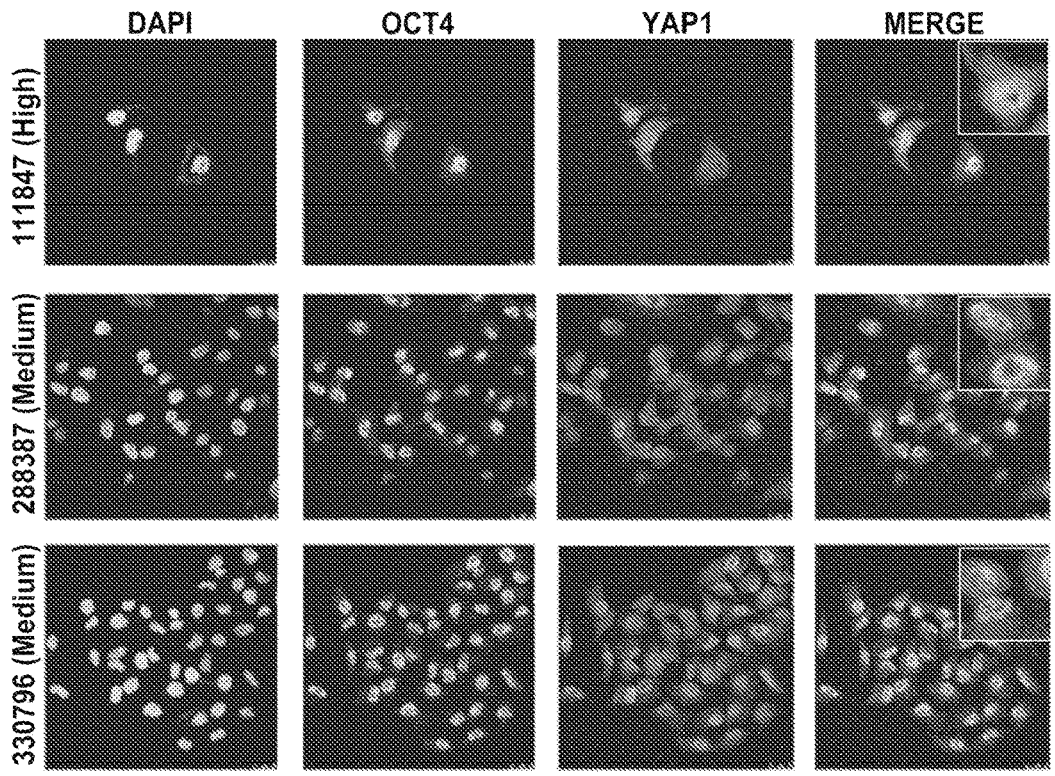
FIG. 12 is a group of cell micrographs showing disruption of YAP1 and Oct4 colocalization by high and medium priority NCI compounds. A double immunofluorescence experiments showing the co-localization of Oct4 and YAP1. Cells were treated with the indicated compounds for 48 hrs and double immunofluorescence experiment was conducted following protocols described in Bora-Singhal et al., *Stem Cells*, 2015, 33(6):1705-18. Co-localization of Oct4 and YAP1 is seen as yellow or orange color in the merged image. This is inhibited by initial NCI hits, as seen by the reduction in the yellow/orange color in co-localization experiment. The inset shows an enlarged nucleus.
Figure 13:
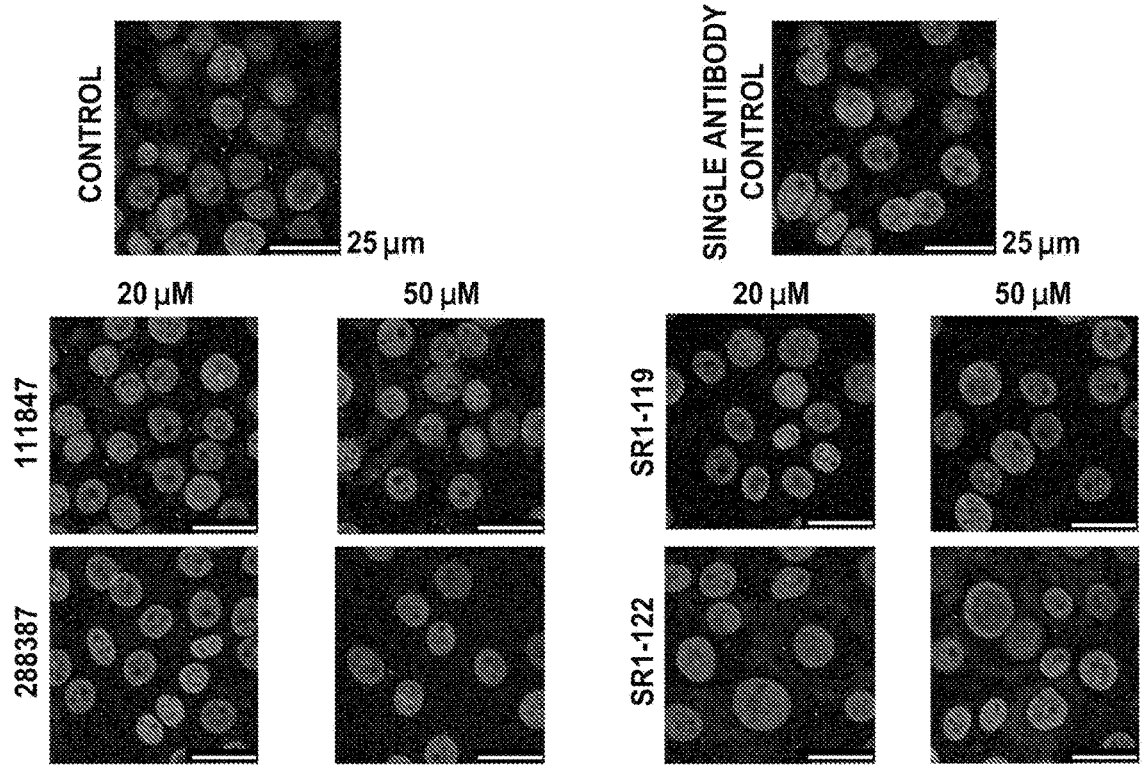
FIG. 13 is a group of cell micrographs showing disruption of YAP1 and Oct4 interaction by NCI compounds and peptidomimetics, as seen by PLA. Proximity ligation assays were conducted to further detect the interaction of Oct4 with YAP1, using protocols described in Bora-Singhal et al., 2015. Each red spot is a foci of interaction. The proximity ligation assay showed the disruption of the Oct4-YAP1 interaction in H1650 cells by the NCI hits, as determined by the absence or reduction of the red spots. Cells were treated with the compounds for 48 hrs.
Figure 14:
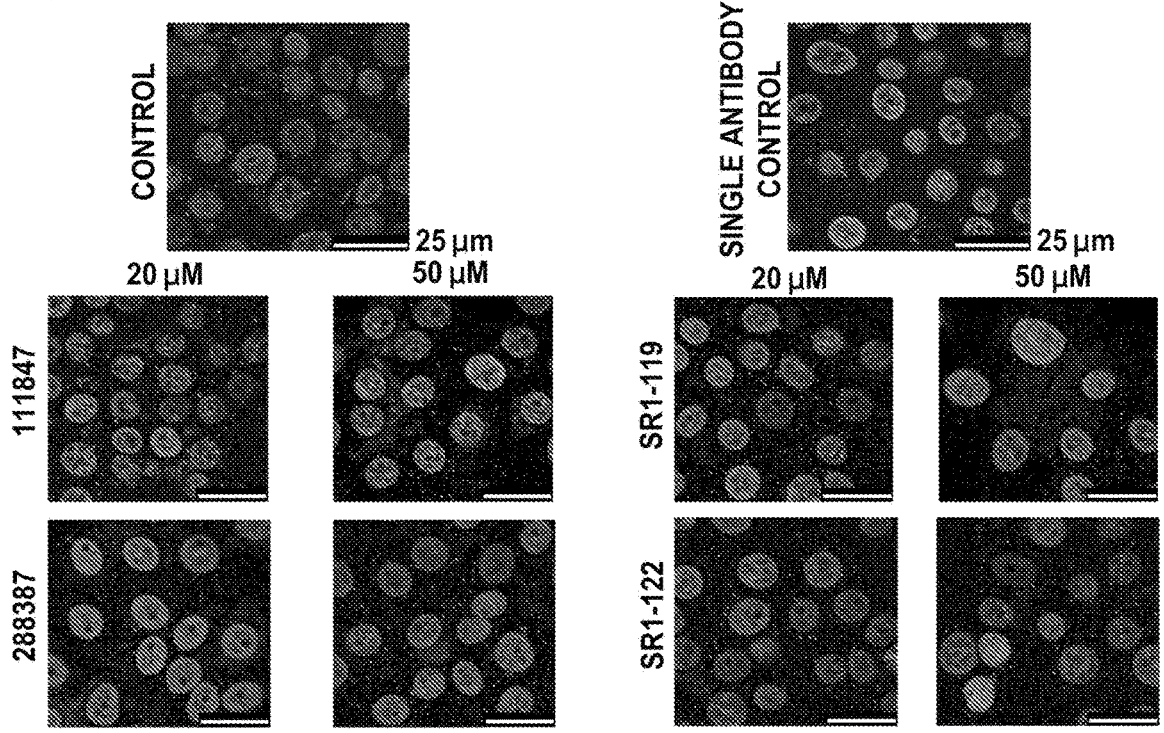
FIG. 14 is a group of cell micrographs showing disruption of YAP1 and Oct4 interaction by NCI compounds and peptidomimetics, as seen by PLA. A proximity ligation assay was used to test if the compounds could inhibit the binding of an unrelated transcription factor, TEAD2, to YAP1. TEAD2 binds to YAP1 through the TEAD binding domain, and not the WW domain of YAP1. Proximity ligation assays using antibodies to YAP1 and TEAD2 showed that the same NCI compounds do not disrupt the binding of YAP1 to TEAD2. Cells were treated with the indicated doses of the compounds for 48 hrs. This is essentially a control experiment, showing the specificity of the drugs in disrupting the OCt4-YAP1 interaction.
Figure 15:
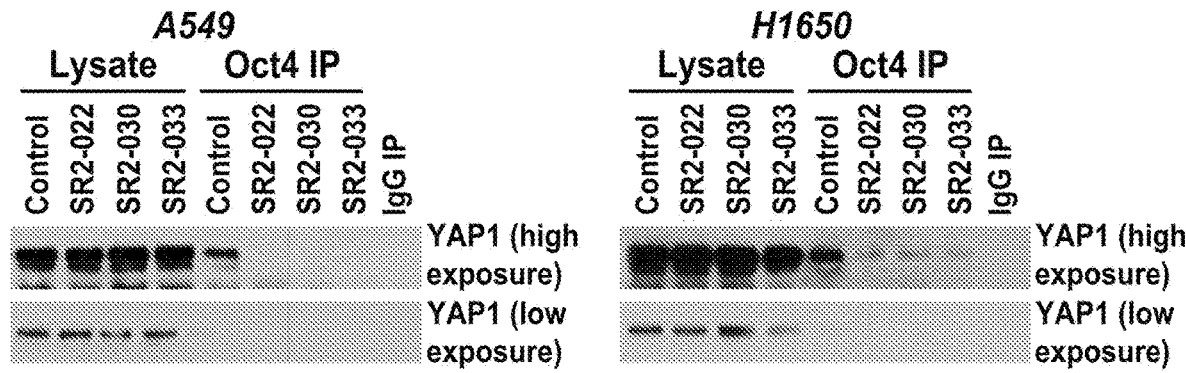
FIG. 15 is a group of gel images showing peptidomimetic compounds SR2-022, SR2-030, and SR2-033 reduced YAP1-Oct4 interaction as detected by IP-WB. An immunoprecipitation-Western blot experiment was conducted to assess if the indicated compounds could disrupt the binding of Oct4 to YAP1. IP-western blots were conducted using the protocols described in Bora-Singhal et al, 2015. Essentially, cells were treated with 5 µM of the indicated compounds for 72 hours. Lysates were prepared from the cells, and immunoprecipitated with an antibody to OCt4, or a control IgG. Lysates as well as the immunoprecipitates were resoled by a polyacrylamide gel and a western blot was conducted using an antibody to YAP1. It can be seen that there is a significant amount of YAP1 associated with Oct4 in the IP from the unreated cells (Control lane, in Oct4 IP); the interaction was completely abolished by the drugs in A549 cells, and significantly reduced in H1650 cells. This shows that the compounds can disrupt the interaction of Oct4 with YAP1.
Figure 16:
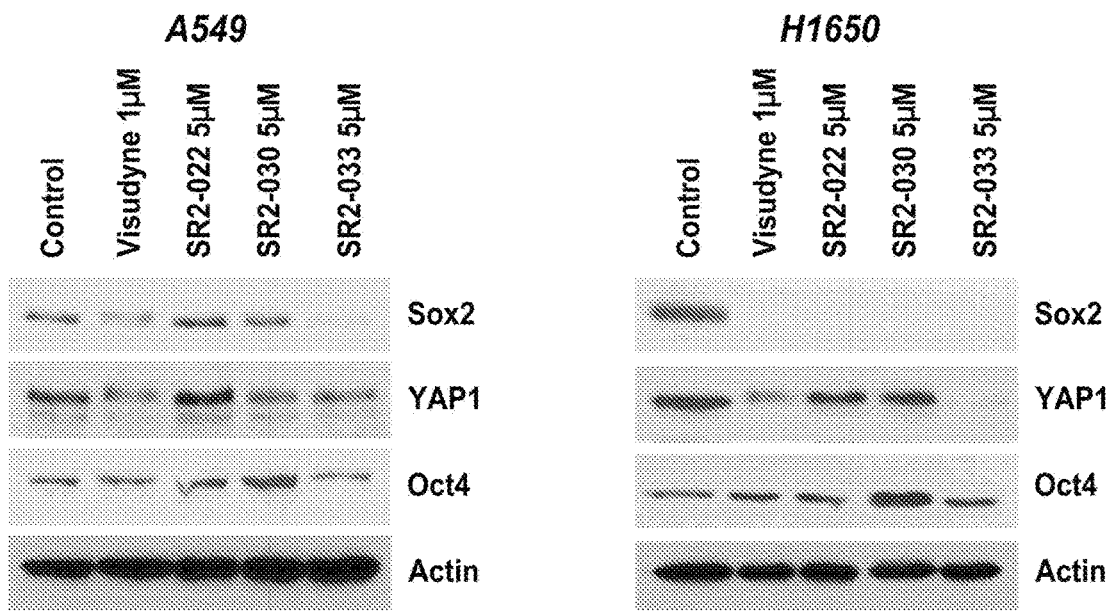
FIG. 16 is a group of gel images showing Sox2 protein expression was reduced by SR-2033 in adenocarcinoma cells.
Figure 17:
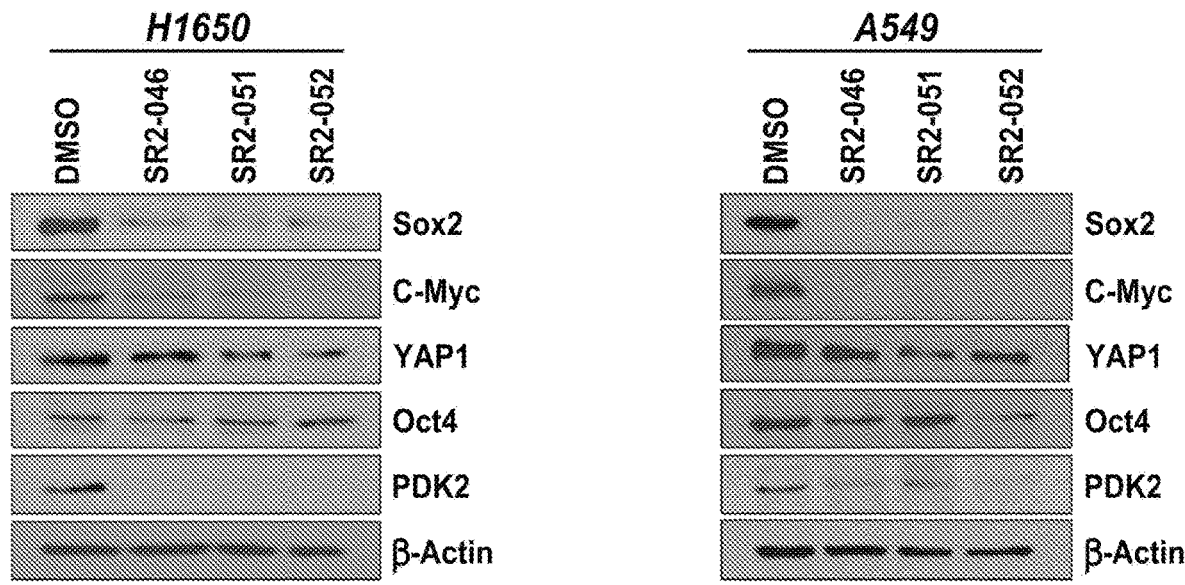
FIG. 17 is a group of gel images showing compounds SR2-046, SR2-051, and SR2-052 reduce Sox2, c-Myc expression in H165 and A549 cells. Cells were treated for 72 hours with the indicated compounds. A western blot showing the reduction of Sox2 expression in H1650 cells and in A549 cells after treatment with 10 uM of the drugs for 72 hours. There was a reduction in the levels of C-myc and phoshodiesterate kinase 2 as well. Western blotting was done using our standard protocols, as published in Bora-Singhal et al., 2015.
Figure 18:
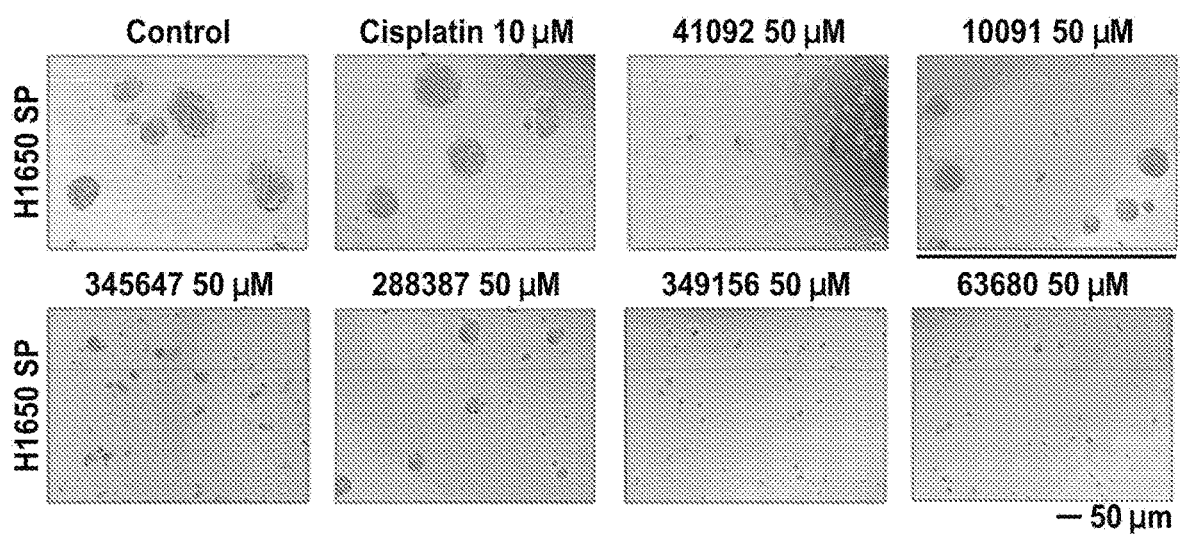
FIG. 18 is a group of cell micrographs showing inhibition of self-renewals by selected compounds in a sphere formation assay. Self-renewal of stem-like side-population (SP) cells was measured by a sphere-formation assay. Essentially, side-population cells were sorted by flow cytometry based on Hoechst 33342 dye exclusion as described in our publications. Isolated SP cells were grown in low-adherence plates in stem-cell selective media for 10 days (Singh and Chellappan, 2012, Bora-Singhal et al., 2015 etc). Self-renewal ability of the stem-like cells can be assessed by the formation of spheres under these conditions; non-stem cells cannot self-renew and form spheres. Inclusion of the indicated disruptors significantly reduced the number of spheres, whereas a standard chemotherapy drug, Cisplatin, had no effect.
Figure 19:
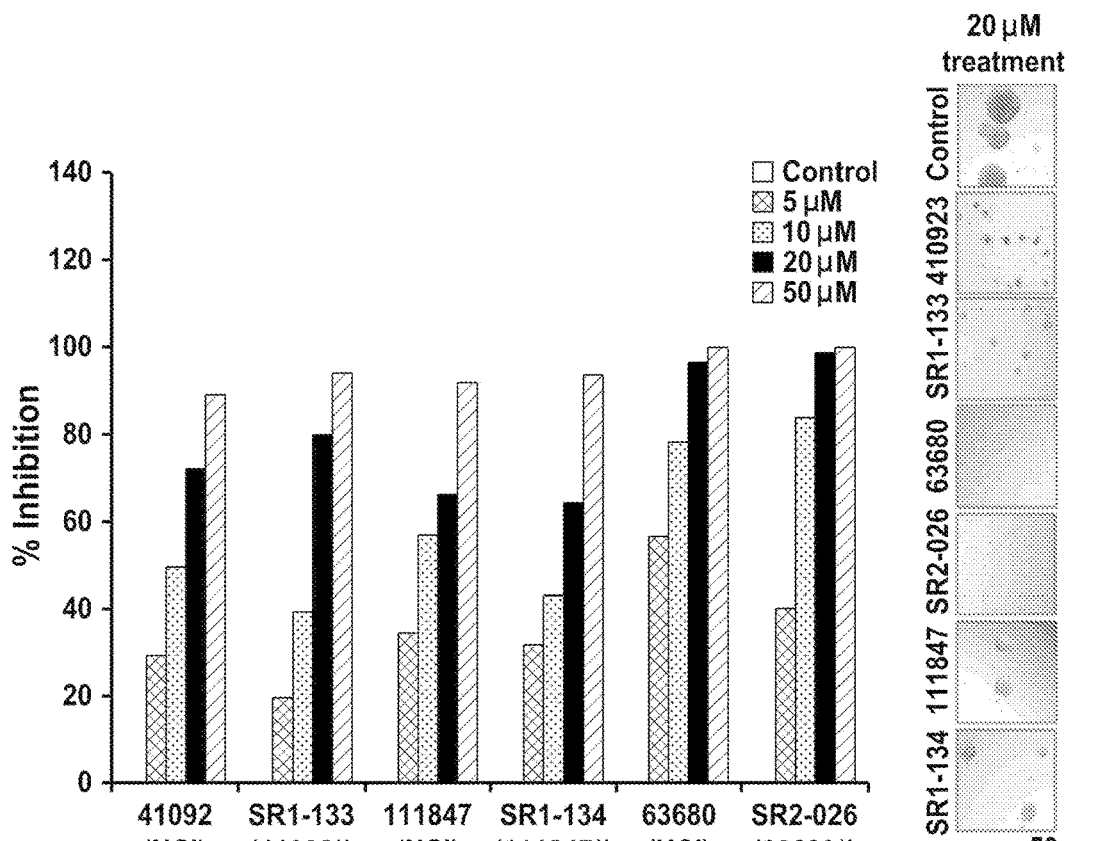
FIG. 19 is a graph showing that 3 hits suppress self-renewal of H1650 SP cells, as seen by a sphere-formation assay. The assay is conducted for 10 days, and the number of spheres larger than 50 µm in diameter is counted. The indicated drugs could significantly inhibit self-renewal.
Figure 20:
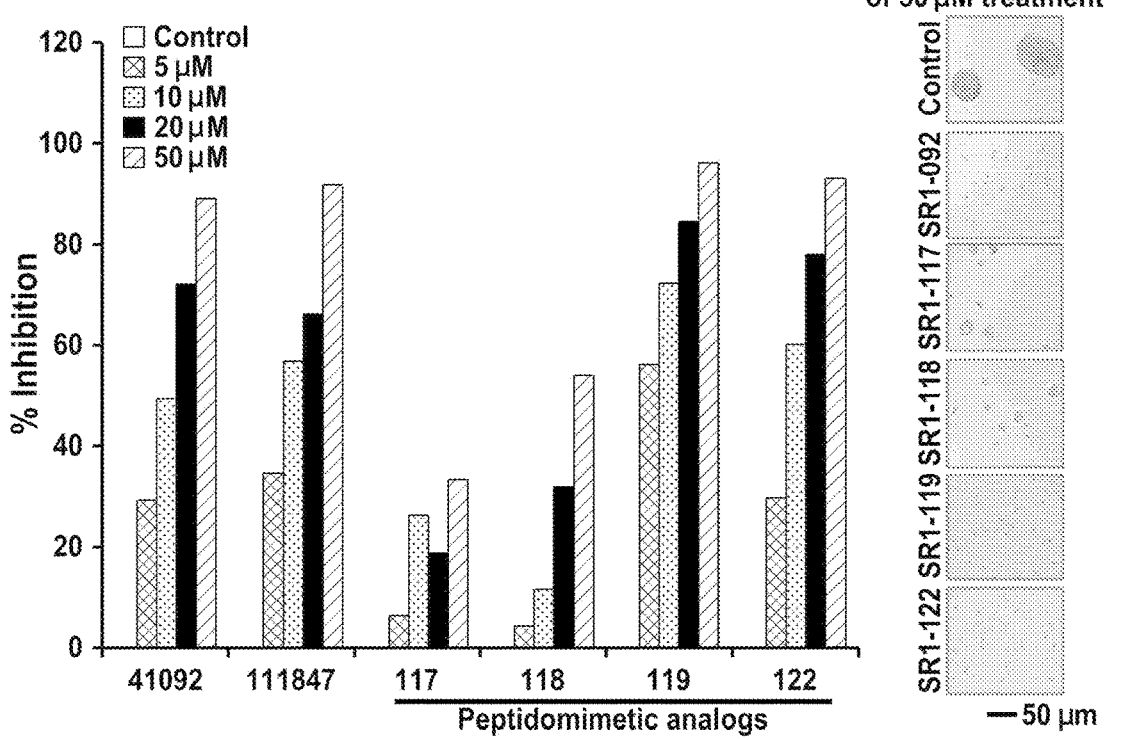
FIG. 20 is a graph showing that PPxY mimetic compounds inhibit self-renewal, as seen by a sphere-formation assay. The assay is conducted for 10 days, and the number of spheres larger than 50 µm in diameter is counted. The indicated drugs could significantly inhibit self-renewal.
Figure 21:
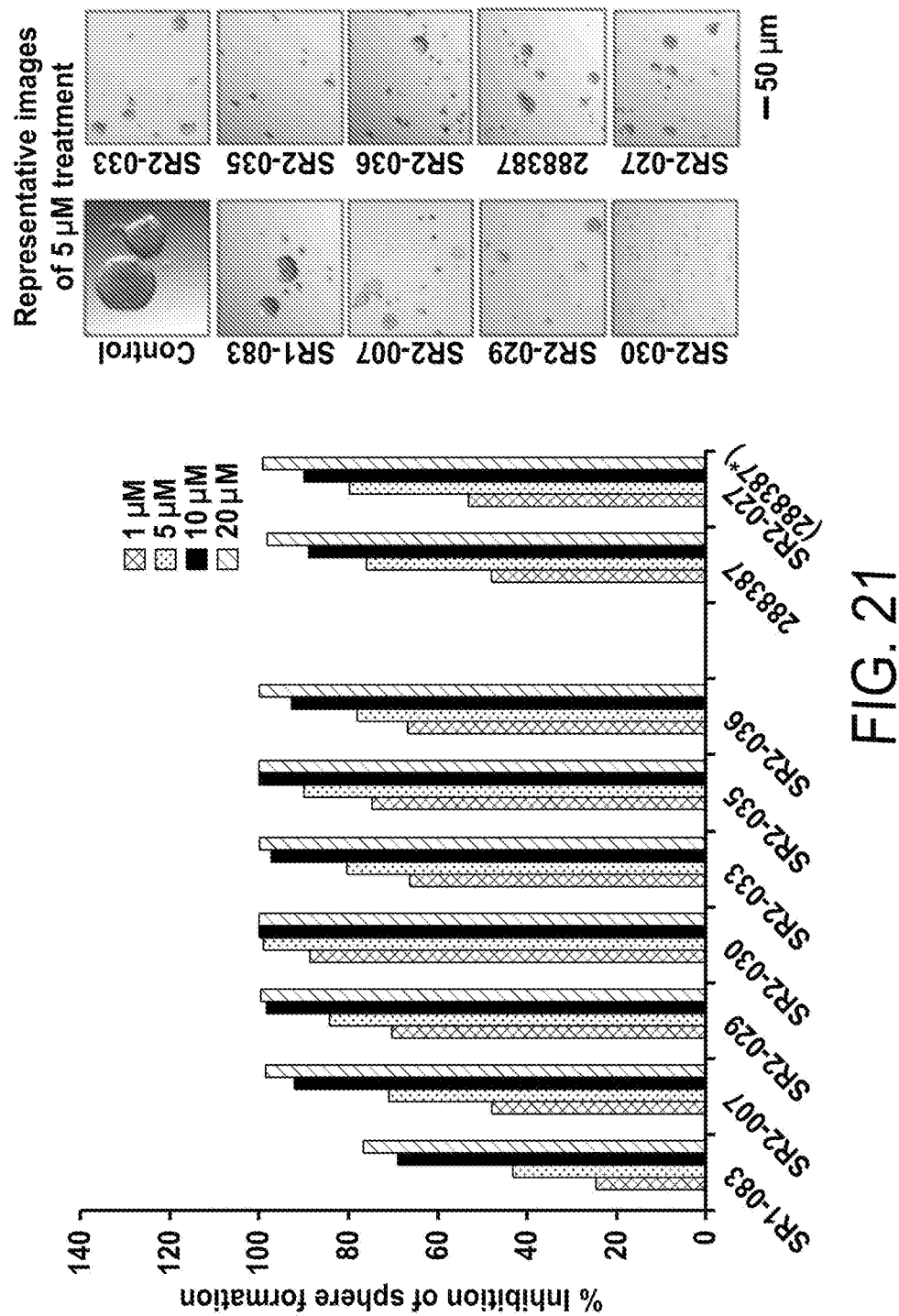
FIG. 21 is a graph showing compounds inhibit self-renewal, as seen by a sphere-formation assay. The assay is conducted for 10 days, and the number of spheres larger than 50 μm in diameter is counted. The indicated drugs could significantly inhibit self-renewal.
Figure 22:
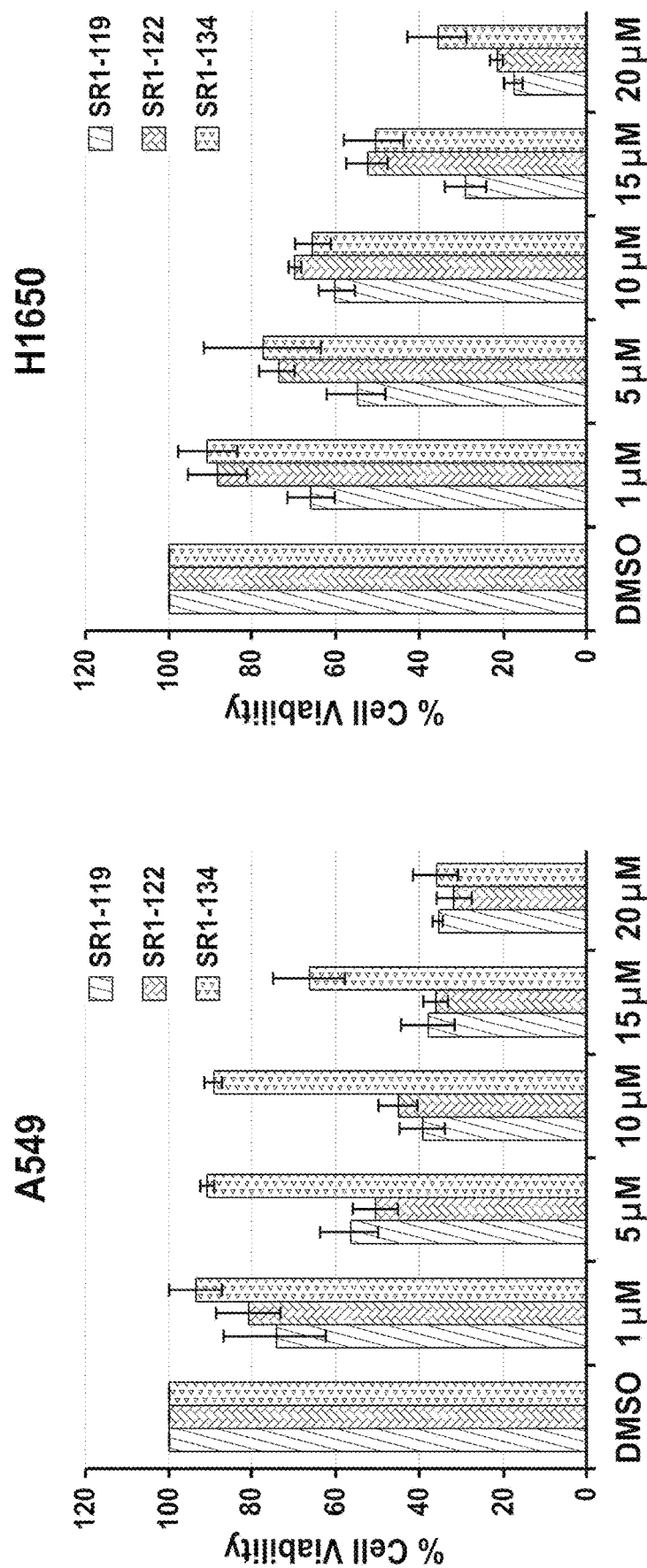
FIG. 22 is a group of graphs showing the ability of the indicated compounds to reduce the viability of A549 and H1650 cells assessed by a MTT assay, using standard protocols. Cells were treated with the indicated doses of the drugs for 72 hrs, and MTT assay was conducted. Viability of both A549 and H1650 cells was markedly reduced by the drugs.
Figure 22:
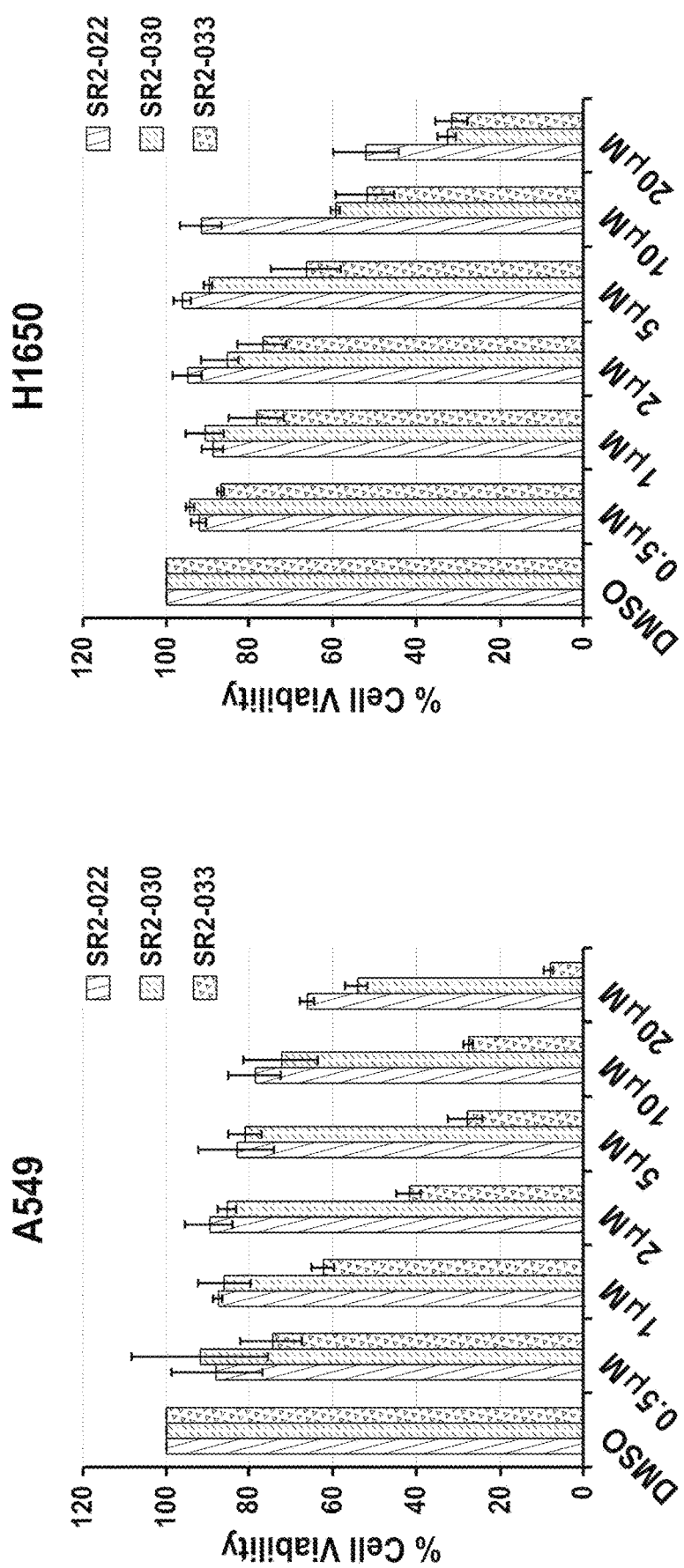
Figure 22:
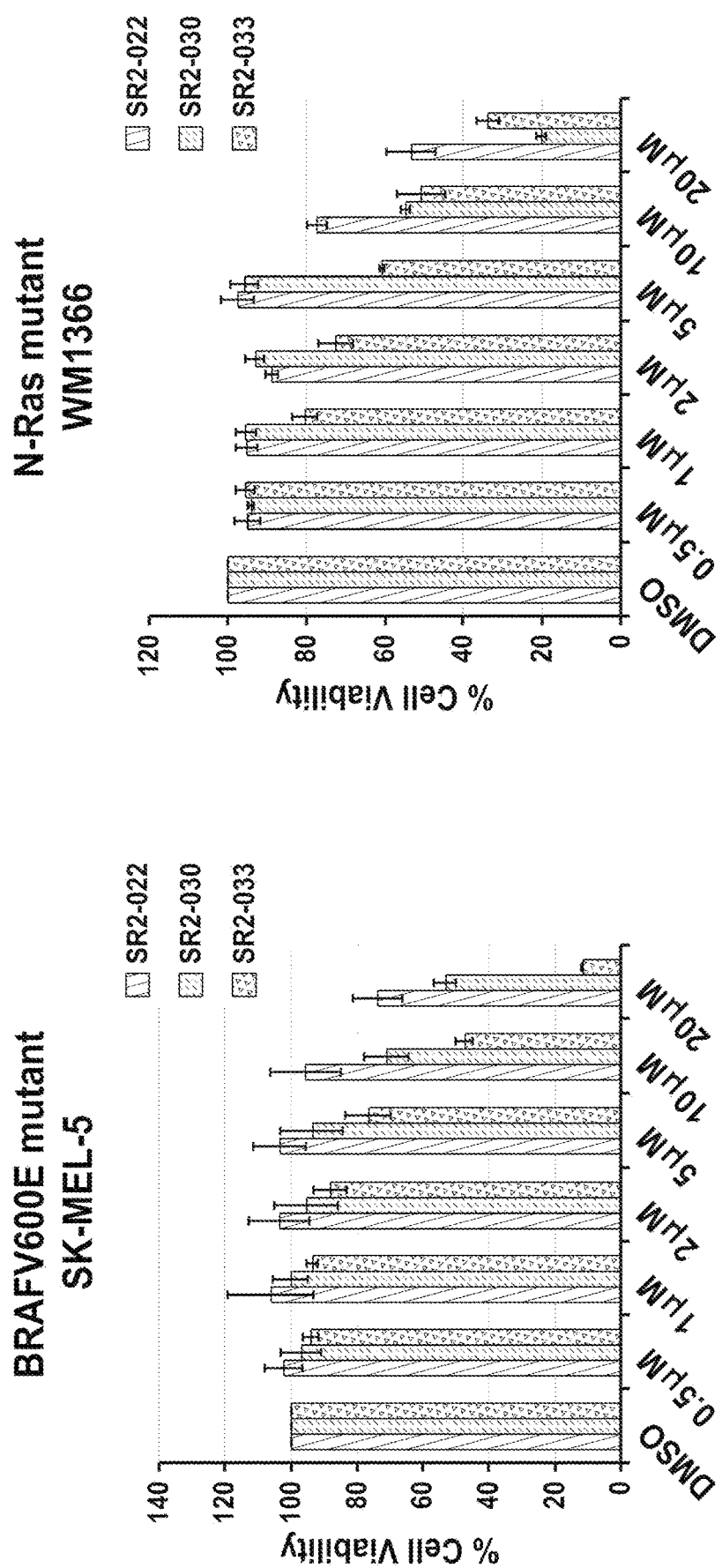
Figure 22:
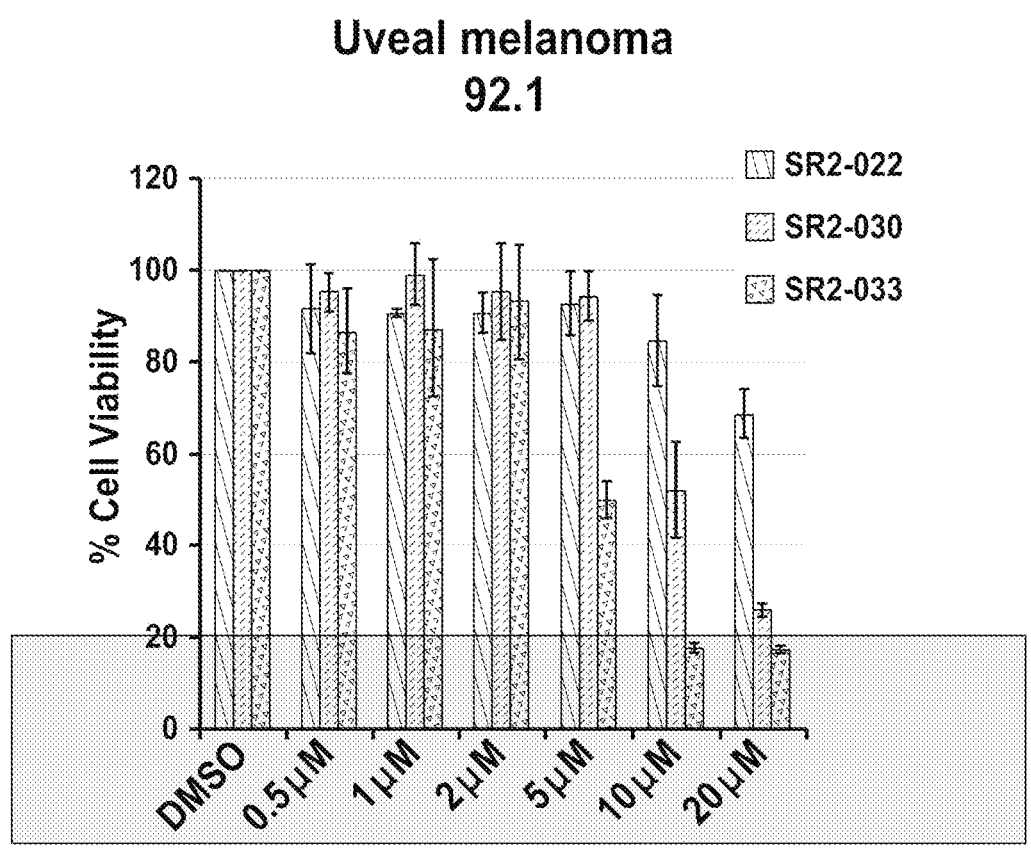
Figure 22:
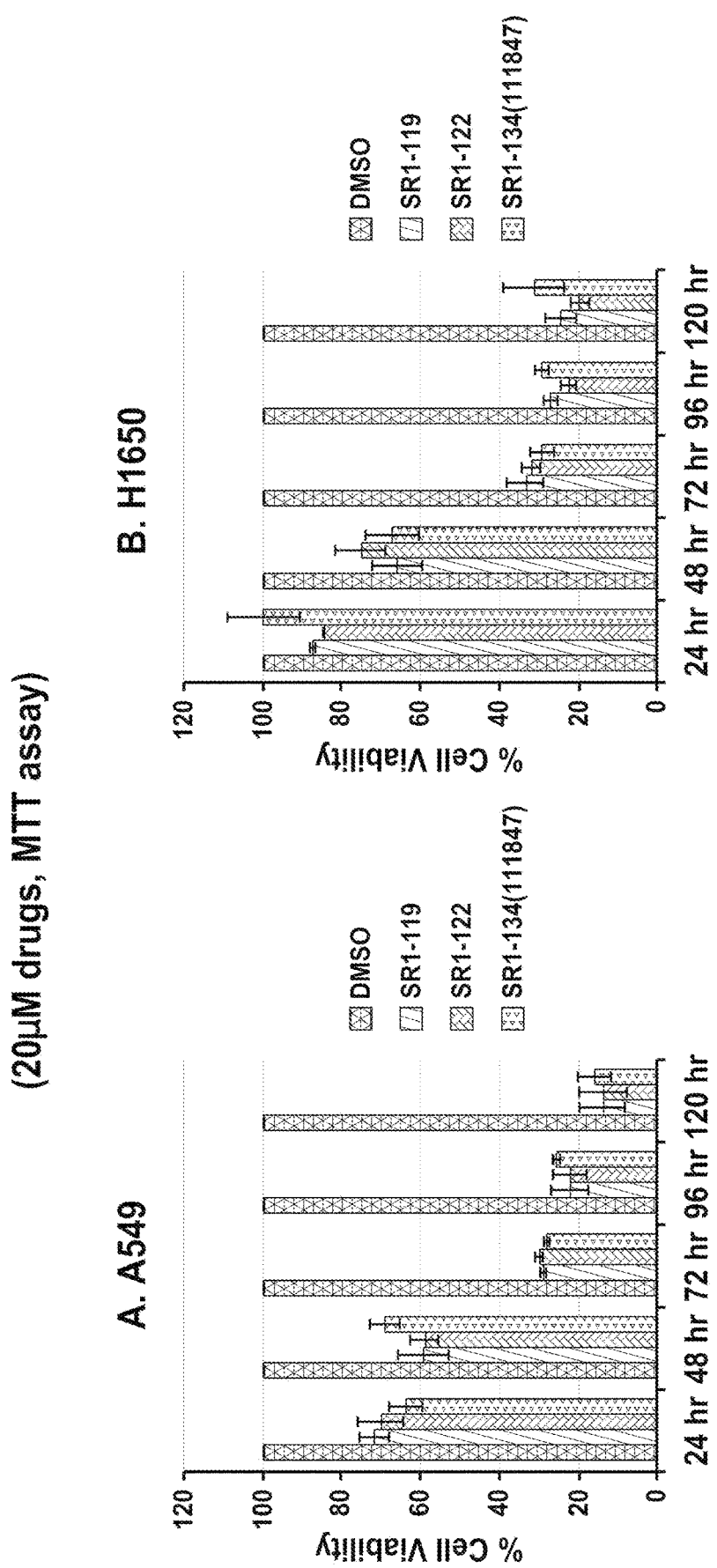
Figure 23:
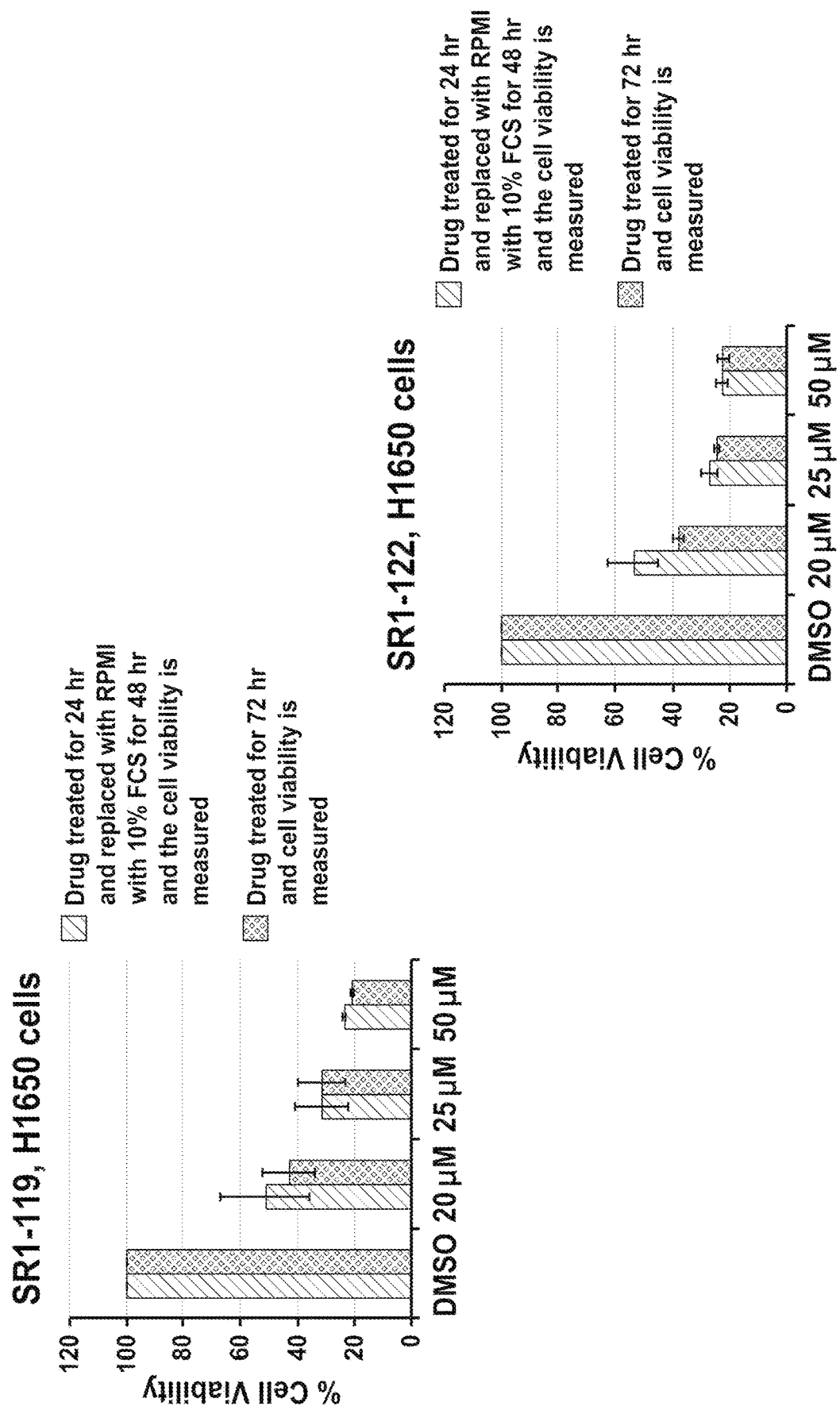
FIG. 23 is a group of graphs showing results from an experiment to check how long the cells should be treated with the drugs to reduce viability. Cells were treated for 24 hours with the drugs (light bars); the drugs were removed and cells were grown in regular growth media for an additional 48 hrs. In parallel, cells were treated with the drugs continuously for 72 hrs (dark bars). It can be seen that treatment with the drugs for 24 hrs can reduce cell viability comparable to continuous treatment for 72 hrs.
Figure 24:
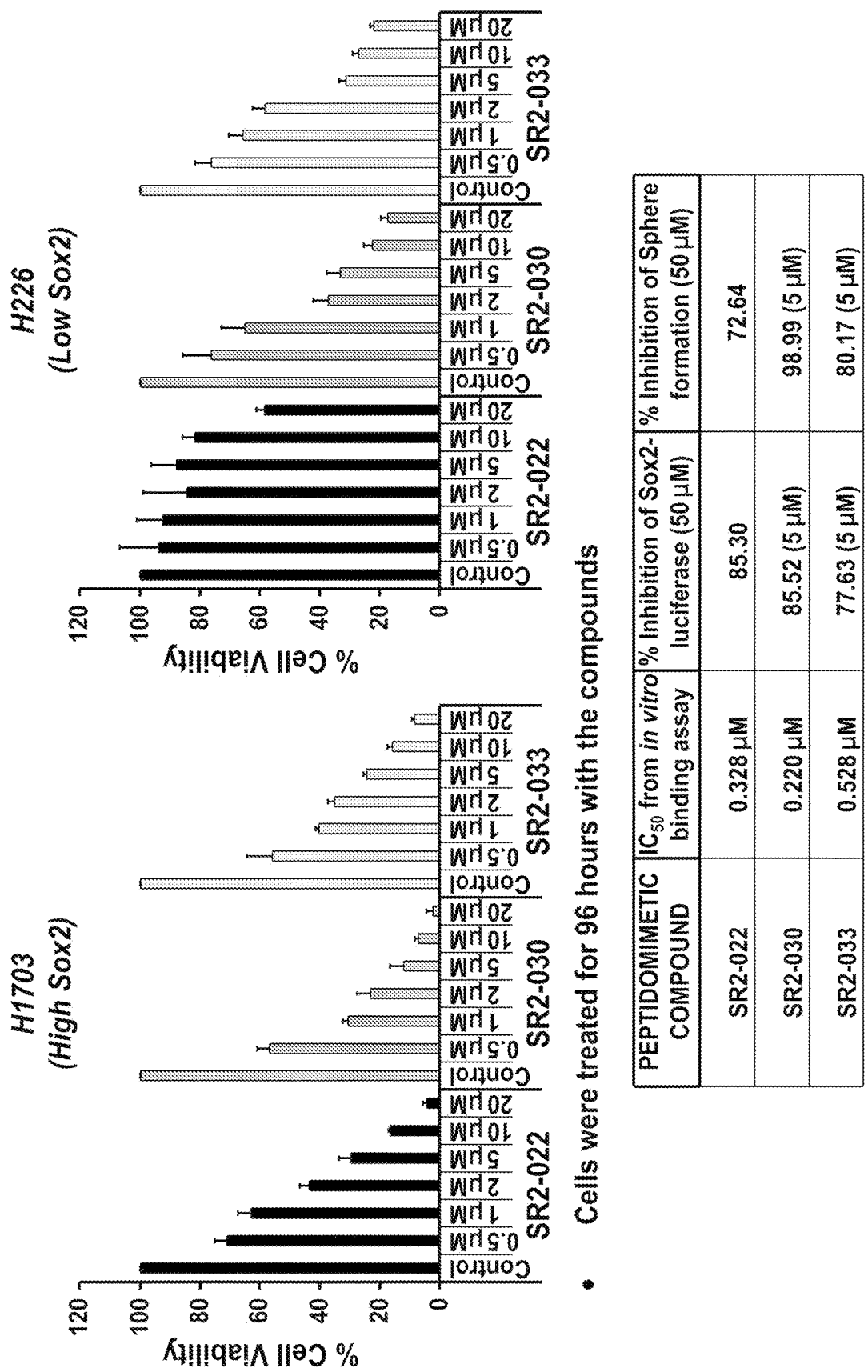
FIG. 24 shows YAP1 inhibitors reduce the viability of squamous cell carcinomas cell lines (from the lung), as measured by a MTT assay. Cells were treated for 96 hrs with the indicated doses of the drugs.
Figure 25:
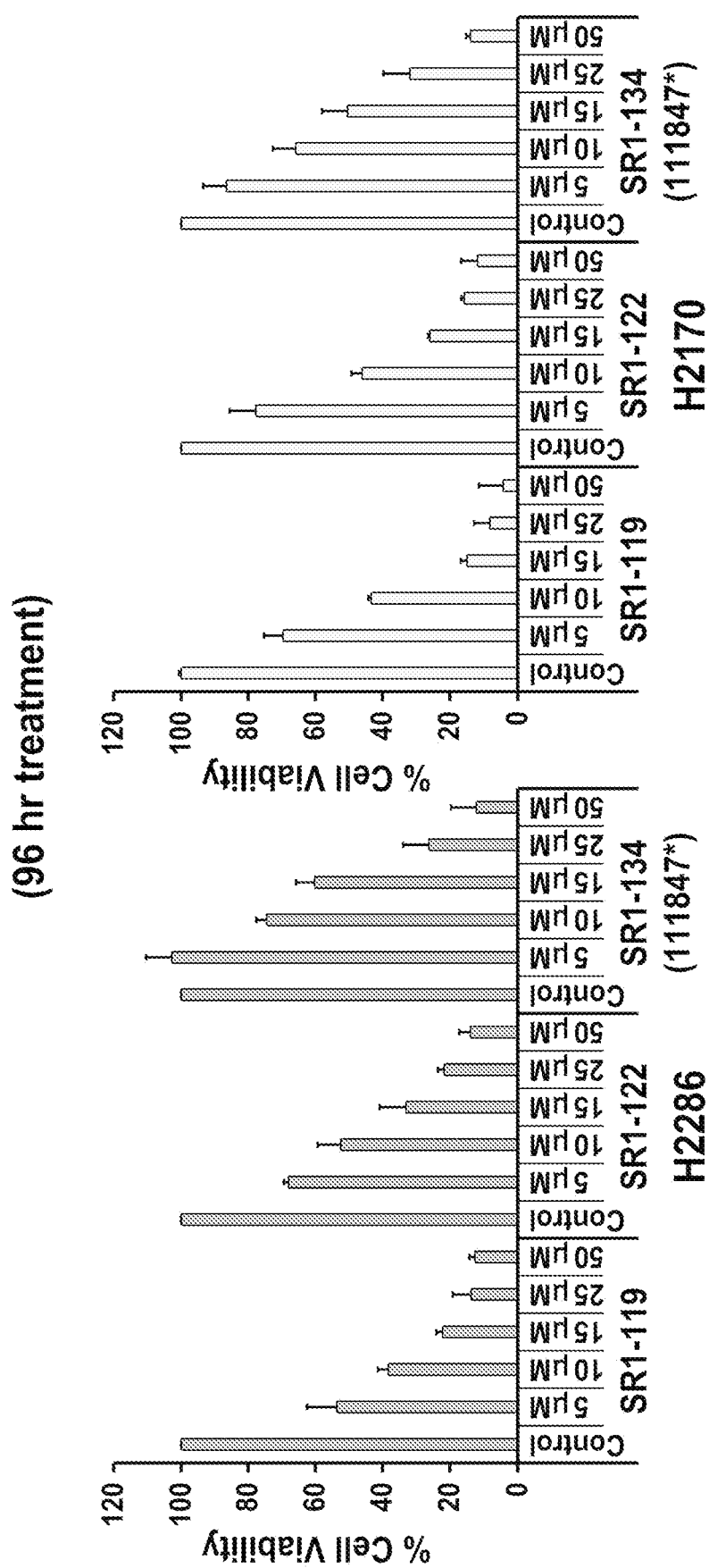
FIG. 25 shows YAP1 inhibitors reduce the viability of squamous cell carcinomas cell lines (from the lung), as measured by a MTT assay. Two different cell lines were treated for 96 hrs with the indicated doses of the drugs.
Figure 26:
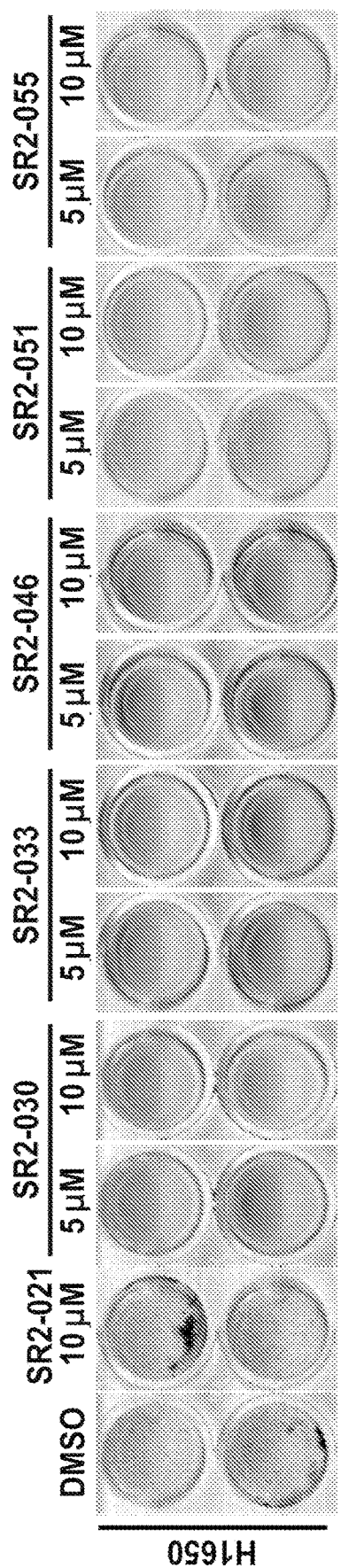
FIG. 26 shows photographs from an assay of adherence-independent growth of H1650 cells in the presence of selected compounds. One feature of cancer cells is their ability to grow in an adherence-independent manner. They do not require survival signals from adhesion to a substratum. Ability to grow in an adherence-independent manner can be measured by growing the cells in soft-agar. The ability of the YAP1 inhibitors to suppress adherence-independent growth of H1650 lung adenocarcinoma cells in soft-agar was tested for 33 days, with new aliquots of the drugs added every three days. Standard protocols were used.
Figure 27:
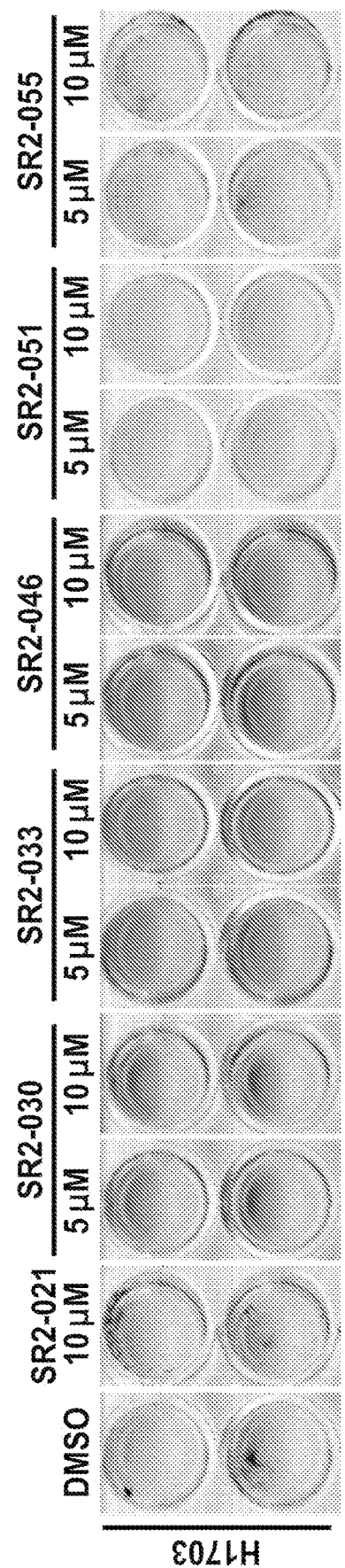
FIG. 27 shows photographs from an assay of adherence-independent growth of H1703 cells in the presence of selected compounds. One feature of cancer cells is their ability to grow in an adherence-independent manner. They do not require survival signals from adhesion to a substratum. Ability to grow in an adherence-independent manner can be measured by growing the cells in soft-agar. The ability of the YAP1 inhibitors to suppress adherence-independent growth of H1703 lung squamous cell carcinoma in soft-agar was tested for 33 days, with new aliquots of the drugs added every three days. Standard protocols were used.
Figure 28:
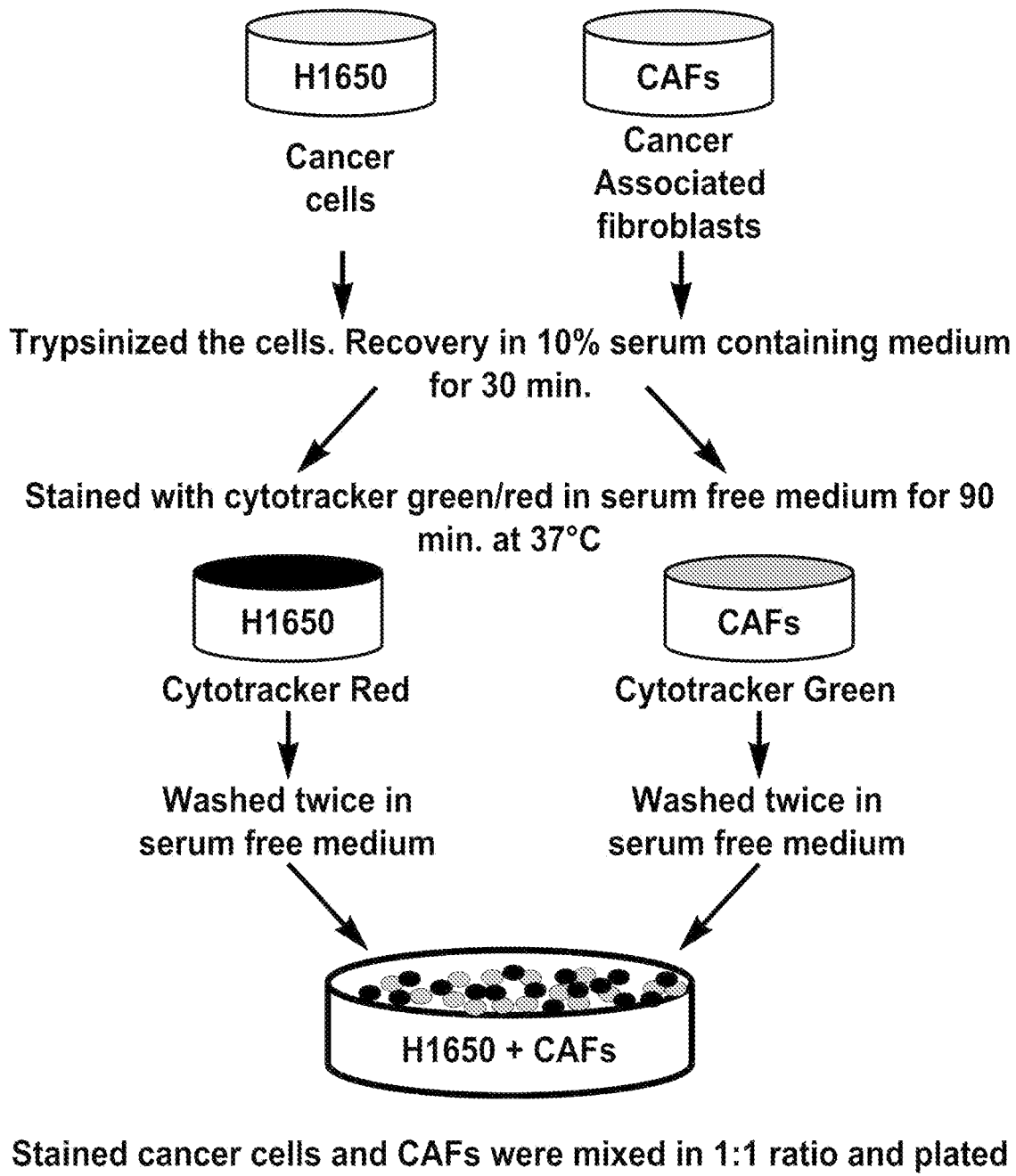
FIG. 28 is a schematic of a study on the effected of compounds on co-cultures. Cancer associated fibroblasts (CAFs) present in the tumor stroma facilitate the growth of tumors and confer resistance to various drugs. This experiment was to test if the YAP1 inhibitors can eliminate cancer cells even when CAFs are present. H1650 cells were labeled with a commercially available cytotracker red dye and CAFs were labeled with cytotracker green dye. Cells can be cultured together and visualized by immunofluorescence microscopy. This co-culture system was used to assess if the YAP1 inhibitors could kill the cancer cells selectively, even in the presence of CAFs.
Figure 29:
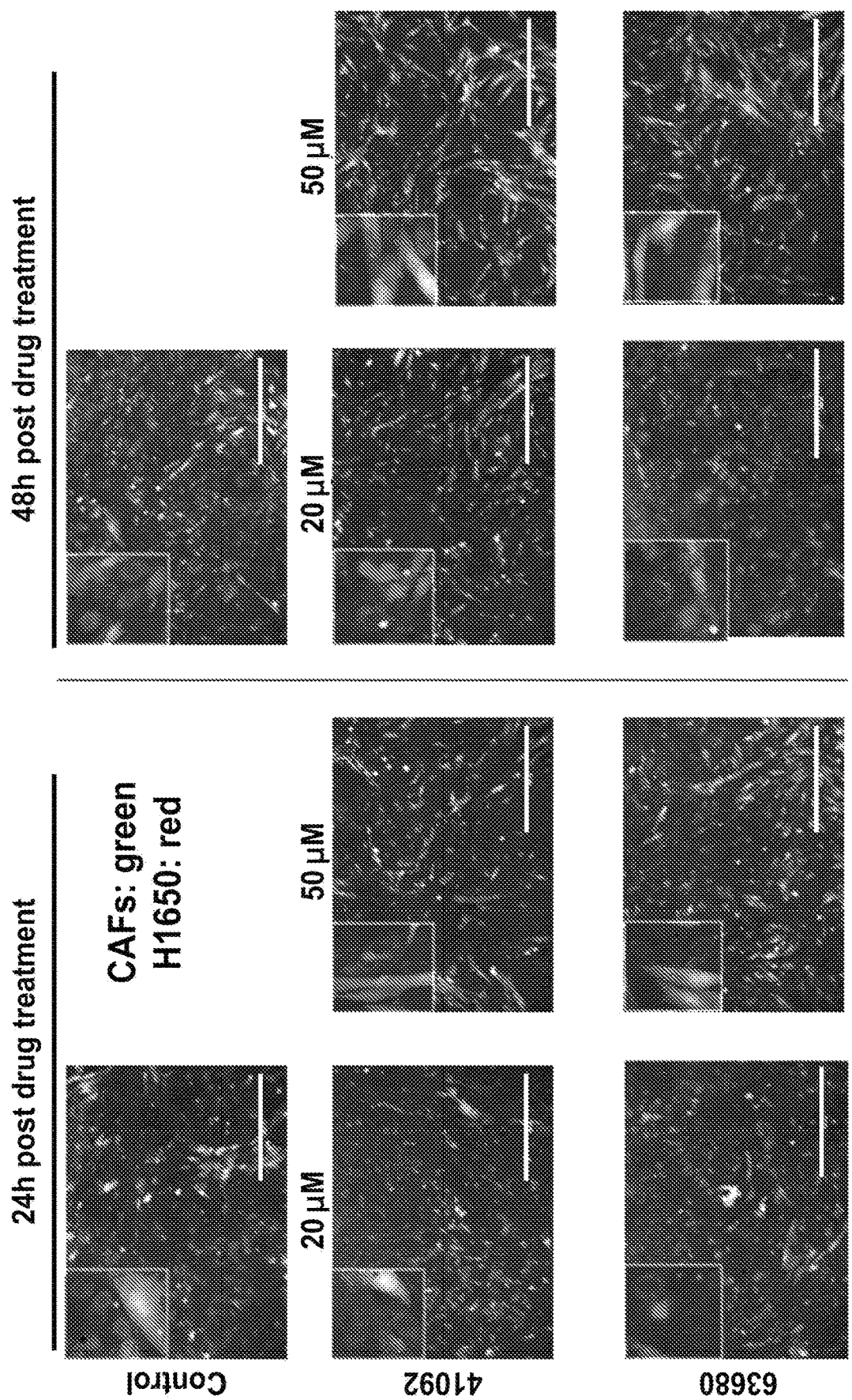
FIG. 29 shows results from H1650 cells cocultured with primary lung cancer associated fibroblasts. Cancer associated fibroblasts (CAFs) present in the tumor stroma facilitate the growth of tumors and confer resistance to various drugs. This experiment was to test if the YAP1 inhibitors can eliminate cancer cells even when CAFs are present. H1650 cells were labeled with a commercially available cytotracker red dye and CAFs were labeled with cytotracker green dye. Cells can be cultured together and visualized by immunofluorescence microscopy. This co-culture system was used to assess if the YAP1 inhibitors could kill the cancer cells selectively, even in the presence of CAFs.
Figure 29:
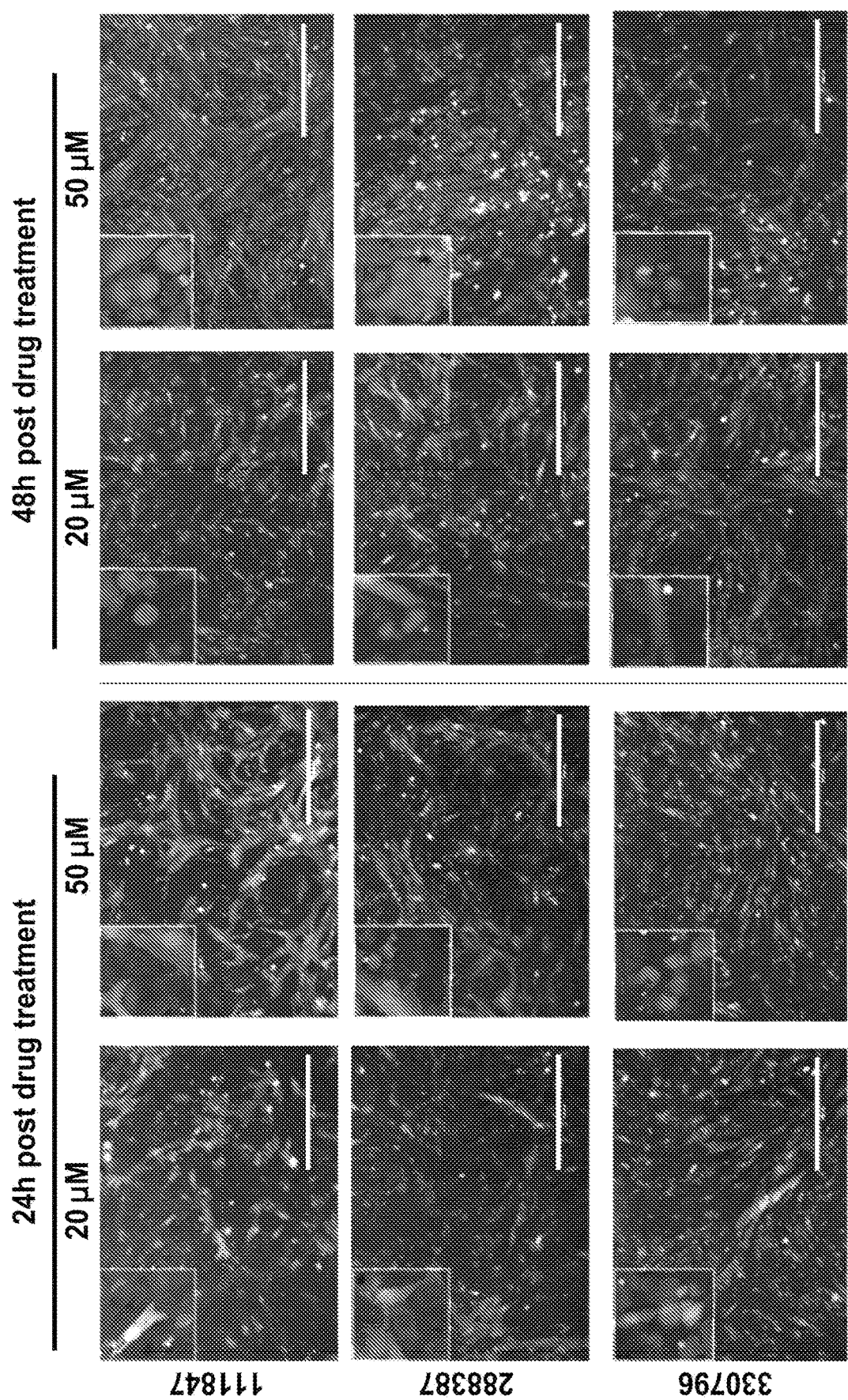
Figure 29:
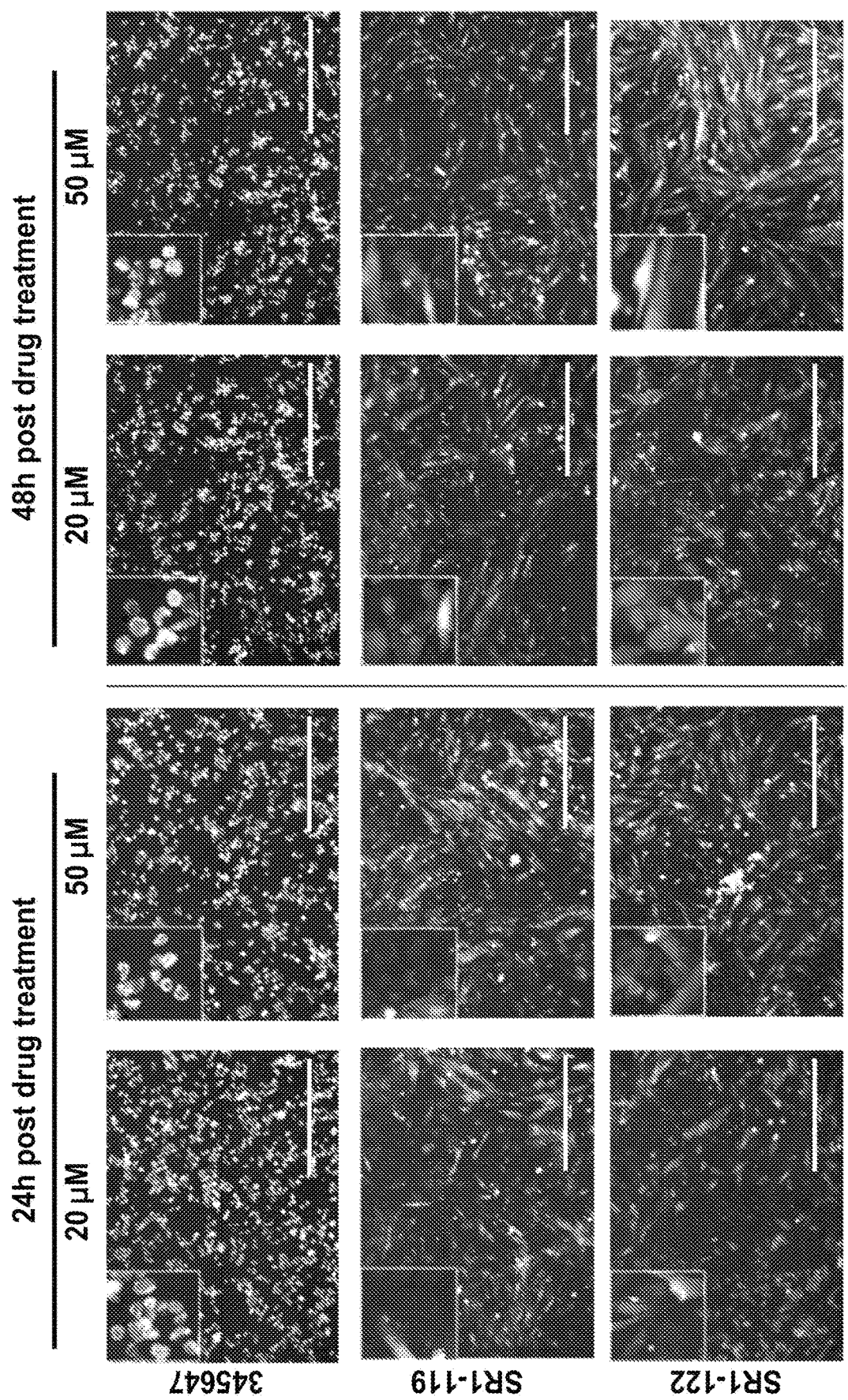
Figure 30:
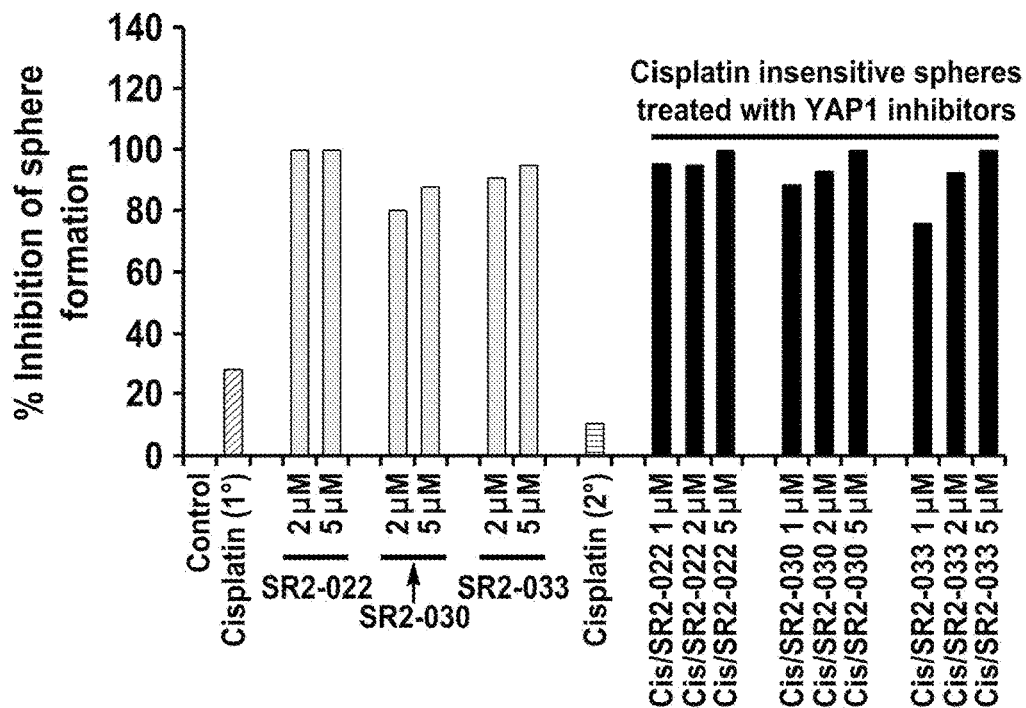
Figure 30:
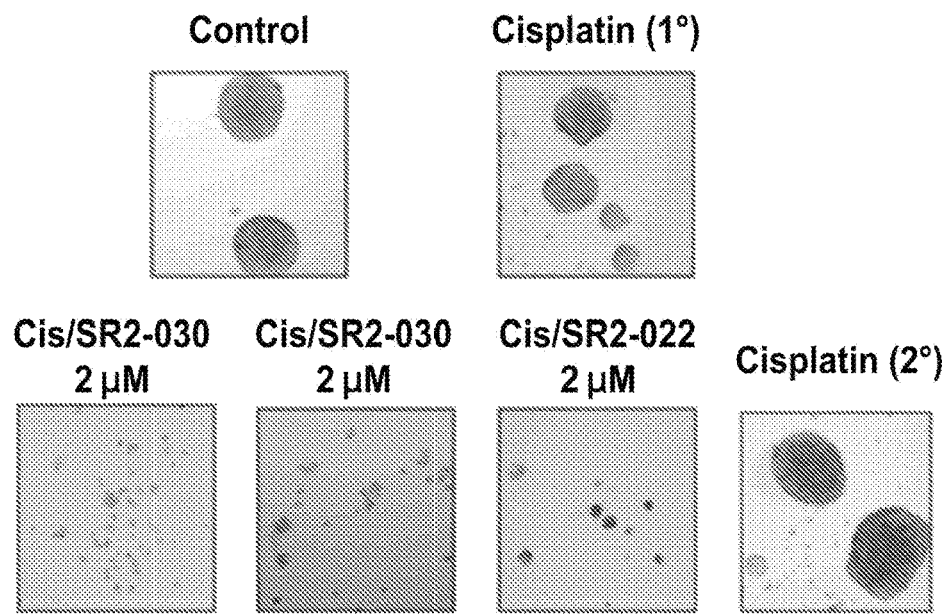

FIG. 30 shows that indentified compounds inhibit self-renewal of cisplatin-insensitive SP cells. One feature of cancer stem cells is their drug resistance. Sphere formation of SP cells from H1650 cells was conduced in the presence of cisplatin; stem-like SP cells can self-renew and form spheres in stem-cell selective media and on low-adherence plates, even in the presence of 5 uM cisplatin (top right image). Dissociating the cisplatin-insensitive spheres and treating them with 2 uM of YAP1 inhibitors inhibited self-renewal completely, as seen by the disappearance of the spheres. In contrast, dissociating the cisplatin-insensitive cells and conducting self-renewal assays again with cisplatin allowed self-renewal and formation of colonies. Shows that the YAP inhibitors can effectively eliminate cisplatin insensitive stem-like cells.

Figure 31:
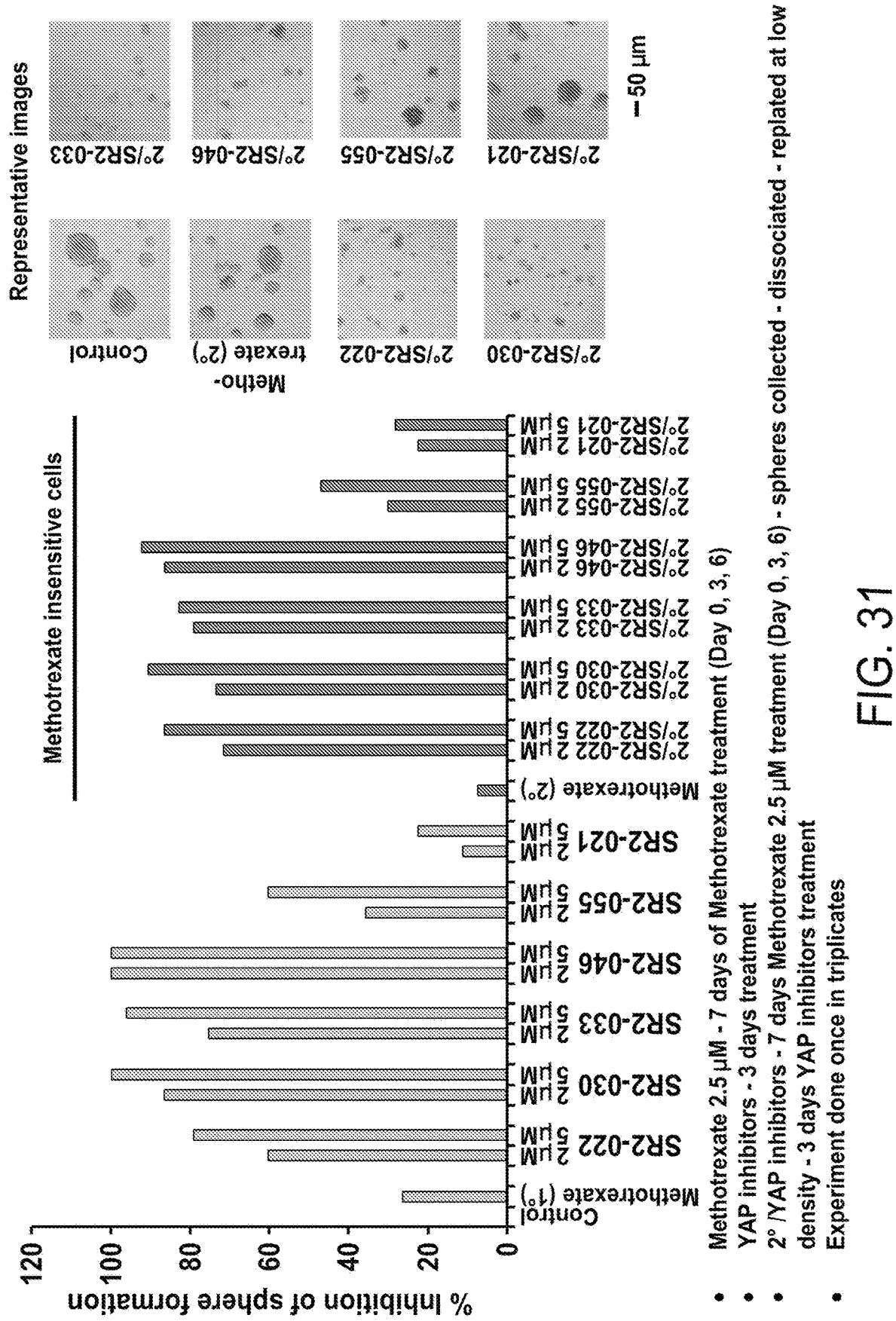

FIG. 31 shows YAP1 inhibitors reduce the self renewal ability of methotrexate insensitive H146 SLCL cells. A similar experiment, where sphere formation of small-cell lung cancer cells, which are insensitive to methotrexate, was inhibited by YAP1 inhibitors. Sphere formation of SP cells from H146 small-cell lung carcinoma cells was conduced in the presence of 2.5 uM methotrexate; stem-like cells can self-renew and form spheres in stem-cell selective media and on low-adherence plates, even in the presence of 2.5 uM methotrexate. Dissociating the methotrexate-insensitive spheres and treating them with 2 uM of YAP1 inhibitors inhibited self-renewal completely, as seen by the disappearance of the spheres. In contrast, dissociating the methotrexate-insensitive cells and conducting self-renewal assays again with methotrexate allowed self-renewal and formation of colonies. Shows that the YAP inhibitors can effectively eliminate methotrexate insensitive stem-like cells.

Figure 32:
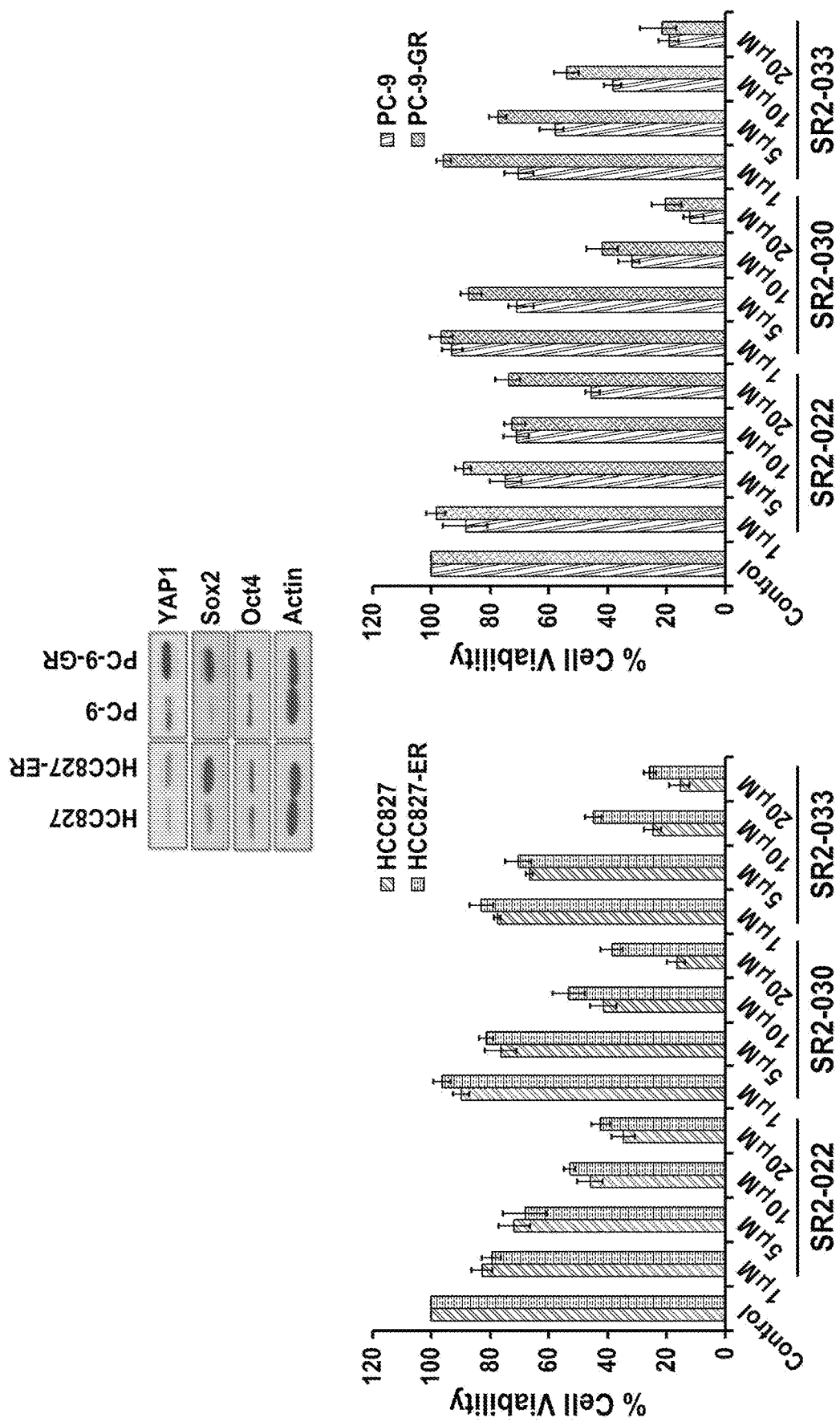

FIG. 32 shows identified compounds can induce cytotoxicity in EGFR-inhibitor resistant cells. EGFR inhibitors like erlotinib and gefitinib are effective against EGFR-mutant lung adenocarcinomas. The patients invariably develop resistance to these inhibitors. HCC827 cells which are erlotinib resistant (HCC827-ER) and gefitinib resistant PC-9 cells (PC-9GR) express higher levels of Sox2 and YAP1. YAP inhibitors can effectively reduce the viability of EGFR-I sensitive parental cells as well as the resistant cells, as measured by a MTT assay. (ER=erlotinib resistant cells; GR=gefitinib resistant cells).

Figure 33:
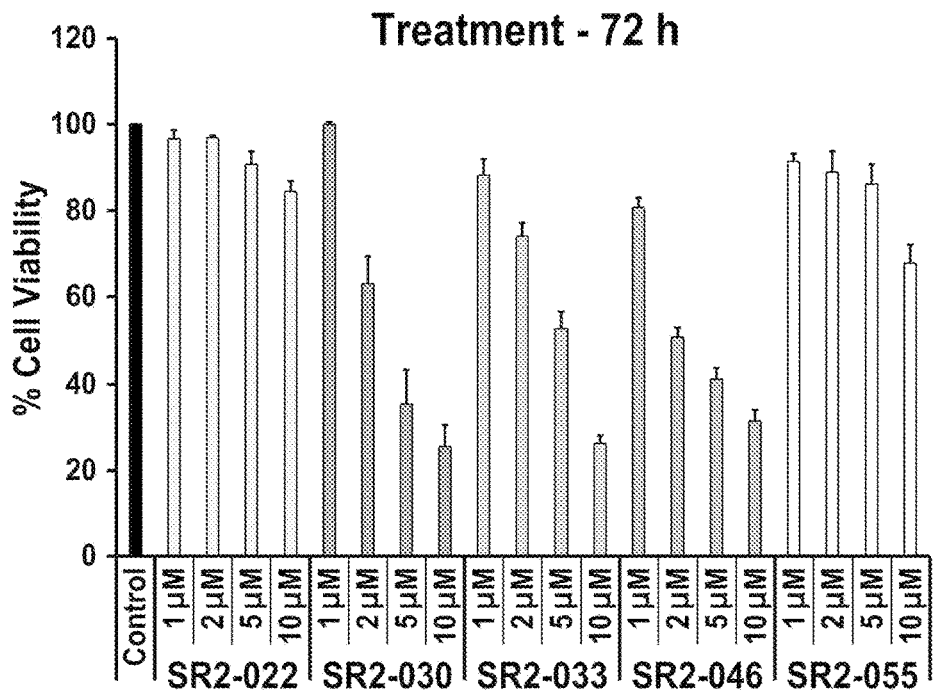

FIG. 33 is a graph showing the identified compounds reduced the viability of H1975 (RGFR T790 M mutant) lung adenocarcinoma cells. H1975 is an EGFR mutant cell line that is resistant to EGFR inhibitors like erlotinib and gefitinib. YAP1 inhibitors could effectively reduce the viability of these cells, as seen by a MTT assay. Drug treatment was for 72 hrs.

Figure 34:
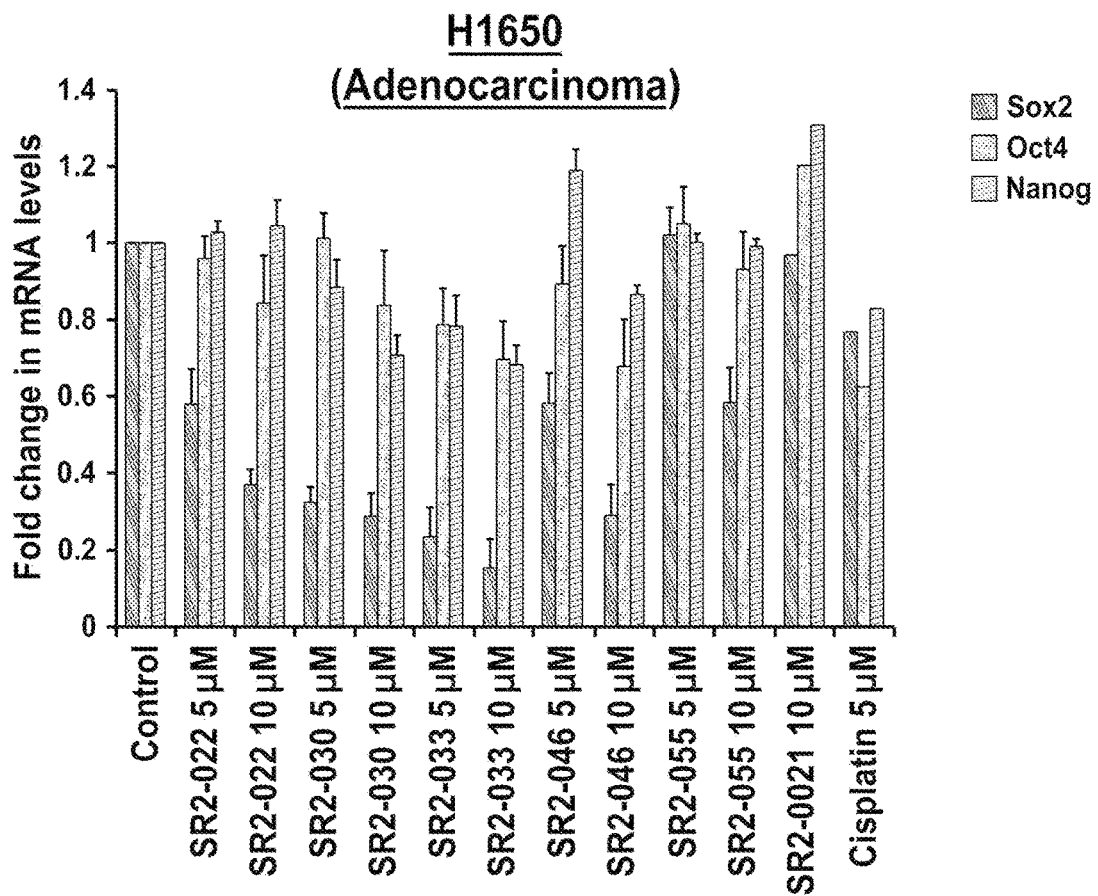
Figure 34:
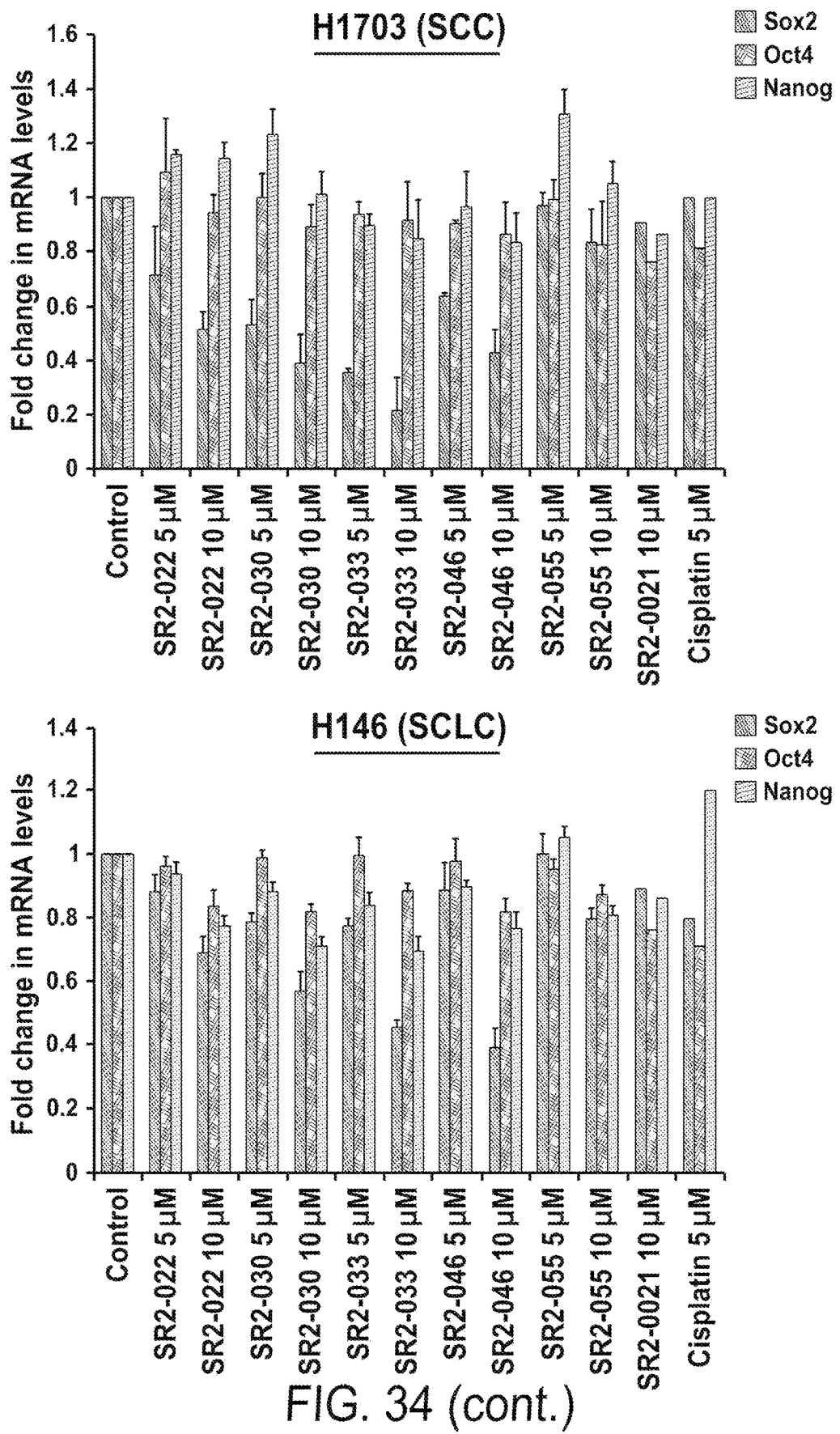

FIG. 34 contains graphs showing the indentified compounds inhibit Sox2 expression in multiple lung cancer cells. Earlier studies had shown that YAP1 regulates the expression of Sox2, with minimal effect on the expression of Oct4 and Nanog transcription factors. RT-PCR experiments show that PPxY mimetics can suppress the expression of Sox2 mRNA after 72 hrs of treatment, but had minimal effect on the expression of Oct4 and Nanog mRNA. Similar results were obtained in H1650 (Lung adenocarcinoma), H1703 (Squamous cell carcinoma) and H146 (Small Cell lung cancer) cell lines.

Figure 35:
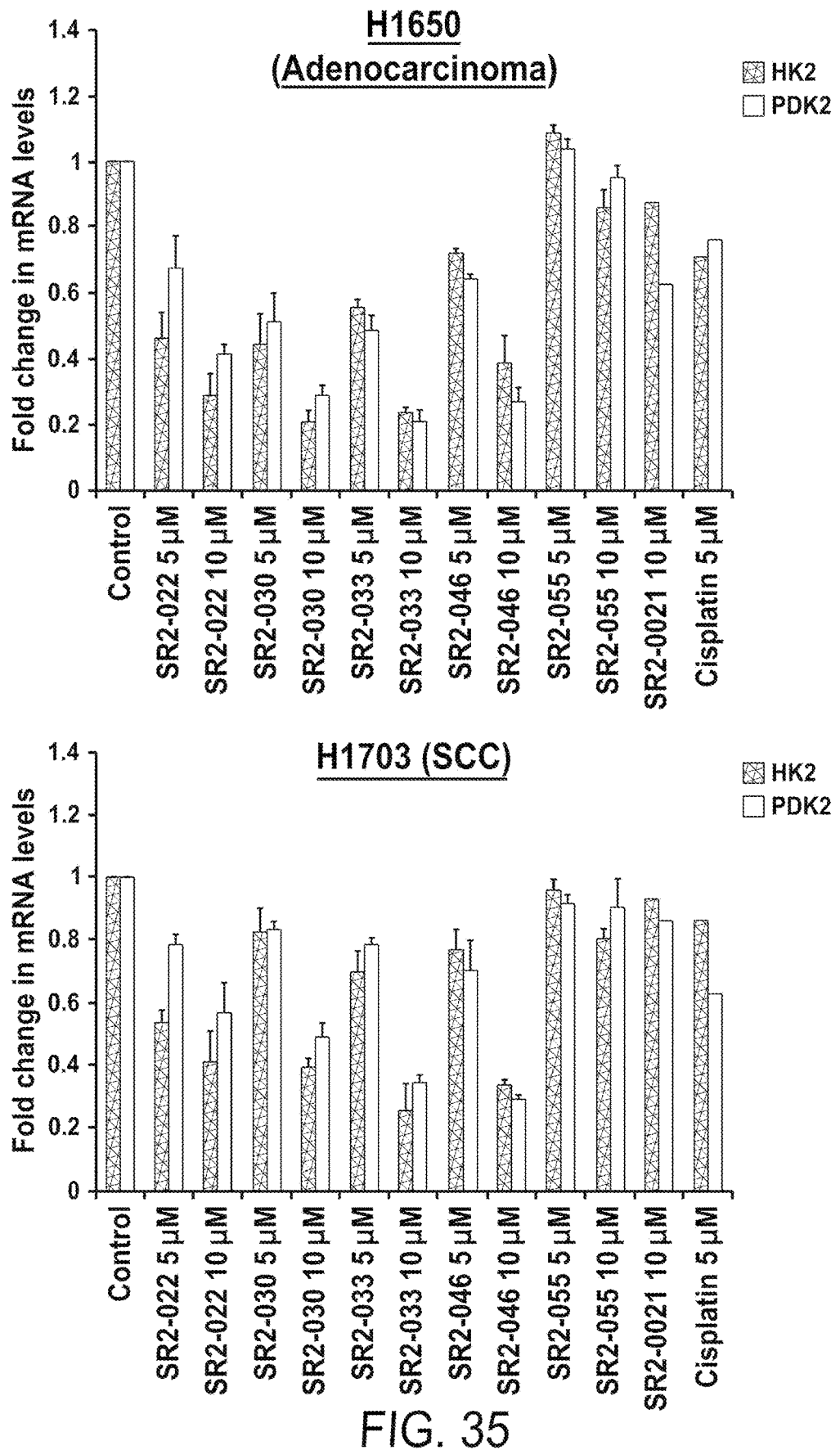
Figure 35:
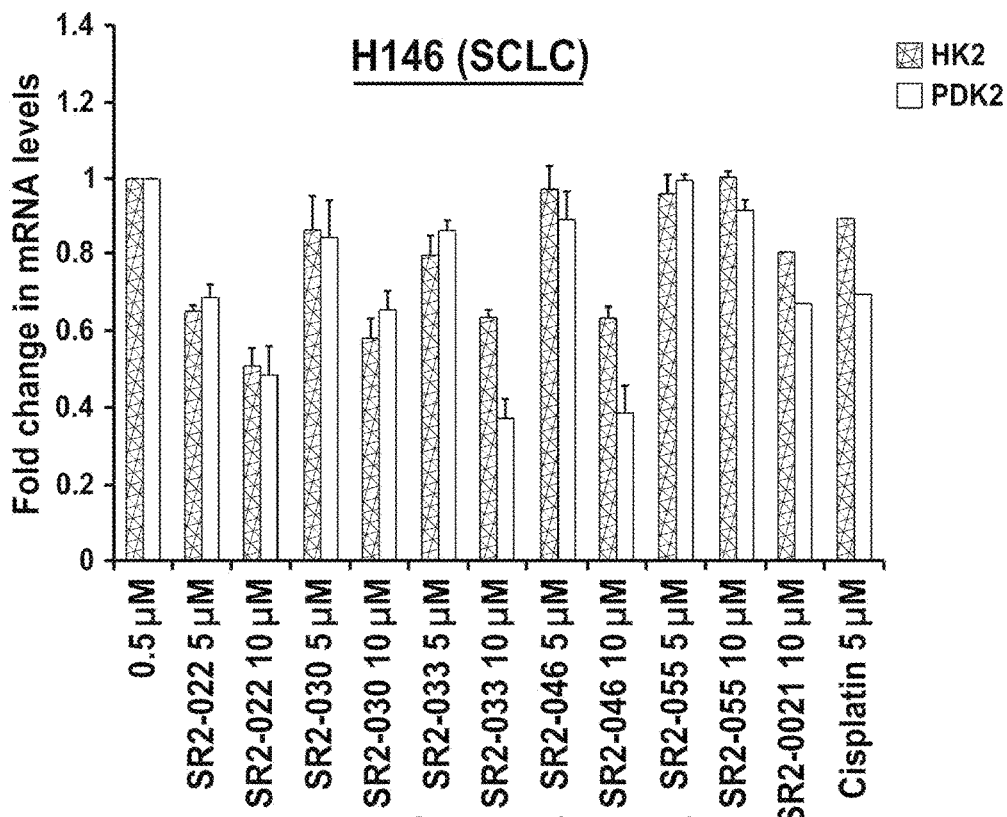

FIG. 35 contains graphs showing the identified compounds inhibit HK2 and PDK2 mRNA expression in lung cancer cells. Suppression of these genes could be the mechanism by which the YAP1 inhibitors suppress cell proliferation and reduce viability. We tested these genes (HK2 and PKD2) since they had Sox2 binding sites on their promoter and appear to be regulated by Sox2. Treatment with the drugs for 72 hrs reduced the expression of Hexokinase 2 and pyruvate dehydrogenase kinase 2, as seen by RT-PCR.

Figure 36:
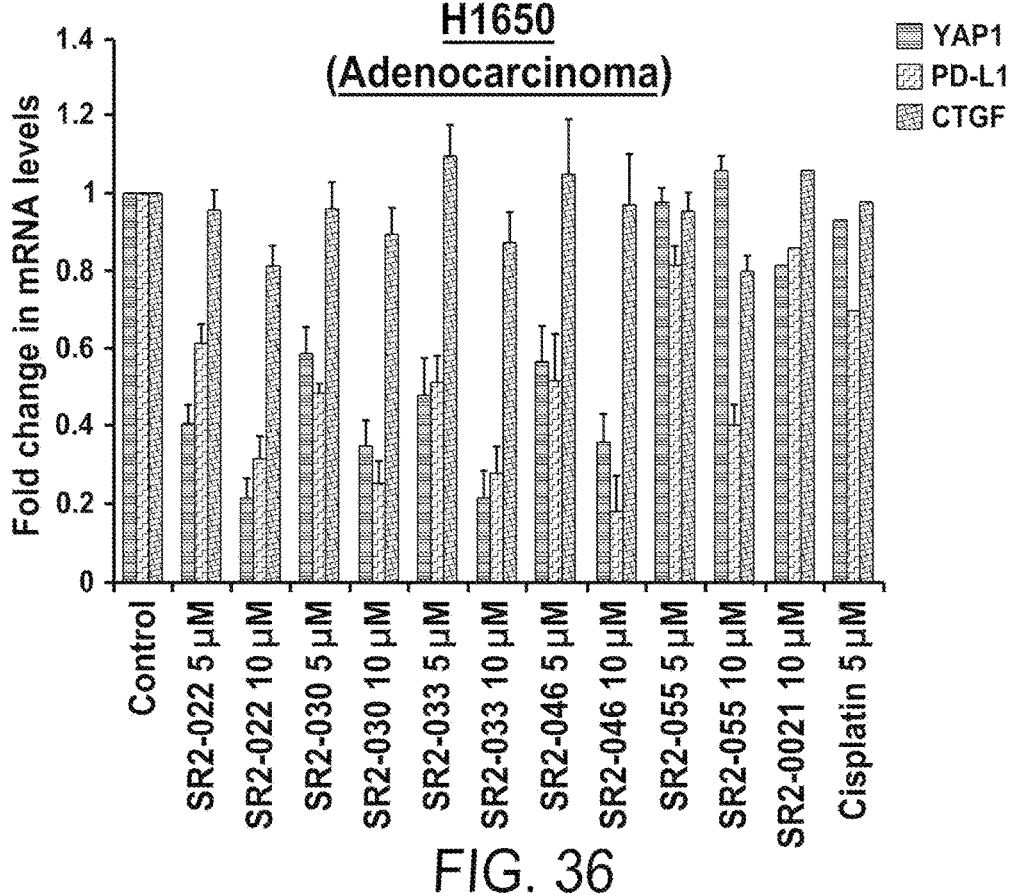
Figure 36:
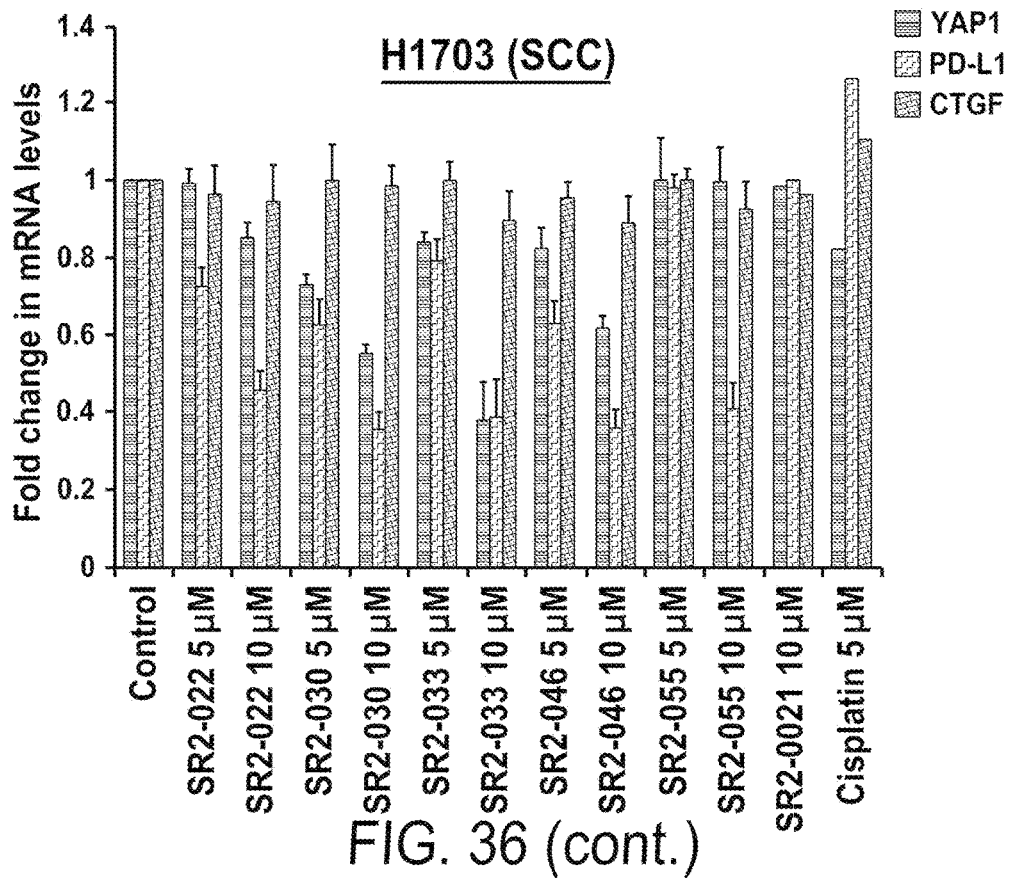

FIG. 36 contains graphs showing certain compounds inhibit PD-L1 but not CTGF (TREAD2 target) expression in lung cancer cells. YAP1 might regulate the expression of PD-L1. YAP1 inhibitors suppressed PD-L1 at the level of transcription after 72 hrs of treatment, as seen by RT-PCR. Expression of a TEAD-2 target gene, CTGF, was not affected by these drugs.

Figure 37:
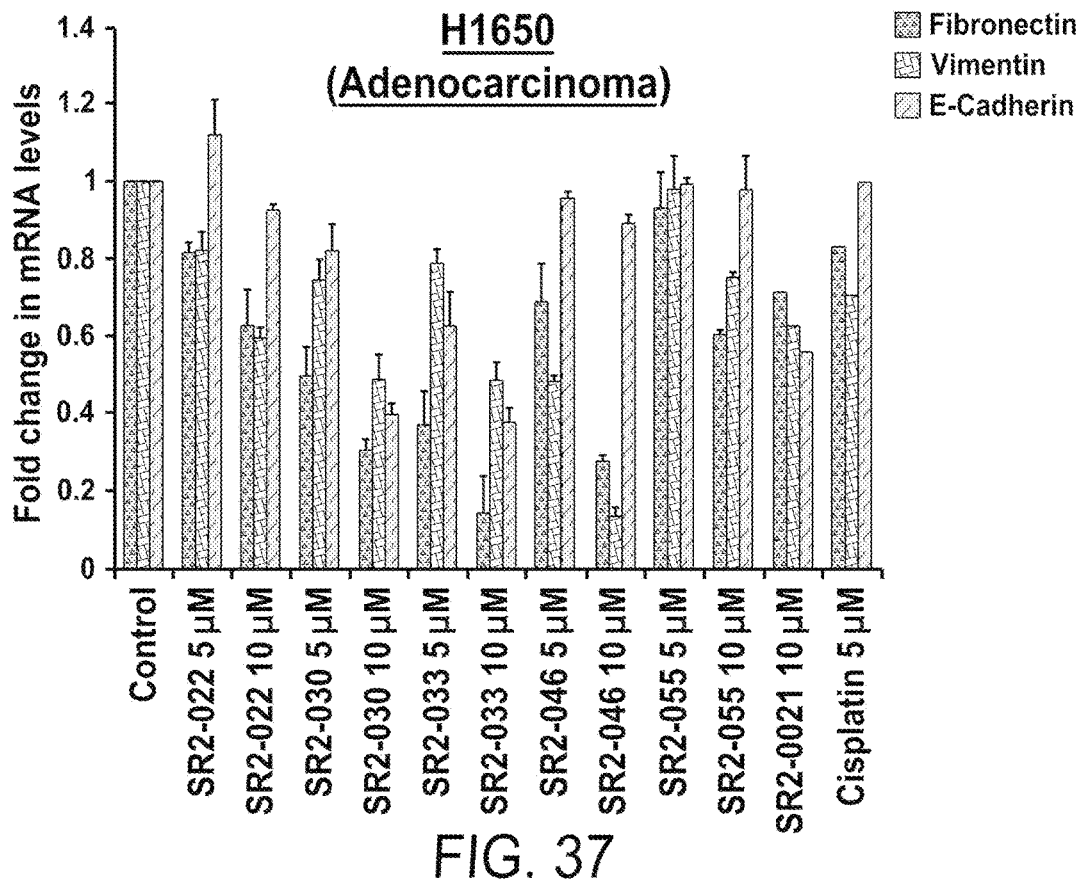
Figure 37:
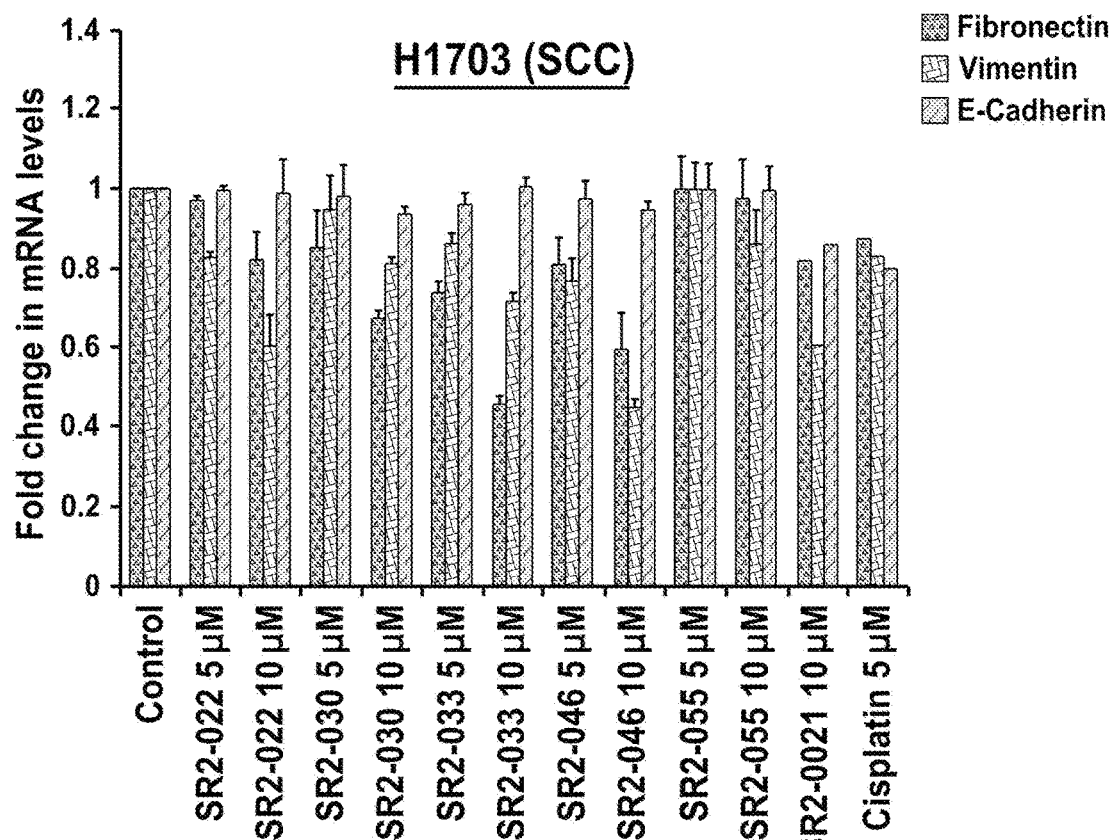

FIG. 37 contains graphs showing certain compounds surpress fibronectin expression in lung cancer cells. Earlier studies had shown that mesenchymal genes like fibronectin and vimentin are targets of YAP1. They are known to promote the progression and metastsis of cancer, by promoting epithelial-mesenchymal transition. RT-PCR experiments showed that the YAP1 inhibitors could suppress the expression of these genes after 72 hrs of treatment.

Figure 38:
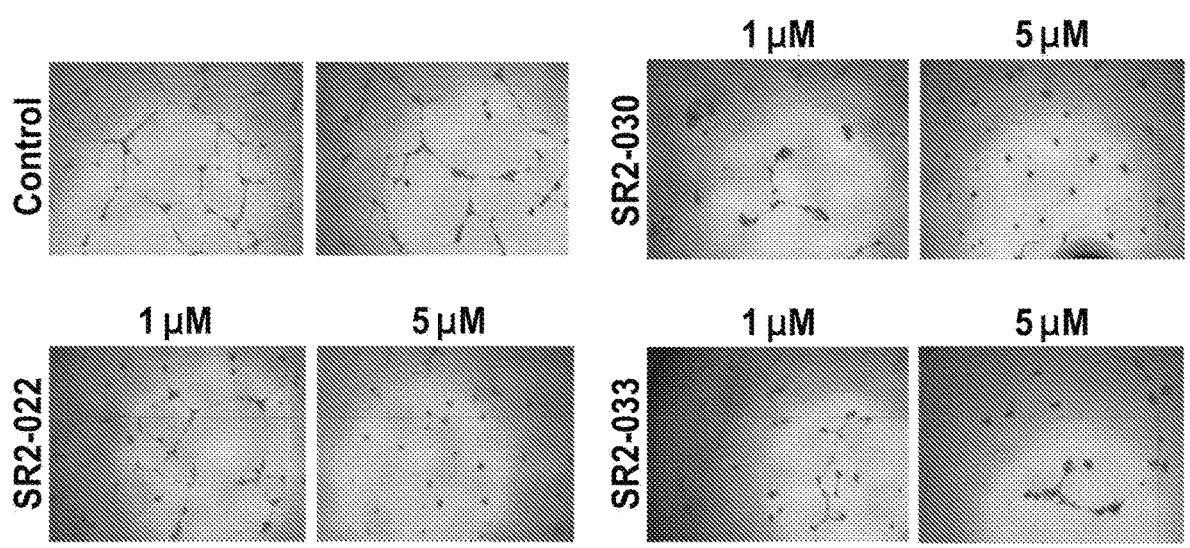

FIG. 38 contains cell micrographs showing certain compounds reduce tubule formation in matrigel by Huvec. Studies show that YAP1 plays a role in angiogenesis. Angiogenesis is necessary for tumor growth and inhibition of angiogenesis is an accepted therapeutic strategy for solid tumors. The results show YAP1 inhibitors could inhibit the angiogenic tubule formation by HUVECs in matrigel, after 18-24 hrs of treatment.

Figure 39:
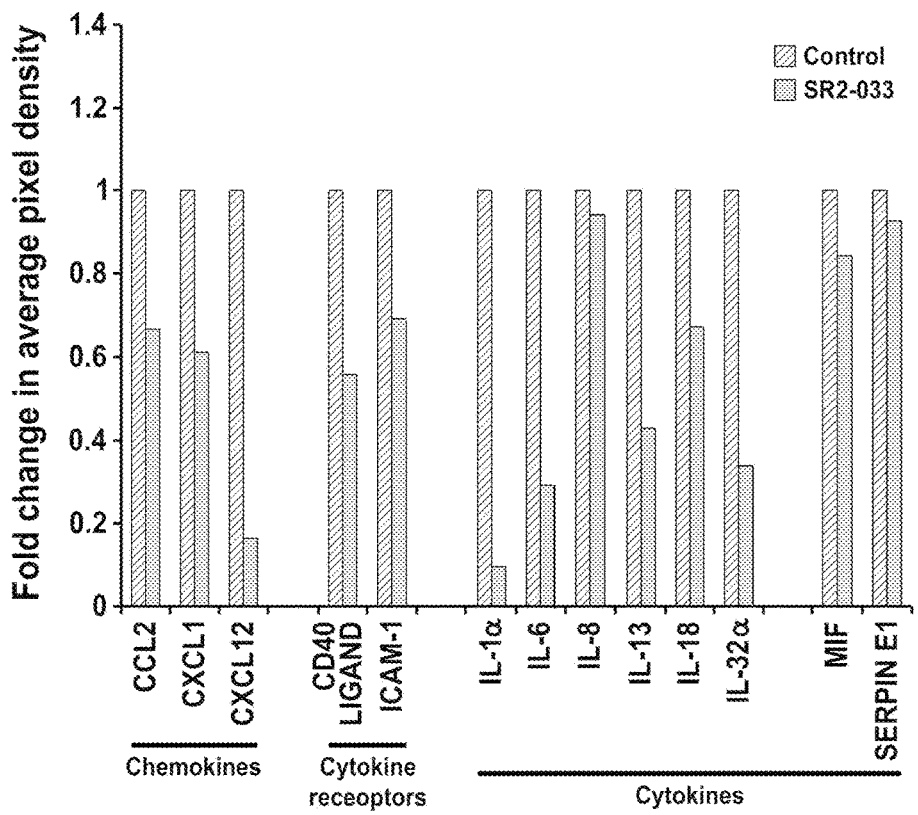

FIG. 39 is a graph showing results from a cytokine array performed on A549 cells treated with SR2-033. Cytokine array experiments show that the levels of secreted cytokines are altered by the YAP1 inhibitors. This data is on A549 lung adenocarcinoma cells.

Figure 40:
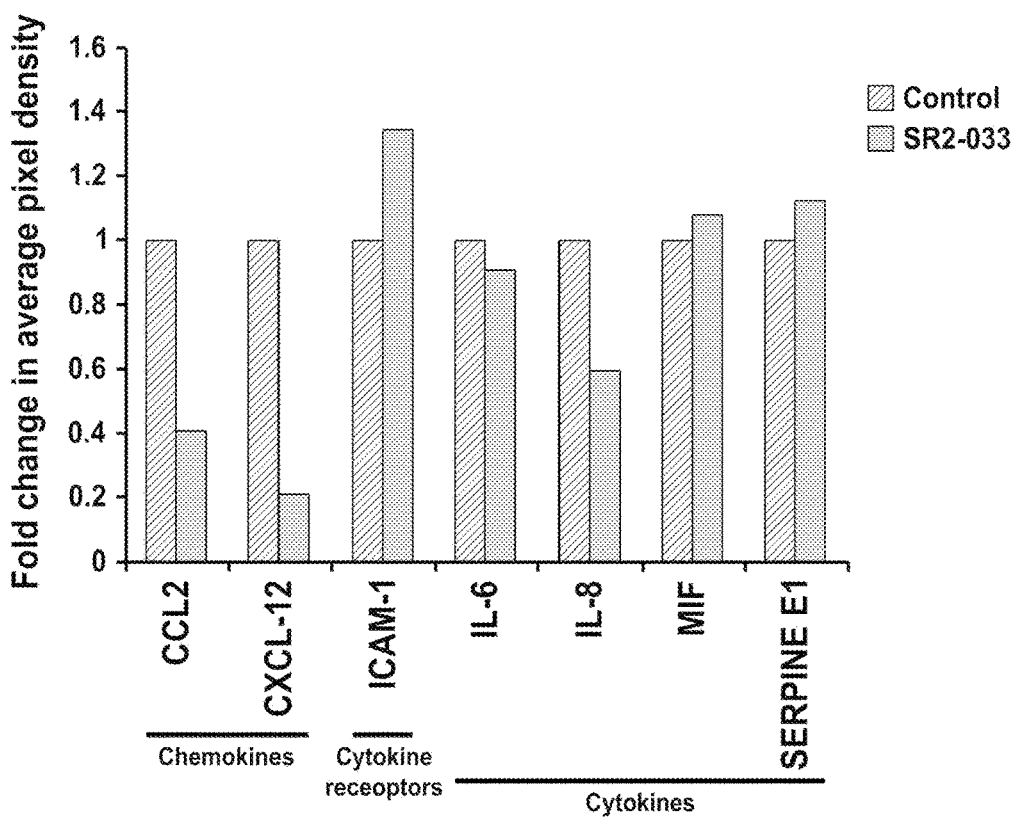

FIG. 40 is a graph showing results from a cytokine array performed on A549 cells treated with SR2-033. Cytokine array experiments show that the levels of secreted cytokines are altered by the YAP1 inhibitors. This data is on primary cancer associated fibroblasts.

DETAILED DESCRIPTION

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A''$ is used herein as merely a generic substituent in the definitions below.

The term "alkoxy" as used herein is an alkyl group bound through a single, terminal ether linkage; that is, an "alkoxy" group can be defined as $—OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O$^-$.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "cyano" as used herein is represented by the formula —CN

The term "azido" as used herein is represented by the formula —N$_3$.

The term "sulfonyl" is used herein to refer to the sulfo-oxo group represented by the formula —S(O)$_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH$_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples and Figures.

Compounds

Disclosed herein are compounds of Formula I.

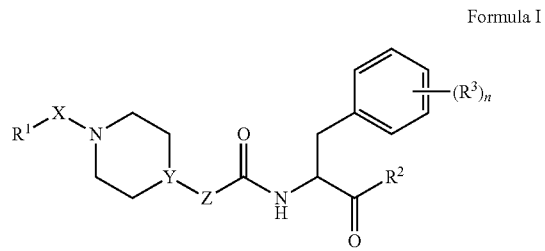

Formula I wherein,

X is C(O), S(O), or $SO_2$;

Y is CH, $CR^6$, or N;

Z is $CH_2$, $CR^6R^7$, or NH;

$R^1$ is $C_1$-$C_8$ alkyl, $C_1$-$C_8$ alkenyl, $C_1$-$C_8$ alkynyl, $C_1$-$C_8$ alkoxyl, $C_1$-$C_8$ heteroalkyl, $C_3$-$C_6$ cycloalkyl, $C_3$-$C_6$ heterocycloalkyl, aryl, or heteroaryl, any of which is optionally substituted with one or more carbonyl (C=O), $C_1$-$C_6$ alkyl, $C_1$-$C_6$ haloalkyl, $C_1$-$C_6$ alkoxyl, amino, —$NR^6R^7$, —C(O)$NR^6R^7$, $C_1$-$C_6$ alkylhydroxy, $C_3$-$C_6$ cycloalkyl, $C_3$-$C_6$ heterocycloalkyl, aryl, heteroaryl, halo, hydroxyl, thiol, cyano, nitro, or radiolabeled isotope (e.g., $^{18}F$, $^{11}C$);

$R^2$ is amino, hydroxyl, $C_1$-$C_8$ alkyl, $C_1$-$C_8$ alkenyl, $C_1$-$C_8$ alkynyl, $C_1$-$C_8$ alkoxyl, $C_1$-$C_8$ heteroalkyl, $C_3$-$C_6$ cycloalkyl, $C_3$-$C_6$ heterocycloalkyl, aryl, or heteroaryl, any of which is optionally substituted with one or more carbonyl (C=O), carboxyl (—$CO_2$—), ester ($CO_2R^6$), $C_1$-$C_6$ alkyl, $C_1$-$C_6$ haloalkyl, $C_1$-$C_6$ alkoxyl, amino, —$NR^6R^7$, —C(O)$NR^6R^7$, $C_1$-$C_6$ alkyl$C_{3-6}$cycloalkyl, $C_3$-$C_6$ cycloalkyl, $C_3$-$C_6$ heterocycloalkyl, aryl, heteroaryl, $C_{1-6}$alkylaryl, halo, hydroxyl, thiol, cyano, nitro, or radiolabeled isotope (e.g., $^{18}F$, $^{11}C$);

each $R^3$ is, independently, hydrogen, halogen, OH, $C_1$-$C_8$ alkyl, $C_1$-$C_8$ alkoxyl, aryl, O-aryl, heteroaryl, O-heteroaryl, O-$CH_2$aryl, or O-$CH_2$heteroaryl; and $R^6$ and $R^7$ are independently selected from hydrogen, $C_1$-$C_8$ alkyl, $C_1$-$C_8$ alkenyl, $C_1$-$C_8$ alkynyl, $C_1$-$C_8$ alkoxide, $C_1$-$C_8$ carboxylate, $C_1$-$C_8$ haloalkyl, $C_1$-$C_8$ haloalkenyl, $C_1$-$C_8$ haloalkynyl, $C_3$-$C_6$ cycloalkyl, $C_3$-$C_6$ heterocloalkyl, aryl, $C_1$-$C_3$ alkylheteroaryl, or heteroaryl; any of which is optionally substituted with a halogen; and n is 1-5.

In preferred examples of Formula I, Z is $CH_2$.

In some embodiments, when X is C(O), the compounds can have Formula I-A

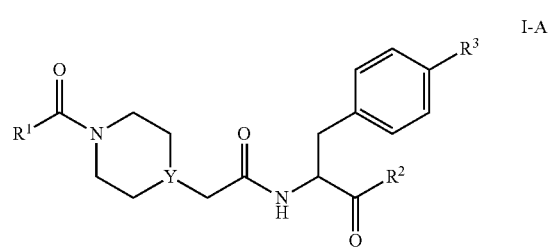

I-A

In some examples when X is S(O), the compound can have Formula I-B

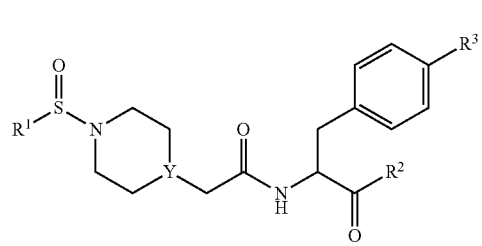

I-B

In some examples, when X is SO₂, the compound can have Formula I-C

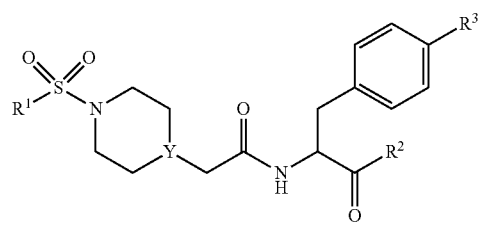

I-C

In some embodiments, when Y is CH and X is C(O), the compounds can have Formula I-D

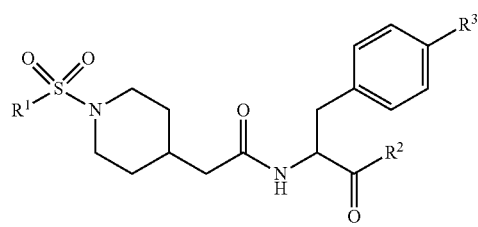

I-D

In some examples, when Y is CH and X is S(O), the compound can have Formula I-E

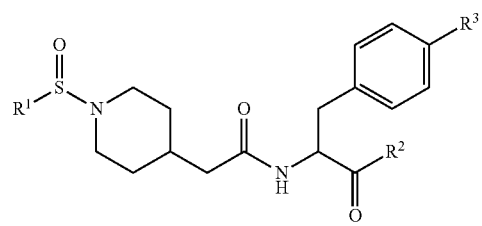

I-E

In some examples, when Y is CH and X is SO₂, the compound can have Formula I-F

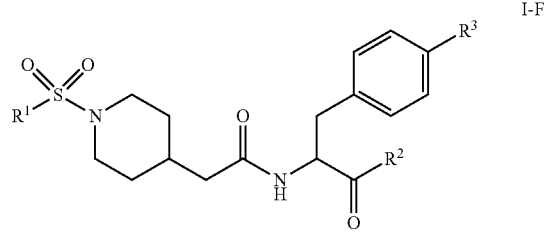

I-F

In some embodiments, when Y is N and X is C(O), the compounds can have Formula I-G

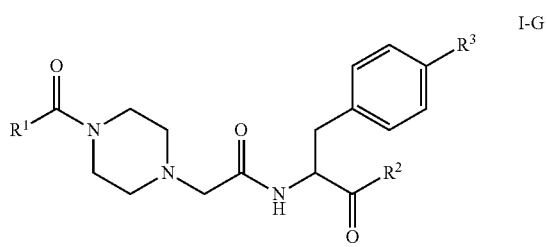

I-G

In some examples, when Y is N and X is S(O), the compound can have Formula I-H

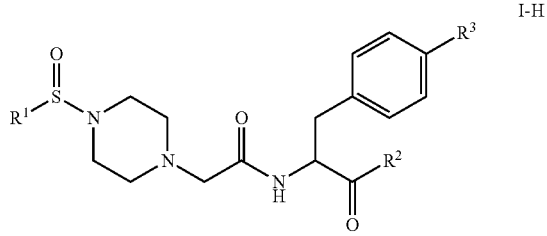

I-H

In some examples, when Y is N and X is SO₂, the compound can have Formula I-I

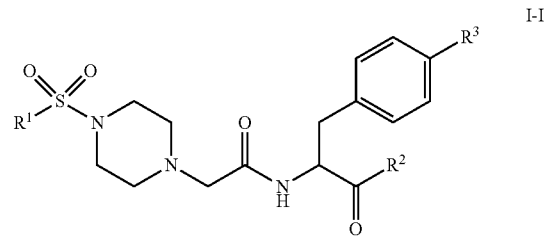

I-I

In some embodiments, when Y is CH and X is C(O), the compounds can have Formula I-J

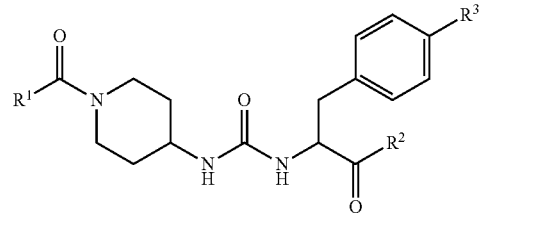

I-J

In some examples when Y is CH and X is S(O), the compound can have Formula I-K

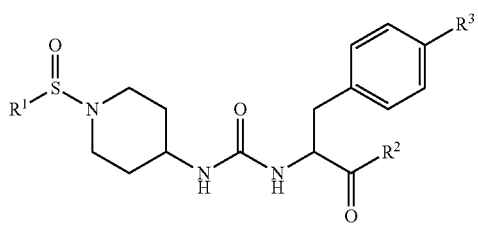

I-K

In some examples, when Y is CH and X is SO$_2$, the compound can have Formula I-L

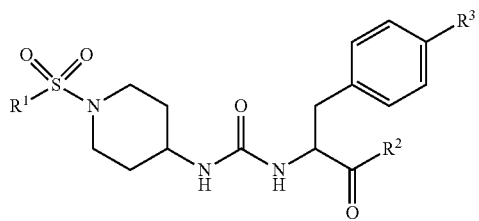

I-L

Formula I-A-I-L where n=1, and R$^3$ is also on the 2, 3, 5 or 6 position are also contemplated.

Also disclosed herein are compounds of Formula II.

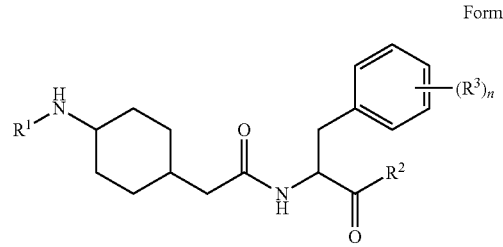

Formula II wherein,
R$^1$ is hydrogen, C$_1$-C$_8$ alkyl, C$_1$-C$_8$ alkenyl, C$_1$-C$_8$ alkynyl, C$_1$-C$_8$ alkoxyl, C$_1$-C$_8$ heteroalkyl, C$_3$-C$_6$ cycloalkyl, C$_3$-C$_6$ heterocycloalkyl, aryl, or heteroaryl, any of which is optionally substituted with one or more carbonyl (C=O), C$_1$-C$_6$ alkyl, C$_1$-C$_6$ haloalkyl, C$_1$-C$_6$ alkoxyl, amino, —NR$^6$R$^7$, —C(O)NR$^6$R$^7$, C$_1$-C$_6$ alkylhydroxy, C$_3$-C$_6$ cycloalkyl, C$_3$-C$_6$ heterocycloalkyl, aryl, heteroaryl, halo, hydroxyl, thiol, cyano, nitro, or radiolabeled isotope (e.g., $^{18}$F, $^{11}$C);

R$^2$ is amino, hydroxyl, C$_1$-C$_8$ alkyl, C$_1$-C$_8$ alkenyl, C$_1$-C$_8$ alkynyl, C$_1$-C$_8$ alkoxyl, C$_1$-C$_8$ heteroalkyl, C$_3$-C$_6$ cycloalkyl, C$_3$-C$_6$ heterocycloalkyl, aryl, or heteroaryl, any of which is optionally substituted with one or more carbonyl (C=O), carboxyl (—CO$_2$—), ester (CO$_2$R$^6$), C$_1$-C$_6$ alkyl, C$_1$-C$_6$ haloalkyl, C$_1$-C$_6$ alkoxyl, amino, —NR$^6$R$^7$, —C(O)NR$^6$R$^7$, C$_1$-C$_6$ alkylC$_{3-6}$cycloalkyl, C$_3$-C$_6$ cycloalkyl, C$_3$-C$_6$ heterocycloalkyl, aryl, heteroaryl, C$_{1-6}$alkylaryl, halo, hydroxyl, thiol, cyano, nitro, or radiolabeled isotope (e.g., $^{18}$F, $^{11}$C);

each R$^3$ is, independently, hydrogen, halogen, OH, C$_1$-C$_8$ alkyl, C$_1$-C$_8$ alkoxyl, aryl, O-aryl, heteroaryl, O-heteroaryl, O-CH$_2$aryl, or O-CH$_2$heteroaryl; and R$^6$ and R$^7$ are independently selected from hydrogen, C$_1$-C$_8$ alkyl, C$_1$-C$_8$ alkenyl, C$_1$-C$_8$ alkynyl, C$_1$-C$_8$ alkoxide, C$_1$-C$_8$ carboxylate, C$_1$-C$_8$ haloalkyl, C$_1$-C$_8$ haloalkenyl, C$_1$-C$_8$ haloalkynyl, C$_3$-C$_6$ cycloalkyl, C$_3$-C$_6$ heterocycloalkyl, aryl, C$_1$-C$_3$ alkylheteroaryl, or heteroaryl; any of which is optionally substituted with a halogen; and n is 1-5.

Also disclosed herein are compounds of Formula III

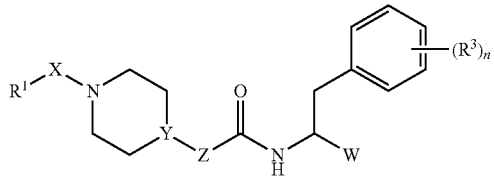

Formula III wherein,
X is C(O), S(O), or SO$_2$;
Y is CH, CR$^6$, or N;
Z is CH$_2$, CR$^6$R$^7$, or NH;
W is cyano, C$_2$-C$_4$ alkyne, or a triazole, tetrazole or oxaxole optionally substituted with one or more carbonyl (C=O), C$_1$-C$_6$ alkyl, C$_1$-C$_6$ haloalkyl, C$_1$-C$_6$ alkoxyl, amino, —NR$^6$R$^7$, —C(O)NR$^6$R$^7$, C$_1$-C$_6$ alkylhydroxy, C$_3$-C$_6$ cycloalkyl, C$_3$-C$_6$ heterocycloalkyl, aryl, heteroaryl, halo, hydroxyl, thiol, cyano, nitro, or radiolabeled isotope (e.g., $^{18}$F, $^{11}$C);

R$^1$ is C$_1$-C$_8$ alkyl, C$_1$-C$_8$ alkenyl, C$_1$-C$_8$ alkynyl, C$_1$-C$_8$ alkoxyl, C$_1$-C$_8$ heteroalkyl, C$_3$-C$_6$ cycloalkyl, C$_3$-C$_6$ heterocycloalkyl, aryl, or heteroaryl, any of which is optionally substituted with one or more carbonyl (C=O), C$_1$-C$_6$ alkyl, C$_1$-C$_6$ haloalkyl, C$_1$-C$_6$ alkoxyl, amino, —NR$^6$R$^7$, —C(O)NR$^6$R$^7$, C$_1$-C$_6$ alkylhydroxy, C$_3$-C$_6$ cycloalkyl, C$_3$-C$_6$ heterocycloalkyl, aryl, heteroaryl, halo, hydroxyl, thiol, cyano, nitro, or radiolabeled isotope (e.g., $^{18}$F, $^{11}$C);

R$^2$ is amino, hydroxyl, C$_1$-C$_8$ alkyl, C$_1$-C$_8$ alkenyl, C$_1$-C$_8$ alkynyl, C$_1$-C$_8$ alkoxyl, C$_1$-C$_8$ heteroalkyl, C$_3$-C$_6$ cycloalkyl, C$_3$-C$_6$ heterocycloalkyl, aryl, or heteroaryl, any of which is optionally substituted with one or more carbonyl (C=O), carboxyl (—CO$_2$—), ester (CO$_2$R$^6$), C$_1$-C$_6$ alkyl, C$_1$-C$_6$ haloalkyl, C$_1$-C$_6$ alkoxyl, amino, —NR$^6$R$^7$, —C(O)NR$^6$R$^7$, C$_1$-C$_6$ alkylC$_{3-6}$cycloalkyl, C$_3$-C$_6$ cycloalkyl, C$_3$-C$_6$ heterocycloalkyl, aryl, heteroaryl, C$_{1-6}$alkylaryl, halo, hydroxyl, thiol, cyano, nitro, or radiolabeled isotope (e.g., $^{18}$F, $^{11}$C);

each R$^3$ is, independently, hydrogen, halogen, OH, C$_1$-C$_8$ alkyl, C$_1$-C$_8$ alkoxyl, aryl, O-aryl, heteroaryl, O-heteroaryl, O-CH$_2$aryl, or O-CH$_2$heteroaryl; and R$^6$ and R$^7$ are independently selected from hydrogen, C$_1$-C$_8$ alkyl, C$_1$-C$_8$ alkenyl, C$_1$-C$_8$ alkynyl, C$_1$-C$_8$ alkoxide, C$_1$-C$_8$ carboxylate, C$_1$-C$_8$ haloalkyl, C$_1$-C$_8$ haloalkenyl, C$_1$-C$_8$ haloalkynyl, C$_3$-C$_6$ cycloalkyl, C$_3$-C$_6$ heterocycloalkyl, aryl, C$_1$-C$_3$ alkylheteroaryl, or heteroaryl; any of which is optionally substituted with a halogen; and n is 1-5.

In any of Formulas I-A through I-L, II, and III, R$^1$, R$^2$, R$^3$, R$^6$ and R$^7$ can be as further defined herein.

In preferred examples, Y is CH. In other examples, Y is N.

In preferred examples, Z is CH$_2$. In other examples, Z is NH.

In specific examples, R$^1$ can be C$_1$-C$_8$ alkoxyl. In other examples, R$^1$ can be OtBu. In other examples, R$^1$ can be phenyl. In still other examples, $R^1$ can be $C_1$-$C_3$ alkyl substituted with aryl, e.g., $(CH_2)_{1-3}Ph$, wherein the aryl is optionally substituted with one or more $C_1$-$C_6$ alkyl, $C_1$-$C_6$ haloalkyl, $C_1$-$C_6$ alkoxyl, amino, halo, hydroxyl, thiol, cyano, nitro, or radiolabeled isotope. In still other examples, $R^1$ can be $CH_2Ph$. In other examples, $R^1$ can be $CH_2CH_2Ph$. In still other examples, $R^1$ can be $CH_2CH_2CH_2Ph$. In further examples, $R^1$ can be $CH(CH_2)Ph$ or $C(CH_3)_2Ph$. In yet further examples, $R^1$ can be $CH_2CH(Ph)_2$. In other examples, $R^1$ can be $CH_2CH_2Ph$, where the phenyl is substituted with one or more $C_1$-$C_6$ alkyl, $C_1$-$C_6$ haloalkyl, $C_1$-$C_6$ alkoxyl, amino, halo, hydroxyl, thiol, cyano, nitro, or radiolabeled isotope. In further examples, $R^1$ is a $C_1$-3 alkyl substituted with a phenyl substituted with one or more halogen, methoxyl, ethoxyl, propoxyl, cyano, and $CF_3$. In further examples, $R^1$ is a $C_{1-3}$ alkyl substituted with a phenyl substituted with a dioxole.

In still other examples, $R^1$ can be $C_{1-3}$ alkenyl substituted with aryl, e.g., CH=CHPh, wherein the aryl is optionally substituted with one or more $C_1$-$C_6$ alkyl, $C_1$-$C_6$ haloalkyl, $C_1$-$C_6$ alkoxyl, amino, halo, hydroxyl, thiol, cyano, nitro, or radiolabeled isotope. In other examples, $R^1$ can be CH=CHPh. In other examples, $R^1$ can be CH=CHPh, where the phenyl is substituted with one or more $C_1$-$C_6$ alkyl, $C_1$-$C_6$ haloalkyl, $C_1$-$C_6$ alkoxyl, amino, halo, hydroxyl, thiol, cyano, nitro, or radiolabeled isotope. In further examples, $R^1$ can be pyridine.

In specific examples, $R^1$ can be $C_1$-$C_8$ heteroalkyl, such as —$CH_2O$—, —$OCH_2$—, —$NHCH_2$—, —$CH_2NH$—, —$CH_2CH_2O$—, —$OCH_2CH_2$—, —$NHCH_2CH_2$—, and —$CH_2CH_2NH$—.

In further examples, $R^1$ can be a $C_{3-6}$ heterocycloalkyl, e.g., a pyrrolidine, piperadine, piperazine, which can be optionally substituted with one or more C=O, $C_{1-6}$ alkyl, and aryl. In some examples, $R^1$ can be a pyrrolidine substituted with $C(O)CH_3$.

In specific examples, $R^2$ can be OMe or OH. In other examples, $R^2$ can be unsubstituted amino. In other examples, $R^2$ can be amino substituted with $C_1$-$C_6$ alkyl, with specific examples including NHmethyl, NHethyl, NHpropyl, and NHi-propyl. In other examples, $R^2$ can be amino substituted with $C_3$-$C_6$ cycloalkyl, with specific examples includes NHcyclopropyl, NHcyclobutyl, NHcyclopentyl, and NHcyclohexyl. In other examples, $R^2$ can be amino substituted with $C_1$-$C_6$ alkyl $C_{3-6}$cycloalkyl, with specific examples including NHCH$_2$cyclopropyl, NHCH$_2$cyclobutyl, NHCH$_2$cyclopentyl, and NHCH$_2$cyclohexyl.

In specific examples, $R^3$ can be hydrogen. In other examples, $R^3$ can be OH. In further examples, $R^3$ can be Obenzyl. In specific examples $R^3$ is in the 4 position. In other examples, $R^3$ is in the 2, 3, 5 or 6 position.

In preferred examples, n is 1. In other examples n is 2, 3, 4, or 5.

Also disclosed are compounds having Formula IV

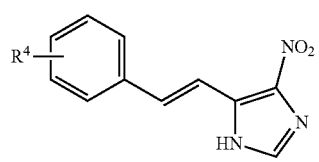

IV wherein
$R^4$ is hydrogen, halo, hydroxyl, cyano, nitro, amino, $C_1$-$C_8$ alkyl, $C_1$-$C_8$ alkenyl, $C_1$-$C_8$ alkynyl, $C_1$-$C_8$ alkoxyl, $C_1$-$C_8$ heteroalkyl, $C_3$-$C_6$ cycloalkyl, $C_3$-$C_6$ heterocycloalkyl, aryl (fused or pendant), or heteroaryl (fused or pendant), any of which is optionally substituted with one or more carbonyl (C=O), $C_1$-$C_6$ alkyl, $C_1$-$C_6$ haloalkyl, $C_1$-$C_6$ alkoxyl, amino, —$NR^6R^7$, —$C(O)NR^6R^7$, $C_1$-$C_6$ alkyl-hydroxy, $C_3$-$C_6$ cycloalkyl, $C_3$-$C_6$ heterocycloalkyl, aryl, heteroaryl, halo, hydroxyl, thiol, cyano, nitro, or radiolabeled isotope (e.g., $^{18}F$, $^{11}C$).

In specific examples of Formula IV, $R^4$ is OH, F, $C_1$, Br, or CN.

Also disclosed are compounds having Formula V.

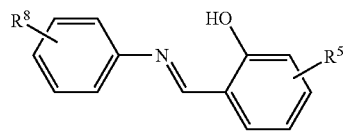

V wherein
$R^5$ is hydrogen, halo, hydroxyl, cyano, nitro, amino, $C_1$-$C_8$ alkyl, $C_1$-$C_8$ alkenyl, $C_1$-$C_8$ alkynyl, $C_1$-$C_8$ alkoxyl, $C_1$-$C_8$ heteroalkyl, $C_3$-$C_6$ cycloalkyl, $C_3$-$C_6$ heterocycloalkyl, aryl (fused or pendant), or heteroaryl (fused or pendant), any of which is optionally substituted with one or more carbonyl (C=O), $C_1$-$C_6$ alkyl, $C_1$-$C_6$ haloalkyl, $C_1$-$C_6$ alkoxyl, amino, —$NR^6R^7$, —$C(O)NR^6R^7$, $C_1$-$C_6$ alkyl-hydroxy, $C_3$-$C_6$ cycloalkyl, $C_3$-$C_6$ heterocycloalkyl, aryl, heteroaryl, halo, hydroxyl, thiol, cyano, nitro, or radiolabeled isotope (e.g., $^{18}F$, $^{11}C$); and
$R^8$ is hydrogen, halo, hydroxyl, cyano, nitro, amino, $C_1$-$C_8$ alkyl, $C_1$-$C_8$ alkenyl, $C_1$-$C_8$ alkynyl, $C_1$-$C_8$ alkoxyl, $C_1$-$C_8$ heteroalkyl, $C_3$-$C_6$ cycloalkyl, $C_3$-$C_6$ heterocycloalkyl, aryl (fused or pendant), or heteroaryl (fused or pendant), any of which is optionally substituted with one or more carbonyl (C=O), $C_1$-$C_6$ alkyl, $C_1$-$C_6$ haloalkyl, $C_1$-$C_6$ alkoxyl, amino, —$NR^6R^7$, —$C(O)NR^6R^7$, $C_1$-$C_6$ alkyl-hydroxy, $C_3$-$C_6$ cycloalkyl, $C_3$-$C_6$ heterocycloalkyl, aryl, heteroaryl, halo, hydroxyl, thiol, cyano, nitro, or radiolabeled isotope (e.g., $^{18}F$, $^{11}C$).

In specific examples of Formula V, $R^5$ is at the 3 position of the phenyl ring. In specific examples, $R^5$ is OH, F, $C_1$, Br, or CN. In other examples, $R^5$ is $C_1$-$C_6$ alkyl or $C_1$-$C_6$ alkoxyl. In specific examples $R^5$ is a fused phenyl. In specific examples $R^5$ is phenyl.

In specific examples, $R^8$ is at the 2 position of the phenyl ring. In other examples, $R^8$ is at the 3 position of the phenyl ring. In specific examples, $R^8$ is hydroxyl, F, $C_1$, or Br. In specific examples, $R^8$ is phenyl or benzyl.

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

In specific examples, the type of cancer is lung cancer.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Piperidine Derivatives:

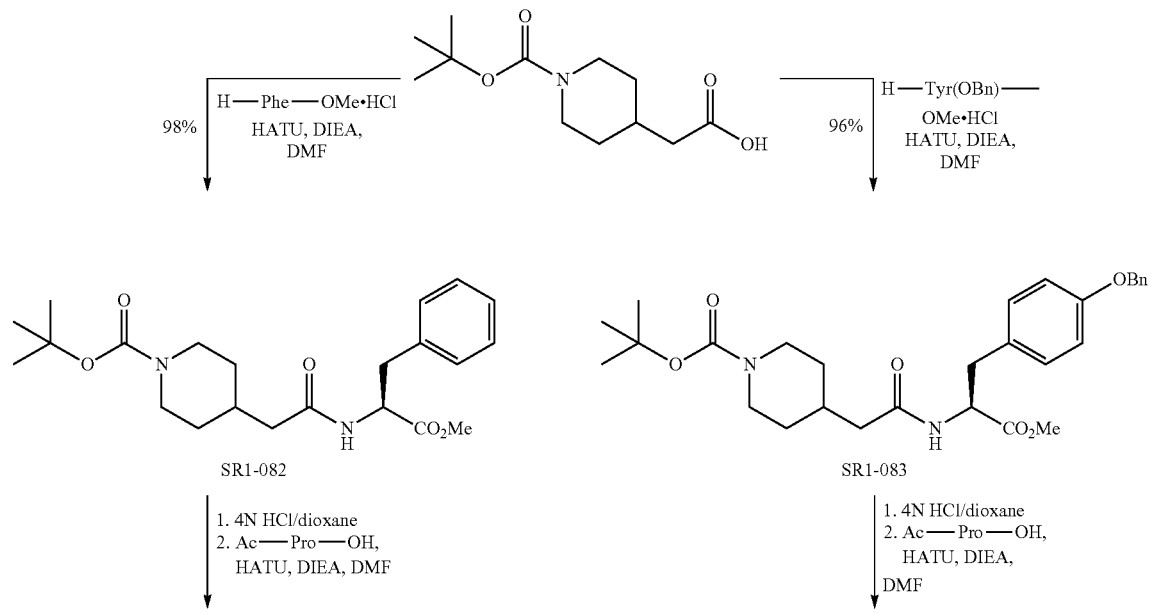

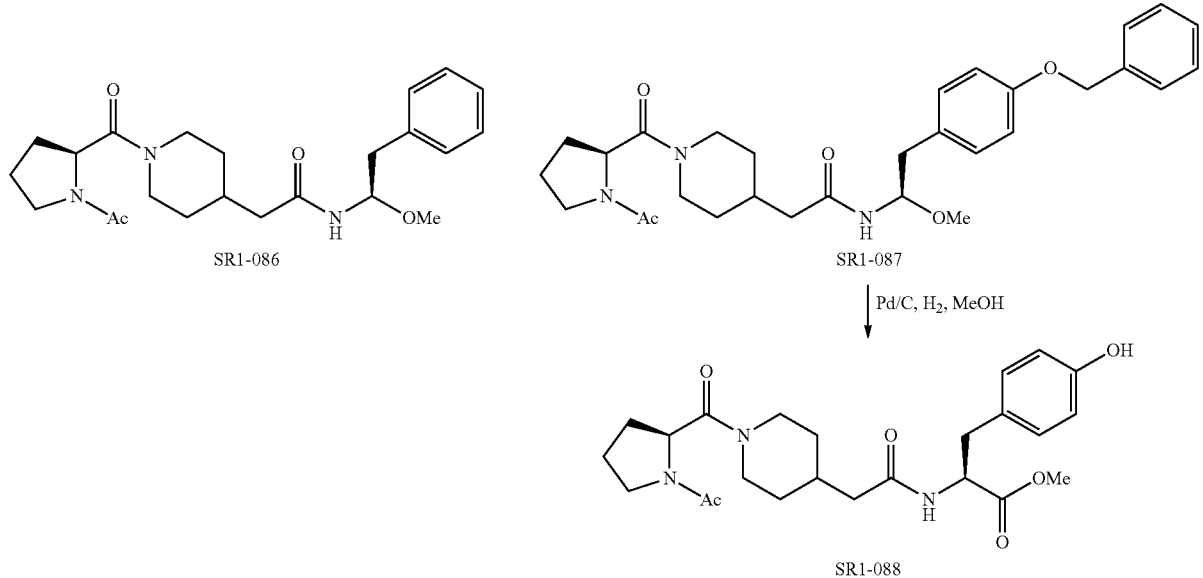

A series of tyrosine derivatives based on mimics of the OCT4 PPPY peptide sequence were prepared based on piperidineacetic acid core. A set of amides were prepared, such as SR1-082 and SR1-083 by coupling with different amino acids and esters. Deprotection of the Boc group provides the NH piperidine which upon acylation provides the prolyl derivatives SR1-086 and SR1-088.

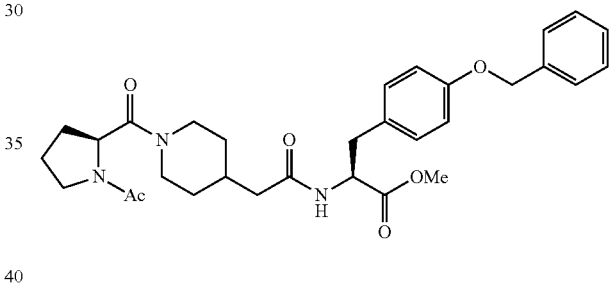

tert-Butyl (S)-4-(2-((3-(4-(benzyloxy)phenyl)-1-methoxy-1-oxopropan-2-yl)amino)-2-oxoethyl)piperidine-1-carboxylate (SR1-083). DIEA (0.472 mL, 2.713 mmol) and HATU (0.563 g, 1.48 mmol) were added into a solution of 2-(1-Boc-piperidin-4-yl)acetic acid (0.300 g, 1.233 mmol) in anhydrous DMF (7 mL) at rt. After stirring for 3 min. H-Tyr(bzl)-OH.HCl (0.476 g, 1.480 mmol) was added to the mixture and stirred for 21 h. The solvent was removed under reduced pressure and the resulting gum dissolved in EtOAc (30 mL). The organic phase was washed with 1N HCl (2×20 mL) followed by sat. NaHCO$_3$ (2×20 mL). Purification by flash column chromatography using EtOAc/hexane (40:60-100:0) as eluent afforded SR1-083 as a white foam (0.602 g, 96%). HPLC: >97% [$t_R$=5.8 min, 80% MeOH, 20% water (with 0.1% TFA), 20 min]. $^1$H NMR (400 MHz, CDCl$_3$-d) δ 7.49-7.30 (m, 5H), 7.00 (d, J=8.7 Hz, 2H), 6.89 (d, J=8.7 Hz, 2H), 5.85 (d, J=7.9 Hz, 1H), 5.03 (s, 2H), 4.87 (dt, J=8.0, 5.9 Hz, 1H), 4.06 (dq, J=13.2, 2.4 Hz, 2H), 3.73 (s, 3H), 3.05 (qd, J=14.0, 5.9 Hz, 2H), 2.74-2.62 (m, 2H), 2.08 (d, J=7.1 Hz, 2H), 1.97-1.70 (m, 2H), 1.60 (m, 2H), 1.44 (s, 9H), 1.09 (m, 2H). HRMS (ESI+): m/z C$_{29}$H$_{38}$N$_2$O$_6$ (M+H)$^+$511.2794; m/z C$_{29}$H$_{38}$N$_2$O$_6$Na (M+Na)$^+$533.2613. HPLC-MS (ESI+): m/z 533.3 [90%, (M+Na)$^+$].

Methyl (S)-2-(2-(1-(acetyl-L-prolyl)piperidin-4-yl)acetamido)-3-(4-(benzyloxy)phenyl)-propanoate (SR1-087). A solution of HCl (3 mL, 4N in dioxane) was added to piperidine methyl ester SR1-083 (0.300 g, 0.507 mmol) at rt. after stirring for 2 h, the reaction mixture was concentrated under reduced pressure to afford a white semi-solid, which then dissolved in anhydrous DMF (5 mL). To the mixture DIEA (0.307 mL, 1.761 mmol), HATU (0.268 g, 0.704 mmol), and Ac-Pro-OH (0.110 g, 0.704 mmol) were added. The mixture was stirred for 20 h and evaporated under reduced pressure. The resulting residue was dissolved in EtOAc (30 mL). The organic phase was washed with 1N HCl (2×20 mL) followed by sat. NaHCO$_3$ (2×20 mL). Purification by flash column chromatography using MeOH/DCM (0:100-10:90) as eluent afforded SR1-087 as a white foam (0.223 g, 69%, 2 steps). HPLC: >99% [$t_R$=18.8 min, 10-95% MeOH in water (with 0.1% TFA), 20 min]. $^1$H NMR (400 MHz, CDCl$_3$-d) δ 7.51-7.27 (m, 5H), 7.02 (m, 2H), 6.90 (m, 2H), 6.19 (bs, 0.5H), 5.84 (bs, 0.5H), 5.03 (s, 2H), 4.85 (m, 2H), 4.52 (bs, 1H), 3.94 (m, 1H), 3.72 (m, 4H), 3.56 (bs, 1H), 3.23-2.90 (m, 3H), 2.82-2.32 (m, 3H), 2.13 (m, 6H), 1.94 (m, 1H), 1.80-1.51 (m, 2H), 1.46 (m, 1H), 1.14 (bs, 1H). HRMS (ESI+): m/z C$_{31}$H$_{39}$N$_3$O$_6$ (M+H)$^+$ 550.2903; m/z C$_{31}$H$_{39}$N$_3$O$_6$Na (M+Na)$^+$572.2716. HPLC-MS (ESI+): m/z 550.4 [100%, (M+H)$^+$], 572.2 [80%, (M+Na)$^+$].

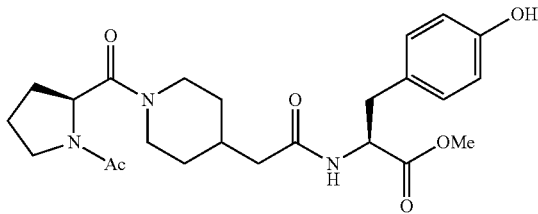 [SMILES: COC(=O)[C@H](Cc1ccc(O)cc1)NC(=O)CC1CCN(C(=O)[C@@H]2CCCN2C(C)=O)CC1]

Methyl (2-(1-(acetyl-L-prolyl)piperidin-4-yl)acetyl)-L-tyrosinate (SR1-088). Benzyl ether methyl ester SR1-087 (0.030 g, 0.055 mmol) was dissolved in MeOH (2.5 mL) and purged with Argon. Palladium on carbon (10%, 0.008 g, 0.15 g/mol) was added and purged with H2 (balloon). The mixture was stirred under H2 for 20 h and filtered through Celite with MeOH/DCM rinsing of the filter bed. The filtrate was evaporated under reduced pressure to afford SR1-088 as a white foam (0.25 g, yield quantitative). HPLC: >99% [$t_R$=6.9 min, 40% MeOH, 60% water (with 0.1% TFA), 20 min]. $^1$H NMR (400 MHz, CDCl$_3$-d) δ 6.91 (d, J=8.3 Hz, 1H), 6.76 (d, J=8.1 Hz, 1H), 6.44 (d, J=8.0 Hz, 0.5H), 6.20 (d, J=8.2 Hz, 0.5H), 4.93-4.70 (m, 2H), 4.44 (m, 1H), 3.92-3.76 (m, 1H), 3.72 (m, 4H), 3.55 (m, 1H), 3.39 (m, 1H), 3.19-2.92 (m, 2H), 2.84 (m, 1H), 2.50 (m, 1H), 2.11 (m, 4H), 2.04-1.75 (m, 4H), 1.60 (m, 1H), 1.53-1.39 (m, 2H), 1.36-1.19 (m, 1H), 1.15-0.81 (m, 2H). HRMS (ESI+): m/z C$_{24}$H$_{33}$N$_3$O$_6$ (M+H)$^+$460.2437; m/z C$_{24}$H$_{33}$N$_3$O$_6$Na (M+Na)$^+$482.2253. HPLC-MS (ESI+): m/z 460.4 [100%, (M+H)$^+$], 919.4 [30%, (2M+H)$^+$].

tert-Butyl (S)-4-(2-((1-methoxy-1-oxo-3-phenylpropan-2-yl)amino)-2-oxoethyl)piperidine-1-carboxylate (SR1-082). The amide SR1-082 (0.491 g, 98%) was prepared in the same way as SR1-083 using H-Phe-OH.HCl (0.300 g, 1.233 mmol) as starting material. HPLC: >97% [$t_R$=6.9 min, 70% MeOH, 30% water (with 0.1% TFA), 20 min]. $^1$H NMR (400 MHz, CDCl$_3$-d) δ 7.33-7.19 (m, 3H), 7.11-7.04 (m, 2H), 5.90 (d, J=7.9 Hz, 1H), 4.91 (m, 1H), 4.03 (m, 2H), 3.73 (d, 3H), 3.16 (dd, J=13.9, 5.6 Hz, 1H), 3.04 (dd, J=13.9, 6.5 Hz, 1H), 2.65 (m, 2H), 2.07 (dd, J=7.1, 4.6 Hz, 2H), 1.88 (m, 1H), 1.61 (m, 1H), 1.52 (m, 1H), 1.44 (s, 9H), 1.14-0.96 (m, 2H). HRMS (ESI+): m/z C$_{22}$H$_{32}$N$_2$O$_5$Na (M+Na)$^+$ 427.2202; m/z C$_{22}$H$_{32}$N$_2$O$_5$K (M+K)$^+$443.1946 HPLC-MS (ESI+): m/z 427.3 [100%, (M+Na)$^+$].

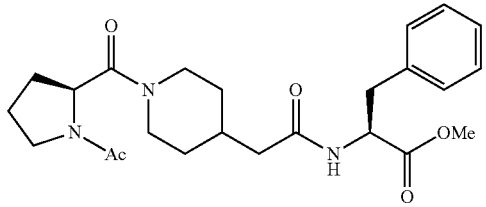 [SMILES: COC(=O)[C@H](Cc1ccccc1)NC(=O)CC1CCN(C(=O)[C@@H]2CCCN2C(C)=O)CC1]

Methyl (2-(1-(acetyl-L-prolyl)piperidin-4-yl)acetyl)-L-phenylalaninate (SR1-086). Amide SR1-086 (0.106 g, 48%, 2 steps) was prepared from SR1-082 (0.200 g, 0.494 mmol), by the same method used to make SR1-087. HPLC: >99% [$t_R$=7.8 min, 50% MeOH, 50% water (with 0.1% TFA), 20 min]. $^1$H NMR (400 MHz, DMSO-d$_6$) δ 8.31 (m, 1H), 7.33-7.15 (m, 5H), 4.87 (m, 0.4H), 4.72 (m, 0.6H), 4.51 (m, 1H), 4.28-4.08 (m, 1H), 3.94-3.71 (m, 1H), 3.61 (s, 3H), 3.49 (t, J=6.6 Hz, 1H), 3.05 (d, J=14.0 Hz, 1H), 3.94 (m, 1H), 2.84 (dd, J=13.8, 10.2 Hz, 1H), 2.45 (m, 1H), 2.34-2.03 (m, 2H), 1.98 (d, J=7.2 Hz, 2H), 1.93 (s, 2H), 1.87 (m, 1H), 1.79 (m, 3H), 1.71 (m, 1H), 1.64 (m, 0.5H), 1.49 (m, 0.5H), 1.41-1.21 (m, 1H), 1.21-0.92 (m, 1H), 0.92-0.74 (m, 1H). HRMS (ESI+): m/z C$_{24}$H$_{33}$N$_3$O$_5$ (M+H)$^+$444.2488; m/z C$_{24}$H$_{33}$N$_3$O$_5$Na (M+Na)$^+$466.2301. HPLC-MS (ESI+): m/z 444.2 [100%, (M+H)$^+$], 466.2 [30%, (M+Na)$^+$], 909.4 [45% (2M+Na)$^+$].

Piperazine Derivatives:

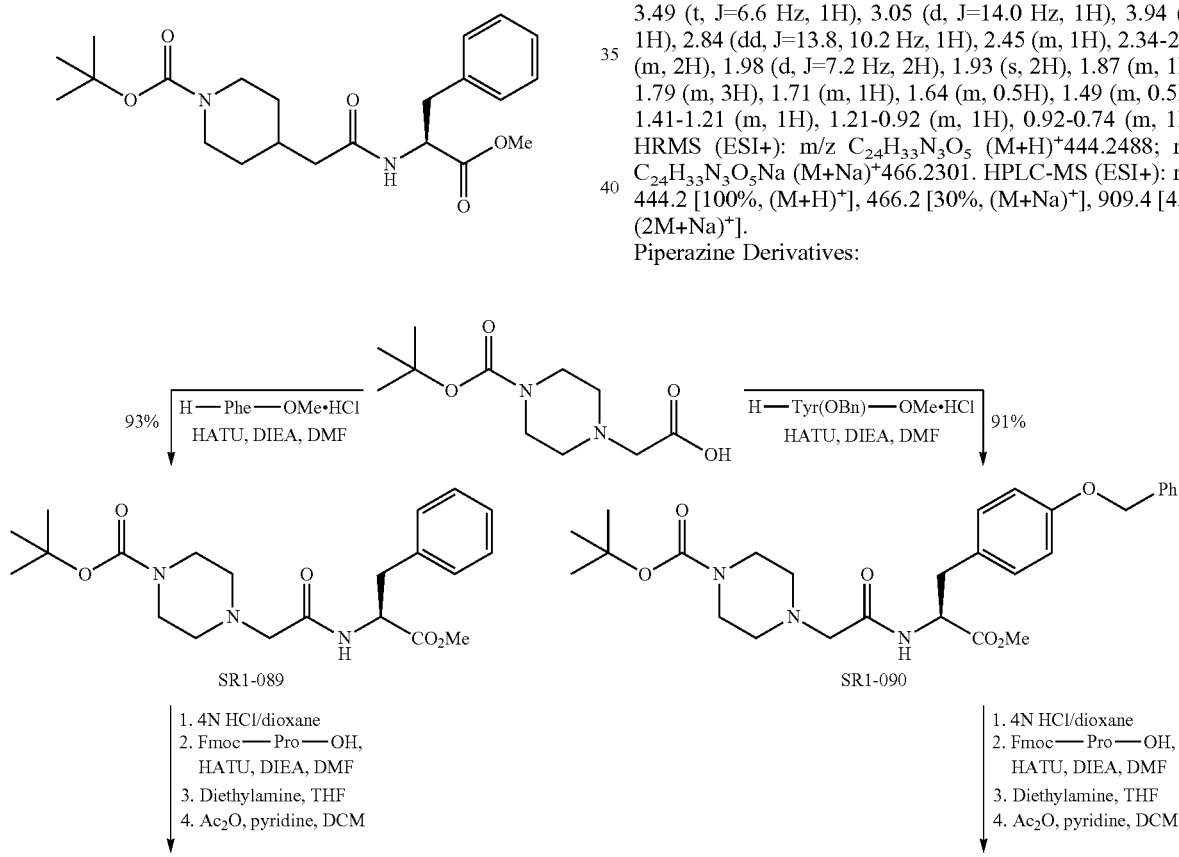

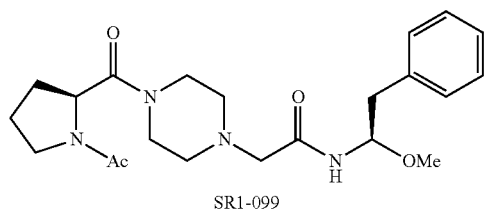
SR1-099

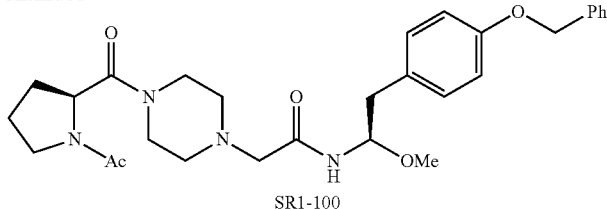
SR1-100

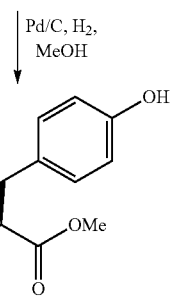
SR1-101

The central piperidyl core of the PPPY mimetics was replaced by piperazine, as shown in the derivatives SR1-099 and SR1-100. The synthesis of SR1-099 and SR1-100 is shown in the Figure above, starting from 4-Bocpiperazine-1-acetic acid, by first amide formation with amino acid derivatives to make SR1-089 and SR1-090. Boc deprotection followed by acylation with Fmoc prolyl derivatives, further Fmoc deprotection and acetylation gave the PPPY mimetics SR1-099 and SR1-100. The tyrosyl benzyl group can be deprotected as shown in the transformation of SR1-100 into SR1-101.

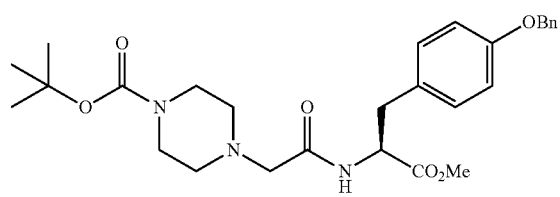 [SMILES: COC(=O)[C@H](Cc1ccc(OCc2ccccc2)cc1)NC(=O)CN1CCN(C(=O)OC(C)(C)C)CC1]

tert-Butyl (S)-4-(2-((3-(4-(benzyloxy)phenyl)-1-methoxy-1-oxopropan-2-yl)amino)-2-oxoethyl)piperazine-1-carboxylate (SR1-090). DIEA (0.534 mL, 3.065 mmol), and HATU (0.560 g, 1.472 mmol) were added into a solution of 4-N-Boc-piperazineacetic acid (0.300 g, 1.223 mmol) in anhydrous DMF (7 mL) at rt and stirring for 3 min. H-Tyr(bzl)-OMe.HCl was added into the mixture and stirred for 18 h and concentrated under reduced pressure. The resulting residue was dissolved in EtOAc and washed with Sat. $NH_4OH$ (2×20 mL) and sat. $NaHCO_3$ (2×20 mL). Purification by flash column chromatography using EtOAc/Hexane (1:1-100:0) as eluent afforded SR1-090 as a white foam (0.569 g, 91%). HPLC: >98% [$t_R$=9.6 min, 60% MeOH, 40% water (with 0.1% TFA), 20 min]. $^1$H NMR (400 MHz, DMSO-$d_6$) δ 7.90 (d, J=8.1 Hz, 1H), 7.47-7.28 (m, 5H), 7.11 (d, J=8.6 Hz, 2H), 6.96-6.89 (m, 2H), 5.06 (s, 2H), 4.54 (td, J=8.7, 5.2 Hz, 1H), 3.64 (s, 3H), 3.24 (m, 4H), 3.03 (dd, J=13.9, 5.2 Hz, 1H), 2.96 (m, 1H), 2.91 (m, 1H), 2.83 (d, J=15.5 Hz, 1H), 2.30-2.11 (m, 4H). HRMS (ESI+): m/z $C_{28}H_{37}N_3O_6$ (M+H)$^+$512.2748; m/z $C_{28}H_{37}N_3O_6Na$ (M+Na)$^+$534.2568. HPLC-MS (ESI+): m/z 512.4 [100%, (M+H)$^+$].

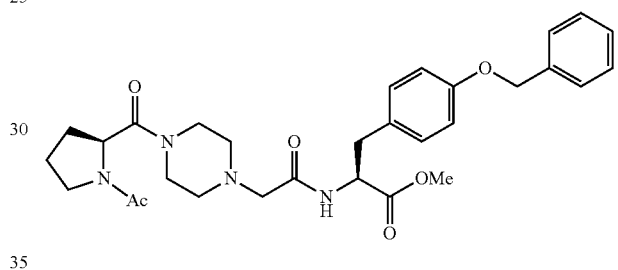

Methyl (S)-2-(2-(4-(acetyl-L-prolyl)piperazin-1-yl)acetamido)-3-(4-(benzyloxy)phenyl)-propanoate (SR1-100). A solution of HCl (4 mL, 4N in dioxane) was added dropwise into SR1-090 (0.350 g, 0.684 mmol) at rt and stirred for 3 h. The resulting residue was dissolved in anhydrous DMF (2 mL) and added into a mixture of DIEA (0.357 mL, 2.052 mmol), HATU (0.312 g, 0.821 mmol), and Fmoc-Pro-OH (0.278 g, 0.821 mmol) in DMF (5 mL). After stirring 16 h, the reaction mixture was evaporated under reduced pressure. The resulting residue was dissolved in EtOAc and washed with Sat. $NH_4OH$ (2×25 mL) and sat. $NaHCO_3$ (2×25 mL). Purification by flash column chromatography using MeOH/DCM (0%-10%) as eluent afforded SR1-094 (Fmoc-Pro-piperazineacetic acid Tyr(bzl)-OMe) as a white foam (0.452 g, 91%). HPLC: >92% [$t_R$=6.4 min, 50% MeOH, 50% water (with 0.1% TFA), 20 min]. $^1$H NMR (400 MHz, DMSO-$d_6$) δ 7.93 (dd, J=8.1, 5.2 Hz, 1H), 7.88 (m, 2H), 7.65 (dd, J=10.2, 7.3 Hz, 1H), 7.56 (J=13.8, 7.5 Hz, 1H), 7.44-7.23 (m, 9H), 7.10 (m, 2H), 6.90 (m, 2H), 5.03 (s, 1H), 4.99 (s, 1H), 4.67-4.56 (m, 1H), 4.52 (m, 1H), 4.30-4.06 (m, 3H), 3.62 (s, 3H), 3.50-3.34 (m, 4H), 3.01 (m, 1H), 2.92 (m, 2H), 2.81 (m, 1H), 2.31 (m, 2H), 2.26-2.02 (m, 4H), 1.76 (m, 4H). HRMS (ESI+): m/z $C_{43}H_{47}N_4O_7$(M+H)$^+$731.5639. HPLC-MS (ESI+): m/z 731.4 [100%, (M+H)$^+$].

Diethylamine (0.269 mL, 2.600 mmol) was added into a mixture of SR1-094 (380 g, 0.519 mmol) in THF (5 mL) at rt. The reaction was stirred for 4 h and the solvent evaporated. The resulting gum was dissolved in DCM (5 mL) and pyridine (0.210 mL, 2.595 mmol) and acetic anhydride (0.245 mL, 2.595) were added. The mixture was stirred at rt for 16 h and evaporated. Purification by flash column Chromatography using MeOH/DCM (5%-10%) as eluent afforded SR1-100 as a white foam (0.052 g, 18%). (Note: the crude mixture partly solidified in the column during purification and much SR1-100 was obtained co-eluting with impurities. Only the pure material was taken to the next step.). The above benzyl ether SR1-100 (0.052, 0.094 mmol) was dissolved in MeOH (1.5 mL) and purged with Argon. Palladium on carbon (10%, 0.015 g, 0.15/mmol) was added and the mixture purged with $H_2$ (balloon). The reaction was stirred for 20 h, filtered through Celite, and concentrated under reduced pressure. Purification by flash column chromatography using MeOH/DCM (3%-12%) as eluent afforded SR1-101 as a white foam (0.035 g, 81%). HPLC: >97% [$t_R$=12.2 min, 10-95% MeOH in water (with 0.1% TFA), 20 min $^1$H NMR (400 MHz, DMSO-$d_6$) δ 9.25 (s, 1H), 7.89 (t, J=7.7 Hz, 1H), 6.97 (d, J=8.5 Hz, 2H), 6.65 (d, J=8.5 Hz, 2H), 4.88 (dd, J=8.6, 3.7 Hz, 0.3H), 4.70 (dd, J=8.6, 3.7 Hz, 0.7H), 4.49 (m, 1H), 3.62 (s, 3H), 3.56-3.34 (m, 4H), 3.26 (m, 2H), 3.00-2.80 (m, 4H), 2.42 (m, 1H), 2.31 (m, 1H), 2.28-2.04 (m, 4H), 1.92 (s, 2H), 1.89-1.60 (m, 3H). HRMS (ESI+): m/z $C_{23}H_{33}N_4O_6$ (M+H)$^+$461.2388; m/z $C_{23}H_{32}N_4O_6$Na (M+Na)$^+$483.2205. HPLC-MS (ESI+): m/z 461.2 [70%, (M+H)$^+$].

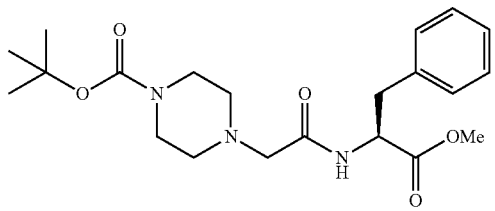 [SMILES: COC(=O)[C@H](Cc1ccccc1)NC(=O)CN1CCN(C(=O)OC(C)(C)C)CC1]

tert-Butyl (S)-4-(2-((1-methoxy-1-oxo-3-phenylpropan-2-yl)amino)-2-oxoethyl)piperazine-1-carboxylate (SR1-089). SR1-089 (0.463 g, 93%) was prepared by following the same method reported for SR1-090 from H-Phe-OMe (0.300 g, 1.228 mmol). HPLC: >99% [$t_R$=4.3 min, 55% MeOH, 45% water (with 0.1% TFA), 20 min]. $^1$H NMR (400 MHz, DMSO-$d_6$) δ 7.94 (d, J=8.3 Hz, 1H), 7.26 (m, 2H), 7.19 (m, 3H), 4.59 (ddd, J=9.4, 8.2, 5.2 Hz, 1H), 3.63 (s, 3H), 3.27-3.14 (m, 4H), 3.09 (dd, J=13.8, 5.1 Hz, 1H), 3.01 (d, J=9.4 Hz, 1H), 2.99-2.75 (m, 2H), 2.26-2.09 (m, 4H), 1.37 (s, 9H). HRMS (ESI+): m/z $C_{21}H_{31}N_3O_5$ (M+H)$^+$ 406.2326; m/z $C_{21}H_{31}N_3O_5$Na (M+Na)$^+$428.2147. HPLC-MS (ESI+): m/z 406.2 [100%, (M+H)$^+$].

SR1-093 (Fmoc-Pro-piperazineacetic acid-Phe-OMe) was obtained as a white foam (0.441 g, 96%) from SR1-089 (0.300 g, 0.740 mmol) by the method used to make SR1-094. HPLC: 87% &13% (two diastereomers) [$t_R$=6.4 min & 5.2 min, 70% MeOH, 30% water (with 0.1% TFA), 20 min]. $^1$H NMR (400 MHz, DMSO-$d_6$) δ 7.98 (t, J=8.7 Hz, 1H), 7.88 (m, 3H), 7.65 (m, 2H), 7.58 (m, 1H), 7.40 (m, 3H), 7.35-7.15 (m, 4H), 4.61 (m, 2H), 4.31-4.01 (m, 3H), 3.63 (s, 3H), 3.50-3.37 (m, 4H), 3.30-3.14 (m, 2H), 3.08 (m, 1H), 3.01 (m, 1H), 2.92 (m, 1H), 2.86-2.70 (m, 1H), 2.32 (m, 1H), 2.17 (m, 3H), 1.78 (m, 4H). HRMS (ESI+): m/z $C_{36}H_{40}N_4O_6$ (M+H)$^+$625.3008; m/z $C_{36}H_{40}N_4O_6$Na (M+Na)$^+$647.2829. HPLC-MS (ESI+): m/z 625.3 [100%, (M+H)+].

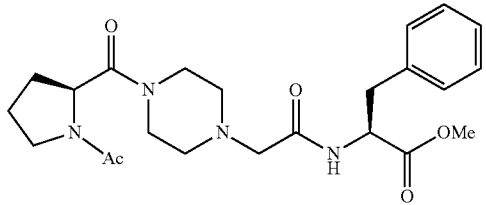 [SMILES: COC(=O)[C@H](Cc1ccccc1)NC(=O)CN1CCN(C(=O)[C@@H]2CCCN2C(C)=O)CC1]

Methyl (2-(4-(acetyl-L-prolyl)piperazin-1-yl)acetyl)-L-phenylalaninate (SR1-099). The amide SR1-099 (0.078 g, 27%) was prepared from SR1-093 (0.410 g, 0.656 mmol) by following the same method reported for SR1-100. HPLC: >98% [$t_R$=13.9 min, 10-95% MeOH in water (with 0.1% TFA), 20 min]. $^1$H NMR (400 MHz, DMSO-$d_6$) δ 8.01 (dd, J=8.2, 6.6 Hz, 1H), 7.29 (m, 2H), 7.21 (m, 3H), 4.89 (dd, J=8.6, 2.8 Hz, 0.3H), 4.72 (dd, J=8.6, 3.7 Hz, 0.7H), 4.61 (m, 1H), 3.65 (s, 3H), 3.57-3.35 (m, 4H), 3.28 (m, 2H), 3.11 (dd, J=13.8, 5.1 Hz, 1H), 3.03 (dd, J=9.9, 3.6 Hz, 1H), 2.963 (m, 1H), 2.85 (m, 1H), 2.44 (m, 1H), 2.32 (m, 1H), 2.26-2.06 (m, 3H), 1.94 (s, 2H), 1.88 (m, 1H), 1.79 (m, 1H), 1.73 (s, 1H), 1.73 (m, 1H). HRMS (ESI+): m/z $C_{23}H_{32}N_4O_5$ (M+H)$^+$ 445.2440; m/z $C_{23}H_{32}N_4O_5$Na (M+Na)$^+$467.2259. HPLC-MS (ESI+): m/z 445.4 [100%, (M+H)$^+$].

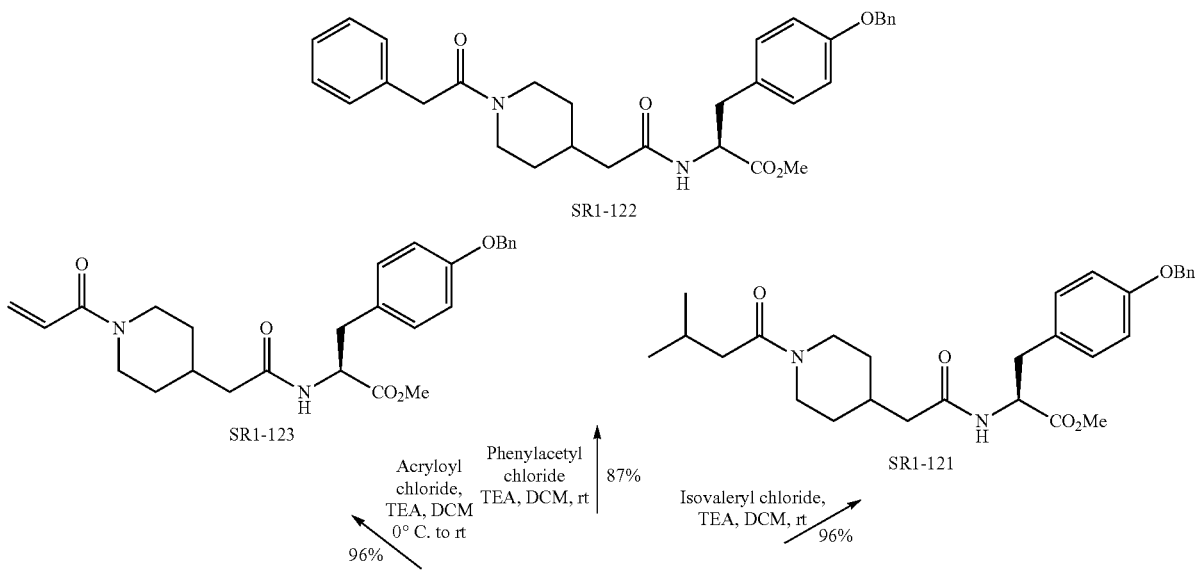

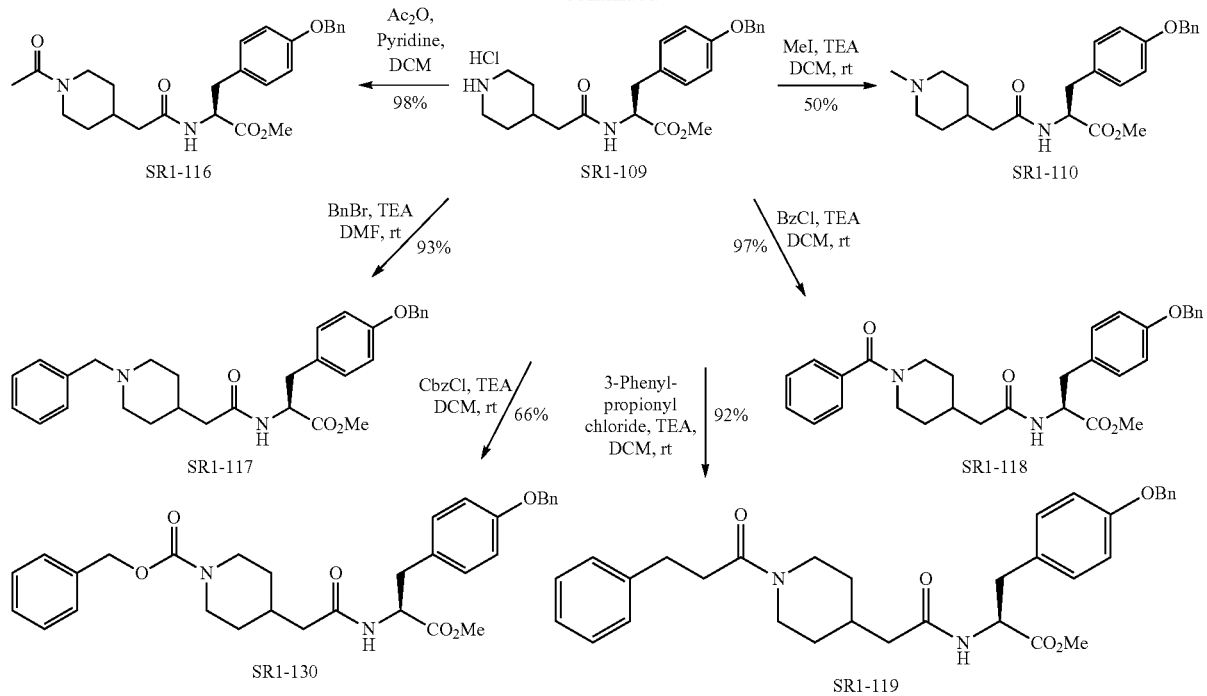

A set of PPPY mimetics can be prepared from the piperidine SR1-109 (made by deprotection of the Boc derivative SR1-083. A set of PPPY mimetics were prepared by alkylation or acylation with a range of acyl and alkyl halides, as shown in the Figure above. The methyl ester group can be further transformed into amides or hydrolyzed to its corresponding carboxylic acid, as shown in the examples below.

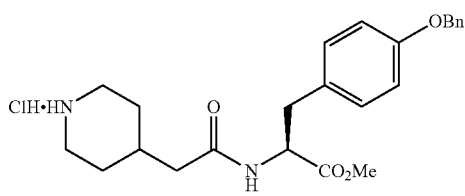

Methyl (S)-3-(4-(benzyloxy)phenyl)-2-(2-(piperidin-4-yl)acetamido)propanoate hydrochloride (SR1-085). A solution of HCl (3 mL, 4N in dioxane) was added slowly to SR1-083 (0.300 g, 0.587 mmol) at rt and stirred for 2 h. The mixture was concentrated under reduced pressure to afford SR2-085 (0.262 g, 99%) as a white solid. HPLC: >99% [$t_R$=4.7 min, 60% MeOH, 40% water (with 0.1% TFA), 20 min]. $^1$H NMR (400 MHz, DMSO-$d_6$) δ 8.68 (s, 1H), 8.46 (s, 1H), 8.35 (d, J=8.7 Hz, 1H), 7.45-7.34 (m, 4H), 7.32 (m, 1H), 7.11 (d, J=8.7 Hz, 2H), 6.90 (d, J=8.7 Hz, 2H), 5.04 (s, 2H), 4.43 (ddd, J=10.1, 8.0, 5.2 Hz, 1H), 3.58 (s, 3H), 3.21-3.05 (m, 2H), 2.96 (dd, J=13.8, 5.2 Hz, 1H), 2.76 (m, 3H), 2.00 (m, 2H), 1.80 (m, 1H), 1.62 (m, 1H), 1.43 (m, 1H), 1.32-1.09 (m, 2H). HRMS (ESI+): m/z $C_{24}H_{30}N_2O_4$ (M+H)$^+$411.2270; m/z $C_{24}H_{30}N_2O_4Na$ (M+Na)$^+$433.2089. HPLC-MS (ESI+): m/z 411.3 [100%, (M+H)+].

General Method A: Synthesis of N-Terminal Variants of SR1-083.

The amine salt SR1-085 (0.055 mmol) was dissolved in DCM (1.5 mL) under argon and DIEA/NEt$_3$ or pyridine (0.167 mmol) added. To this mixture corresponding alkyl halide or substituted carbonyl halide (0.067 mmol) was added and stirred at rt for 14-20 h and concentrated under reduced pressure. The resulting residue was directly purified by column chromatography.

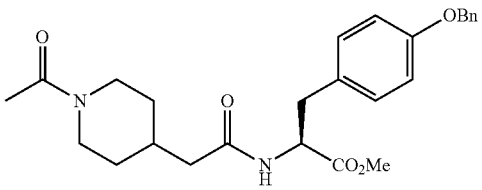 [SMILES: COC(=O)[C@H](Cc1ccc(OCc2ccccc2)cc1)NC(=O)CC1CCN(C(C)=O)CC1]

Methyl (S)-2-(2-(1-acetylpiperidin-4-yl)acetamido)-3-(4-(benzyloxy)phenyl)propanoate (SR1-116). The N-acetyl derivative SR1-116 (0.025 g, 98%) was prepared using method A, from SR1-085 (0.025 g, 0.056 mmol), acetyl chloride (8 μL, 0.084 mmol) and pyridine (13.5 μL, 0.167 mmol). HPLC: >99% [$t_R$=10.24 min, 60% MeOH, 40% water (with 0.1% TFA), 20 min]. $^1$H NMR (400 MHz, DMSO-$d_6$) δ 8.25 (d, J=8.0 Hz, 1H), 7.42 (m, 2H), 7.36 (m, 2H), 7.31 (m, 1H), 7.11 (d, J=8.2 Hz, 2H), 6.90 (m, 2H), 5.04 (s, 2H), 4.43 (m, 1H), 4.22 (m, 1H), 3.65 (m, 1H), 3.58 (s, 3H), 2.96 (dd, J=13.8, 5.2 Hz, 1H), 2.86 (m, 1H), 2.75 (dd, J=13.4, 10.6 Hz 1H), 2.36 (m, 1H), 1.93 (m, 5H), 1.71 (m, 1H), 1.47 (m, 1H), 1.28 (m, 1H), 1.04-0.63 (m, 2H). HRMS (ESI+): m/z $C_{26}H_{32}N_2O_4$ (M+H)$^+$453.2395; m/z $C_{26}H_{32}N_2O_4Na$ (M+Na)$^+$475.2203. HPLC-MS (ESI+): m/z 453.3 [100%, (M+H)$^+$], 475.3 [40%, (M+Na)$^+$].

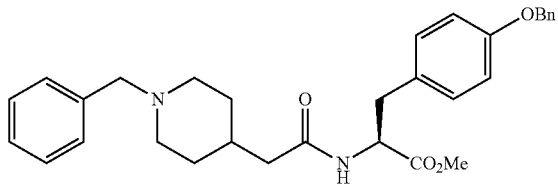 [SMILES: COC(=O)[C@H](Cc1ccc(OCc2ccccc2)cc1)NC(=O)CC1CCN(Cc2ccccc2)CC1]

Methyl (S)-3-(4-(benzyloxy)phenyl)-2-(2-(1-benzylpiperidin-4-yl)acetamido)propanoate (SR1-117). The N-benzyl derivative SR1-117 (0.026 g, 93%) was prepared using general method A from SR1-085 (0.025 g, 0.056 mmol) benzyl chloride (8 µL, 0.067 mmol) and triethylamine (23 µL, 0.167 mmol). HPLC: >95% [$t_R$=7.79 min, 60% MeOH, 40% water (with 0.1% TFA), 20 min]. $^1$H NMR (400 MHz, CDCl$_3$-d) δ 7.57 (bs, 1H), 7.49-7.28 (m, 10H), 7.01 (d, J=8.6 Hz, 1H), 6.89 (d, J=8.7 Hz, 1H), 6.12 (s, 0.7H), 5.92 (s, 0.3H), 5.03 (s, 2H), 4.85 (dt, J=8.0, 6.0 Hz, 0.2H), 4.78 (td, J=7.4, 5.5 Hz, 0.8H), 4.28 (bs, 0.4H), 4.06 (bs, 1.6H), 3.69 (s, 1H), 3.36 (m, 1H), 3.06 (dd, J=14.1, 5.5 Hz, 1H), 2.96 (dd, J=14.2, 7.1 Hz, 1H), 2.56 (m, 1H), 2.24-2.07 (m, 2H), 2.07-1.89 (m, 3H), 1.78 (m, 2H), 1.65 (m, 1H). HRMS (ESI+): m/z C$_{31}$H$_{36}$N$_2$O$_4$ (M+H)$^+$501.2740; m/z C$_{31}$H$_{36}$N$_2$O$_4$Na (M+Na)$^+$523.2559. HPLC-MS (ESI+): m/z 501.3 [95%, (M+H)$^+$].

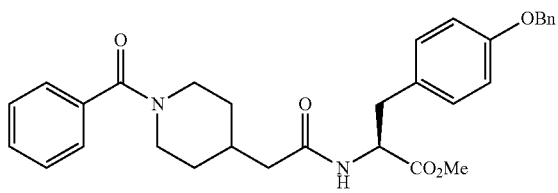 [SMILES: COC(=O)[C@H](Cc1ccc(OCc2ccccc2)cc1)NC(=O)CC1CCN(C(=O)c2ccccc2)CC1]

Methyl (S)-2-(2-(1-benzoylpiperidin-4-yl)acetamido)-3-(4-(benzyloxy)phenyl)propanoate (SR1-118). The N-benzoyl derivative SR1-118 (0.028 g, 97%) was prepared using general method A, from SR1-085 (0.025 g, 0.056 mmol) benzoyl chloride (8 µL, 0.067 mmol) and triethylamine (23 µL, 0.167 mmol). HPLC: >95% [$t_R$=6.5 min, 70% MeOH, 30% water (with 0.1% TFA), 20 min]. $^1$H NMR (400 MHz, DMSO-d$_6$) δ 8.25 (d, J=8.0 Hz, 1H), 7.54-7.25 (m, 10H), 7.10 (d, J=8.7 Hz, 2H), 6.86 (bs, 2H), 4.98 (bs, 2H), 4.44 (ddd, J=10.3, 8.0, 5.1 Hz, 1H), 4.34 (bs, 1H), 3.58 (s, 3H), 3.42 (m, 1H), 3.06-2.83 (m, 2H), 2.82-2.54 (m, 2H), 1.98 (m, 2H), 1.77 (m, 1H), 1.67-1.16 (m, 2H), 1.07-0.86 (m, 2H). RMS (ESI+): m/z C$_{31}$H$_{34}$N$_2$O$_5$ (M+H)$^+$515.2544; m/z C$_{31}$H$_{34}$N$_2$O$_5$Na (M+Na)$^+$537.2353. HPLC-MS (ESI+): m/z 515.3 [95%, (M+H)$^+$], 537.3 [30%, (M+Na)$^+$].

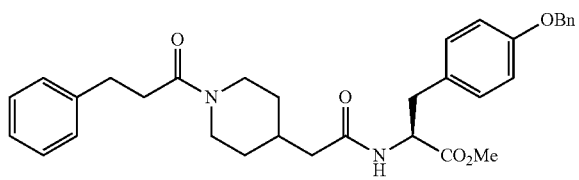 [SMILES: COC(=O)[C@H](Cc1ccc(OCc2ccccc2)cc1)NC(=O)CC1CCN(C(=O)CCc2ccccc2)CC1]

Methyl (S)-3-(4-(benzyloxy)phenyl)-2-(2-(1-(3-phenylpropanoyl)piperidin-4-yl)acetamido)propanoate (SR1-119). The N-phenylpropanoyl derivative SR1-119 (0.028 g, 92%) was prepared using general method A, from SR1-085 (0.025 g, 0.056 mmol) 3-phenylpropionyl chloride (10 µL, 0.067 mmol) and triethylamine (23 µL, 0.167 mmol). HPLC: >98% [$t_R$=10.8 min, 70% MeOH, 30% water (with 0.1% TFA), 20 min]. $^1$H NMR (400 MHz, CDCl$_3$-d) δ 7.44-7.35 (m, 4H), 7.35-7.25 (m, 3H), 7.25-7.15 (m, 3H), 7.00 (d, J=8.7 Hz, 2H), 6.89 (d, J=8.7 Hz, 2H), 5.94 (d, J=7.9 Hz, 1H), 5.03 (s, 2H), 4.90-4.78 (m, 1H), 3.73 (s, 3H), 3.09 (dd, J=14.1, 5.7 Hz, 1H), 3.03-2.88 (m, 5H), 2.83-2.47 (m, 4H), 2.04 (d, J=6.9 Hz, 2H), 2.02-1.92 (m, 1H), 1.64 (dd, J=26.6, 13.2 Hz, 2H), 0.94 (bs, 2H). HRMS (ESI+): m/z C$_{33}$H$_{39}$N$_2$O$_5$ (M+H)$^+$543.2841; m/z C$_{33}$H$_{38}$N$_2$O$_5$Na (M+Na)$^+$565.2659. HPLC-MS (ESI+): m/z 543.3 [100%, (M+H)$^+$], 565.4 [50%, (M+Na)$^+$].

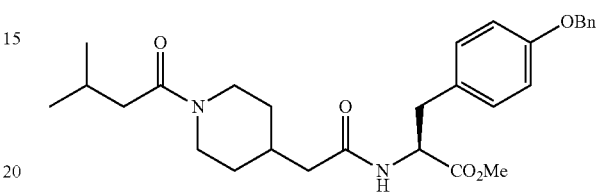

Methyl (S)-3-(4-(benzyloxy)phenyl)-2-(2-(1-(3-methylbutanoyl)piperidin-4-yl)acetamido)-propanoate (SR1-121). The N-methylbutanoyl derivative SR1-121 (0.032 g, 96%) was prepared using general method A, from SR1-085 (0.025 g, 0.056 mmol), isovaleryl chloride (11 µL, 0.087 mmol) and triethylamine (23 µL, 0.167 mmol). HPLC: >99% [$t_R$=8.0 min, 70% MeOH, 30% water (with 0.1% TFA), 20 min]. $^1$H NMR (400 MHz, CDCl$_3$-d) δ 7.46-7.30 (m, 5H), 7.00 (d, J=8.6 Hz, 2H), 6.89 (d, J=8.6 Hz, 2H), 5.88 (d, J=8.0 Hz, 1H), 5.03 (s, 2H), 4.86 (dt, J=8.0, 5.9 Hz, 1H), 4.70-4.0 (m, 2H), 3.73 (s, 3H), 3.09 (dd, J=14.1, 5.7 Hz, 1H), 3.01 (dd, J=14.1, 6.2 Hz, 1H), 2.90-2.62 (m, 2H), 2.21 (d, J=7.0 Hz, 2H), 2.17-1.95 (m, 4H), 1.77-1.62 (m, 2H), 1.15-1.00 (m, 1.5H), 0.99-0.92 (m, 6.5H). HRMS (ESI+): m/z C$_{29}$H$_{39}$N$_2$O$_5$ (M+H)$^+$495.2846; m/z C$_{29}$H$_{38}$N$_2$O$_5$Na (M+Na)$^+$517.2655. HPLC-MS (ESI+): m/z 495.3 [100%, (M+H)$^+$], 517.3 [30%, (M+Na)$^+$].

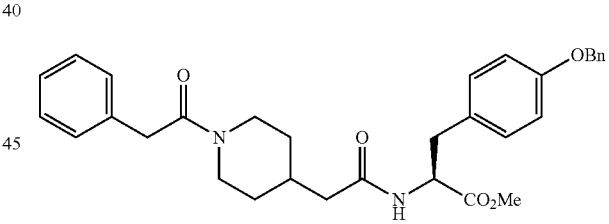

Methyl (S)-3-(4-(benzyloxy)phenyl)-2-(2-(1-(2-phenylacetyl)piperidin-4-yl)acetamido)-propanoate (SR1-122). The N-phenylacetyl derivative SR1-122 (0.033 g, 87%) was prepared using general method A, from SR1-085 (0.032 g, 0.072 mmol), phenylacetyl chloride (12 µL, 0.093 mmol) and triethylamine (30 µL, 0.215 mmol). HPLC: >98% [$t_R$=7.9 min, 70% MeOH, 30% water (with 0.1% TFA), 20 min]. $^1$H NMR (400 MHz, DMSO-d$_6$) δ 8.22 (d, J=8.0 Hz, 1H), 7.44-7.23 (m, 7H), 7.24-7.14 (m, 3H), 7.10 (d, J=8.2 Hz, 2H), 6.88 (d, J=8.5 Hz, 2H), 5.03 (s, 2H), 4.43 (m, 1H), 4.26 (m, 1H), 3.91-3.72 (m, 1H), 3.64 (s, 2H), 3.58 (s, 3H), 2.94 (dd, J=13.9, 5.0 Hz, 1H), 2.92-2.80 (m, 1H), 2.74 (dd, J=13.8, 10.1 Hz, 1H), 2.44-2.31 (m, 1H), 1.91 (d, J=7.2 Hz, 2H), 1.78-1.64 (m, 1H), 1.51-1.37 (m, 1H), 1.32-1.20 (m, 1H), 0.91-0.61 (m, 2H). HRMS (ESI+): m/z C$_{32}$H$_{36}$N$_2$O$_5$ (M+H)$^+$529.2687; m/z C$_{32}$H$_{36}$N$_2$O$_5$Na (M+Na)$^+$551.2508. HPLC-MS (ESI+): m/z 529.3 [80%, (M+H)$^+$], 551.3 [100%, (M+Na)$^+$].

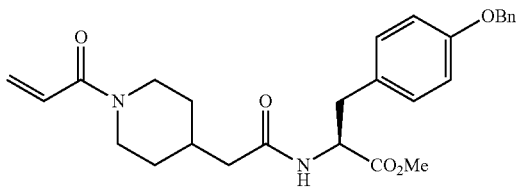 [SMILES: C=CC(=O)N1CCC(CC(=O)N[C@@H](Cc2ccc(OCc3ccccc3)cc2)C(=O)OC)CC1]

Methyl (S)-2-(2-(1-acryloylpiperidin-4-yl)acetamido)-3-(4-(benzyloxy)phenyl)propanoate (SR1-123). The N-acryloyl derivative SR1-123 (0.030 g, 96%) was prepared using general method A, from SR1-085 (0.030 g, 0.067 mmol), acryloyl chloride (7 uL, 0.087 mmol) and triethylamine (28 μL, 0.201 mmol). HPLC: >99% [$t_R$=4.6 min, 70% MeOH, 30% water (with 0.1% TFA), 20 min]. $^1$H NMR (400 MHz, Chloroform-d) δ 7.46-7.29 (m, 5H), 7.00 (d, J=8.5 Hz, 2H), 6.93-6.86 (m, 2H), 6.55 (dd, J=17.0, 10.6 Hz, 1H), 6.25 (dd, J=16.8, 1.9 Hz, 1H), 5.86 (d, J=7.9 Hz, 1H), 5.66 (dd, J=10.6, 1.9 Hz, 1H), 5.03 (s, 2H), 4.86 (m, 1H), 4.49-4.02 (m, 2H), 3.74 (s, 3H), 3.10 (dd, J=14.1, 5.7 Hz, 1H), 3.06-2.96 (m, 1H), 2.93-2.54 (m, 2H), 2.14-1.96 (m, 2H), 1.89 (m, 1H), 1.78-1.61 (m, 2H), 1.19-1.01 (m, 2H). HRMS (ESI+): m/z $C_{27}H_{32}N_2O_5$ (M+H)$^+$465.2376; m/z $C_{27}H_{32}N_2O_5Na$ (M+Na)$^+$487.2192. HPLC-MS (ESI+): m/z 465.3 [50%, (M+H)$^+$], 487.3 [100%, (M+Na)$^+$].

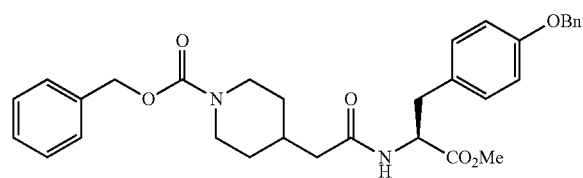 [SMILES: COC(=O)[C@H](Cc1ccc(OCc2ccccc2)cc1)NC(=O)CC1CCN(C(=O)OCc2ccccc2)CC1]

Benzyl (S)-4-(2-((3-(4-(benzyloxy)phenyl)-1-methoxy-1-oxopropan-2-yl)amino)-2-oxoethyl)piperidine-1-carboxylate (SR1-130). The N-benzylcarbamate derivative SR1-130 (0.024 g, 66%) was prepared using general method A from SR1-085 (0.030 g, 0.067 mmol), benzyl chloroformate (13 μL, 0.087 mmol) and triethylamine (28 μL, 0.201 mmol). HPLC: >99% [$t_R$=4.4 min, 80% MeOH, 20% water (with 0.1% TFA), 20 min]. $^1$H NMR (400 MHz, CDCl$_3$-d) δ 7.46-7.29 (m, 10H), 6.99 (d, J=8.7 Hz, 2H), 6.89 (d, J=8.7 Hz, 2H), 5.83 (d, J=8.3 Hz, 1H), 5.11 (s, 2H), 5.02 (s, 2H), 4.86 (m, 1H), 4.15 (m, 2H), 3.73 (s, 3H), 3.09 (dd, J=13.7, 5.6 Hz, 1H), 3.01 (dd, J=14.2, 6.1 Hz, 1H), 2.75 (m, 2H), 2.08 (dd, J=6.9, 1.8 Hz, 2H), 1.94 (m, 1H), 1.62 (m, 2H), 1.11 (m, 2H). HRMS (ESI+): m/z $C_{32}H_{36}N_2O_6$ (M+H)$^+$ 545.2645; m/z $C_{32}H_{36}N_2O_6Na$ (M+Na)$^+$567.2462. HPLC-MS (ESI+): m/z 545.4 [60%, (M+H)$^+$], 567.3 [100%, (M+Na)$^+$].

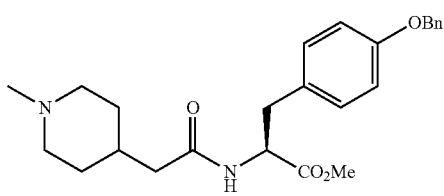 [SMILES: COC(=O)[C@H](Cc1ccc(OCc2ccccc2)cc1)NC(=O)CC1CCN(C)CC1]

Methyl (S)-3-(4-(benzyloxy)phenyl)-2-(2-(1-methylpiperidin-4-yl)acetamido)propanoate (SR1-110). N-methyl derivative SR1-110 (0.014 g, 49%, separated from N,N'-dimethylated by-product) was prepared using general method A from SR1-085 (0.030 g, 0.067 mmol), methyl iodide (2.5 eq. 10 μL) and K$_2$CO$_3$ (5 eq., 0.046 g) and DMF (1.2 mL) as solvent. HPLC: >97% [$t_R$=11.3 min, 50% MeOH, 50% water (with 0.1% TFA), 20 min]. $^1$H NMR (400 MHz, DMSO-d$_6$) δ 8.35 (d, J=7.9 Hz, 1H), 7.45-7.28 (m, 5H), 7.11 (d, J=8.6 Hz, 2H), 6.90 (d, J=8.7 Hz, 2H), 5.04 (s, 3H), 4.43 (ddd, J=9.9, 7.9, 5.2 Hz, 1H), 3.58 (s, 3H), 3.34-3.20 (m, 2H), 2.96 (dd, J=13.8, 5.2 Hz, 1H), 2.86-2.73 (m, 3H), 2.66 (s, 3H), 1.99 (dd, J=7.2, 2.3 Hz, 2H), 1.74 (m, 1H), 1.66 (m, 1H), 1.50 (m, 2H), 1.40-1.15 (m, 2H). HRMS (ESI+): m/z $C_{25}H_{32}N_2O_4$ (M+H)$^+$425.2423; m/z $C_{25}H_{32}N_2O_4Na$ (M+Na)$^+$447.2240. HPLC-MS (ESI+): m/z 425.3 [100%, (M+H)$^+$].

Synthesis of C-Terminal Variants of SR1-083.

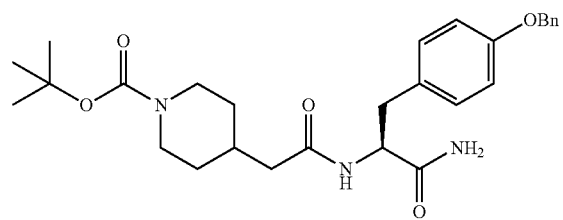 [SMILES: CC(C)(C)OC(=O)N1CCC(CC(=O)N[C@@H](Cc2ccc(OCc3ccccc3)cc2)C(=O)O)CC1]

tert-Butyl (S)-4-(2-((1-amino-3-(4-(benzyloxy)phenyl)-1-oxopropan-2-yl)amino)-2-oxoethyl)piperidine-1-carboxylate (SR1-136). Ammonia (1.25 mL, 30% aqueous solution) was premixed with MeOH (1.25 mL) and added to SR1-083 (0.050 g, 0.098 mmol) at rt. The mixture was stirred for 4 h and solvents removed under reduced pressure. Purification by flash column chromatography using MeOH/DCM (3:97-1:9) as eluent afforded SR1-136 as a white solid (0.033 g, 68%). HPLC: >99% [$t_R$=7.4 min, 70% MeOH, 30% water (with 0.1% TFA), 20 min]. $^1$H NMR (400 MHz, DMSO-d$_6$) δ 7.93 (d, J=8.7 Hz, 1H), 7.50-7.25 (m, 5H), 7.13 (d, J=8.6 Hz, 2H), 7.01 (m, 1H), 6.88 (d, J=8.7 Hz, 2H), 5.02 (s, 2H), 4.42 (ddd, J=10.6, 8.7, 4.3 Hz, 1H), 3.78 (m, 2H), 2.93 (dd, J=13.8, 4.3 Hz, 1H), 2.61 (dd, J=13.8, 10.5 Hz, 1H), 2.5 (m, 2H), 1.97-1.84 (m, 2H), 1.70-1.49 (m, 1H), 1.36 (s, 9H), 1.24-1.05 (m, 1H), 0.93-0.65 (m, 2H). HRMS (ESI+): m/z $C_{28}H_{37}N_3O_5Na$ (M+Na)$^+$518.2611; m/z $C_{28}H_{37}N_3O_5K$ (M+K)$^+$534.2358. HPLC-MS (ESI+): m/z 518.3 [70%, (M+Na)$^+$].

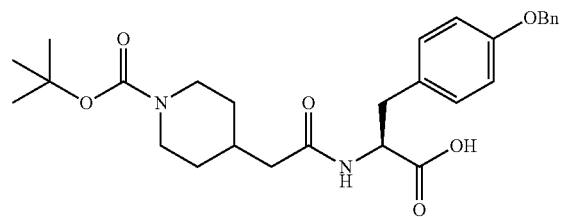

(S)-3-(4-(benzyloxy)phenyl)-2-(2-(1-(tert-butoxycarbonyl)piperidin-4-yl)acetamido)-propanoic acid (SR1-152). The methyl ester SR1-083 (0.025 g, 0.049 mmol) was dissolved in MeOH (1 mL) and sodium hydroxide (0.50 mL of a 2N aqueous solution, 20 eq.) added into the mixture. The reaction was stirred for 1.5 h and concentrated under reduced pressure. The resulting aqueous layer was diluted with water (3 mL) and washed with Et$_2$O (2×15 mL). The aqueous layer was acidified with 1N HCl (to pH-3.0) and then extracted with EtOAc (2×20 mL). The combined organic layers was dried (Na$_2$SO$_4$) and evaporated to afford SR1-152 as a white semi-solid (0.024 g, 98%). HPLC: >99% [t$_R$=9.5 min, 70% MeOH, 30% water (with 0.1% TFA), 20 min]. $^1$H NMR (400 MHz, DMSO-d$_6$) δ 12.62 (bs, 1H), 8.08 (d, J=8.3 Hz, 1H), 7.47-7.23 (m, 5H), 7.11 (d, J=8.6 Hz, 2H), 6.88 (d, J=8.6 Hz, 2H), 5.02 (s, 3H), 4.38 (ddd, J=10.3, 8.2, 4.6 Hz, 1H), 3.78 (m, 3H), 2.98 (dd, J=13.9, 4.6 Hz, 1H), 2.70 (dd, J=13.8, 10.4 Hz, 1H), 2.67-2.49 (m, 2H), 1.92 (d, J=7.2 Hz, 2H), 1.62 (d, J=3.6 Hz, 1H), 1.42 (m, 1H), 1.34 (s, 9H), 1.21 (m, 1H), 0.94-0.70 (m, 2H). HRMS (ESI+): m/z C$_{28}$H$_{36}$N$_2$O$_6$ (M)$^+$496.2581; m/z C$_{28}$H$_{36}$N$_2$O$_6$Na (M+Na)$^+$519.2444. HPLC-MS (ESI+): m/z 519.3 [50%, (M+Na)$^+$], m/z 441.2 [100%, (M-t-Bu+1)]$^+$.

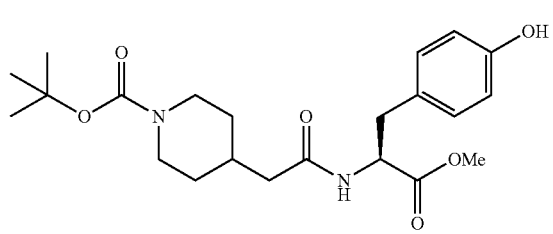 [SMILES: COC(=O)[C@H](Cc1ccc(O)cc1)NC(=O)CC1CCN(C(=O)OC(C)(C)C)CC1]

tert-Butyl (S)-4-(2-((3-(4-hydroxyphenyl)-1-methoxy-1-oxopropan-2-yl)amino)-2-oxoethyl)piperidine-1-carboxylate (SR1-153). The benzyl ether SR1-083 (0.030 g, 0.059 mmol) was dissolved in MeOH (1.5 mL) and purged with argon. Palladium on carbon (10%, 0.009 g, 0.15 g/mmol) was added into the mixture, purged with H$_2$ (balloon), and stirred at rt for 2 h. The suspension was filtered through Celite and the filter bed rinsed with MeOH/DCM. The filtrate was evaporated under reduced pressure to afford SR1-153 (0.025 g, quantitative yield) as a white foam. HPLC: >98% [t$_R$=5.0 min, 60% MeOH, 40% water (with 0.1% TFA), 20 min]. $^1$H NMR (400 MHz, Chloroform-d) δ 6.93 (d, J=8.5 Hz, 2H), 6.75 (d, J=8.5 Hz, 2H), 5.98 (d, J=8.1 Hz, 1H), 4.91-4.81 (m, 1H), 4.00 (m, 2H), 3.73 (d, J=1.9 Hz, 3H), 3.11 (dd, J=14.1, 5.4 Hz, 1H), 2.91 (dd, J=14.1, 7.3 Hz, 1H), 2.62 (m, 2H), 2.15-1.96 (m, 2H), 1.84 (m, 1H), 1.61-1.48 (m, 1H), 1.45-143 (m, 1H, overlap with t-Bu), 1.44 (d, J=2.0 Hz, 9H), 0.99 (s, 2H). HRMS (ESI+): m/z C$_{22}$H$_{32}$N$_2$O$_6$Na (M+Na)$^+$443.2143; m/z C$_{22}$H$_{32}$N$_2$O$_6$K (M+K)$^+$459.1878. HPLC-MS (ESI+): m/z 443.3 [90%, (M+Na)$^+$], m/z 365.2 [100%, (M-t-Bu+1)]$^+$.

General Method B: Synthesis of C-Terminal Amide Variants of SR1-083.

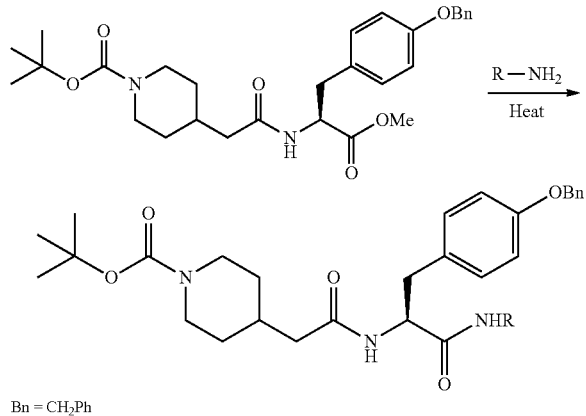

The methyl ester SR1-083 (0.050-0.100 g, 0.098-0.196 mmol) was placed in a sealed microwave vial (2.5 mL size) and dissolved in selected alkylamine (1.0 mL). The mixture was heated at 90-100° C. for 20-36 h and allowed to cool to room temperature. The mixture was evaporated under reduced pressure and the resulting residue was dissolved in EtOAc (25 mL). The organic layer was washed with 1N HCl (3×15 mL) and evaporated. Purification by flash column chromatography using either MeOH/DCM (0:100-10:100) or EtOAc/Hexane (4:6-100:0) as eluents afforded the following C-terminal amidated products.

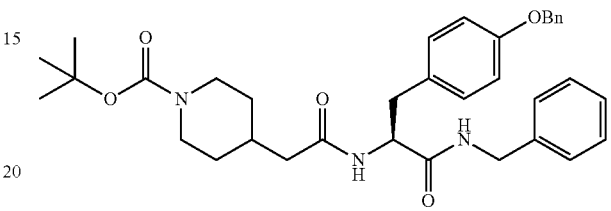

tert-Butyl (S)-4-(2-((1-(benzylamino)-3-(4-(benzyloxy) phenyl)-1-oxopropan-2-yl)amino)-2-oxoethyl)piperidine-1-carboxylate (SR1-160). SR1-160 was obtained as a white foam (0.046 g, 80%) from SR1-083 (0.050 g, 0.097 mmol) according to general method B using benzylamine. HPLC: >99% [t$_R$=5.4 min, 80% MeOH, 20% water (with 0.1% TFA), 20 min]. $^1$H NMR (400 MHz, DMSO-d$_6$) δ 8.48 (t, J=6.0 Hz, 1H), 8.08 (d, J=8.6 Hz, 1H), 7.47-7.41 (m, 2H), 7.38 (ddd, J=7.9, 6.9, 1.1 Hz, 2H), 7.35-7.30 (m, 1H), 7.29 (d, J=1.6 Hz, 1H), 7.27 (t, J=1.1 Hz, 1H), 7.26-7.19 (m, 1H), 7.19-7.12 (m, 4H), 6.89 (d, J=8.7 Hz, 1H), 5.04 (s, 2H), 4.54 (ddd, J=10.0, 8.6, 4.9 Hz, 1H), 4.27 (d, J=5.9 Hz, 2H), 3.79 (m, 2H), 2.95 (dd, J=13.5, 4.9 Hz, 1H), 2.68 (dd, J=13.6, 10.3 Hz, 1H), 2.60-2.52 (m, 2H), 2.02-1.87 (m, 2H), 1.62 (m, 1H), 1.39 (m, 1H), 1.37 (s, 9H), 1.29-1.12 (m, 1H), 0.97-0.71 (m, 2H). HRMS (ESI+): m/z C$_{35}$H$_{44}$N$_3$O$_5$ (M+H)$^+$586.3266; m/z C$_{35}$H$_{43}$N$_3$O$_5$Na (M+Na)$^+$608.3084. HPLC-MS (ESI+): m/z 608.2 [50%, (M+Na)$^+$].

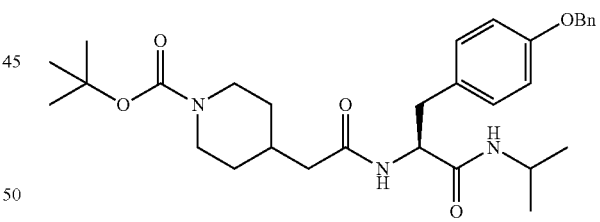

tert-butyl (S)-4-(2-((3-(4-(benzyloxy)phenyl)-1-(isopropylamino)-1-oxopropan-2-yl)amino)-2-oxoethyl)piperidine-1-carboxylate (SR1-167). SR1-167 was obtained as a foam (0.053 g, 50%) and recovered starting material (0.036 g, 36%) from SR1-083 (0.100 g, 0.195 mmol) according to general method B using isopropylamine. HPLC: >99% [t$_R$=4.5 min, 80% MeOH, 20% water (with 0.1% TFA), 20 min]. $^1$H NMR (400 MHz, chloroform-d) δ 7.45-7.27 (m, 5H), 7.12 (d, J=8.6 Hz, 2H), 6.89 (d, J=8.6 Hz, 2H), 6.52 (bs, 1H), 5.59 (bs, 1H), 5.03 (s, 2H), 4.51 (m, 1H), 4.05 (m, 2H), 3.93 (m, 1H), 3.02 (ddd, J=13.7, 6.3, 1.6 Hz, 1H), 2.87 (dd, J=13.6, 8.5 Hz, 1H), 2.66 (m, 2H), 2.16-2.05 (m, 2H), 1.96-1.85 (m, 1H), 1.66-1.52 (m, 2H), 1.44 (s, 9H), 1.16-1.08 (m, 1H), 1.05 (s, 1H), 1.03 (s, 1H), 0.95 (s, 1H), 0.93 (s, 1H). HRMS (ESI+): m/z C$_{31}$H$_{44}$N$_3$O$_5$ (M+H)$^+$538.3275;

m/z $C_{31}H_{43}N_3O_5Na$ (M+Na)$^+$560.3093. HPLC-MS (ESI+): m/z 457.4 [40% (M+H)$^+$], m/z 560.4 [80%, (M+Na)$^+$].

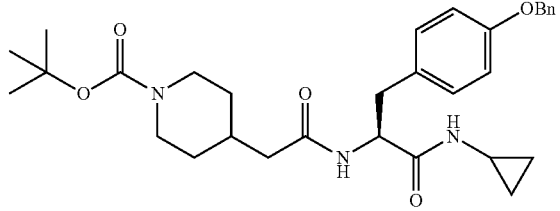 [SMILES: CC(C)(C)OC(=O)N1CCC(CC(=O)N[C@@H](Cc2ccc(OCc3ccccc3)cc2)C(=O)NC2CC2)CC1]

tert-Butyl (S)-4-(2-((3-(4-(benzyloxy)phenyl)-1-(cyclopropylamino)-1-oxopropan-2-yl)amino)-2-oxoethyl)piperidine-1-carboxylate (SR1-168). SR1-168 was obtained as a foam (0.052 g, 50%) and recovered starting material (0.014 g, 14%) from SR1-083 (0.100 g, 0.195 mmol) according to general method B using cyclopropylamine along with DMF (1 mL) as co-solvent. HPLC: >99% [$t_R$=11.2 min, 70% MeOH, 30% water (with 0.1% TFA), 20 min]. $^1$H NMR (400 MHz, DMSO-d$_6$) δ 8.03 (d, J=4.2 Hz, 1H), 7.99 (d, J=8.7 Hz, 1H), 7.47-7.27 (m, 5H), 7.11 (d, J=8.7 Hz, 2H), 6.88 (d, J=8.7 Hz, 2H), 5.03 (s, 2H), 4.39 (m, 1H), 3.79 (m, 2H), 2.83 (dd, J=13.6, 5.0 Hz, 1H), 2.71-2.51 (m, 4H), 1.92 (m, 2H), 1.61 (m, 1H), 1.45-1.37 (m, 1H), 1.36 (s, 9H), 1.29-1.12 (m, 1H), 0.84 (m, 2H), 0.66-0.53 (m, 2H), 0.44-0.25 (m, 2H). HRMS (ESI+): m/z $C_{31}H_{42}N_3O_5$ (M+H)$^+$ 536.3112; m/z $C_{31}H_{41}N_3O_5Na$ (M+Na)$^+$558.2939. HPLC-MS (ESI+): m/z 536.4 [100% (M+H)$^+$], m/z 558.4 [80%, (M+Na)$^+$].

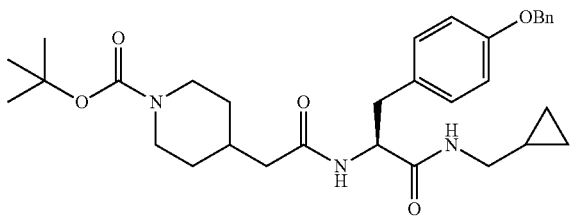 [SMILES: CC(C)(C)OC(=O)N1CCC(CC(=O)N[C@@H](Cc2ccc(OCc3ccccc3)cc2)C(=O)NCC2CC2)CC1]

tert-Butyl (S)-4-(2-((3-(4-(benzyloxy)phenyl)-1-((cyclopropylmethyl)amino)-1-oxopropan-2-yl)amino)-2-oxoethyl)piperidine-1-carboxylate (SR1-172). SR1-172 was obtained as a foam (0.068 g, 84%) from SR1-083 (0.075 g, 0.147 mmol) according to general method B using cyclopropanemethylamine. HPLC: >95% [$t_R$=7.9 min, 75% MeOH, 25% water (with 0.1% TFA), 20 min]. $^1$H NMR (400 MHz, DMSO-d$_6$) δ 8.11-7.93 (m, 2H), 7.47-7.27 (m, 5H), 7.14 (d, J=8.6 Hz, 2H), 6.89 (d, J=8.7 Hz, 2H), 5.04 (s, 2H), 4.48 (ddd, J=10.2, 8.9, 4.7 Hz, 1H), 3.90-3.69 (m, 2H), 2.99-2.85 (m, 3H), 2.69-2.52 (m, 3H), 2.03-1.84 (m, 2H), 1.62 (m, 1H), 1.37-1.50 (m, 1H), 1.37 (s, 9H), 1.19 (m, 2H), 0.98-0.80 (m, 1H), 0.78 (m, 0.5H), 0.67-0.57 (m, 0.5H), 0.44-0.33 (m, 2H), 0.20-0.08 (m, 2H). HRMS (ESI+): m/z $C_{32}H_{44}N_3O_5$ (M+H)$^+$550.3283; m/z $C_{32}H_{43}N_3O_5Na$ (M+Na)$^+$572.3108. HPLC-MS (ESI+): m/z 550.4 [40% (M+H)$^+$], m/z 495.2 [60%, (M-t-Bu+1)$^+$].

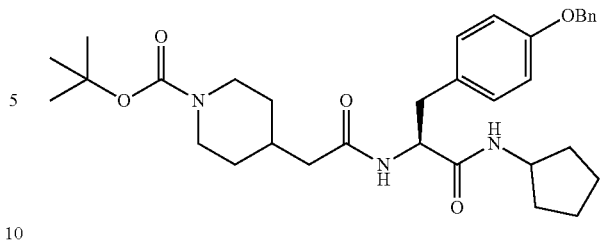

tert-Butyl (S)-4-(2-((3-(4-(benzyloxy)phenyl)-1-(cyclopentylamino)-1-oxopropan-2-yl)amino)-2-oxoethyl)piperidine-1-carboxylate (SR1-174). SR1-174 was obtained as a foam (0.067 g, 81%) from SR1-083 (0.075 g, 0.147 mmol) according to general method B using cyclopentylamine. HPLC: >99% [$t_R$=5.8 min, 80% MeOH, 20% water (with 0.1% TFA), 20 min]. $^1$H NMR (400 MHz, DMSO-d$_6$) δ 7.96 (d, J=8.7 Hz, 1H), 7.87 (d, J=7.3 Hz, 1H), 7.46-7.41 (m, 2H), 7.41-7.35 (m, 2H), 7.34-7.29 (m, 1H), 7.13 (d, J=8.6 Hz, 2H), 6.88 (d, J=8.7 Hz, 2H), 5.03 (s, 2H), 4.46 (td, J=9.4, 5.0 Hz, 1H), 3.94 (m, 1H), 3.80 (m, 2H), 2.82 (dd, J=13.7, 5.1 Hz, 1H), 2.68-2.53 (m, 3H), 2.01-1.86 (m, 2H), 1.83-1.66 (m, 2H), 1.66-1.43 (m, 5H), 1.42-1.35 (m, 2H), 1.36 (s, 9H), 1.30-1.11 (m, 2H), 0.95-0.70 (m, 2H). HRMS (ESI+): m/z $C_{33}H_{46}N_3O_5$ (M+H)$^+$564.3432; m/z $C_{33}H_{45}N_3O_5Na$ (M+Na)$^+$586.3248. HPLC-MS (ESI+): m/z 564.4 [90% (M+H)$^+$], m/z 586.4 [100%, (M+Na)$^+$].

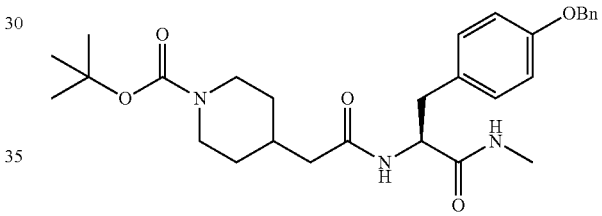

tert-Butyl (S)-4-(2-((3-(4-(benzyloxy)phenyl)-1-(methylamino)-1-oxopropan-2-yl)amino)-2-oxoethyl)piperidine-1-carboxylate (SR1-177). SR1-177 was obtained as a white foam (0.032 g, 80%) from SR1-083 (0.040 g, 0.073 mmol) according to the general method B using 40% aqueous solution of methylamine. HPLC: >99% [$t_R$=9.1 min, 70% MeOH, 30% water (with 0.1% TFA), 20 min]. $^1$H NMR (400 MHz, DMSO-d$_6$) δ 7.99 (d, J=8.7 Hz, 1H), 7.88 (d, J=4.7 Hz, 1H), 7.45-7.39 (m, 2H), 7.36 (m, 2H), 7.33-7.28 (m, 1H), 7.11 (d, J=8.6 Hz, 2H), 6.87 (d, J=8.7 Hz, 2H), 5.02 (s, 2H), 4.46-4.35 (m, 1H), 3.77 (m, 2H), 2.89 (dd, J=13.7, 4.5 Hz, 1H), 2.68-2.58 (m, 1H), 2.55 (d, J=4.5 Hz, 3H), 2.55-2.45 (m, 2H), 1.98-1.86 (m, 2H), 1.67-1.50 (m, 1H), 1.40-1.34 (m, 1H), 1.35 (s, 9H), 1.19-1.02 (m, 1H), 0.79 (m, 2H). HRMS (ESI+): m/z $C_{29}H_{40}N_3O_5$ (M+H)$^+$510.2945; m/z $C_{29}H_{39}N_3O_5Na$ (M+Na)$^+$532.2771. HPLC-MS (ESI+): m/z 510.4 [100% (M+H)$^+$], m/z 532.4 [50%, (M+Na)$^+$].

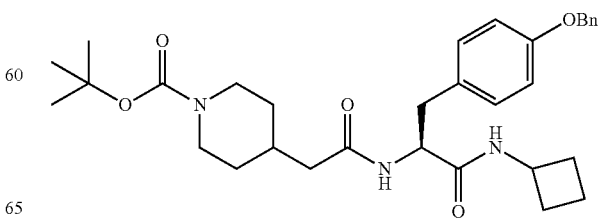

tert-Butyl (S)-4-(2-((3-(4-(benzyloxy)phenyl)-1-(cyclobutylamino)-1-oxopropan-2-yl)amino)-2-oxoethyl)piperidine-1-carboxylate (SR1-178). SR1-178 was obtained as foam (0.068 g, 79%) from SR1-083 (0.040 g, 0.073 mmol) according to general method B using cyclobutylamine. HPLC: >99% [$t_R$=2.6 min, 75% MeOH, 25% water (with 0.1% TFA), 20 min]. $^1$H NMR (400 MHz, DMSO-d$_6$) δ 8.17 (d, J=7.8 Hz, 1H), 7.96 (d, J=8.7 Hz, 1H), 7.45-7.39 (m, 2H), 7.39-7.33 (m, 2H), 7.33-7.28 (m, 1H), 7.10 (d, J=8.7 Hz, 2H), 6.87 (d, J=8.7 Hz, 2H), 5.02 (s, 2H), 4.40 (ddd, J=10.1, 8.6, 4.9 Hz, 1H), 4.21-4.05 (m, 1H), 3.87-3.66 (m, 2H), 2.82 (dd, J=13.7, 4.9 Hz, 1H), 2.65-2.50 (m, 3H), 2.18-2.02 (m, 2H), 1.99-1.68 (m, 4H), 1.58 (m, 3H), 1.44-1.35 (m, 1H), 1.35 (s, 9H), 1.28-1.03 (m, 1H), 0.94-0.68 (m, 2H). HRMS (ESI+): m/z C$_{32}$H$_{44}$N$_3$O$_5$ (M+H)$^+$550.3280; m/z C$_{32}$H$_{43}$N$_3$O$_5$Na (M+Na)$^+$572.3104. HPLC-MS (ESI+): m/z 550.4 [100% (M+H)$^+$], m/z 572.4 [80%, (M+Na)$^+$].

tert-Butyl (S)-4-(2-((3-(4-(benzyloxy)phenyl)-1-(cyclohexylamino)-1-oxopropan-2-yl)amino)-2-oxoethyl)piperidine-1-carboxylate (SR1-181). SR1-181 was obtained as a white foam (0.051 g, 93%) from SR1-083 (0.050 g, 0.098 mmol) according to general method B using cyclohexylamine. HPLC: >99% [$t_R$=5.6 min, 80% MeOH, 20% water (with 0.1% TFA), 20 min]. $^1$H NMR (400 MHz, DMSO-d$_6$) δ 7.96 (d, J=8.8 Hz, 1H), 7.79 (d, J=7.9 Hz, 1H), 7.43 (dt, J=6.1, 1.6 Hz, 2H), 7.41-7.35 (m, 2H), 7.35-7.29 (m, 1H), 7.13 (d, J=8.7 Hz, 2H), 6.88 (d, J=8.7 Hz, 2H), 5.03 (s, 2H), 4.47 (td, J=9.3, 4.9 Hz, 1H), 3.91-3.68 (m, 2H), 3.54-3.42 (m, 1H), 2.83 (dd, J=13.7, 4.9 Hz, 1H), 2.69-2.52 (m, 3H), 2.00-1.84 (m, 2H), 1.77-1.48 (m, 6H), 1.37-1.44 (m, 1H), 1.37 (d, 9H), 1.30-0.98 (m, 6H), 0.97-0.71 (m, 2H). HRMS (ESI+): m/z C$_{34}$H$_{48}$N$_3$O$_5$ (M+H)$^+$578.3575; m/z C$_{34}$H$_{47}$N$_3$O$_5$Na (M+Na)$^+$600.3393. HPLC-MS (ESI+): m/z 578.5 [70% (M+H)$^+$], m/z 600.4 [40%, (M+Na)$^+$].

C Terminal Analogs of SR1-119

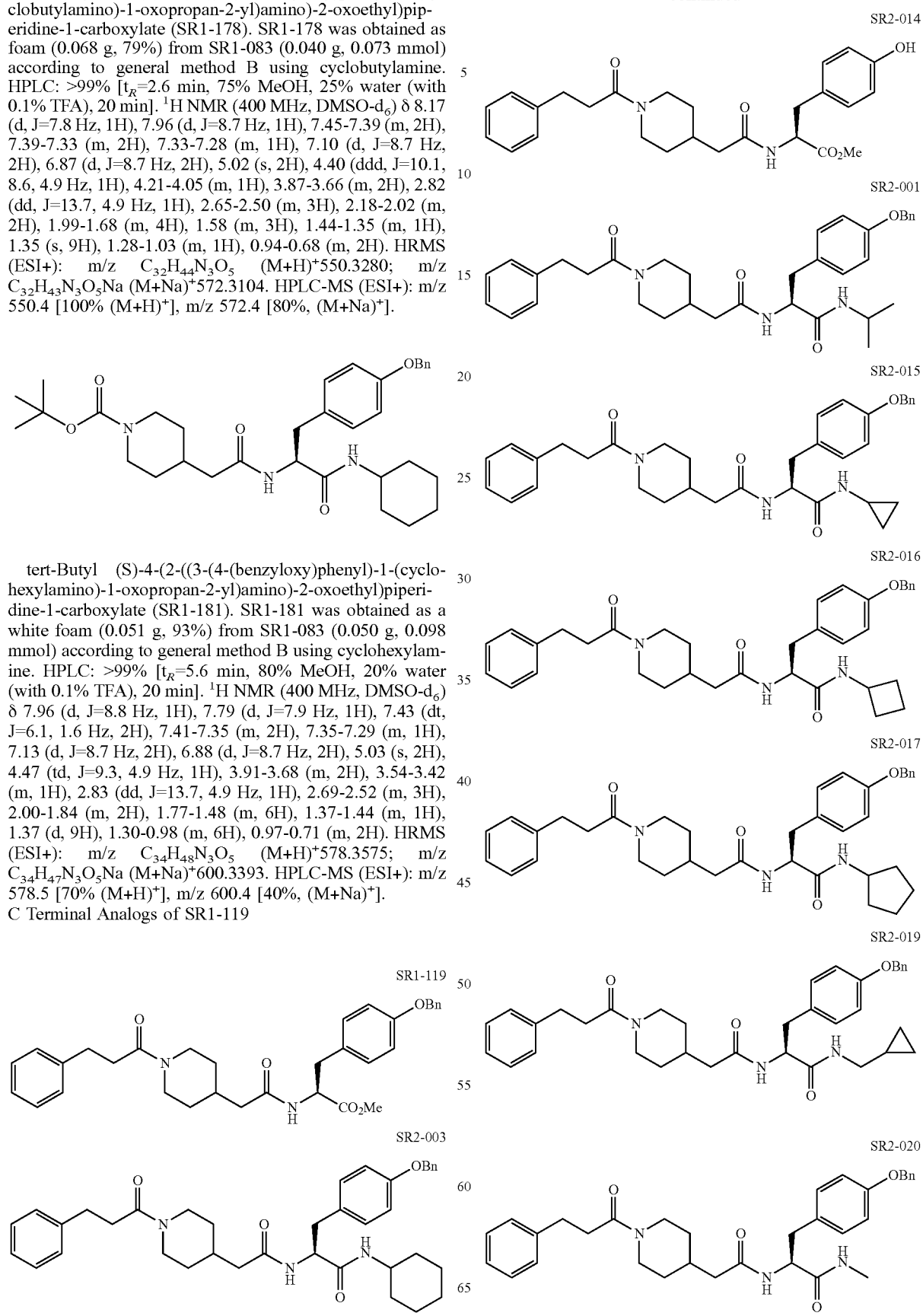

-continued

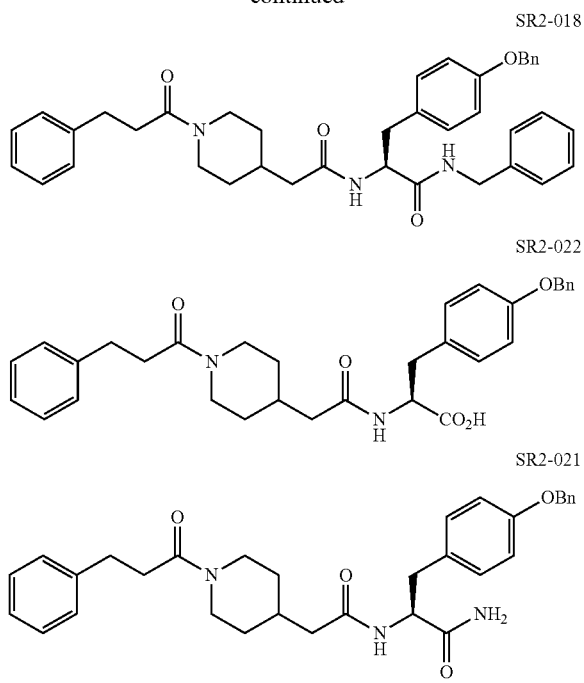

SR2-018

SR2-022

SR2-021

Synthesis of C-Terminal Variants of SR1-119.

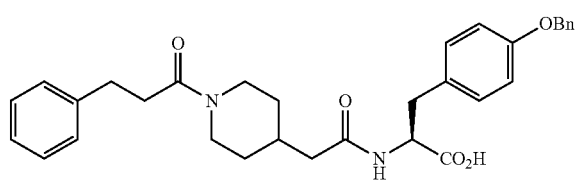 [SMILES: O=C(CC1CCN(C(=O)CCc2ccccc2)CC1)N[C@@H](Cc1ccc(OCc2ccccc2)cc1)C(=O)O]

(S)-3-(4-(Benzyloxy)phenyl)-2-(2-(1-(3-phenylpropanoyl)piperidin-4-yl)acetamido)propan-oic acid (SR2-022). The methyl ester SR1-119 (0.050 g, 0.092 mmol) was dissolved in MeOH (1 mL) and sodium hydroxide (1.0 mL of a 2N aqueous solution) added to the mixture. The reaction was stirred for 1.5 h at rt and concentrated under reduced pressure. The resulting aqueous layer was diluted with water (3 mL) and washed with Et$_2$O (2×15 mL). The aqueous layer was acidified with 1N HCl (to pH~3.0) and then extracted with EtOAc (2×20 mL). The combined organic layers were dried (Na$_2$SO$_4$) and the solvent evaporated to afford SR2-022 as a white semi-solid (0.046 g, 94%). HPLC: >98% [$t_R$=6.3 min, 70% MeOH, 30% water (with 0.1% TFA), 20 min]. $^1$H NMR (400 MHz, DMSO-d$_6$) δ 12.58 (bs, 1H), 8.08 (d, J=8.2 Hz, 1H), 7.48-7.29 (m, 5H), 7.28-7.14 (m, 5H), 7.11 (d, J=8.6 Hz, 2H), 6.88 (d, J=8.6 Hz, 2H), 5.02 (s, 2H), 4.38 (td, J=9.3, 8.7, 4.1 Hz, 1H), 4.26 (m, 1H), 3.76-3.59 (m, 1H), 2.98 (dd, J=13.9, 4.6 Hz, 1H), 2.87-2.62 (m, 5H), 2.62-2.51 (m, 1H), 2.45-2.30 (m, 1H), 1.92 (d, 7.2 Hz, 2H), 1.69 (m, 1H), 1.44 (m, 1H), 1.31-1.19 (m, 2H), 0.92-0.67 (m, 2H). HRMS (ESI+): m/z C$_{32}$H$_{37}$N$_2$O$_5$ (M+H)$^+$ 529.2690; m/z C$_{32}$H$_{36}$N$_2$O$_5$Na (M+Na)$^+$551.2504. HPLC-MS (ESI+): m/z 529.3 [40% (M+H)$^+$], m/z 551.3 [40%, (M+Na)$^+$], HPLC-MS (ESI–): m/z 527.3 [100% (M–H)$^-$].

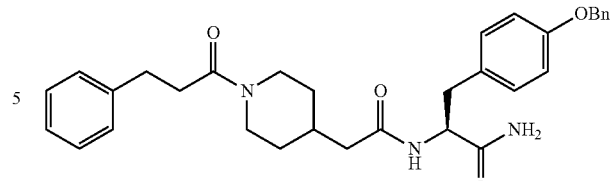

(S)-3-(4-(Benzyloxy)phenyl)-2-(2-(1-(3-phenylpropanoyl)piperidin-4-yl)acetamido)propan-amide (SR2-021). Ammonia (30% aqueous solution, 1.25 mL) was premixed with MeOH (1.25 mL) and added to SR1-119 (0.050 g, 0.092 mmol) at rt. The mixture was stirred for 4 h and solvents removed under reduced pressure. Purification of the residue by flash column chromatography using MeOH/DCM (3:97-10:90) gave SR2-021 as a white solid (0.033 g, 69%). HPLC: >99% [$t_R$=6.2 min, 70% MeOH, 30% water (with 0.1% TFA), 20 min]. $^1$H NMR (400 MHz, DMSO-d$_6$) δ 7.93 (d, J=8.6 Hz, 1H), 7.50-7.28 (m, 6H), 7.22 (m, 5H), 7.12 (d, J=8.5 Hz, 2H), 7.01 (s, 1H), 6.87 (d, J=8.7 Hz, 2H), 5.04-4.97 (m, 2H), 4.40 (td, J=8.6, 7.8, 3.7 Hz, 1H), 4.24 (m, 1H), 3.67 (m, 1H), 2.92 (dd, J=13.8, 4.5 Hz, 1H), 2.76 (m, 3H), 2.61 (m, 1H), 2.54 (m, 2H), 2.44-2.29 (m, 1H), 1.90 (dd, J=7.3, 4.2 Hz, 2H), 1.65 (m, 1H), 1.37 (m, 1H), 1.16 (m, 1H), 0.87-0.61 (m, 2H). HRMS (ESI+): m/z C$_{32}$H$_{38}$N$_3$O$_4$ (M+H)$^+$528.2862; m/z C$_{32}$H$_{37}$N$_3$O$_4$Na (M+Na)$^+$550.2681. HPLC-MS (ESI+): m/z 528.3 [100% (M+H)$^+$], m/z 550.3 [90%, (M+Na)$^+$].

Methyl (2-(1-(3-phenylpropanoyl)piperidin-4-yl)acetyl)-L-tyrosinate (SR2-014). The benzyl ether SR2-014 (0.020 g, 0.037 mmol) was dissolved in MeOH (1.5 mL) and purged with argon. Palladium on carbon (10%, 0.005 g, 0.15 g/mmol) was added to the mixture and purged with H$_2$ (balloon). After stirring for 2 h at room temperature, the suspension was filtered through Celite and the filter bed rinsed with MeOH/DCM. The filtrate was evaporated under reduced pressure to afford SR2-014 (0.015 g, 90%) as a white foam. HPLC: >98% [$t_R$=2.6 min, 70% MeOH, 30% water (with 0.1% TFA), 20 min]. $^1$H NMR (400 MHz, CDCl$_3$-d) δ 7.27 (m, 3H), 7.24-7.16 (m, 3H), 6.94 (d, J=8.5 Hz, 2H), 6.77 (dd, J=8.3 Hz, 2H), 5.84 (d, J=8.1 Hz, 1H), 4.91-4.81 (m, 1H), 4.44 (m, 1H), 3.75 (m, 4H), 3.14 (dd, J=13.8, 5.2 Hz, 1H), 3.02-2.73 (m, 4H), 2.70-2.20 (m, 3H), 2.14-2.02 (m, 1H), 1.94 (m, 2H), 1.65-1.34 (m, 1H), 1.25 (d, 1H), 0.97-0.73 (m, 2H). HRMS (ESI+): m/z C$_{26}$H$_{33}$N$_2$O$_5$ (M+H)$^+$453.2386; m/z C$_{26}$H$_{32}$N$_2$O$_5$Na (M+Na)$^+$475,2204. HPLC-MS (ESI+): m/z 453.2 [80% (M+H)$^+$], m/z 475.2 [100%, (M+Na)$^+$], HPLC-MS (ESI–): m/z 451.2 [100% (M–H)$^-$].

General Method C: Synthesis of C-Terminal Amide Variants of SR1-119.

The methyl ester SR1-119 (0.050-0.100 g, 0.092-0.184 mmol) was placed in a sealed microwave vial (2.5 mL) and dissolved in selected alkylamine (1.0 mL). The mixture was heated at 90-100° C. for 20-36 h and then cooled to room temperature. The mixture was evaporated under reduced pressure and the resulting residue was dissolved in EtOAc (25 mL). The organic layer was washed with 1N HCl (3×15 mL) and evaporated. Purification by flash column chromatography using either MeOH/DCM (0:100-10:90) or EtOAc/ hexane (4:6-100:0) as eluents afforded corresponding C-terminal amidated products.

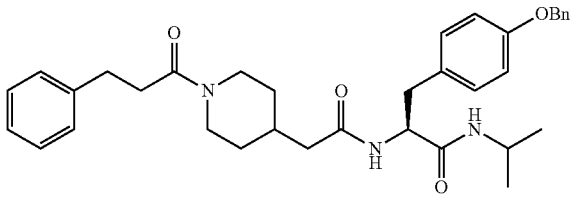 [SMILES: CC(C)NC(=O)[C@H](Cc1ccc(OCc2ccccc2)cc1)NC(=O)CC1CCN(C(=O)CCc2ccccc2)CC1]

(S)-3-(4-(Benzyloxy)phenyl)-N-isopropyl-2-(2-(1-(3-phenylpropanoyl)piperidin-4-yl)acet-amido)propanamide (SR2-001). The amide SR2-001 was obtained as a foam (0.039 g, 74%) using general method C from SR1-119 (0.050 g, 0.092 mmol), isopropylamine and DMF as co-solvent. HPLC: >98% [$t_R$=5.1 min, 50% MeOH, 50% water (with 0.1% TFA), 20 min]. HRMS (ESI+): m/z $C_{35}H_{44}N_3O_4$ (M+H)$^+$570.3337; m/z $C_{35}H_{43}N_3O_4Na$ (M+Na)$^+$592.3151. HPLC-MS (ESI+): m/z 570.4 [100% (M+H)$^+$], m/z 592.3 [100%, (M+Na)$^+$].

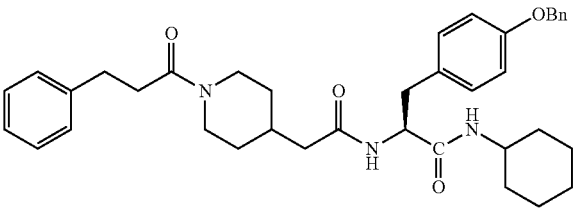 [SMILES: O=C(CC1CCN(C(=O)CCc2ccccc2)CC1)N[C@@H](Cc1ccc(OCc2ccccc2)cc1)C(=O)NC1CCCCC1]

(S)-3-(4-(Benzyloxy)phenyl)-N-cyclohexyl-2-(2-(1-(3-phenylpropanoyl)piperidin-4-yl)acetamido)propanamide (SR2-003). The amide SR2-003 was obtained as a white foam (0.048 g, 83%) using general method C from SR1-119 (0.050 g, 0.092 mmol), cyclohexylamine. HPLC: >98% [$t_R$=5.8 min, 80% MeOH, 20% water (with 0.1% TFA), 20 min]. HRMS (ESI+): m/z $C_{38}H_{48}N_3O_4$ (M+H)$^+$610.3629; m/z $C_{38}H_{47}N_3O_4Na$ (M+Na)$^+$632.3451. HPLC-MS (ESI+): m/z 632.4 [100%, (M+Na)$^+$].

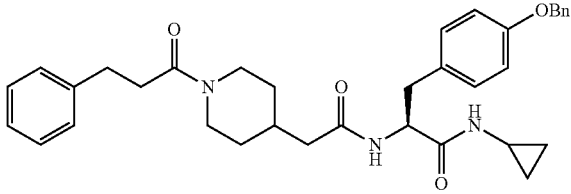 [SMILES: O=C(CC1CCN(C(=O)CCc2ccccc2)CC1)N[C@@H](Cc1ccc(OCc2ccccc2)cc1)C(=O)NC1CC1]

(S)-3-(4-(Benzyl oxy)phenyl)-N-cyclopropyl-2-(2-(1-(3-phenylpropanoyl)piperid in-4-yl)acetamido)propanamide (SR2-015). The amide SR2-015 was obtained as a white foam (0.034 g, 65% (isolated)) using general method C from SR1-119 (0.050 g, 0.092 mmol), cyclopropylamine and DMF as co-solvent. HPLC: >99% [$t_R$=3.0 min, 20% MeOH, 80% water (with 0.1% TFA), 20 min]. $^1$H NMR (400 MHz, DMSO-$d_6$) δ 8.17-7.87 (m, 7H), 7.47-7.28 (m, 2H), 7.27-7.12 (m, 3H), 7.09 (d, J=8.1 Hz, 2H), 6.86 (d, J=8.7 Hz, 2H), 5.02 (s, J=1.8 Hz, 1H), 4.99 (s, 1H), 4.36 (td, J=10.4, 8.6, 3.5 Hz, 1H), 4.24 (m, 1H), 3.68 (m, 4H), 2.91-2.69 (m, 4H), 2.67-2.50 (m, 1H), 2.46-2.29 (m, 1H), 2.01-1.83 (m, 2H), 1.69 (m, 1H), 1.40 (m, 1H), 1.19 (m, 1H), 0.89-0.66 (m, 1H), 0.65-0.55 (m, 2H), 0.47 (m, 1H), 0.38 (m, 1H), 0.35-0.25 (m, 1H). HRMS (ESI+): m/z $C_{35}H_{42}N_3O_4$ (M+H)$^+$ 568.3171; m/z $C_{35}H_{41}N_3O_4Na$ (M+Na)$^+$590.2988. HPLC-MS (ESI+): m/z 568.2 [80% (M+H)$^+$], m/z 590.4 [70%, (M+Na)$^+$].

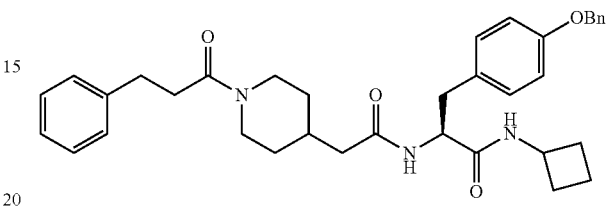

(S)-3-(4-(Benzyloxy)phenyl)-N-cyclobutyl-2-(2-(1-(3-phenylpropanoyl)piperidin-4-yl)acetamido)propanamide (SR2-016). The amide SR2-016 was obtained as a white solid (0.044 g, 82%) using general method C from SR1-119 (0.050 g, 0.092 mmol) and cyclobutylamine. HPLC: >99% [$t_R$=11.5 min, 20% MeOH, 70% water (with 0.1% TFA), 20 min]. $^1$H NMR (400 MHz, DMSO-$d_6$) δ 8.18 (d, J=7.9 Hz, 1H), 7.98 (d, J=8.6 Hz, 1H), 7.48-7.29 (m, 6H), 7.29-7.14 (m, 4H), 7.12 (d, J=8.0 Hz, 2H), 6.88 (d, J=8.7 Hz, 2H), 5.04 (s, 1H), 5.01 (s, 1H), 4.47-4.35 (m, 1H), 4.25 (m, 1H), 4.15 (m, 1H), 3.69 (m, 1H), 2.88-2.73 (m, 4H), 2.69-2.52 (m, 3H), 2.46-2.29 (m, 1H), 2.11 (dtd, J=14.0, 7.3, 3.2 Hz, 2H), 2.00-1.73 (m, 4H), 1.72-1.51 (m, 3H), 1.40 (m, 1H), 1.30-1.12 (m, 1H), 0.94-0.64 (m, 2H). HRMS (ESI+): m/z $C_{36}H_{44}N_3O_4$ (M+H)$^+$582.3327; m/z $C_{36}H_{43}N_3O_4Na$ (M+Na)$^+$604.3144. HPLC-MS (ESI+): m/z 582.4 [70% (M+H)$^+$], m/z 604.3 [80%, (M+Na)$^+$].

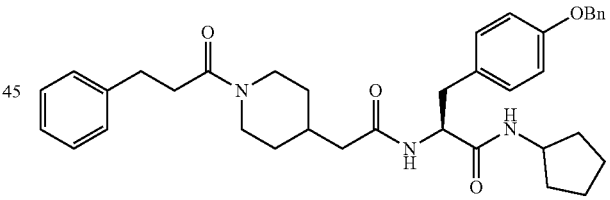

(S)-3-(4-(benzyloxy)phenyl)-N-cyclopentyl-2-(2-(1-(3-phenylpropanoyl)piperidin-4-yl)acetamido)propanamide (SR2-017). The amide SR2-017 was obtained as a white solid (0.043 g, 80%) using general method C from SR1-119 (0.050 g, 0.092 mmol) and cyclopentylamine. HPLC: >98% [$t_R$=4.9 min, 80% MeOH, 20% water (with 0.1% TFA), 20 min]. $^1$H NMR (400 MHz, DMSO-$d_6$) δ 7.97 (d, J=8.6 Hz, 1H), 7.88 (m, 1H), 7.47-7.29 (m, 5H), 7.29-7.14 (m, 5H), 7.12 (d, J=7.3 Hz, 2H), 6.88 (d, J=8.7 Hz, 2H), 5.04 (m, 1H), 5.01 (m, 1H), 4.45 (m, 1H), 4.26 (m, 1H), 3.93 (m, 1H), 3.77-3.62 (m, 1H), 2.79 (m, 4H), 2.71-2.52 (m, 3H), 2.47-2.31 (m, 1H), 2.01-1.86 (m, 2H), 1.83-1.65 (m, 2H), 1.65-1.32 (m, 7H), 1.25 (m, 2H), 0.78 (m, 2H). HRMS (ESI+): m/z $C_{37}H_{46}N_3O_4$ (M+H)$^+$596.3484; m/z $C_{37}H_{45}N_3O_4Na$ (M+Na)$^+$618.3302. HPLC-MS (ESI+): m/z 596.4 [80% (M+H)$^+$], m/z 618.2 [80%, (M+Na)$^+$].

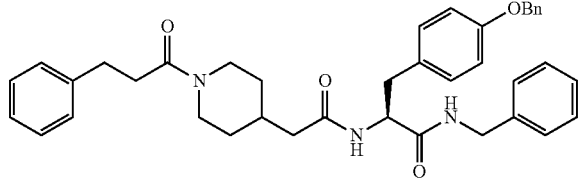 [SMILES: O=C(CC1CCN(C(=O)CCc2ccccc2)CC1)N[C@@H](Cc1ccc(OCc2ccccc2)cc1)C(=O)NCc1ccccc1]

(S)—N-benzyl-3-(4-(benzyloxy)phenyl)-2-(2-(1-(3-phenylpropanoyl)piperidin-4-yl)acetamido)propanamide (SR2-018). The amide SR2-018 was obtained as a white foam (0.046 g, 81%) using general method C from SR1-119 (0.050 g, 0.092 mmol) and benzylamine. HPLC: >98% [$t_R$=4.3 min, 70% MeOH, 30% water (with 0.1% TFA), 20 min]. $^1$H NMR (400 MHz, DMSO-d$_6$) δ 8.47 (t, J=6.0 Hz, 1H), 8.06 (d, J=8.5 Hz, 1H), 7.46-7.08 (m, 17H), 6.87 (d, J=8.7 Hz, 2H), 5.03 (s, 1H), 5.00 (m, 1H), 4.51 (m, 1H), 4.33-4.17 (m, 3H), 3.67 (m, 1H), 2.93 (m, 1H), 2.85-2.71 (m, 3H), 2.66 (dd, J=13.6, 10.1 Hz, 1H), 2.61-2.50 (m, J=7.8 Hz, 2H), 2.45-2.27 (m, 1H), 2.02-1.83 (m, 2H), 1.74-1.59 (m, 1H), 1.39 (m, 1H), 1.26-1.12 (m, 1H), 0.90-0.62 (m, 2H). HRMS (ESI+): m/z C$_{39}$H$_{44}$N$_3$O$_4$ (M+H)$^+$618.3328; m/z C$_{39}$H$_{43}$N$_3$O$_4$Na (M+Na)$^+$640.3146. HPLC-MS (ESI+): m/z 618.2 [40% (M+H)$^+$], m/z 640.2 [100%, (M+Na)$^+$].

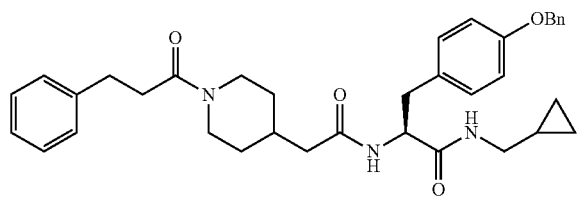 [SMILES: O=C(CC1CCN(C(=O)CCc2ccccc2)CC1)N[C@@H](Cc1ccc(OCc2ccccc2)cc1)C(=O)NCC1CC1]

(S)-3-(4-(benzyloxy)phenyl)-N-(cyclopropylmethyl)-2-(2-(1-(3-phenylpropanoyl)piperidin-4-yl)acetamido)propanamide (SR2-019). The amide SR2-019 was obtained as a white foam (0.040 g, 75%) using general method C from SR1-119 (0.050 g, 0.092 mmol) and cyclopropanemethylamine. HPLC: >99% [$t_R$=9.2 min, 70% MeOH, 30% water (with 0.1% TFA), 20 min]. $^1$H NMR (400 MHz, DMSO-d$_6$) δ 8.16-7.96 (m, 2H), 7.47-7.30 (m, 4H), 7.30-7.16 (m, 6H), 7.14 (d, J=7.6 Hz, 2H), 6.88 (d, J=8.7 Hz, 2H), 5.04 (s, 1H), 5.01 (s, 1H), 4.53-4.41 (m, 1H), 4.25 (m, 1H), 3.76-3.63 (m, 1H), 3.31 (m, 2H), 3.01-2.83 (m, 3H), 2.77 (m, 2H), 2.63 (dd, J=13.8, 10.3 Hz, 1H), 2.58-2.52 (m, 1H), 2.47-2.29 (m, 1H), 2.02-1.83 (m, 2H), 1.67 (m, 1H), 1.40 (m, 1H), 1.21 (m, 1H), 0.94-0.56 (m, 3H), 0.46-0.34 (m, 2H), 0.22-0.05 (m, 2H). HRMS (ESI+): m/z C$_{36}$H$_{44}$N$_3$O$_4$ (M+H)$^+$582.3317; m/z C$_{36}$H$_{43}$N$_3$O$_4$Na (M+Na)$^+$604.3139. HPLC-MS (ESI+): m/z 582.4 [90% (M+H)$^+$], m/z 604.48 [100%, (M+Na)$^+$].

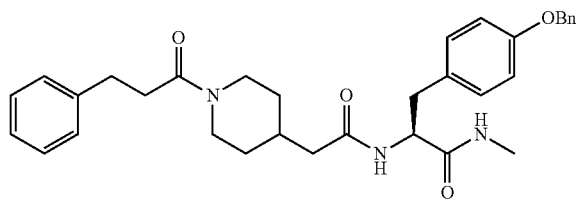 [SMILES: CNC(=O)[C@H](Cc1ccc(OCc2ccccc2)cc1)NC(=O)CC1CCN(C(=O)CCc2ccccc2)CC1]

(S)-3-(4-(benzyloxy)phenyl)-N-methyl-2-(2-(1-(3-phenylpropanoyl)piperidin-4-yl)acetamido)propanamide (SR2-020). The amide SR2-020 was obtained as a white solid (0.033 g, 66%) using general method C from SR1-119 (0.050 g, 0.092 mmol) and methylamine (40% in water). HPLC: >99% [$t_R$=6.7 min, 70% MeOH, 30% water (with 0.1% TFA), 20 min]. $^1$H NMR (400 MHz, DMSO-d$_6$) δ 8.02 (d, J=8.4 Hz, 1H), 7.90 (d, J=5.1 Hz, 1H), 7.48-7.27 (m, 6H), 7.27-7.15 (m, 4H), 7.12 (d, J=8.1 Hz, 2H), 6.88 (d, J=8.7 Hz, 2H), 5.04 (s, 1H), 5.01 (s, 1H), 4.47-4.37 (m, 1H), 4.31-4.21 (m, 1H), 3.68 (m, 1H), 2.90 (dd, J=14.2, 4.2 Hz, 1H), 2.86-2.71 (m, 3H), 2.62 (m, 1H), 2.57 (d, J=4.7 Hz, 2H, major rotamer of N-methyl group), 2.59-2.55 (m, 1H), 2.53 (d, J=4.7 Hz, 1H, minor rotamer of N-methyl group), 2.54-2.52 (m, 1H), 2.46-2.30 (m, 1H), 2.00-1.84 (m, 2H), 1.73-1.59 (m, 1H), 1.39 (m, 1H), 1.25-1.10 (m, 1H), 0.92-0.62 (m, 2H). HRMS (ESI+): m/z C$_{33}$H$_{40}$N$_3$O$_4$ (M+H)$^+$ 542.3015; m/z C$_{33}$H$_{39}$N$_3$O$_4$Na (M+Na)$^+$564.2834. HPLC-MS (ESI+): m/z 542.2 [90% (M+H)$^+$], m/z 564.3 [100%, (M+Na)$^+$].

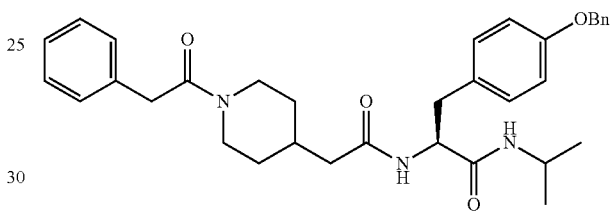

(S)-3-(4-(benzyloxy)phenyl)-N-isopropyl-2-(2-(1-(2-phenylacetyl)piperidin-4-yl)acetamido)propanamide (SR2-012). The amide SR2-012 was obtained as a white foam (0.051 g, 96%) using general method C from SR1-119 (0.050 g, 0.092 mmol), isopropylamine and DMF as co-solvent (1:1). HPLC: >98% [$t_R$=5.7 min, 50% MeOH, 50% water (with 0.1% TFA), 20 min]. HRMS (ESI+): m/z C$_{34}$H$_{42}$N$_3$O$_4$ (M+H)$^+$556.3172; m/z C$_{34}$H$_{41}$N$_3$O$_4$Na (M+Na)$^+$578.2989. HPLC-MS (ESI+): m/z 556.2 [80% (M+H)$^+$], m/z 578.2 [100%, (M+Na)$^+$].

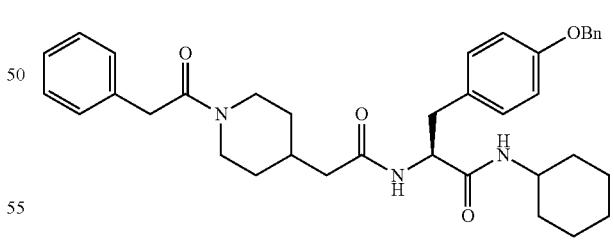

(S)-3-(4-(benzyloxy)phenyl)-N-cyclohexyl-2-(2-(1-(2-phenylacetyl)piperidin-4-yl)acetamido)propanamide (SR1-013). The amide SR2-013 was obtained as a white foam (0.032 g, 57%) using general method C from SR1-119 (0.050 g, 0.092 mmol) and cyclohexylamine. HPLC: >98% [$t_R$=5.1 min, 80% MeOH, 20% water (with 0.1% TFA), 20 min]. HRMS (ESI+): m/z C$_{37}$H$_{46}$N$_3$O$_4$ (M+H)$^+$596.3475; m/z C$_{37}$H$_{45}$N$_3$O$_4$Na (M+Na)$^+$618.3297. HPLC-MS (ESI+): m/z 596.2 [50% (M+H)$^+$], m/z 618.4 [100%, (M+Na)$^+$].

General Method D: Synthesis of N-Terminal Modified Analogs of SR1-119

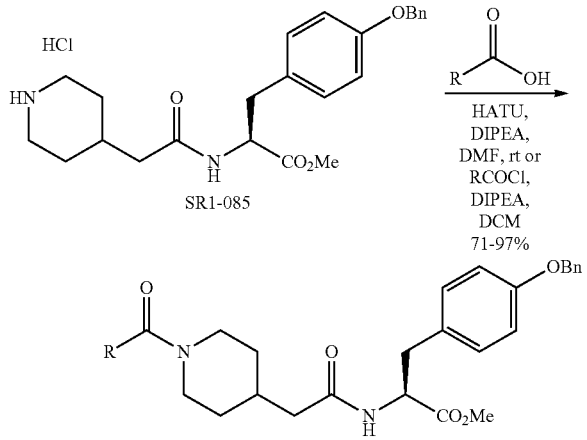

The amine salt SR1-085 (0.050 g, 0.112 mmol, 1 eq.) was dissolved in DMF (1.5-2.0 mL) under argon and DIEA (2.0 eq.), HATU (1.2 eq.), and corresponding propionic acid (1.2 eq.) were added. The mixture was stirred at room temperature for 18-24 h and concentrated under reduced pressure. The resulting thick oil was dissolved in EtOAc and washed with 1N HCl (2×20 mL) and sat. aq. NaHCO₃ (2×20 mL). The organic layer was dried (Na₂SO₄) and evaporated. Purification by flash column chromatography using MeOH/DCM (0:100-10:90) as eluent afforded the corresponding N-terminal amidated products.

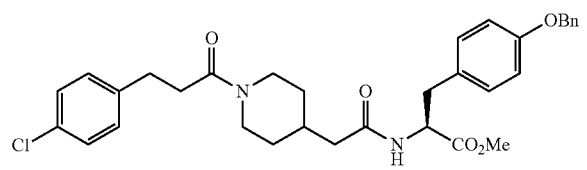 [SMILES: COC(=O)[C@H](Cc1ccc(OCc2ccccc2)cc1)NC(=O)CC1CCN(C(=O)CCc2ccc(Cl)cc2)CC1]

Methyl (S)-3-(4-(benzyloxy)phenyl)-2-(2-(1-(3-(4-chlorophenyl)propanoyl)piperidin-4-yl)acetamido)propanoate (SR2-004). Amide SR2-004 was obtained as a white foam (0.037 g, 71%) from 3-(4-chlorophenyl)propionic acid (0.020 g, 0.109 mmol, 1.2 eq.) using general method D. HPLC: >97% [$t_R$=4.9 min, 80% MeOH, 20% water (with 0.1% TFA), 20 min]. ¹H NMR (400 MHz, CDCl₃-d) δ 7.47-7.30 (m, 5H), 7.24 (d, J=8.4 Hz, 2H), 7.14 (d, J=8.6 Hz, 2H), 6.99 (d, J=8.7 Hz, 2H), 6.89 (d, J=8.7 Hz, 2H), 5.83 (d, J=7.9 Hz, 1H), 5.03 (s, 2H), 4.86 (dt, J=7.9, 5.9 Hz, 1H), 4.73-4.44 (m, 1H), 3.84-3.60 (m, 1H), 3.73 (s, 3H), 3.09 (dd, J=14.0, 5.7 Hz, 1H), 3.01 (dd, J=14.1, 6.1 Hz, 1H), 2.97-2.87 (m, 2H), 2.57 (t, J=7.7 Hz, 2H), 2.57-2.31 (m, 1H), 2.28-1.87 (m, 4H), 1.64 (m, 2H), 1.15-0.72 (m, 2H). HRMS (ESI+): m/z C₃₃H₃₈ClN₂O₅ (M+H)⁺577.2480; m/z C₃₃H₃₇ClN₂O₅Na (M+Na)⁺599.2297. HPLC-MS (ESI+): m/z 577.2 [40% (M+H)⁺], m/z 599.2 [100%, (M+Na)⁺].

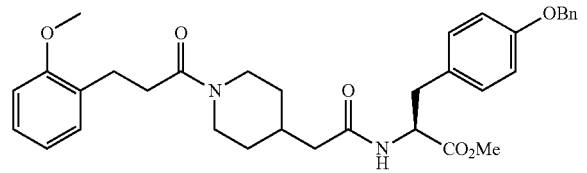 [SMILES: COC(=O)[C@H](Cc1ccc(OCc2ccccc2)cc1)NC(=O)CC1CCN(C(=O)CCc2ccccc2OC)CC1]

Methyl (S)-3-(4-(benzyloxy)phenyl)-2-(2-(1-(3-(2-methoxyphenyl)propanoyl)piperidin-4-yl)acetamido)propanoate (SR2-006). Amide SR2-006 was obtained as a white foam (0.059 g, 92%) from 3-(2-methoxyphenyl)propionic acid (0.024 g, 0.134 mmol, 1.2 eq.) using general method D. HPLC: >96% [$t_R$=4.9 min, 70% MeOH, 30% water (with 0.1% TFA), 20 min]. ¹H NMR (400 MHz, CDCl₃-d) δ 7.49-7.29 (m, 5H), 7.22-7.14 (m, 2H), 6.99 (d, J=8.7 Hz, 2H), 6.95-6.80 (m, 4H), 5.81 (d, J=7.9 Hz, 1H), 5.03 (d, J=2.3 Hz, 2H), 4.91-4.81 (m, 1H), 4.75-4.27 (m, 1H), 3.81 (s, 3H), 3.78-3.50 (m, 1H), 3.73 (s, 3H), 3.09 (dd, J=14.2, 5.7 Hz, 1H), 3.02 (dd, J=14.1, 6.0 Hz, 1H), 2.94 (t, J=8.0 Hz, 2H), 2.93-2.75 (m, 1H), 2.61 (dd, J=9.3, 6.7 Hz, 2H), 2.61-2.39 (m, 1H), 2.05 (d, J=4.8 Hz, 2H), 2.00-1.76 (m, 1H), 1.74-1.59 (m, 2H), 1.17-0.74 (m, 2H). HRMS (ESI+): m/z C₃₄H₄₁N₂O₆ (M+H)⁺573.2949; m/z C₃₄H₄₀N₂O₆Na (M+Na)⁺595.2767. HPLC-MS (ESI+): m/z 573.2 [80% (M+H)⁺], m/z 595.2 [100%, (M+Na)⁺].

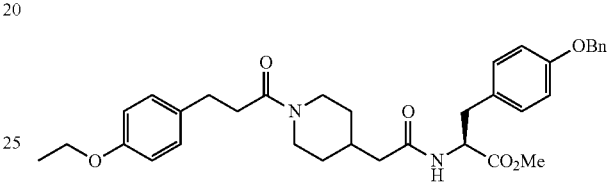

Methyl (S)-3-(4-(benzyloxy)phenyl)-2-(2-(1-(3-(4-ethoxyphenyl)propanoyl)piperidin-4-yl)acetamido)propanoate (SR2-007). Amide SR2-007 was obtained as a white foam (0.046 g, 72%) from 3-(4-ethoxyphenyl)propionic acid (0.026 g, 0.134 mmol, 1.2 eq.) using general method D. HPLC: >96% [$t_R$=10.4 min, 75% MeOH, 25% water (with 0.1% TFA), 20 min]. ¹H NMR (400 MHz, DMSO-d₆) δ 8.24 (d, J=8.0 Hz, 1H), 7.47-7.25 (m, 5H), 7.14-7.05 (m, 4H), 6.89 (d, J=8.4 Hz, 2H), 6.78 (dd, J=8.6, 4.1 Hz, 2H), 5.03 (s, 1H), 5.00 (m, 1H), 4.48-4.37 (m, 1H), 4.30-4.19 (m, 1H), 3.98-3.89 (m, 2H), 3.81-3.63 (m, 1H), 3.58 (s, 3H), 2.95 (dd, J=13.7, 5.1 Hz, 1H), 2.88-2.73 (m, 1H), 2.72-2.63 (m, 2H), 2.50 (m, 2H), 2.42-2.29 (m, 1H), 1.93 (d, J=7.2 Hz, 2H), 1.82-1.61 (m, 1H), 1.44 (m, 1H), 1.31-1.24 (m, 4H), 0.95-0.71 (m, 2H). HRMS (ESI+): m/z C₃₅H₄₂N₂O₆ (M+H)⁺ 587.3107; m/z C₃₅H₄₂N₂O₆Na (M+Na)⁺609.2932. HPLC-MS (ESI+): m/z 587.2 [90% (M+H)⁺], m/z 609.2 [100%, (M+Na)⁺].

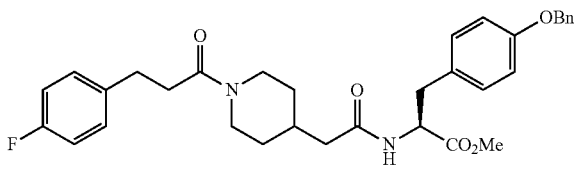 [SMILES: COC(=O)[C@H](Cc1ccc(OCc2ccccc2)cc1)NC(=O)CC1CCN(C(=O)CCc2ccc(F)cc2)CC1]

Methyl (S)-3-(4-(benzyloxy)phenyl)-2-(2-(1-(3-(4-fluorophenyl)propanoyl)piperidin-4-yl)acetamido)propanoate (SR2-008). Amide SR2-008 was obtained as a white foam (0.059 g, 93%) from 3-(4-fluorophenyl)propionic acid (0.023 g, 0.134 mmol, 1.2 eq.) using general method D. HPLC: >95% [$t_R$=6.1 min, 75% MeOH, 25% water (with 0.1% TFA), 20 min]. ¹H NMR (400 MHz, CDCl₃-d) δ 7.48-7.30 (m, 5H), 7.19-7.12 (m, 2H), 6.99 (d, J=8.6 Hz, 2H), 6.96 (t, J=8.7 Hz, 2H), 6.89 (d, J=8.7 Hz, 2H), 5.83 (d, J=7.9 Hz, 1H), 5.03 (s, 2H), 4.85 (dt, J=8.0, 5.9 Hz, 1H), 4.78-4.28 (m, 1H), 3.73 (s, 1H), 3.80-3.42 (m, 1H), 3.09 (dd, J=14.1, 5.7 Hz, 1H), 3.01 (dd, J=14.1, 6.2 Hz, 1H), 2.92 (t, J=7.7 Hz, 2H), 2.92-2.74 (m, 1H), 2.65-2.26 (m, 3H), 2.15-1.86 (m, 3H), 1.75-1.54 (m, 2H), 1.15-0.68 (m, 2H). $^{19}$F NMR (376 MHz, CDCl$_3$-d) δ -117.27 (ddd, J=14.1, 8.9, 5.4 Hz). HRMS (ESI+): m/z C$_{33}$H$_{38}$FN$_2$O$_5$ (M+H)$^+$ 561.2753; m/z C$_{33}$H$_{37}$FN$_2$O$_5$Na (M+Na)$^+$583.2573. HPLC-MS (ESI+): m/z 561.2 [60% (M+H)$^+$], m/z 583.2 [100%, (M+Na)$^+$].

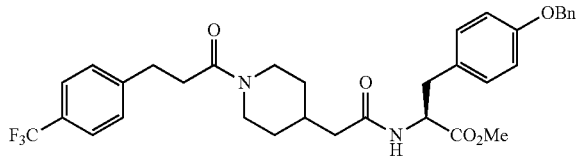 [SMILES: COC(=O)[C@H](Cc1ccc(OCc2ccccc2)cc1)NC(=O)CC1CCN(C(=O)CCc2ccc(C(F)(F)F)cc2)CC1]

Methyl (S)-3-(4-(benzyloxy)phenyl)-2-(2-(1-(3-(4-(trifluoromethyl)phenyl)propanoyl)-piperidin-4-yl)acetamido)propanoate (SR2-009). Amide SR2-009 was obtained as a white foam (0.066 g, 97%) from 3-(4-trifluorophenyl)propionic acid (0.029 g, 0.134 mmol, 1.2 eq.) using general method D. HPLC: >99% [t$_R$=4.9 min, 80% MeOH, 20% water (with 0.1% TFA), 20 min]. $^1$H NMR (400 MHz, DMSO-d$_6$) δ 8.25 (d, J=8.0 Hz, 1H), 7.61 (dd, J=7.9, 5.4 Hz, 2H), 7.49-7.26 (m, 7H), 7.12 (d, J=8.6 Hz, 2H), 6.90 (d, J=8.2 Hz, 2H), 5.05 (s, 1H), 5.03 (s, 1H), 4.45 (dt, J=8.9, 4.6 Hz, 1H), 4.27 (m, 1H), 3.81-3.67 (m, 1H), 3.60 (s, 3H), 2.97 (dd, J=13.8, 5.1 Hz, 1H), 2.87 (td, J=7.5, 4.0 Hz, 2H), 2.76 (dd, J=13.9, 10.2 Hz, 1H), 2.69-2.53 (m, 2H), 2.50 (m, 1H), 2.47-2.27 (m, 1H), 1.95 (d, J=7.1 Hz, 2H), 1.72 (m, 1H), 1.47 (m, 1H), 1.39-1.19 (m, 1H), 0.98-0.70 (m, 2H). $^{19}$F NMR (376 MHz, DMSO-d$_6$) δ -60.70 (d, J=3.2 Hz). HRMS (ESI+): m/z C$_{34}$H$_{38}$F$_3$N$_2$O$_5$ (M+H)$^+$611.2718; m/z C$_{34}$H$_{37}$F$_3$N$_2$O$_5$Na (M+Na)$^+$633.2537. HPLC-MS (ESI+): m/z 611.2 [70% (M+H)$^+$], m/z 633.2 [100%, (M+Na)$^+$].

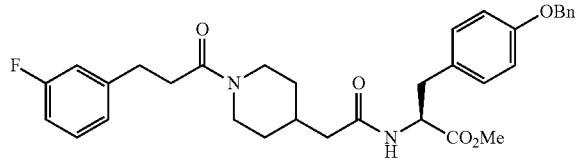

Methyl (S)-3-(4-(benzyloxy)phenyl)-2-(2-(1-(3-(3-fluorophenyl)propanoyl)piperidin-4-yl)acetamido)propanoate (SR2-010). Amide SR2-010 was obtained as a white foam (0.060 g, 95%) from 3-(3-fluorophenyl)propionic acid (0.023 g, 0.134 mmol, 1.2 eq.) using general method D. HPLC: >99% [t$_R$=9.5 min, 70% MeOH, 30% water (with 0.1% TFA), 20 min]. $^1$H NMR (400 MHz, Chloroform-d) δ 7.47-7.29 (m, 5H), 7.25-7.19 (m, 1H), 6.99 (m, 3H), 6.94-6.84 (m, 4H), 5.81 (d, J=7.9 Hz, 1H), 5.03 (s, 2H), 4.86 (dt, J=7.9, 5.9 Hz, 1H), 4.77-4.36 (m, 1H), 3.86-3.54 (m, 1H), 3.74 (s, 3H), 3.09 (dd, J=14.0, 5.7 Hz, 1H), 3.01 (dd, J=14.1, 6.1 Hz, 1H), 3.00-2.88 (m, 3H), 2.64-2.57 (m, 3H), 2.12-1.75 (m, 3H), 1.73-1.56 (m, 2H), 1.19-0.78 (m, 2H). $^{19}$F NMR (376 MHz, CDCl$_3$-d) δ -113.45-113.57 (m). HRMS (ESI+): m/z C$_{33}$H$_{38}$FN$_2$O$_5$ (M+H)$^+$561.2754; m/z C$_{33}$H$_{37}$FN$_2$O$_5$Na (M+Na)$^+$583.2581; HPLC-MS (ESI+): m/z 561.2 [50% (M+H)$^+$], m/z 583.2 [100%, (M+Na)$^+$].

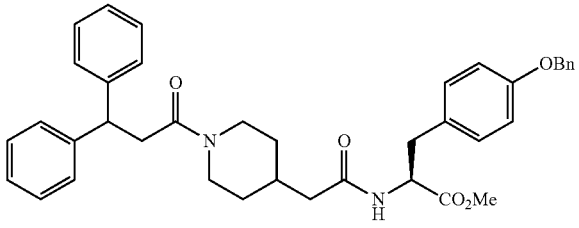

Methyl (S)-3-(4-(benzyloxy)phenyl)-2-(2-(1-(3,3-diphenylpropanoyl)piperidin-4-yl)acetamido)propanoate (SR2-029). Amide SR2-029 was obtained as a white foam (0.063 g, 91%) from 3-(3,3-diphenyl)propionic acid (0.030 g, 0.134 mmol, 1.2 eq.) using general method D. HPLC: >99% [t$_R$=5.6 min, 80% MeOH, 20% water (with 0.1% TFA), 20 min]. $^1$H NMR (400 MHz, DMSO-d$_6$) δ 8.25 (d, J=8.0 Hz, 1H), 7.45-7.39 (m, 2H), 7.39-7.19 (m, 11H), 7.18-7.08 (m, 4H), 6.90 (dd, J=8.7, 3.3 Hz, 2H), 5.04 (s, 2H), 4.53-4.37 (m, 2H), 4.18 (m, 1H), 3.91 (m, 1H), 3.59 (s, 3H), 3.16-3.03 (m, 1H), 3.05-2.90 (m, 2H), 2.89-2.65 (m, 2H), 2.34 (m, 1H), 1.91 (d, J=7.2 Hz, 2H), 1.78-1.58 (m, 1H), 1.49-1.36 (m, 1H), 1.35-1.12 (m, 1H), 0.94-0.55 (m, 2H). HRMS (ESI+): m/z C$_{39}$H$_{43}$N$_2$O$_5$ (M+H)$^+$619.3157; m/z C$_{39}$H$_{42}$N$_2$O$_5$Na (M+Na)$^+$641.2979; HPLC-MS (ESI+): m/z 619.2 [60% (M+H)$^+$], m/z 641.2 [100%, (M+Na)$^+$].

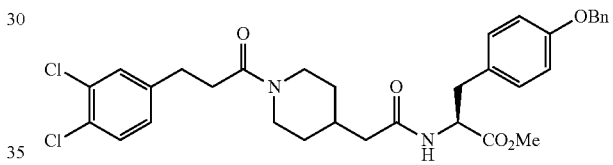

Methyl (S)-3-(4-(benzyloxy)phenyl)-2-(2-(1-(3-(3,4-dichlorophenyl)propanoyl)piperidin-4-yl)acetamido)propanoate (SR2-030). Amide SR2-030 was obtained as a white foam (0.060 g, 88%) from 3-(3,4-dichlorophenyl)propionic acid (0.029 g, 0.134 mmol, 1.2 eq.) using general method D. HPLC: >98% [t$_R$=6.4 min, 80% MeOH, 20% water (with 0.1% TFA), 20 min]. $^1$H NMR (400 MHz, DMSO-d$_6$) δ 8.24 (d, J=8.0 Hz, 1H), 7.54-7.45 (m, 2H), 7.44-7.25 (m, 5H), 7.22 (m, 1H), 7.11 (d, J=8.5 Hz, 2H), 6.89 (d, J=7.7 Hz, 2H), 5.03 (s, 1H), 5.01 (s, 1H), 4.43 (td, J=9.5, 9.1, 4.7 Hz, 1H), 4.30-4.19 (m, 1H), 3.80-3.63 (m, 1H), 3.58 (s, 3H), 2.96 (dd, J=13.8, 5.1 Hz, 1H), 2.90-2.70 (m, 4H), 2.66 (m, 1H), 2.61-2.52 (m, 1H), 2.45-2.29 (m, 1H), 1.94 (d, J=7.1 Hz, 2H), 1.80-1.61 (m, 1H), 1.53-1.38 (m, 1H), 1.36-1.19 (m, 1H), 1.02-0.62 (m, 2H). HRMS (ESI+): m/z C$_{33}$H$_{37}$C$_{12}$N$_2$O$_5$ (M+H)$^+$611.2048; m/z C$_{33}$H$_{36}$N$_2$O$_5$Na (M+Na)$^+$633.1876; HPLC-MS (ESI+): m/z 611.2 [50% (M+H)$^+$], m/z 633.2 [100%, (M+Na)$^+$].

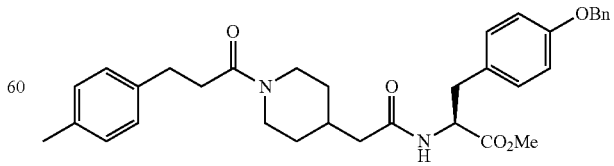

Methyl (S)-3-(4-(benzyloxy)phenyl)-2-(2-(1-(3-(p-tolyl)propanoyl)piperidin-4-yl)acetamido)propanoate (SR2-031). Amide SR2-031 was obtained as a white foam (0.054 g, 87%) from 3-(p-tolyl)propionic acid (0.022 g, 0.134 mmol, 1.2 eq.) using general method D. HPLC: >98% [$t_R$=4.8 min, 80% MeOH, 20% water (with 0.1% TFA), 20 min]. $^1$H NMR (400 MHz, DMSO-$d_6$) δ 8.24 (d, J=8.0 Hz, 1H), 7.46-7.24 (m, 5H), 7.11 (d, J=8.7 Hz, 2H), 7.08-6.99 (m, 4H), 6.89 (d, J=8.6 Hz, 2H), 5.03 (s, 1H), 5.00 (s, 1H), 4.43 (ddd, J=10.5, 8.2, 5.2 Hz, 1H), 4.32-4.18 (m, 1H), 3.77-3.63 (m, 1H), 3.58 (s, 3H), 2.95 (dd, J=13.8, 5.0 Hz, 1H), 2.87-2.64 (m, 5H), 2.51 (m, 1H), 2.45-2.30 (m, 1H), 2.22 (s, 3H), 1.93 (d, J=7.2 Hz, 2H), 1.83-1.56 (m, 1H), 1.54-1.36 (m, 1H), 1.33-1.17 (m, 1H), 0.93-0.66 (m, 2H). HRMS (ESI+): m/z $C_{34}H_{41}N_2O_5$ (M+H)$^+$557.3002; m/z $C_{34}H_{40}N_2O_5Na$ (M+Na)$^+$579.2825; HPLC-MS (ESI+): m/z 557.2 [60% (M+H)$^+$], m/z 579.2 [100%, (M+Na)$^+$].

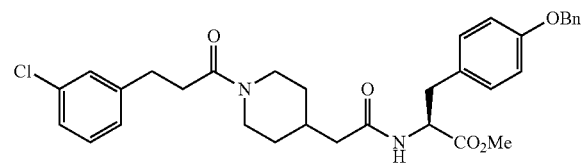 [SMILES: COC(=O)[C@H](Cc1ccc(OCc2ccccc2)cc1)NC(=O)CC1CCN(C(=O)CCc2cccc(Cl)c2)CC1]

Methyl (S)-3-(4-(benzyloxy)phenyl)-2-(2-(1-(3-(3-chlorophenyl)propanoyl)piperidin-4-yl)acetamido)propanoate (SR2-032). Amide SR2-032 was obtained as a white foam (0.052 g, 81%) from 3-(3-chlorophenyl)propionic acid (0.025 g, 0.134 mmol, 1.2 eq.) using general method D. HPLC: >98% [$t_R$=4.9 min, 80% MeOH, 20% water (with 0.1% TFA), 20 min]. $^1$H NMR (400 MHz, DMSO-$d_6$) δ 8.24 (d, J=8.0 Hz, 1H), 7.46-7.32 (m, 4H), 7.32-7.28 (m, 2H), 7.26 (dd, J=7.6, 3.8 Hz, 1H), 7.23-7.14 (m, 2H), 7.11 (d, J=8.6 Hz, 2H), 6.89 (d, J=8.5 Hz, 2H), 5.04 (s, 1H), 5.02 (m, 1H), 4.43 (ddd, J=12.9, 9.7, 5.0 Hz, 1H), 4.31-4.21 (m, 1H), 3.79-3.64 (m, 1H), 3.58 (s, 3H), 2.95 (dd, J=13.8, 5.1 Hz, 1H), 2.88-2.69 (m, 5H), 2.63-2.51 (m, 1H), 2.45-2.28 (m, 1H), 1.93 (d, J=7.3 Hz, 2H), 1.80-1.58 (m, 1H), 1.54-1.39 (m, 1H), 1.35-1.17 (m, 1H), 0.94-0.70 (m, 2H). HRMS (ESI+): m/z $C_{33}H_{38}ClN_2O_5$ (M+H)$^+$577.2454; m/z $C_{33}H_{37}ClN_2O_5Na$ (M+Na)$^+$599.2274 HPLC-MS (ESI+): m/z 577.2 [50% (M+H)$^+$], m/z 599.2 [100%, (M+Na)$^+$].

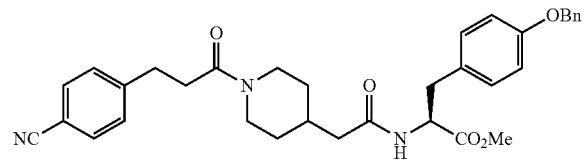 [SMILES: COC(=O)[C@H](Cc1ccc(OCc2ccccc2)cc1)NC(=O)CC1CCN(C(=O)CCc2ccc(C#N)cc2)CC1]

Methyl (S)-3-(4-(benzyloxy)phenyl)-2-(2-(1-(3-(4-cyanophenyl)propanoyl)piperidin-4-yl)acetamido)propanoate (SR2-033). Amide SR2-033 was obtained as a white foam (0.055 g, 87%) from 3-(4-cyanophenyl)propionic acid (0.024 g, 0.134 mmol, 1.2 eq.) using general method D. HPLC: >99% [$t_R$=4.1 min, 75% MeOH, 25% water (with 0.1% TFA), 20 min]. $^1$H NMR (400 MHz, DMSO-$d_6$) δ 8.26 (d, J=8.0 Hz, 1H), 7.71 (dd, J=8.3, 6.5 Hz, 2H), 7.47-7.27 (m, 7H), 7.12 (d, J=8.7 Hz, 2H), 6.90 (d, J=7.8 Hz, 2H), 5.04 (s, 1H), 5.01 (m, 1H), 4.50-4.38 (m, 1H), 4.31-4.20 (m, 1H), 3.81-3.64 (m, 1H), 3.59 (s, 3H), 2.97 (dd, J=13.8, 5.0 Hz, 1H), 2.90-2.70 (m, 4H), 2.69-2.54 (m, 2H), 2.47-2.30 (m, 1H), 1.95 (d, J=7.2 Hz, 2H), 1.82-1.63 (m, 1H), 1.52-1.42 (m, 1H), 1.40-1.20 (m, 1H), 0.96-0.70 (m, 2H). HRMS (ESI+): m/z $C_{34}H_{38}N_3O_5$ (M+H)$^+$568.2793; m/z $C_{34}H_{37}N_3O_5Na$ (M+Na)$^+$590.2618; HPLC-MS (ESI+): m/z 568.2 [50% (M+H)$^+$], m/z 599.2 [100%, (M+Na)$^+$].

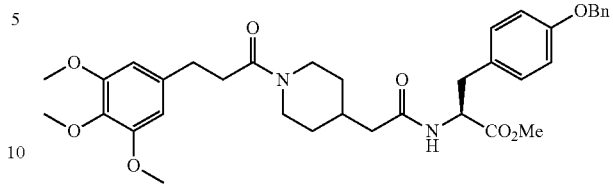

Methyl (S)-3-(4-(benzyloxy)phenyl)-2-(2-(1-(3-(3,4,5-trimethoxyphenyl)propanoyl)piperid-in-4-yl)acetamido) propanoate (SR2-034). Amide SR2-034 was obtained as a white foam (0.052 g, 85%) from 3-(3,4,5-trimethoxyphenyl)propionic acid (0.032 g, 0.134 mmol, 1.2 eq.) using general method D. HPLC: >99% [$t_R$=7.3 min, 70% MeOH, 30% water (with 0.1% TFA), 20 min]. $^1$H NMR (400 MHz, DMSO-$d_6$) δ 8.24 (d, J=8.0 Hz, 1H), 7.46-7.25 (m, 5H), 7.11 (d, J=8.7 Hz, 2H), 6.89 (d, J=8.6 Hz, 2H), 6.51 (s, 2H), 5.03 (s, 1H), 5.00 (m, 1H), 4.43 (ddd, J=13.0, 9.8, 5.1 Hz, 1H), 4.34-4.21 (m, 1H), 3.79-3.67 (m, 1H), 3.72 (s, 6H), 3.58 (s, 3H), 3.57 (s, 3H), 2.95 (dd, J=13.9, 5.1 Hz, 1H), 2.89-2.79 (m, 1H), 2.79-2.63 (m, 4H), 2.64-2.49 (m, 1H), 2.45-2.30 (m, 1H), 1.94 (d, J=7.1 Hz, 2H), 1.84-1.61 (m, 1H), 1.52-1.40 (m, 1H), 1.37-1.17 (m, 1H), 0.93-0.68 (m, 2H). HRMS (ESI+): m/z $C_{36}H_{45}N_2O_8$ (M+H)$^+$633.3162; m/z $C_{36}H_{44}N_2O_8Na$ (M+Na)$^+$655.2980; HPLC-MS (ESI+): m/z 633.2 [70% (M+H)$^+$], m/z 655.2 [100%, (M+Na)$^+$].

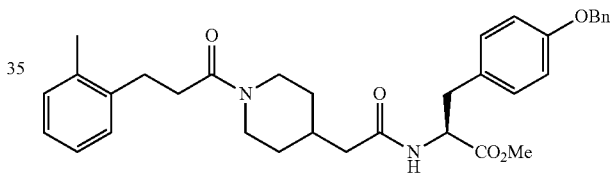

Methyl (S)-3-(4-(benzyloxy)phenyl)-2-(2-(1-(3-(o-tolyl) propanoyl)piperidin-4-yl)acetamido)propanoate (SR2-035). Amide SR2-035 was obtained as a white foam (0.047 g, 74%) from 3-(2-methylphenyl)propionic acid (0.022 g, 0.134 mmol, 1.2 eq.) using general method D. HPLC: >99% [$t_R$=7.9 min, 75% MeOH, 25% water (with 0.1% TFA), 20 min]. $^1$H NMR (400 MHz, DMSO-$d_6$) δ 8.26 (d, J=8.0 Hz, 1H), 7.47-7.28 (m, 5H), 7.23-7.04 (m, 6H), 6.90 (d, J=7.4 Hz, 2H), 5.05 (s, 11H), 5.02 (m, 1H), 4.44 (ddd, J=13.2, 9.9, 5.0 Hz, 1H), 4.33-4.25 (m, 1H), 3.81-3.66 (m, 1H), 3.60 (s, 3H), 2.97 (dd, J=13.8, 4.6 Hz, 1H), 2.88-2.75 (m, 3.5H), 2.75-2.64 (m, 1.5H), 2.54 (m, 1H), 2.47-2.35 (m, 1H), 2.26 (s, 3H), 1.95 (d, J=7.1 Hz, 2H), 1.82-1.61 (m, 1H), 1.54-1.39 (m, 1H), 1.36-1.20 (m, 1H), 0.95-0.65 (m, 2H). HRMS (ESI+): m/z $C_{34}H_{41}N_2O_5$ (M+H)$^+$557.3006; m/z $C_{34}H_{40}N_2O_5Na$ (M+Na)$^+$579.2822; HPLC-MS (ESI+): m/z 557.2 [80% (M+H)$^+$], m/z 579.2 [100%, (M+Na)$^+$].

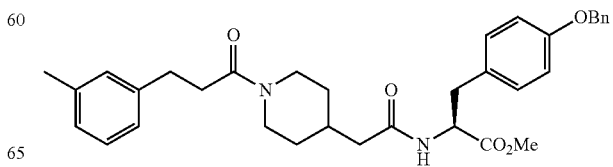

Methyl (S)-3-(4-(benzyloxy)phenyl)-2-(2-(1-(3-(m-tolyl)propanoyl)piperidin-4-yl)acetamido)propanoate (SR2-036). Amide SR2-036 was obtained as a white foam (0.046 g, 74%) from 3-(3-methylphenyl)propionic acid (0.022 g, 0.134 mmol, 1.2 eq.) using general method D. HPLC: >99% [$t_R$=7.5 min, 75% MeOH, 25% water (with 0.1% TFA), 20 min]. $^1$H NMR (400 MHz, DMSO-$d_6$) δ 8.26 (d, J=8.0 Hz, 1H), 7.37 (m, 5H), 7.15 (m, 1H), 7.12 (d, J=8.5 Hz, 2H), 7.06-6.95 (m, 3H), 6.90 (d, J=8.6 Hz, 2H), 5.05 (s, 1H), 5.02 (s, 1H), 4.44 (ddd, J=13.3, 4.7, 2.5 Hz, 1H), 4.33-4.24 (m, 1H), 3.79-3.67 (m, 1H), 3.60 (s, 3H), 2.97 (dd, J=13.9, 5.1 Hz, 1H), 2.89-2.65 (m, 5H), 2.63-2.52 (m, 1H), 2.41 (m, 1H), 2.25 (s, 3H), 1.95 (d, J=7.2 Hz, 2H), 1.79-1.63 (m, 1H), 1.54-1.37 (m, 1H), 1.34-1.20 (m, 1H), 0.94-0.71 (m, 2H). HRMS (ESI+): m/z $C_{34}H_{41}N_2O_5$ (M+H)$^+$557.3009; m/z $C_{34}H_{40}N_2O_5Na$ (M+Na)$^+$579.2826; HPLC-MS (ESI+): m/z 557.2 [60% (M+H)$^+$], m/z 579.2 [100%, (M+Na)$^+$].

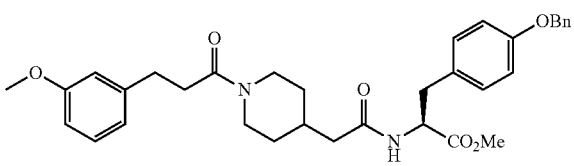 [SMILES: COC(=O)[C@H](Cc1ccc(OCc2ccccc2)cc1)NC(=O)CC1CCN(C(=O)CCc2cccc(OC)c2)CC1]

Methyl (S)-3-(4-(benzyloxy)phenyl)-2-(2-(1-(4-(4-methoxyphenyl)-4-oxobutanoyl)piperidin-4-yl)acetamido)propanoate (SR2-037). Amide SR2-037 was obtained as a white foam (0.061 g, 91%) from 3-(4-methoxybenzyl)propionic acid (0.028 g, 0.134 mmol, 1.2 eq.) using general method D. HPLC: >98% [$t_R$=5.0 min, 75% MeOH, 25% water (with 0.1% TFA), 20 min]. $^1$H NMR (400 MHz, DMSO-$d_6$) δ 8.28 (d, J=8.0 Hz, 1H), 7.94 (dd, J=8.8, 1.9 Hz, 2H), 7.41 (d, J=7.0 Hz, 2H), 7.38-7.24 (m, 3H), 7.12 (dd, J=8.6, 3.8 Hz, 2H), 7.07-7.00 (m, 2H), 6.90 (t, J=8.2 Hz, 2H), 5.04 (s, 2H), 4.50-4.39 (m, 1H), 4.25-4.16 (m, 1H), 3.88-3.74 (m, 1H), 3.83 (s, 3H), 3.59 (s, 3H), 3.11 (m, 2H), 2.97 (dd, J=13.8, 5.1 Hz, 1H), 2.92-2.83 (m, 1H), 2.76 (dd, J=13.8, 10.3 Hz, 1H), 2.70-2.55 (m, 2H), 2.46-2.25 (m, 1H), 1.97 (d, J=7.2 Hz, 2H), 1.80-1.65 (m, 1H), 1.49 (m, 1H), 1.40-1.17 (m, 1H), 1.11-0.70 (m, 2H). HRMS (ESI+): m/z $C_{35}H_{41}N_2O_7$ (M+H)$^+$601.2900; m/z $C_{35}H_{40}N_2O_7Na$ (M+Na)$^+$623.2723; HPLC-MS (ESI+): m/z 601.2 [30% (M+H)$^+$], m/z 623.2 [100%, (M+Na)$^+$].

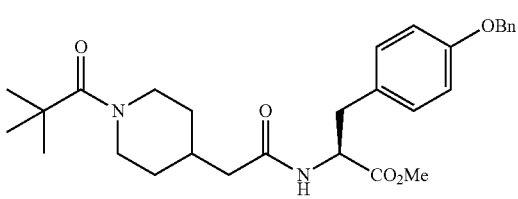 [SMILES: COC(=O)[C@H](Cc1ccc(OCc2ccccc2)cc1)NC(=O)CC1CCN(C(=O)C(C)(C)C)CC1]

Methyl (S)-3-(4-(benzyloxy)phenyl)-2-(2-(1-pivaloylpiperidin-4-yl)acetamido)propanoate (SR2-039). Amide SR2-039 was obtained as a white foam (0.043 g, 78%) from trimethylacetic acid (0.014 g, 0.134 mmol, 1.2 eq.) using general method D. HPLC: >99% [$t_R$=8.5 min, 70% MeOH, 30% water (with 0.1% TFA), 20 min]. $^1$H NMR (400 MHz, DMSO-$d_6$) δ 8.26 (d, J=8.0 Hz, 1H), 7.47-7.40 (m, 2H), 7.42-7.34 (m, 2H), 7.36-7.27 (m, 1H), 7.13 (d, J=8.6 Hz, 2H), 6.91 (d, J=8.6 Hz, 2H), 5.05 (s, 2H), 4.46 (ddd, J=10.2, 8.0, 5.1 Hz, 1H), 4.15 (m, 2H), 3.60 (s, 3H), 2.98 (dd, J=13.9, 5.0 Hz, 1H), 2.76 (dd, J=13.8, 10.3 Hz, 1H), 2.73-2.58 (m, 2H), 1.96 (d, J=7.2 Hz, 2H), 1.84-1.68 (m, 1H), 1.55-1.44 (m, 1H), 1.35-1.26 (m, 1H), 1.15 (s, 9H), 1.00-0.72 (m, 2H). HRMS (ESI+): m/z $C_{29}H_{39}N_2O_5$ (M+H)$^+$495.2853; m/z $C_{29}H_{38}N_2O_5Na$ (M+Na)$^+$517.2671; HPLC-MS (ESI+): m/z 495.2 [50% (M+H)$^+$], m/z 517.2 [100%, (M+Na)$^+$].

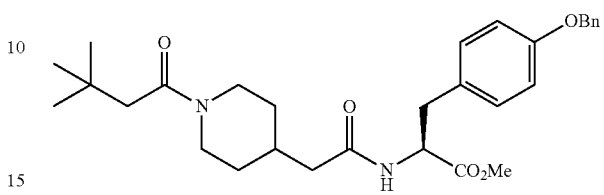

Methyl (S)-3-(4-(benzyloxy)phenyl)-2-(2-(1-(3,3-dimethylbutanoyl)piperidin-4-yl)acetamido)propanoate (SR2-040). Amide SR2-040 was obtained as a white foam (0.051 g, 90%) from tert-butylacetic acid (0.017 μL, 0.134 mmol, 1.2 eq.) using general method D. HPLC: >98% [$t_R$=10.1 min, 70% MeOH, 30% water (with 0.1% TFA), 20 min]. $^1$H NMR (400 MHz, DMSO-$d_6$) δ 8.24 (d, J=8.0 Hz, 1H), 7.43 (m, 2H), 7.37 (m, 2H), 7.34-7.26 (m, 1H), 7.12 (d, J=8.2 Hz, 2H), 6.90 (d, J=8.7 Hz, 2H), 5.04 (s, 2H), 4.50-4.38 (m, 1H), 4.32 (m, 1H), 3.91-3.71 (m, 1H), 3.59 (s, 3H), 2.96 (dd, J=13.8, 5.1 Hz, 1H), 2.91-2.79 (m, 1H), 2.75 (dd, J=13.8, 10.2 Hz, 1H), 2.45-2.28 (m, 1H), 2.24-2.08 (m, 2H), 1.96 (dd, J=7.6, 5.3 Hz, 2H), 1.81-1.64 (m, 1H), 1.55-1.41 (m, 1H), 1.37-1.20 (m, 1H), 0.95 (s, 4.5H), 0.93 (s, 4.5), 0.93-0.69 (m, 2H). HRMS (ESI+): m/z $C_{30}H_{41}N_2O_5$ (M+H)$^+$509.3016; m/z $C_{30}H_{40}N_2O_5Na$ (M+Na)$^+$531.2839; HPLC-MS (ESI+): m/z 509.4 [40% (M+H)$^+$], m/z 531.2 [100%, (M+Na)$^+$].

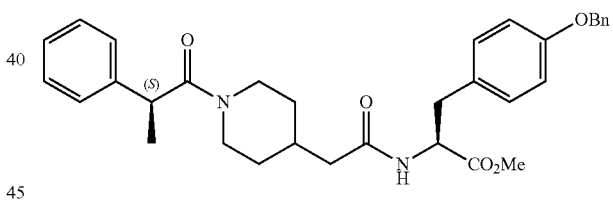

Methyl (S)-3-(4-(benzyloxy)phenyl)-2-(2-(1-((S)-2-phenylpropanoyl)piperidin-4-yl)acetamido)propanoate (SR2-041). Amide SR2-041 was obtained as a white foam (0.054 g, 89%) from (S)-(+)-2-phenylpropionic acid (0.018 μL, 0.134 mmol, 1.2 eq.) using general method D. HPLC: >99% (88:11 two isomers (S:R)) [$t_R$=8.2 and 8.8 min, 70% MeOH, 30% water (with 0.1% TFA), 20 min]. $^1$H NMR (400 MHz, DMSO-$d_6$) δ 8.24 (d, J=8.0 Hz, 0.4H), 8.16 (d, J=7.9 Hz, 0.6H), 7.51-7.16 (m, 10H), 7.10 (d, J=8.7 Hz, 1H), 7.06 (d, J=8.7 Hz, 1H), 6.88 (d, J=8.7 Hz, 1H), 6.85 (d, J=8.6 Hz, 1H), 5.04 (s, 2H), 4.47-4.20 (m, 2H), 4.11-3.92 (m, 1H), 3.79 (m, 1H), 3.58 (s, 1.0H), 3.56 (s, 2H), 2.92 (m, 0.7H), 2.88-2.76 (m, 0.3H), 2.76-2.63 (m, 1H), 2.63-2.51 (m, 1H), 2.48-2.26 (m, 1H), 1.96 (d, J=7.2 Hz, 2H), 1.74 (d, J=7.4 Hz, 1H), 1.71-1.57 (m, 1H), 1.49-1.35 (m, 1H), 1.24 (d, J=6.8 Hz, 1.5H), 1.22 (d, 6.7 Hz, 1.5H), 1.09-0.89 (m, 1H), 0.89-0.54 (m, 0.6H), 0.15--0.07 (m, 0.4H). HRMS (ESI+): m/z $C_{33}H_{39}N_2O_5$ (M+H)$^+$543.2860; m/z $C_{33}H_{38}N_2O_5Na$ (M+Na)$^+$565.2683; HPLC-MS (ESI+): m/z 543.2 [40% (M+H)$^+$], m/z 565.2 [100%, (M+Na)$^+$].

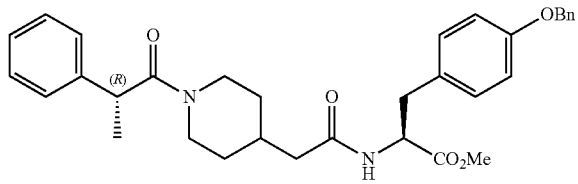

Methyl (S)-3-(4-(benzyloxy)phenyl)-2-(2-(1-((R)-2-phenylpropanoyl)piperidin-4-yl)-acetamido)propanoate (SR2-056). Amide SR2-056 was obtained as a white foam (0.052 g, 86%) from (R)-(+)-2-phenylpropionic acid (0.020 g, 0.134 mmol, 1.2 eq.) using general method D. HPLC: >99% (95:4.5 two isomers (R:S)) [$t_R$=8.6 and 9.0 min, 70% MeOH, 30% water (with 0.1% TFA), 20 min]. $^1$H NMR (400 MHz, DMSO-$d_6$) δ 8.25 (d, J=7.9 Hz, 0.4H), 8.16 (d, J=8.0 Hz, 0.6H), 7.50-7.25 (m, 6H), 7.25-7.15 (m, 4H), 7.14-7.03 (m, 2H), 6.94-6.82 (m, 2H), 5.04 (s, 2H), 4.48-4.21 (m, 2H), 4.08-3.94 (m, 1H), 3.87-3.71 (m, 1H), 3.57 (s, 1H), 3.55 (s, 2H), 3.01-2.63 (m, 2H), 2.62-2.48 (m, 1H), 2.46-2.30 (m, 1H), 1.95 (d, J=7.1 Hz, 1H), 1.74 (d, J=6.3 Hz, 1H), 1.72-1.57 (m, 2H), 1.50-1.33 (m, 0.5H), 1.23 (m, 3H), 1.19-1.11 (m, 0.5H), 1.10-0.76 (m, 1H), 0.73-0.50 (m, 0.5H), 0.15--0.07 (m, 0.5H). HRMS (ESI+): m/z $C_{33}H_{39}N_2O_5$ (M+H)$^+$543.2866; m/z $C_{33}H_{38}N_2O_5Na$ (M+Na)$^+$565.2684; HPLC-MS (ESI+): m/z 543.3 [30% (M+H)$^+$], m/z 565.3 [100%, (M+Na)$^+$].

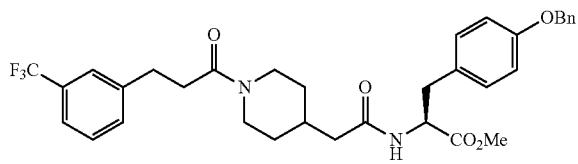 [SMILES: COC(=O)[C@H](Cc1ccc(OCc2ccccc2)cc1)NC(=O)CC1CCN(C(=O)CCc2cccc(C(F)(F)F)c2)CC1]

Methyl (S)-3-(4-(benzyloxy)phenyl)-2-(2-(1-(3-(3-(trifluoromethyl)phenyl)propanoyl)-piperid-in-4-yl)acetamido)propanoate (SR2-042). Amide SR2-042 was obtained as a white foam (0.061 g, 91%) from 3-(3-trifluromethylphenyl) propionic acid (0.029 g, 0.134 mmol, 1.2 eq.) using general method D. HPLC: >99% [$t_R$=11.3 min, 70% MeOH, 30% water (with 0.1% TFA), 20 min]. $^1$H NMR (400 MHz, DMSO-$d_6$) δ 8.25 (d, J=8.0 Hz, 1H), 7.58 (d, J=4.7 Hz, 1H), 7.55-7.44 (m, 3H), 7.44-7.24 (m, 5H), 7.11 (d, J=8.7 Hz, 2H), 6.89 (d, J=8.6 Hz, 2H), 5.04 (s, 1H), 5.01 (s, 1H), 4.43 (ddd, J=13.1, 10.0, 5.2 Hz, 1H), 4.31-4.19 (m, 1H), 3.80-3.67 (m, 1H), 3.58 (s, 3H), 2.96 (dd, J=13.8, 5.1 Hz, 1H), 2.91-2.70 (m, 4H), 2.70-2.52 (m, 2H), 2.47-2.29 (m, 1H), 1.93 (d, J=7.2 Hz, 2H), 1.82-1.59 (m, 1H), 1.53-1.40 (m, 1H), 1.35-1.17 (m, 1H), 0.97-0.67 (m, 2H). $^{19}$F NMR (376 MHz, DMSO-$d_6$) δ −60.90. HRMS (ESI+): m/z $C_{34}H_{38}F_3N_2O_5$ (M+H)$^+$611.2739; m/z $C_{34}H_{37}F_3N_2O_5Na$ (M+Na)$^+$633.2559; HPLC-MS (ESI+): m/z 611.2 [60% (M+H)$^+$], m/z 633.2 [100%, (M+Na)$^+$].

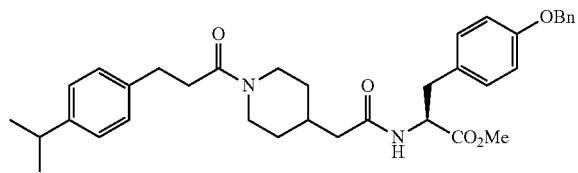 [SMILES: COC(=O)[C@H](Cc1ccc(OCc2ccccc2)cc1)NC(=O)CC1CCN(C(=O)CCc2ccc(C(C)C)cc2)CC1]

Methyl (S)-3-(4-(benzyloxy)phenyl)-2-(2-(1-(3-(4-isopropylphenyl)propanoyl)piperidin-4-yl)acetamido)propanoate (SR2-043). Amide SR2-043 was obtained as a white foam (0.064 g, 98%) from 3-(4-isopropylphenyl)propionic acid (0.026 g, 0.134 mmol, 1.2 eq.) using general method D. HPLC: >98% [$t_R$=10.5 min, 75% MeOH, 25% water (with 0.1% TFA), 20 min]. $^1$H NMR (400 MHz, DMSO-$d_6$) δ 8.22 (d, J=8.0 Hz, 1H), 7.34 (m, 5H), 7.11-7.07 (m, 6H), 6.87 (d, J=8.6 Hz, 2H), 5.02 (s, 1H), 4.99 (s, 1H), 4.42 (dt, J=9.5, 4.7 Hz, 1H), 4.30-4.17 (m, 1H), 3.77-3.62 (m, 1H), 3.57 (s, 3H), 2.94 (dd, J=13.8, 5.1 Hz, 1H), 2.85-2.62 (m, 6H), 2.59-2.49 (m, 1H), 2.44-2.27 (m, 1H), 1.92 (d, J=7.2 Hz, 2H), 1.79-1.59 (m, 1H), 1.51-1.34 (m, 1H), 1.31-1.19 (m, 1H), 1.17-1.11 (m, 6H), 0.93-0.68 (m, 2H). HRMS (ESI+): m/z $C_{36}H_{45}N_2O_5$ (M+H)$^+$585.3327; m/z $C_{36}H_{44}N_2O_5Na$ (M+Na)$^+$607.3135; HPLC-MS (ESI+): m/z 585.2 [40% (M+H)$^+$], m/z 607.2 [100%, (M+Na)$^+$].

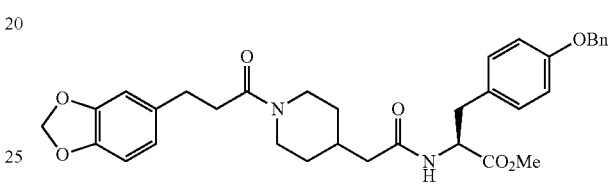

Methyl (S)-2-(2-(1-(3-(benzo[d][1,3]dioxol-5-yl)propanoyl)piperidin-4-yl)acetamido)-3-(4-(benzyloxy)phenyl) propanoate (SR2-044). Amide SR2-044 was obtained as a white foam (0.059 g, 89%) from 3-(3,4-methylenedioxyphenyl)propionic acid (0.026 g, 0.134 mmol, 1.2 eq.) using general method D. HPLC: >98% [$t_R$=7.8 min, 70% MeOH, 30% water (with 0.1% TFA), 20 min]. $^1$H NMR (400 MHz, DMSO-$d_6$) δ 8.25 (d, J=8.0 Hz, 1H), 7.46-7.26 (m, 5H), 7.11 (d, J=8.6 Hz, 2H), 6.89 (d, J=8.7 Hz, 2H), 6.81 (dd, J=4.8, 1.7 Hz, 1H), 6.77 (dd, J=7.8, 4.4 Hz, 1H), 6.65 (ddd, J=8.0, 3.7, 1.7 Hz, 1H), 5.93 (1, 1H), 5.92 (s, 1H), 5.04 (s, 1H), 5.02 (s, 1H), 4.43 (dt, J=9.2, 4.6 Hz, 1H), 4.31-4.22 (m, 1H), 3.80-3.65 (m, 1H), 3.59 (s, 3H), 2.96 (dd, J=13.8, 5.1 Hz, 1H), 2.88-2.63 (m, 4H), 2.52 (m, 2H), 2.47-2.32 (m, 1H), 1.94 (d, J=7.2 Hz, 2H), 1.77-1.64 (m, 1H), 1.50-1.39 (m, 1H), 1.35-1.19 (m, 1H), 0.96-0.67 (m, 2H). HRMS (ESI+): m/z $C_{34}H_{39}N_2O_7$ (M+H)$^+$587.2755; m/z $C_{34}H_{38}N_2O_7Na$ (M+Na)$^+$609.2575; HPLC-MS (ESI+): m/z 587.4 [40% (M+H)$^+$], m/z 609.2 [100%, (M+Na)$^+$].

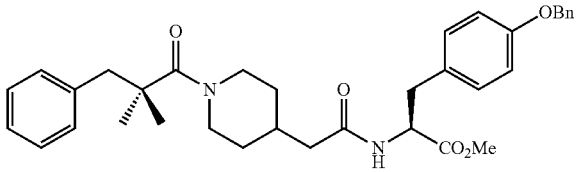

Methyl (S)-3-(4-(benzyloxy)phenyl)-2-(2-(1-(2-methyl-2-phenylpropanoyl)piperidin-4-yl)acetamido)propanoate (SR2-045). Amide SR2-045 was obtained as a white foam (0.058 g, 93%) from 2-methyl-2-phenylpropionic acid (0.022 g, 0.134 mmol, 1.2 eq.) using general method D. HPLC: >99% [$t_R$=4.1 min, 80% MeOH, 20% water (with 0.1% TFA), 20 min]. $^1$H NMR (500 MHz, DMSO-$d_6$, at 65° C.) δ 7.97 (d, J=8.0 Hz, 1H), 7.44 (d, J=7.3 Hz, 2H), 7.39 (t, J=7.5 Hz, 2H), 7.37-7.29 (m, 3H), 7.22 (d, J=7.4 Hz, 1H), 7.18 (d, J=7.9 Hz, 2H), 7.08 (d, J=8.6 Hz, 2H), 6.87 (d, J=8.6 Hz, 2H), 5.06 (s, 2H), 4.44 (ddd, J=9.6, 7.8, 5.3 Hz, 1H), 4.00-3.64 (m, 1H), 3.58 (s, 3H), 3.43-3.20 (m, 1H), 2.95 (dd, J=14.0, 5.4 Hz, 1H), 2.77 (dd, J=13.9, 9.6 Hz, 1H), 2.46 (m, 2H), 1.89 (d, J=7.1 Hz, 2H), 1.69-1.56 (m, 1H), 1.42 (s, 6H), 1.32-1.12 (m, 2H), 0.67 (m, 2H). HRMS (ESI+): m/z $C_{34}H_{41}N_2O_5$ (M+H)$^+$557.3022; m/z $C_{34}H_{40}N_2O_5Na$ (M+Na)$^+$579.2840; HPLC-MS (ESI+): m/z 557.4 [50% (M+H)$^+$], m/z 579.2 [100%, (M+Na)$^+$].

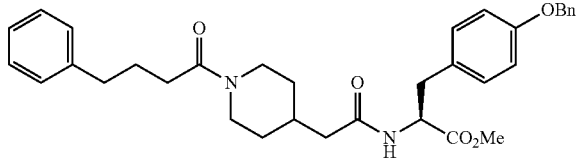 [SMILES: COC(=O)[C@H](Cc1ccc(OCc2ccccc2)cc1)NC(=O)CC1CCN(C(=O)CCCc2ccccc2)CC1]

Methyl (S)-3-(4-(benzyloxy)phenyl)-2-(2-(1-(4-phenylbutanoyl)piperidin-4-yl)acetamido)-propanoate (SR2-046). Amide SR2-046 was obtained as a white foam (0.058 g, 93%) from 4-phenylbutyric acid (0.022 g, 0.134 mmol, 1.2 eq.) using general method D. HPLC: >98% [$t_R$=6.5 min, 75% MeOH, 25% water (with 0.1% TFA), 20 min]. $^1$H NMR (400 MHz, DMSO-d$_6$) δ 8.26 (d, J=8.0 Hz, 1H), 7.47-7.41 (m, 2H), 7.40-7.35 (m, 2H), 7.34-7.24 (m, 3H), 7.17 (m, 3H), 7.13 (d, J=8.2 Hz, 2H), 6.90 (dd, J=8.6, 2.1 Hz, 2H), 5.06 (s, 1H), 5.04 (s, 1H), 4.46 (ddd, J=10.2, 8.0, 5.1 Hz, 1H), 4.33-4.23 (m, 1H), 3.76-3.62 (m, 1H), 3.60 (s, 3H), 2.98 (ddd, J=14.0, 5.4, 1.8 Hz, 1H), 2.92-2.64 (m, 2H), 2.61-2.53 (m, 2H), 2.47-2.35 (m, 1H), 2.34-2.15 (m, 2H), 2.01-1.92 (m, 1H), 1.82-1.65 (m, 3H), 1.48 (d, J=13.2 Hz, 1H), 1.34-1.22 (m, 1H), 1.00-0.71 (m, 2H). HRMS (ESI+): m/z $C_{34}H_{41}N_2O_5$ (M+H)$^+$557.3018; m/z $C_{34}H_{40}N_2O_5Na$ (M+Na)$^+$579.2834; HPLC-MS (ESI+): m/z 557.3 [80% (M+H)$^+$], m/z 579.2 [100%, (M+Na)$^+$].

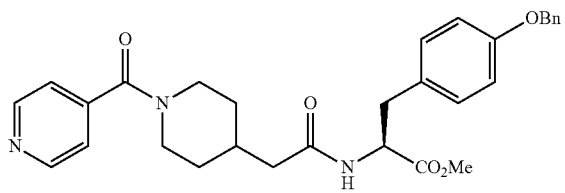 [SMILES: COC(=O)[C@H](Cc1ccc(OCc2ccccc2)cc1)NC(=O)CC1CCN(C(=O)c2ccncc2)CC1]

Methyl (S)-3-(4-(benzyloxy)phenyl)-2-(2-(1-isonicotinoylpiperidin-4-yl)acetamido)propan-oate (SR2-050). Amide SR2-050 was obtained as a white foam (0.051 g, 88%) from isonicotinic acid (0.016 g, 0.134 mmol, 1.2 eq.) using general method D. HPLC: >98% [$t_R$=4.4 min, 60% MeOH, 40% water (with 0.1% TFA), 20 min]. $^1$H NMR (400 MHz, DMSO-d$_6$) δ 8.63 (d, J=5.9 Hz, 1H), 8.27 (d, J=8.0 Hz, 1H), 7.44-7.27 (m, 7H), 7.11 (dd, J=8.3, 6.0 Hz, 2H), 6.86 (dd, J=22.5, 8.2 Hz, 2H), 5.02 (s, 1H), 4.95 (s, 1H), 4.45 (m, 1H), 4.41-4.27 (m, 1H), 3.58 (s, 3H), 3.30 (m, 1H), 3.02-2.86 (m, 2H), 2.75 (dd, J=13.9, 10.1 Hz, 1H), 2.72-2.61 (m, 1H), 1.98 (d, J=6.1 Hz, 2H), 1.89-1.71 (m, 1H), 1.65-1.53 (m, 1H), 1.45-1.34 (m, 1H), 1.29-1.17 (m, 1H), 1.14-0.84 (m, 2H). HRMS (ESI+): m/z $C_{30}H_{34}N_3O_5$ (M+H)$^+$516.2504; m/z $C_{30}H_{33}N_3O_5Na$ (M+Na)$^+$538.2316; HPLC-MS (ESI+): m/z 516.2 [100% (M+H)$^+$].

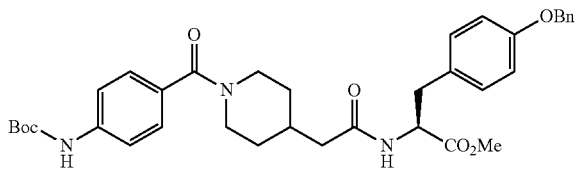 [SMILES: COC(=O)[C@H](Cc1ccc(OCc2ccccc2)cc1)NC(=O)CC1CCN(C(=O)c2ccc(NC(=O)OC(C)(C)C)cc2)CC1]

Methyl (S)-3-(4-(benzyloxy)phenyl)-2-(2-(1-(4-((tert-butoxycarbonyl)amino)benzoyl) piperidin-4-yl)acetamido) propanoate (SR2-051). Amide SR2-051 was obtained as a white foam (0.068 g, 96%) from 4-(Boc-amino)benzoic acid (0.032 g, 0.134 mmol, 1.2 eq.) using general method D. HPLC: >98% [$t_R$=5.7 min, 75% MeOH, 25% water (with 0.1% TFA), 20 min]. $^1$H NMR (400 MHz, DMSO-d$_6$) δ 8.63 (d, J=5.9 Hz, 1H), 8.27 (d, J=8.0 Hz, 1H), 7.44-7.27 (m, 7H), 7.11 (dd, J=8.3, 6.0 Hz, 2H), 6.86 (dd, J=22.5, 8.2 Hz, 2H), 5.02 (s, 1H), 4.95 (s, 1H), 4.45 (m, 1H), 4.41-4.27 (m, 1H), 3.58 (s, 3H), 3.30 (m, 1H), 3.02-2.86 (m, 2H), 2.75 (dd, J=13.9, 10.1 Hz, 1H), 2.72-2.61 (m, 1H), 1.98 (d, J=6.1 Hz, 2H), 1.89-1.71 (m, 1H), 1.65-1.53 (m, 1H), 1.45-1.34 (m, 1H), 1.29-1.17 (m, 1H), 1.14-0.84 (m, 2H). HRMS (ESI+): m/z $C_{36}H_{44}N_3O_7$ (M+H)$^+$630; 3184 m/z $C_{36}H_{43}N_3O_7Na$ (M+Na)$^+$652.3001; HPLC-MS (ESI+): m/z 630.4 [100% (M+H)$^+$], m/z 652.3 [90%, (M+Na)$^+$].

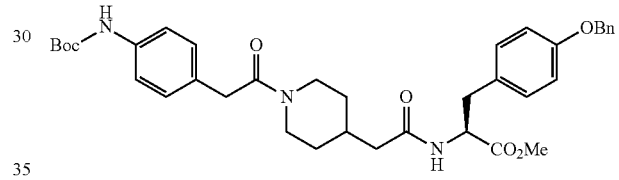

Methyl (S)-3-(4-(benzyloxy)phenyl)-2-(2-(1-(2-(4-((tert-butoxycarbonyl)amino)phenyl) acetyl)piperidin-4-yl)acetamido)propanoate (SR2-052). Amide SR2-052 was obtained as a white foam (0.058 g, 81%) from 4-(Boc-amino)phenylacetic acid (0.034 g, 0.134 mmol, 1.2 eq.) using general method D. HPLC: >96% [$t_R$=6.0 min, 75% MeOH, 25% water (with 0.1% TFA), 20 min]. $^1$H NMR (400 MHz, DMSO-d$_6$) δ 9.27 (s, 1H), 8.23 (d, J=7.8 Hz, 1H), 7.46-7.23 (m, 7H), 7.10 (d, J=8.6 Hz, 2H), 7.05 (dd, J=8.5, 4.6 Hz, 1H), 6.88 (d, J=8.6 Hz, 2H), 5.03 (s, 2H), 4.48-4.35 (m, 1H), 4.29-4.19 (m, 1H), 3.79 (m, 1H), 3.57 (s, 3H), 3.58-3.49 (m, 2H), 3.29 (m, 1H), 2.94 (dd, J=13.9, 5.1 Hz, 1H), 2.90-2.79 (m, 1H), 2.74 (dd, J=13.8, 10.1 Hz, 1H), 2.66 (m, 1H), 2.46-2.35 (m, 1H), 1.91 (d, J=7.1 Hz, 2H), 1.80-1.61 (m, 1H), 1.44 (s, 9H), 1.33-1.20 (m, 2H), 0.91-0.65 (m, 2H). HRMS (ESI+): m/z $C_{37}H_{46}N_3O_7$ (M+H)$^+$644.3337 m/z $C_{37}H_{45}N_3O_7Na$ (M+Na)$^+$666.3156; HPLC-MS (ESI+): m/z 644.4 [50% (M+H)$^+$], m/z 666.2 [80%, (M+Na)$^+$].

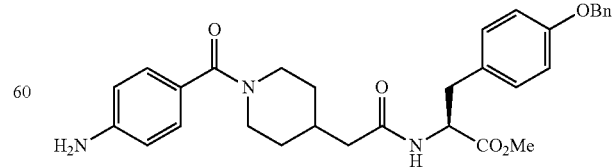

Methyl (S)-2-(2-(1-(4-aminobenzoyl)piperidin-4-yl)acetamido)-3-(4-(benzyloxy)phenyl)-propanoate (SR2-057). SR2-051 (0.032 g, 0.508 mmol) was dissolved in DCM (1 mL) and HCl (4N in dioxane, 2.0 mL) was added at room temperature. The mixture was stirred for 3 h and concentrated. The resulting residue was dissolved in EtOAc (1×15 mL) and washed with sat. NaHCO$_3$ (1×10 mL). The organic layer was extracted with EtOAc (1×10 mL). The combined organic layer was dried (Na$_2$SO$_4$) and evaporated. Purification by flash column chromatography using MeOH/DCM (0:100-10:90) as eluent afforded SR2-057 as a white solid (0.026 g, 96%). HPLC: >97% [$t_R$=5.0 min, 60% MeOH, 40% water (with 0.1% TFA), 20 min]. $^1$H NMR (400 MHz, DMSO-d$_6$) δ 8.22 (d, J=8.0 Hz, 1H), 7.46-7.34 (m, 4H), 7.34-7.28 (m, 1H), 7.12 (d, J=8.6 Hz, 2H), 7.07 (d, J=8.5 Hz, 2H), 6.89 (d, J=8.7 Hz, 2H), 6.54 (d, J=8.5 Hz, 2H), 5.43 (s, 2H), 5.02 (s, 2H), 4.47 (ddd, J=10.0, 8.0, 5.2 Hz, 1H), 4.09-3.90 (m, 1H), 3.60 (s, 3H), 3.29-3.23 (m, 1H), 2.98 (dd, J=13.8, 5.1 Hz, 1H), 2.78 (dd, J=13.9, 10.1 Hz, 1H), 2.73-2.64 (m, 1H), 2.50 (m, 1H), 2.00 (d, J=7.2 Hz, 2H), 1.85-1.68 (m, 1H), 1.49 (m, 1H), 1.35 (m, 1H), 1.15-0.85 (m, 2H). HRMS (ESI+): m/z C$_{31}$H$_{36}$N$_3$O$_5$ (M+H)$^+$530.2661 m/z C$_{31}$H$_{35}$N$_3$O$_5$Na (M+Na)$^+$552.2475; HPLC-MS (ESI+): m/z 530.2 [100% (M+H)$^+$], m/z 552.2 [40%, (M+Na)$^+$].

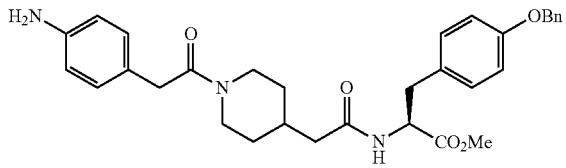 [SMILES: COC(=O)[C@H](Cc1ccc(OCc2ccccc2)cc1)NC(=O)CC1CCN(C(=O)Cc2ccc(N)cc2)CC1]

Methyl (S)-2-(2-(1-(2-(4-aminophenyl)acetyl)piperidin-4-yl)acetamido)-3-(4-(benzyloxy)-phenyl)propanoate (SR2-058). The aniline SR2-058 was obtained from SR2-052 (0.040 g, 0.062 mmol) as a white solid (0.031 g, 92%) by following the same method used to make SR2-057. HPLC: >96% [$t_R$=11.5 min, 50% MeOH, 50% water (with 0.1% TFA), 20 min]. $^1$H NMR (400 MHz, DMSO-d$_6$) δ 8.18 (d, J=7.9 Hz, 1H), 7.41 (m, 2H), 7.36 (m, 2H), 7.33-7.25 (m, 1H), 7.10 (d, J=8.7 Hz, 2H), 6.89 (d, J=8.6 Hz, 2H), 6.83 (dd, J=8.4, 2.4 Hz, 2H), 6.47 (d, J=8.3 Hz, 2H), 5.04 (s, 2H), 4.86 (s, 2H), 4.43 (td, J=8.39, 4.8 Hz, 1H), 4.29-4.19 (m, 1H), 3.86-3.72 (m, 1H), 3.58 (s, 3H), 3.43 (bs, 2H), 2.94 (dd, J=14.0, 5.1 Hz, 1H), 2.90-2.63 (m, 2H), 2.45-2.28 (m, 1H), 1.91 (d, J=7.2 Hz, 2H), 1.77-1.56 (m, 1H), 1.53-1.36 (m, 1H), 1.33-1.20 (m, 1H), 0.92-0.60 (m, 2H). HRMS (ESI+): m/z C$_{32}$H$_{38}$N$_3$O$_5$ (M+H)$^+$544.2818 m/z C$_{32}$H$_{37}$N$_3$O$_5$Na (M+Na)$^+$566.2634; HPLC-MS (ESI+): m/z 544.2 [100% (M+H)$^+$], m/z 566.2 [50%, (M+Na)$^+$].

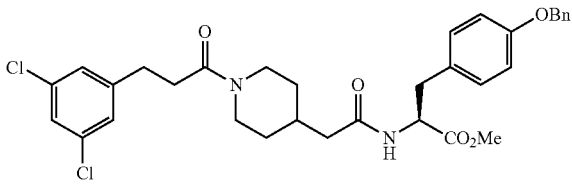 [SMILES: COC(=O)[C@H](Cc1ccc(OCc2ccccc2)cc1)NC(=O)CC1CCN(C(=O)CCc2cc(Cl)cc(Cl)c2)CC1]

Methyl (S)-3-(4-(benzyloxy)phenyl)-2-(2-(1-(3-(3,5-dichlorophenyl)propanoyl)piperidin-4-yl)acetamido)propanoate (SR2-106). The amide SR2-106 was obtained as a white foam (0.066 g, 96%) from 3-(3,5-dichlorophenyl)propionic acid (0.029 g, 0.134 mmol, 1.2 eq.) using general method D. HPLC: >98% [$t_R$=7.0 min, 80% MeOH, 20% water (with 0.1% TFA), 20 min]. $^1$H NMR (500 MHz, DMSO-d$_6$) δ 8.23 (dd, J=7.9, 1.7 Hz, 1H), 7.45-7.31 (m, 5H), 7.31-7.28 (m, 3H), 7.11 (d, J=8.6 Hz, 2H), 6.89 (d, J=8.5 Hz, 2H), 5.04 (s, 1H), 5.02 (s, 1H), 4.44 (m, 1H), 4.25 (m, 1H), 3.80-3.66 (m, 1H), 3.58 (s, 3H), 2.96 (dd, J=13.9, 5.1 Hz, 1H), 2.89-2.72 (m, 4H), 2.68-2.51 (m, 2H), 2.46-2.33 (m, 1H), 1.94 (d, J=7.1 Hz, 2H), 1.79-1.64 (m, 1H), 1.49-1.42 (m, 1H), 1.36-1.19 (m, 1H), 0.97-0.65 (m, 2H). HRMS (ESI+): m/z C$_{33}$H$_{36}$Cl$_2$N$_2$O$_5$ (M)$^+$610.2001; m/z C$_{33}$H$_{36}$Cl$_2$N$_2$O$_5$Na (M+Na)$^+$633.1889; HPLC-MS (ESI+): m/z 633.2 [100%, (M+Na)$^+$].

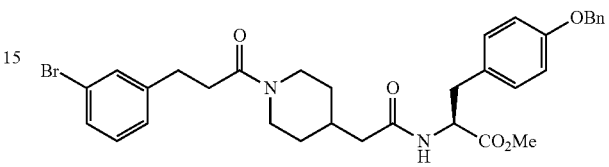

Methyl (S)-3-(4-(benzyloxy)phenyl)-2-(2-(1-(3-(3-bromophenyl)propanoyl)piperidin-4-yl)acetamido)propanoate (SR2-107). Amide SR2-107 was obtained as a white foam (0.068 g, 97%) from 3-(3-bromophenyl)propionic acid (0.031 g, 0.134 mmol, 1.2 eq.) using general method D. HPLC: >97% [$t_R$=4.9 min, 80% MeOH, 20% water (with 0.1% TFA), 20 min]. $^1$H NMR (500 MHz, DMSO-d$_6$) δ 8.22 (d, J=8.0 Hz, 1H), 7.45-7.37 (m, 3H), 7.35 (m, 3H), 7.30 (m, 1H), 7.21 (m, 2H), 7.11 (d, J=8.6 Hz, 2H), 6.89 (d, J=8.6 Hz, 2H), 5.04 (s, 1H), 5.02 (s, 1H), 4.43 (ddd, J=13.3, 10.2, 5.2 Hz, 1H), 4.32-4.21 (m, 1H), 3.81-3.62 (m, 1H), 3.58 (s, 3H), 2.96 (dd, J=13.8, 5.1 Hz, 1H), 2.90-2.70 (m, 4H), 2.64-2.50 (m, 2H), 2.47-2.33 (m, 1H), 1.94 (d, J=7.2 Hz, 2H), 1.71 (m, 1H), 1.45 (m, 1H), 1.35-1.21 (m, 1H), 0.94-0.68 (m, 2H). HRMS (ESI+): m/z C$_{33}$H$_{38}$BrN$_2$O$_5$ (M+H)$^+$621.1959; m/z C$_{33}$H$_{37}$BrN$_2$O$_5$Na (M+Na)$^+$643.1774; HPLC-MS (ESI+): m/z 621.2 [40%, (M+H)$^+$], m/z 643.2 [100%, (M+Na)$^+$].

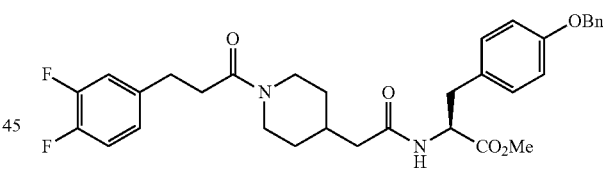

Methyl (S)-3-(4-(benzyloxy)phenyl)-2-(2-(1-(3-(3,4-difluorophenyl)propanoyl)piperidin-4-yl)acetamido)propanoate (SR2-109). The amide SR2-109 was obtained as a white foam (0.058 g, 90%) from 3-(3,4-difluorophenyl)propionic acid (0.025 g, 0.134 mmol, 1.2 eq.) using general method D. HPLC: >99% [$t_R$=12.6 min, 70% MeOH, 30% water (with 0.1% TFA), 20 min]. $^1$H NMR (500 MHz, DMSO-d$_6$) δ 8.22 (d, J=8.0 Hz, 1H), 7.40 (m, 2H), 7.35 (m, 2H), 7.32-7.23 (m, 3H), 7.11 (d, J=8.6 Hz, 2H), 7.04 (m, 1H), 6.89 (d, J=7.6 Hz, 2H), 5.03 (s, 1H), 5.01 (m, 1H), 4.44 (ddd, J=10.1, 8.0, 5.1 Hz, 1H), 4.31-4.21 (m, 1H), 3.72 (m, 1H), 3.58 (s, 3H), 2.96 (dd, J=13.8, 5.1 Hz, 1H), 2.88-2.70 (m, 4H), 2.64-2.50 (m, 2H), 2.45-2.32 (m, 1H), 1.94 (d, J=7.2 Hz, 2H), 1.78-1.63 (m, 1H), 1.51-1.40 (m, 1H), 1.36-1.20 (m, 1H), 0.95-0.71 (m, 2H). HRMS (ESI+): m/z C$_{33}$H$_{37}$F$_2$N$_2$O$_5$ (M)$^+$ 578.2592; m/z C$_{33}$H$_{36}$F$_2$N$_2$O$_5$Na (M+Na)$^+$601.2481; HPLC-MS (ESI+): m/z 579.2 [30%, (M+H)$^+$], m/z 601.2 [100%, (M+Na)$^+$].

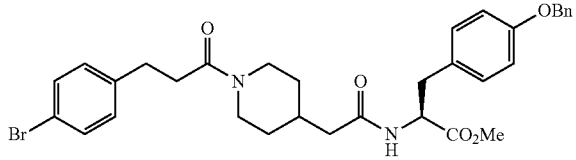 [SMILES: COC(=O)[C@H](Cc1ccc(OCc2ccccc2)cc1)NC(=O)CC1CCN(C(=O)CCc2ccc(Br)cc2)CC1]

Methyl (S)-3-(4-(benzyloxy)phenyl)-2-(2-(1-(3-(4-bromophenyl)propanoyl)piperidin-4-yl)acetamido)propanoate (SR2-110). The amide SR2-110 was obtained as a white foam (0.055 g, 79%) from 3-(4-bromophenyl)propionic acid (0.031 g, 0.134 mmol, 1.2 eq.) using general method D. HPLC: >99% [$t_R$=9.4 min, 75% MeOH, 25% water (with 0.1% TFA), 20 min]. $^1$H NMR (500 MHz, DMSO-$d_6$) δ 8.25 (d, J=8.0 Hz, 1H), 7.46-7.40 (m, 4H), 7.39-7.35 (m, 2H), 7.34-7.27 (m, 1H), 7.19 (dd, J=8.4, 6.9 Hz, 2H), 7.13 (d, J=8.6 Hz, 2H), 6.91 (d, J=8.6 Hz, 2H), 5.06 (s, 1H), 5.04 (s, 1H), 4.46 (ddd, J=10.0, 8.1, 4.7 Hz, 1H), 4.33-4.21 (m, 1H), 3.73 (m, 1H), 3.61 (s, 3H), 2.98 (dd, J=13.8, 5.1 Hz, 1H), 2.90-2.71 (m, 4H), 2.65-2.52 (m, 2H), 2.49-2.37 (m, 1H), 1.96 (d, J=7.2 Hz, 2H), 1.81-1.67 (m, 1H), 1.47 (d, J=13.0 Hz, 1H), 1.37-1.22 (m, 1H), 0.96-0.70 (m, 2H). HRMS (ESI+): m/z $C_{33}H_{37}BrN_2O_5$ (M+H)$^+$621.1951; m/z $C_{33}H_{37}BrN_2O_5Na$ (M+Na)$^+$643.1767; HPLC-MS (ESI+): m/z 622.0 [80%, (M+H)$^+$], m/z 643.2 [100%, (M+Na)$^+$].

General Method E: Synthesis of N-Terminal Sulfinamides and Sulfonamides

The amine SR1-085 (0.050 g, 0.112 mmol, 1 eq.) was dissolved in DCM (1.5-2.0 mL) under argon. To the solution, triethylamine (0.336 mmol, 0.047 mL, 3.0 eq) and corresponding sulfinyl or sulfonyl chloride (1.2 eq.) were added. The mixture was stirred at room temperature for 18-24 h and concentrated under reduced pressure. The resulting thick oil was dissolved in EtOAc and washed with sat. $NH_4Cl$ (2×15 mL). The organic layer was dried ($Na_2SO_4$) and evaporated. Purification by flash column chromatography using MeOH/DCM (0:10-1:9) as eluent afforded corresponding N-terminal sulfinyl and sulfonyl products.

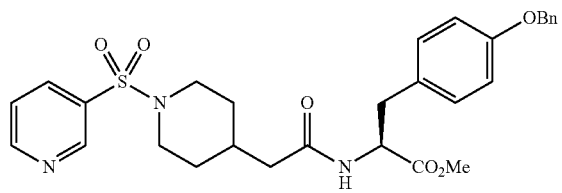 [SMILES: COC(=O)[C@H](Cc1ccc(OCc2ccccc2)cc1)NC(=O)CC1CCN(S(=O)(=O)c2ccccc2)CC1]

Methyl (S)-3-(4-(benzyloxy)phenyl)-2-(2-(1-(pyridin-3-ylsulfonyl)piperidin-4-yl)acetamido)-propanoate (SR2-075). The sulfonamide SR2-075 was obtained as a white foam (0.045 g, 73%) from piperidine-3-sulfonylchloride (0.024 g, 0.134 mmol, 1.2 eq.) using general method E. HPLC: >98% [$t_R$=3.8 min, 70% MeOH, 30% water (with 0.1% TFA), 20 min]. $^1$H NMR (500 MHz, DMSO-$d_6$) δ 8.86 (m, 2H), 8.22 (d, J=8.0 Hz, 1H), 8.09 (dt, J=8.0, 1.9 Hz, 1H), 7.64 (ddd, J=8.0, 4.8, 0.8 Hz, 1H), 7.43 (m, 2H), 7.38 (m, 2H), 7.32 (m, 2H), 7.09 (d, J=8.6 Hz, 2H), 6.88 (d, J=8.7 Hz, 2H), 5.04 (s, 1H), 4.42 (ddd, J=10.1, 8.0, 5.2 Hz, 1H), 3.57 (s, 3H), 3.54 (m, 2H), 2.94 (dd, J=13.9, 5.1 Hz, 1H), 2.73 (dd, J=13.9, 10.1 Hz, 1H), 2.30-2.19 (m, 2H), 1.93 (dd, J=7.1, 2.0 Hz, 2H), 1.56-1.42 (m, 2H), 1.40-1.21 (m, 1H), 1.13-0.92 (m, 2H). HRMS (ESI+): m/z $C_{29}H_{34}N_3O_6S$ (M+H)$^+$552.2173; m/z $C_{29}H_{33}N_3O_6SNa$ (M+Na)$^+$574.1985 HPLC-MS (ESI+): m/z 552.2 [100% (M+H)$^+$], m/z 574.2 [50%, (M+Na)$^+$].

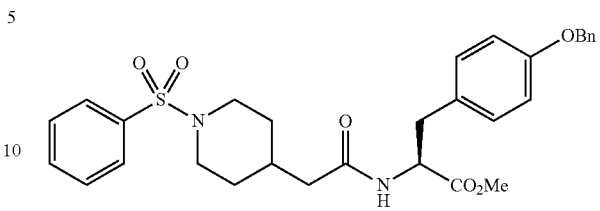

Methyl (S)-3-(4-(benzyloxy)phenyl)-2-(2-(1-(phenylsulfonyl)piperidin-4-yl)acetamido)-propanoate (SR3-078). The sulfonamide SR2-078 was obtained as a white foam (0.060 g, 97%) from benzenesulfonyl chloride (0.017 μL, 0.134 mmol, 1.2 eq.) using general method E. HPLC: >98% [$t_R$=4.7 min, 70% MeOH, 30% water (with 0.1% TFA), 20 min]. $^1$H NMR (500 MHz, DMSO-$d_6$) δ 8.21 (d, J=8.0 Hz, 1H), 7.67 (m, 3H), 7.59 (m, 2H), 7.44 (m, 2H), 7.38 (m, 2H), 7.33 (m, 1H), 7.09 (d, J=8.6 Hz, 2H), 6.87 (d, J=8.7 Hz, 2H), 5.04 (s, 2H), 4.42 (ddd, J=10.1, 8.0, 5.1 Hz, 1H), 3.57 (s, 3H), 3.52 (m, 2H), 2.95 (dd, J=13.9, 5.1 Hz, 1H), 2.73 (dd, J=13.8, 10.2 Hz, 1H), 2.11 (m, 2H), 1.92 (d, J=7.0 Hz, 2H), 1.56-1.37 (m, 2H), 1.32 (dd, J=12.8, 3.1 Hz, 1H), 1.13-0.93 (m, 2H). HRMS (ESI+): m/z $C_{30}H_{35}N_2O_6S$ (M+H)$^+$551.2214; m/z $C_{30}H_{34}N_2O_6SNa$ (M+Na)$^+$573.2040 HPLC-MS (ESI+): m/z 551.2 [50% (M+H)$^+$], m/z 573.2 [100%, (M+Na)$^+$].

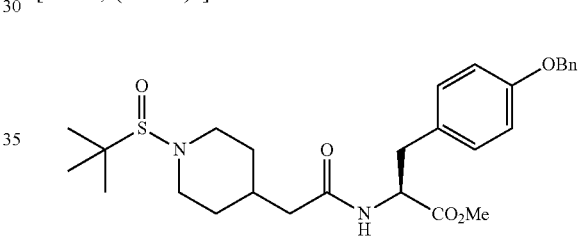

Methyl (2S)-3-(4-(benzyloxy)phenyl)-2-(2-(1-(tert-butylsulfinyl)piperidin-4-yl)acetamido)-propanoate (SR3-079). The sulfonamide SR2-079 was obtained as a white foam (0.041 g, 71%) from tert-butylsulfinyl chloride (0.017 μL, 0.134 mmol, 1.2 eq.) using general method E. HPLC: >98% [$t_R$=7.6 min, 70% MeOH, 30% water (with 0.1% TFA), 20 min]. $^1$H NMR (500 MHz, DMSO-$d_6$) δ 8.21 (d, J=8.0 Hz, 1H), 7.67 (m, 3H), 7.59 (m, 2H), 7.44 (m, 2H), 7.38 (m, 2H), 7.33 (m, 1H), 7.09 (d, J=8.6 Hz, 2H), 6.87 (d, J=8.7 Hz, 2H), 5.04 (s, 2H), 4.42 (ddd, J=10.1, 8.0, 5.1 Hz, 1H), 3.57 (s, 3H), 3.52 (m, 2H), 2.95 (dd, J=13.9, 5.1 Hz, 1H), 2.73 (dd, J=13.8, 10.2 Hz, 1H), 2.11 (m, 2H), 1.92 (d, J=7.0 Hz, 2H), 1.56-1.37 (m, 2H), 1.32 (dd, J=12.8, 3.1 Hz, 1H), 1.13-0.93 (m, 2H). HRMS (ESI+): m/z $C_{28}H_{39}N_2O_5S$ (M+H)$^+$515.2585; m/z $C_{28}H_{38}N_2O_5SNa$ (M+Na)$^+$537.2406 HPLC-MS (ESI+): m/z 515.2 [40% (M+H)$^+$], m/z 537.2 [100%, (M+Na)$^+$].

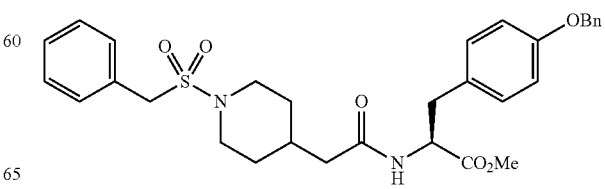

Methyl (S)-3-(4-(benzyloxy)phenyl)-2-(2-(1-(benzylsulfonyl)piperidin-4-yl)acetamido)-propanoate (SR2-082). The sulfonamide SR2-082 was obtained as a white foam (0.046 g, 73%) from alpha-toluenesulfonyl chloride (0.026 g, 0.134 mmol, 1.2 eq.) using general method E. HPLC: >98% [$t_R$=7.1 min, 70% MeOH, 30% water (with 0.1% TFA), 20 min]. $^1$H NMR (400 MHz, DMSO-d$_6$) δ 8.24 (d, J=8.0 Hz, 1H), 7.46-7.27 (m, 10H), 7.10 (d, J=8.2 Hz, 2H), 6.88 (d, J=8.3 Hz, 2H), 5.02 (s, 2H), 4.43 (td, J=9.3, 5.3 Hz, 1H), 4.31 (s, 2H), 3.58 (s, 3H), 3.51-3.23 (m, 2H), 2.95 (dd, J=13.9, 5.1 Hz, 1H), 2.74 (dd, J=13.8, 10.1 Hz, 1H), 2.65-2.39 (m, 2H), 1.95 (d, J=7.3 Hz, 2H), 1.49 (d, J=13.4 Hz, 2H), 1.34-1.20 (m, 1H), 1.08-0.78 (m, 2H). HRMS (ESI+): m/z $C_{31}H_{37}N_2O_6S$ (M+H)$^+$565.2374; m/z $C_{31}H_{36}N_2O_6SNa$ (M+Na)$^+$587.2198 HPLC-MS (ESI+): m/z 587.2 [100%, (M+Na)$^+$].

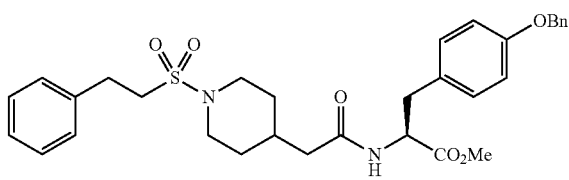 [SMILES: COC(=O)[C@H](Cc1ccc(OCc2ccccc2)cc1)NC(=O)CC1CCN(S(=O)(=O)CCc2ccccc2)CC1]

Methyl (S)-3-(4-(benzyloxy)phenyl)-2-(2-(1-(phenethylsulfonyl)piperidin-4-yl)acetamido)-propanoate (SR2-083). The sulfonamide SR2-083 was obtained as a white foam (0.049 g, 76%) from 2-phenylethanesulfonyl chloride (0.027 g, 0.134 mmol, 1.2 eq.) using general method E. HPLC: >99% [$t_R$=11.6 min, 70% MeOH, 30% water (with 0.1% TFA), 20 min]. $^1$H NMR (400 MHz, DMSO-d$_6$) δ 8.26 (d, J=8.0 Hz, 1H), 7.45-7.40 (m, 2H), 7.40-7.34 (m, 2H), 7.34-7.25 (m, 5H), 7.22 (m, 1H), 7.13 (d, J=8.6 Hz, 2H), 6.91 (d, J=8.6 Hz, 2H), 5.04 (s, 2H), 4.46 (ddd, J=10.0, 7.9, 5.0 Hz, 1H), 3.60 (s, 3H), 3.58-3.45 (m, 2H), 3.29-3.20 (m, 2H), 3.02-2.86 (m, 3H), 2.80-2.62 (m, 3H), 1.99 (d, J=7.2 Hz, 2H), 1.70-1.51 (m, 1H), 1.45-1.30 (m, 2H), 1.14-0.91 (m, 2H). HRMS (ESI+): m/z $C_{32}H_{39}N_2O_6S$ (M+H)$^+$ 579.2530; m/z $C_{32}H_{38}N_2O_6SNa$ (M+Na)$^+$601.2354 HPLC-MS (ESI+): m/z 601.2 [100%, (M+Na)$^+$].

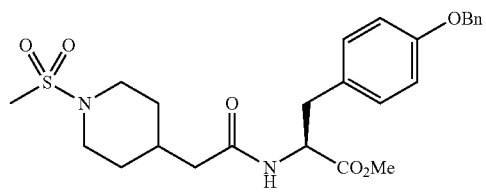 [SMILES: COC(=O)[C@H](Cc1ccc(OCc2ccccc2)cc1)NC(=O)CC1CCN(S(C)(=O)=O)CC1]

Methyl (S)-3-(4-(benzyloxy)phenyl)-2-(2-(1-(methylsulfonyl)piperidin-4-yl)acetamido)-propanoate (SR2-089). The sulfonamide SR2-089 was obtained as a white foam (0.043 g, 79%) from methanesulfonyl chloride (0.011 μL, 0.134 mmol, 1.2 eq.) using general method E. HPLC: >97% [$t_R$=5.9 min, 70% MeOH, 30% water (with 0.1% TFA), 20 min]. $^1$H NMR (500 MHz, DMSO-d$_6$) δ 8.28 (d, J=7.9 Hz, 1H), 7.45-7.41 (m, 2H), 7.41-7.35 (m, 2H), 7.34-7.30 (m, 1H), 7.13 (d, J=8.6 Hz, 2H), 6.91 (d, J=8.7 Hz, 2H), 5.04 (s, 2H), 4.46 (ddd, J=10.1, 8.0, 5.1 Hz, 1H), 3.60 (s, 3H), 3.44 (m, 2H), 2.98 (dd, J=13.8, 5.1 Hz, 1H), 2.80 (s, 3H), 2.79-2.73 (m, 1H), 2.65-2.53 (m, 2H), 2.01 (dd, J=7.1, 1.5 Hz, 2H), 1.68-1.55 (m, 2H), 1.44-1.36 (m, 1H), 1.16-0.97 (m, 2H). HRMS (ESI+): m/z $C_{25}H_{33}N_2O_6S$ (M+H)$^+$ 489.2063; m/z $C_{25}H_{32}N_2O_6SNa$ (M+Na)$^+$511.1879 HPLC-MS (ESI+): m/z 511.2 [100%, (M+Na)$^+$].

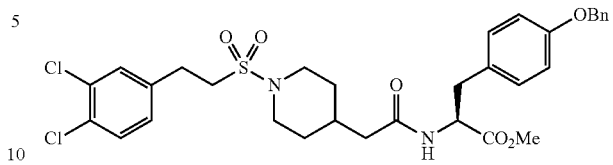

Methyl (S)-3-(4-(benzyloxy)phenyl)-2-(2-(1-((3,4-dichlorophenethyl)sulfonyl)piperidin-4-yl)acetamido)propanoate (SR2-112). The sulfonamide SR2-112 was obtained as a white foam (0.023 g, 32%) from 2-(3,4-dichlorophenyl)ethane-1-sulfonyl chloride (0.037 g, 0.134 mmol, 1.2 eq.) using general method E. HPLC: >97% [$t_R$=6.9 min, 75% MeOH, 25% water (with 0.1% TFA), 20 min]. $^1$H NMR (500 MHz, DMSO-d$_6$) δ 8.29-8.23 (m, 1H), 7.60 (d, J=2.0 Hz, 1H), 7.53 (d, J=8.3 Hz, 1H), 7.45-7.26 (m, 6H), 7.11 (d, J=8.5 Hz, 2H), 6.89 (d, J=8.6 Hz, 2H), 5.04 (s, 1H), 5.02 (s, 1H), 4.45 (ddd, J=10.1, 7.9, 5.1 Hz, 1H), 3.59 (s, 3H), 3.55-3.43 (m, 2H), 3.33-3.25 (m, 2H), 3.01-2.86 (m, 3H), 2.82-2.64 (m, 3H), 1.98 (d, J=7.2 Hz, 2H), 1.63 (m, 0.5H), 1.57-1.49 (m, 0.5H), 1.40-1.18 (m, 1.5H), 1.10-0.83 (m, 2H). HRMS (ESI+): m/z $C_{32}H_{36}Cl_2N_2O_6S$ (M)$^+$646.1671; HPLC-MS (ESI+): m/z 669.0 [100%, (M+Na)$^+$].

Synthesis of Cyclohexylacetic Acid Containing N-Terminal Variants

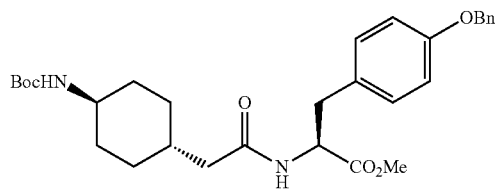 [SMILES: COC(=O)[C@H](Cc1ccc(OCc2ccccc2)cc1)NC(=O)C[C@H]1CC[C@H](NC(=O)OC(C)(C)C)CC1]

Methyl (S)-3-(4-(benzyloxy)phenyl)-2-(2-((1r,4S)-4-((tert-butoxycarbonyl)amino) cyclo-hexyl)acetamido)propanoate (SR2-087). The amide SR2-087 was obtained as a white foam (0.674 g, 83%) from trans-4-(Boc-amino)cyclohexane acetic acid (0.400 g, 1.554 mmol, 1.2 eq.) by following the method used to make SR1-083. HPLC: >99% [$t_R$=10.3 min, 70% MeOH, 30% water (with 0.1% TFA), 20 min]. $^1$H NMR (400 MHz, DMSO-d$_6$) δ 8.17 (d, J=8.0 Hz, 1H), 7.46-7.26 (m, 5H), 7.10 (d, J=8.6 Hz, 2H), 6.88 (d, J=8.6 Hz, 2H), 6.61 (d, J=8.1 Hz, 1H), 5.02 (s, 2H), 4.41 (ddd, J=9.9, 7.8, 5.1 Hz, 1H), 3.57 (s, 3H), 3.16-3.00 (m, 1H), 2.94 (dd, J=13.8, 5.1 Hz, 1H), 2.75 (dd, J=13.8, 10.0 Hz, 1H), 1.89 (d, J=7.1 Hz, 2H), 1.73-1.57 (m, 2H), 1.51 (m, 1H), 1.46-1.26 (m, 2H), 1.34 (s, 9H), 1.03 (dd, J=17.9, 7.6 Hz, 2H), 0.90-0.70 (m, 2H). HRMS (ESI+): m/z $C_{30}H_{41}N_2O_6$ (M+H)$^+$525.2958; m/z $C_{30}H_{40}N_2O_6Na$ (M+Na)$^+$547.2784 found 547.2793; HPLC-MS (ESI+): m/z 547.2 [100%, (M+Na)$^+$].

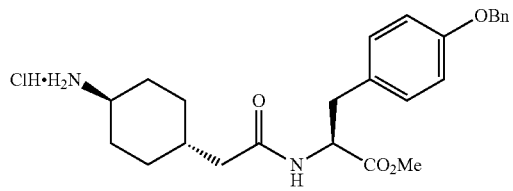

Methyl (S)-2-(2-trans-4-aminocyclohexyl)acetamido)-3-(4-(benzyloxy)phenyl)propanoate hydrochloride (SR2-088). The amine salt SR2-088 was obtained from SR2-087 (0.365 g, 0.695 mmol) as a white foam (0.280 g, 88%) by following the method used to make SR1-087. HPLC: >97% [$t_R$=10.8 min, 50% MeOH, 50% water (with 0.1% TFA), 20 min]. $^1$H NMR (500 MHz, DMSO-$d_6$) δ 8.24 (d, J=7.9 Hz, 1H), 7.81 (s, 3H), 7.44-7.40 (m, 2H), 7.40-7.35 (m, 2H), 7.33-7.28 (m, 1H), 7.11 (d, J=8.6 Hz, 2H), 6.89 (d, J=8.6 Hz, 2H), 5.04 (s, 2H), 4.41 (ddd, J=9.9, 7.9, 5.2 Hz, 1H), 3.58 (s, 3H), 2.94 (dd, J=13.8, 5.2 Hz, 1H), 2.91-2.82 (m, 1H), 2.76 (dd, J=13.9, 9.9 Hz, 1H), 1.95-1.90 (m, 2H), 1.88-1.80 (m, 2H), 1.64-1.54 (m, 1H), 1.54-1.42 (m, 2H), 1.29-1.11 (m, 2H), 0.98-0.79 (m, 2H). HRMS (ESI+): m/z $C_{25}H_{34}N_2O_4$ (M+H)$^+$425.2447; m/z $C_{25}H_{33}N_2O_4$Na (M+Na)$^+$447.2288; HPLC-MS (ESI+): m/z 425.2 [100%, (M+H)$^+$].

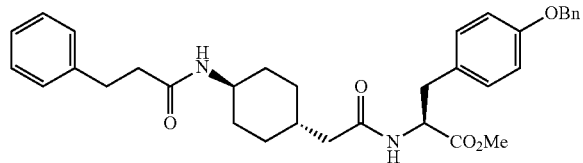 [SMILES: COC(=O)[C@H](Cc1ccc(OCc2ccccc2)cc1)NC(=O)C[C@H]1CC[C@H](NC(=O)CCc2ccccc2)CC1]

Methyl (S)-3-(4-(benzyloxy)phenyl)-2-(2-trans-4-(3-phenylpropanamido)cyclohexyl)-acetamido)propanoate (SR2-090). The amide SR2-090 was obtained as a white foam (0.054 g, 90%) from 3-phenylpropionyl chloride (0.019 µL, 0.130 mmol, 1.2 eq.) using general method E. HPLC: >98% [$t_R$=10.9 min, 70% MeOH, 30% water (with 0.1% TFA), 20 min]. $^1$H NMR (500 MHz, DMSO-$d_6$) δ 8.21 (d, J=7.9 Hz, 1H), 7.63 (d, J=7.9 Hz, 1H), 7.45-7.40 (m, 2H), 7.39-7.35 (m, 2H), 7.34-7.28 (m, 1H), 7.29-7.21 (m, 3H), 7.20-7.15 (m, 2H), 7.12 (d, J=8.7 Hz, 2H), 6.90 (d, J=8.7 Hz, 2H), 5.04 (s, 2H), 4.43 (ddd, J=10.0, 7.9, 5.1 Hz, 1H), 3.59 (s, 3H), 3.41 (m, 1H), 2.96 (dd, J=13.9, 5.2 Hz, 1H), 2.81-2.74 (m, 3H), 2.30 (dd, J=8.7, 6.9 Hz, 2H), 1.92 (dd, J=7.2, 4.0 Hz, 2H), 1.70-1.60 (m, 2H), 1.59-1.51 (m, 1H), 1.51-1.41 (m, 1H), 1.42-1.32 (m, 1H), 1.09-0.93 (m, 2H), 0.94-0.74 (m, 2H). HRMS (ESI+): m/z $C_{34}H_{41}N_2O_5$ (M+H)$^+$557.3013; m/z $C_{34}H_{40}N_2O_5$Na (M+Na)$^+$579.2831; HPLC-MS (ESI+): m/z 579.2 [100%, (M+Na)$^+$].

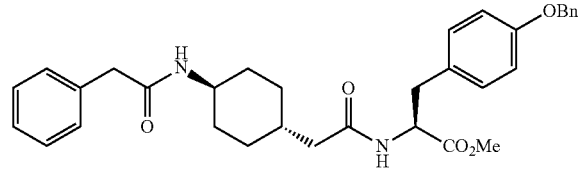 [SMILES: COC(=O)[C@H](Cc1ccc(OCc2ccccc2)cc1)NC(=O)C[C@H]1CC[C@H](NC(=O)Cc2ccccc2)CC1]

Methyl (S)-3-(4-(benzyloxy)phenyl)-2-(2-trans-4-(2-phenylacetamido)cyclohexyl)-acetamido)propanoate (SR2-091). The amide SR2-091 was obtained as a white solid (0.042 g, 72%) from phenylacetyl chloride (0.017 µL, 0.130 mmol, 1.2 eq.) using the general method E. HPLC: >97% [$t_R$=15.6 min, 65% MeOH, 35% water (with 0.1% TFA), 20 min]. $^1$H NMR (500 MHz, DMSO-$d_6$) δ 8.19 (d, J=8.0 Hz, 1H), 7.89 (d, J=7.9 Hz, 1H), 7.42-7.38 (m, 2H), 7.37-7.33 (m, 2H), 7.33-7.15 (m, 6H), 7.10 (d, J=8.6 Hz, 2H), 6.88 (d, J=8.7 Hz, 2H), 5.02 (s, 2H), 4.41 (ddd, J=10.1, 7.9, 5.1 Hz, 1H), 3.58 (s, 3H), 3.41-3.33 (m, 1H), 3.32 (s, 2H), 2.94 (dd, J=13.8, 5.1 Hz, 1H), 2.75 (dd, J=13.8, 10.0 Hz, 1H), 1.90 (dd, J=7.2, 4.6 Hz, 2H), 1.73-1.62 (m, 2H), 1.60-1.51 (m, 1H), 1.52-1.41 (m, 1H), 1.37 (m, 1H), 1.15-0.95 (m, 2H), 0.92-0.74 (m, 2H). HRMS (ESI+): m/z $C_{33}H_{39}N_2O_5$ (M+H)$^+$543.2863; m/z $C_{33}H_{38}N_2O_5$Na (M+Na)$^+$565.2677; HPLC-MS (ESI+): m/z 543.4 [60%, (M+H)$^+$], m/z 565.2 [100%, (M+Na)$^+$].

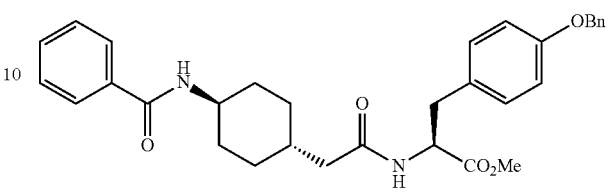

Methyl (S)-2-(2-trans-4-benzamidocyclohexyl)acetamido)-3-(4-(benzyloxy)phenyl)-propanoate (SR2-092). The amide SR2-092 was obtained as a white solid (0.051 g, 89%) from benzyl chloride (0.015 µL, 0.130 mmol, 1.2 eq.) using the general method E. HPLC: >97% [$t_R$=4.7 min, 75% MeOH, 25% water (with 0.1% TFA), 20 min]. $^1$H NMR (500 MHz, DMSO-$d_6$) δ 8.21 (d, J=8.0 Hz, 1H), 8.15 (d, J=8.0 Hz, 1H), 7.82-7.79 (m, 2H), 7.53-7.46 (m, 1H), 7.45-7.33 (m, 4H), 7.32-7.22 (m, 3H), 7.12 (d, J=8.6 Hz, 2H), 6.89 (d, J=8.7 Hz, 2H), 5.01 (s, 2H), 4.45 (ddd, J=10.2, 8.0, 5.0 Hz, 1H), 3.74-3.61 (m, 1H), 3.59 (s, 3H), 2.97 (dd, J=13.8, 5.1 Hz, 1H), 2.76 (dd, J=13.8, 10.2 Hz, 1H), 1.93 (dd, J=7.1, 4.0 Hz, 2H), 1.80-1.68 (m, 2H), 1.62-1.53 (m, 1H), 1.55-1.40 (m, 1H), 1.41-1.31 (m, 1H), 1.32-1.14 (m, 2H), 0.98-0.78 (m, 2H). HRMS (ESI+): m/z $C_{32}H_{36}N_2O_5$ (M+H)$^+$529.2698; m/z $C_{32}H_{36}N_2O_5$Na (M+Na)$^+$551.2514; HPLC-MS (ESI+): m/z 529.8 [70%, (M+H)$^+$], m/z 551.2 [100%, (M+Na)$^+$].

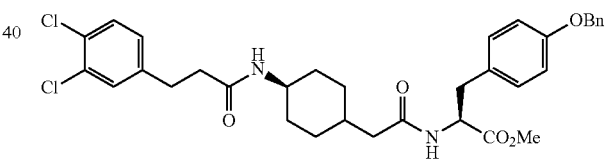

Methyl (S)-3-(4-(benzyloxy)phenyl)-2-(2-trans-4-(3-(3,4-dichlorophenyl)propanamido)-cyclohexyl)acetamido)propanoate (SR2-093). The amide SR2-093 was obtained as a white solid (0.059 g, 87%) from 3-(3,4-dichlorophenyl) propionic acid (0.028 g, 0.130 mmol, 1.2 eq.) by following the method used to make SR1-083. HPLC: >97% [$t_R$=6.2 min, 80% MeOH, 20% water (with 0.1% TFA), 20 min]. $^1$H NMR (500 MHz, DMSO-$d_6$) δ 8.19 (d, J=8.0 Hz, 1H), 7.63 (d, J=7.9 Hz, 1H), 7.49 (d, J=8.2 Hz, 1H), 7.44-7.38 (m, 3H), 7.38-7.32 (m, 2H), 7.32-7.27 (m, 1H), 7.16 (dd, J=8.2, 2.1 Hz, 1H), 7.11 (d, J=8.6 Hz, 2H), 6.88 (d, J=8.6 Hz, 2H), 5.02 (s, 2H), 4.41 (ddd, J=10.0, 7.9, 5.1 Hz, 1H), 3.58 (s, 3H), 3.43-3.33 (m, 1H), 2.94 (dd, J=13.8, 5.2 Hz, 1H), 2.80-2.73 (m, 3H), 2.29 (t, J=7.5 Hz, 2H), 1.90 (dd, J=7.1, 4.4 Hz, 2H), 1.70-1.57 (m, 2H), 1.57-1.49 (m, 1H), 1.49-1.32 (m, 2H), 1.07-0.90 (m, 2H), 0.92-0.73 (m, 2H). HRMS (ESI+): m/z $C_{34}H_{39}Cl_2N_2O_5$ (M+H)$^+$625.2221; m/z $C_{34}H_{38}Cl_2N_2O_5$Na (M+Na)$^+$647.2039; HPLC-MS (ESI+): m/z 647.2 [40%, (M+Na)$^+$].

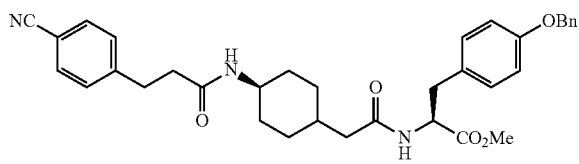

Methyl (S)-3-(4-(benzyloxy)phenyl)-2-(2-trans-4-(3-(4-cyanophenyl)propanamido)-cyclohexyl)acetamido)propanoate (SR2-094). The amide SR2-094 was obtained as a white solid (0.061 g, 97%) from 3-(4-cyanophenyl)propionic acid (0.023 g, 0.130 mmol, 1.2 eq.) by following the method used to make SR1-083. HPLC: >97% [$t_R$=6.6 min, 70% MeOH, 30% water (with 0.1% TFA), 20 min].]. $^1$H NMR (500 MHz, DMSO-$d_6$) δ 8.16 (d, J=7.9 Hz, 1H), 7.72 (d, J=8.3 Hz, 2H), 7.61 (d, J=7.9 Hz, 1H), 7.45-7.34 (m, 6H), 7.33-7.28 (m, 1H), 7.13 (d, J=8.6 Hz, 2H), 6.91 (d, J=8.7 Hz, 2H), 5.05 (s, 2H), 4.45 (ddd, J=9.9, 7.9, 5.2 Hz, 1H), 3.60 (s, 3H), 3.47-3.36 (m, 1H), 2.97 (dd, J=13.9, 5.2 Hz, 1H), 2.88 (t, J=7.6 Hz, 2H), 2.79 (dd, J=13.9, 9.9 Hz, 1H), 2.35 (t, J=7.6 Hz, 2H), 1.93 (dd, J=7.1, 3.5 Hz, 2H), 1.70-1.61 (m, 2H), 1.61-1.53 (m, 1H), 1.52-1.37 (m, 2H), 1.09-0.95 (m, 2H), 0.94-0.77 (m, 2H). HRMS (ESI+): m/z $C_{35}H_{40}N_3O_5$ (M+H)$^+$582.2958; m/z $C_{35}H_{39}N_3O_5Na$ (M+Na)$^+$604.2776; HPLC-MS (ESI+): m/z 582.4 [30%, (M+H)$^+$], m/z 604.2 [100%, (M+Na)$^+$].

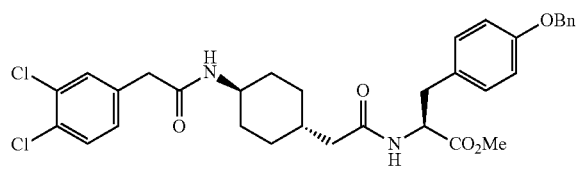 [SMILES: COC(=O)[C@H](Cc1ccc(OCc2ccccc2)cc1)NC(=O)C[C@H]1CC[C@H](NC(=O)Cc2ccc(Cl)c(Cl)c2)CC1]

Methyl (S)-3-(4-(benzyloxy)phenyl)-2-(2-trans-4-(2-(3,4-dichlorophenyl)acetamido)-cyclohexyl)acetamido)propanoate (SR2-100). The amide SR2-100 was obtained as a white solid (0.058 g, 88%) from 3-(3,4-dichlorophenyl)acetic acid (0.027 g, 0.130 mmol, 1.2 eq.) by following the method used to make SR1-083. HPLC: >97% [$t_R$=4.9 min, 80% MeOH, 20% water (with 0.1% TFA), 20 min]. $^1$H NMR (500 MHz, DMSO-$d_6$) δ 8.21 (d, J=7.9 Hz, 1H), 7.96 (d, J=7.9 Hz, 1H), 7.53 (d, J=8.3 Hz, 1H), 7.49 (d, J=2.0 Hz, 1H), 7.44-7.39 (m, 2H), 7.39-7.34 (m, 2H), 7.34-7.28 (m, 1H), 7.21 (dd, J=8.2, 2.1 Hz, 1H), 7.12 (d, J=8.6 Hz, 2H), 6.90 (d, J=8.7 Hz, 2H), 5.03 (s, 2H), 4.43 (ddd, J=10.0, 7.9, 5.1 Hz, 1H), 3.59 (s, 3H), 3.38 (s, 2H), 2.96 (dd, J=13.8, 5.1 Hz, 1H), 2.77 (dd, J=13.8, 10.0 Hz, 1H), 1.92 (dd, J=7.1, 5.0 Hz, 2H), 1.73-1.63 (m, 2H), 1.60-1.52 (m, 1H), 1.53-1.42 (m, 1H), 1.42-1.33 (m, 1H), 1.19-0.98 (m, 2H), 0.95-0.72 (m, 2H). HRMS (ESI+): m/z $C_{33}H_{36}Cl_2N_2O_5$ (M)$^+$ 610.1999; m/z $C_{33}H_{36}Cl_2N_2O_5Na$ (M+Na)$^+$633.1890; HPLC-MS (ESI+): m/z 633.1 [80%, (M+Na)$^+$].

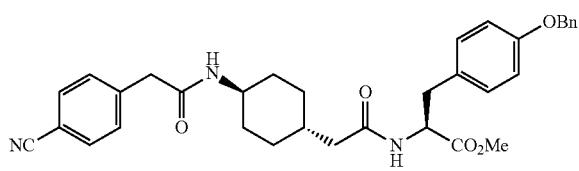 [SMILES: COC(=O)[C@H](Cc1ccc(OCc2ccccc2)cc1)NC(=O)C[C@H]1CC[C@H](NC(=O)Cc2ccc(C#N)cc2)CC1]

Methyl (S)-3-(4-(benzyloxy)phenyl)-2-(2-trans-4-(2-(4-cyanophenyl)acetamido)cyclohexyl)-acetamido)propanoate (SR2-108). The amide SR2-108 was obtained as a white solid (0.059 g, 96%) using (4-cyanophenyl)acetic acid (0.021 g, 0.130 mmol, 1.2 eq.) by following the methods used to make SR1-083. HPLC: >98% [$t_R$=5.6 min, 70% MeOH, 30% water (with 0.1% TFA), 20 min]. $^1$H NMR (500 MHz, DMSO-$d_6$) δ 8.19 (d, J=8.0 Hz, 1H), 7.99 (d, J=7.8 Hz, 1H), 7.72 (d, J=8.3 Hz, 2H), 7.44-7.37 (m, 4H), 7.37-7.33 (m, 2H), 7.32-7.26 (m, 1H), 7.10 (d, J=8.6 Hz, 2H), 6.88 (d, J=8.7 Hz, 2H), 5.01 (s, 2H), 4.41 (ddd, J=10.1, 7.9, 5.1 Hz, 1H), 3.58 (s, 3H), 3.45 (s, 2H), 3.36 (m, 1H), 2.94 (dd, J=13.8, 5.1 Hz, 1H), 2.75 (dd, J=13.8, 10.0 Hz, 1H), 1.90 (dd, J=7.1, 4.8 Hz, 2H), 1.74-1.64 (m, 2H), 1.54 (m, 1H), 1.53-1.41 (m, 1H), 1.41-1.31 (m, 1H), 1.16-0.97 (m, 2H), 0.93-0.74 (m, 2H). HRMS (ESI+): m/z $C_{34}H_{38}N_3O_5$ (M+H)$^+$568.2802; m/z $C_{34}H_{37}N_3O_5Na$ (M+Na)$^+$590.2620; HPLC-MS (ESI+): m/z 568.2 [100%, (M+H)$^+$], m/z 590.2 [100%, (M+Na)$^+$].

Synthesis of D-Tyrosine Containing Analogs

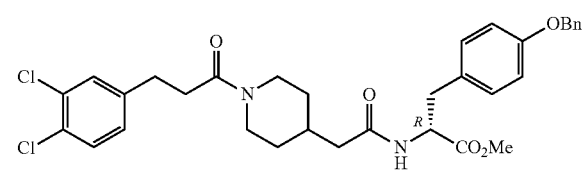

Methyl (R)-3-(4-(benzyloxy)phenyl)-2-(2-(1-(3-(3,4-dichlorophenyl)propanoyl)piperidin-4-yl)acetamido)propanoate (SR2-134). The amide SR2-134 was obtained as a white foam (0.140 g, 97%) from 3-(3,4-dichlorophenyl)propionic acid (0.029 g, 0.134 mmol, 1.2 eq.) and SR2-132 (the enantiomer of SR1-085 made in the same way as SR1-085) using general method D. HPLC: >98% [$t_R$=6.4 min, 80% MeOH, 20% water (with 0.1% TFA), 20 min]. HRMS (ESI+): m/z $C_{33}H_{37}Cl_2N_2O_5$ (M+H)$^+$611.2081; m/z $C_{33}H_{36}Cl_2N_2O_5Na$ (M+Na)$^+$633.1899 found 633.1899; HPLC-MS (ESI+): m/z 633.2 [100%, (M+Na)$^+$].

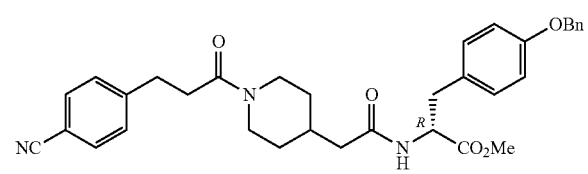

Methyl (R)-3-(4-(benzyloxy)phenyl)-2-(2-(1-(3-(4-cyanophenyl)propanoyl)piperidin-4-yl)acetamido)propanoate (SR2-135). The amide SR2-135 was obtained as a white foam (0.063 g, 99%) from 3-(4-cyanophenyl)propionic acid (0.024 g, 0.134 mmol, 1.2 eq.) and SR2-132 (0.050 g, 0.112 mmol) using the method D. $^1$H NMR (500 MHz, DMSO-$d_6$) δ 8.25 (d, J=8.0 Hz, 1H), 7.55-7.48 (m, 2H), 7.47-7.35 (m, 5H), 7.34-7.29 (m, 1H), 7.24 (dd, J=8.7, 7.2 Hz, 1H), 7.13 (d, J=8.6 Hz, 2H), 6.91 (dd, J=8.6, 1.9 Hz, 2H), 5.06 (s, 1H), 5.04 (s, 1H), 4.46 (ddd, J=13.2, 10.2, 5.2 Hz, 1H), 4.32-4.21 (m, 1H), 3.82-3.70 (m, 1H), 3.61 (s, 3H), 2.98 (dd, J=13.8, 5.1 Hz, 1H), 2.89-2.74 (m, 4H), 2.68-2.53 (m, 2H), 2.47-2.35 (m, 1H), 1.96 (d, J=7.2 Hz, 2H), 1.83-1.64 (m, 1H), 1.48 (m, 1H), 1.37-1.27 (m, 1H), 0.97-0.68 (m, 2H). HPLC: >97% [$t_R$=6.5 min, 70% MeOH, 30% water (with 0.1% TFA), 20 min]. HRMS (ESI+): m/z $C_{34}H_{38}N_3O_5$ (M+H)$^+$ 568.2805; m/z $C_{34}H_{37}N_3O_5Na$ (M+Na)$^+$590.2628; HPLC-MS (ESI+): m/z 568.2 [40% (M+H)$^+$], m/z 599.2 [100%, (M+Na)$^+$].

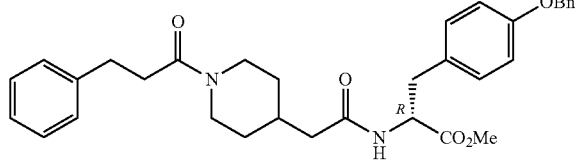

Methyl (R)-3-(4-(benzyloxy)phenyl)-2-(2-(1-(3-phenylpropanoyl)piperidin-4-yl)acetamido)propanoate (SR3-138). The N-phenylpropanoyl derivative SR3-138 (0.059 g, 97%) was prepared from 3-phenylpropionyl chloride (0.020 µL, 0.134 mmol, 1.2 eq.) and SR2-132 (0.050 g, 0.112 mmol) using the general method A. HPLC: >99% [$t_R$=9.6 min, 70% MeOH, 30% water (with 0.1% TFA), 20 min]. $^1$H NMR (500 MHz, DMSO-d$_6$) δ 8.25 (d, J=8.0 Hz, 1H), 7.43 (dd, J=12.2, 7.2 Hz, 2H), 7.40-7.35 (m, 2H), 7.32 (m, 1H), 7.29-7.20 (m, 4H), 7.21-7.15 (m, 1H), 7.13 (d, J=8.3 Hz, 2H), 6.91 (d, J=8.6 Hz, 2H), 5.06 (s, 1H), 5.04 (s, 1H), 4.46 (ddd, J=12.8, 9.8, 4.8 Hz, 1H), 4.35-4.25 (m, 1H), 3.80-3.69 (m, 1H), 3.61 (s, 3H), 2.98 (dd, J=13.8, 5.1 Hz, 1H), 2.91-2.72 (m, 4H), 2.67-2.52 (m, 2H), 2.48-2.35 (m, 1H), 1.96 (d, J=7.2 Hz, 2H), 1.81-1.64 (m, 1H), 1.51-1.43 (m, 1H), 1.35-1.23 (m, 1H), 0.95-0.71 (m, 2H). HRMS (ESI+): m/z $C_{33}H_{38}N_2O_5$ (M+H)$^+$543.2853; m/z $C_{33}H_{38}N_2O_5Na$ (M+Na)$^+$565.2682. HPLC-MS (ESI+): m/z 543.4 [30%, (M+H)$^+$], 565.2 [100%, (M+Na)$^+$].

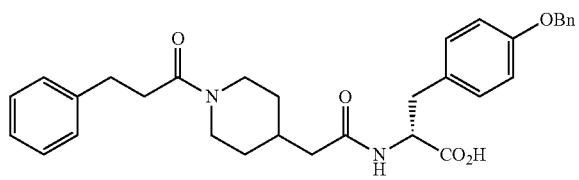

(R)-3-(4-(benzyloxy)phenyl)-2-(2-(1-(3-phenylpropanoyl)piperidin-4-yl)acetamido)propan-oic acid (SR2-148). The carboxylic acid SR2-148 (25.0 mg, 95%), isolated as a white foam was prepared from the methyl ester SR3-138 (27.0 mg) by the same method used to make SR2-022. HPLC: >98% [$t_R$=4.4 min, 70% MeOH, 30% water (with 0.1% TFA), 20 min]. $^1$H NMR (500 MHz, DMSO-d$_6$) δ 12.63 (bs, 1H), 8.10 (d, J=8.3 Hz, 1H), 7.47-7.34 (m, 4H), 7.33-7.29 (m, 1H), 7.28-7.20 (m, 4H), 7.18 (m, 1H), 7.14 (d, J=8.5 Hz, 2H), 6.91 (d, J=8.6 Hz, 2H), 5.06 (s, 1H), 5.03 (s, 1H), 4.41 (ddd, J=9.7, 6.0, 4.1 Hz, 1H), 4.34-4.22 (m, 1H), 3.78-3.66 (m, 1H), 3.01 (dd, J=14.3, 3.6 Hz, 1H), 2.89-2.69 (m, 4H), 2.64-2.51 (m, 2H), 2.47-2.34 (m, 1H), 1.95 (d, J=7.2 Hz, 2H), 1.81-1.64 (m, 1H), 1.54-1.38 (m, 1H), 1.34-1.20 (m, 1H), 0.93-0.71 (m, 2H). HRMS (ESI+): m/z $C_{32}H_{37}N_2O_5$ (M+H)$^+$529.2698; m/z $C_{32}H_{36}N_2O_5Na$ (M+Na)$^+$551.2514. HPLC-MS (ESI+): m/z 529.2 [80% (M+H)$^+$], m/z 551.2 [100%, (M+Na)$^+$], HPLC-MS (ESI−): m/z 527.3 [100% (M−H)$^-$].

Synthesis of Tyr(OMe) Containing Derivatives

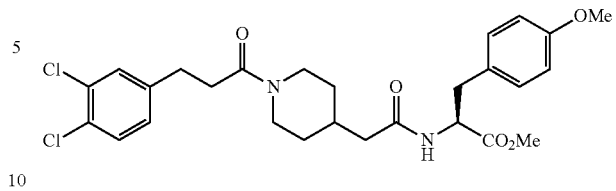

Methyl (S)-2-(2-(1-(3-(3,4-dichlorophenyl)propanoyl)piperidin-4-yl)acetamido)-3-(4-methoxyphenyl)propanoate (SR2-136). The amide SR2-136 was obtained as a white foam (0.140 g, 97%) from the HCl salt of methyl (S)-3-(4-methoxyphenyl)-2-(2-(piperidin-4-yl)acetamido)propanoate (0.100 g, 0.269 mmol) and 3-(3,4-dichlorophenyl)propionic acid (0.071 g, 0.323 mmol, 1.2 eq.) using general method D. HPLC: >94% [$t_R$=6.5 min, 70% MeOH, 30% water (with 0.1% TFA), 20 min]. $^1$H NMR (500 MHz, DMSO-d$_6$) δ 8.24 (d, J=8.0 Hz, 1H), 7.55-7.50 (m, 2H), 7.25 (dt, J=8.4, 2.5 Hz, 1H), 7.12 (d, J=8.5 Hz, 2H), 6.82 (d, J=8.5 Hz, 2H), 4.49-4.40 (m, 1H), 4.30-4.20 (m, 1H), 3.80-3.70 (m, 1H), 3.71 (s, 1.5H), 3.68 (s, 1.5H), 3.60 (s, 3H), 2.97 (dd, J=13.8, 5.1 Hz, 1H), 2.89-2.73 (m, 4H), 2.68-2.53 (m, 2H), 2.47-2.36 (m, 1H), 1.96 (d, J=7.6 Hz, 2H), 1.81-1.66 (m, 1H), 1.54-1.43 (m, 1H), 1.36-1.22 (m, 1H), 0.97-0.66 (m, 2H). HRMS (ESI+): m/z $C_{27}H_{33}Cl_2N_2O_5$ (M+H)$^+$535.1757; m/z $C_{27}H_{32}Cl_2N_2O_5Na$ (M+Na)$^+$557.1582; HPLC-MS (ESI+): m/z 535.2 [30% (M+H)$^+$], m/z 557.2 [100%, (M+Na)$^+$].

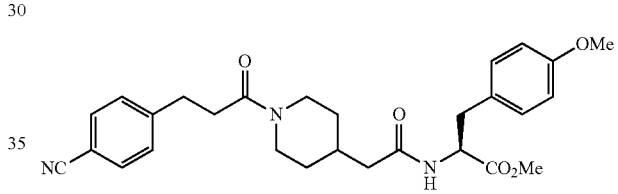

Methyl (S)-2-(2-(1-(3-(4-cyanophenyl)propanoyl)piperidin-4-yl)acetamido)-3-(4-methoxy-phenyl)propanoate (SR2-137). The amide SR2-136 was obtained as a white foam (0.140 g, 97%) from the HCl salt of methyl (S)-3-(4-methoxyphenyl)-2-(2-(piperidin-4-yl)acetamido)propanoate (0.100 g, 0.269 mmol) and 3-(4-cyanophenyl)propionic acid (0.071 g, 0.323 mmol, 1.2 eq.) using general method D. HPLC: >98% [$t_R$=4.7 min, 60% MeOH, 40% water (with 0.1% TFA), 20 min]. $^1$H NMR (500 MHz, DMSO-d$_6$) δ 8.25 (d, J=8.0 Hz, 1H), 7.74 (dd, J=8.3, 2.4 Hz, 2H), 7.46 (dd, J=8.2, 2.5 Hz, 2H), 7.13 (d, J=8.5 Hz, 2H), 6.83 (d, J=8.5 Hz, 2H), 4.45 (m, 1H), 4.25 (m, 1H), 3.84-3.70 (m, 1H), 3.72 (s, 1.5H), 3.68 (s, 1.5H), 3.61 (s, 3H), 2.98 (dd, J=13.8, 5.1 Hz, 1H), 2.93-2.81 (m, 3H), 2.77 (dd, J=13.8, 10.1 Hz, 1H), 2.67-2.58 (m, 2H), 2.48-2.35 (m, 1H), 1.96 (d, J=7.2 Hz, 2H), 1.81-1.68 (m, 1H), 1.54-1.43 (m, 1H), 1.37-1.21 (m, 1H), 0.99-0.70 (m, 2H). HRMS (ESI+): m/z $C_{28}H_{34}N_3O_5$ (M+H)$^+$492.2494; m/z $C_{28}H_{33}N_3O_5Na$ (M+Na)$^+$514.2317; HPLC-MS (ESI+): m/z 492.2 [80% (M+H)$^+$], m/z 514.2 [100%, (M+Na)$^+$].

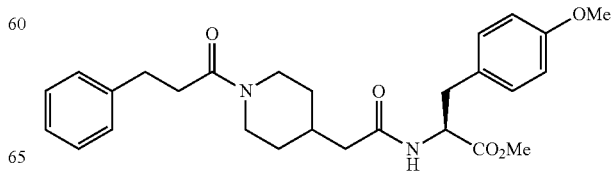

Methyl (S)-3-(4-methoxyphenyl)-2-(2-(1-(3-phenylpropanoyl)piperidin-4-yl)acetamido)-propanoate (SR2-139). The amide SR2-139 was obtained as a white foam (0.101 g, 81%) from HCl salt of methyl (S)-3-(4-methoxyphenyl)-2-(2-(piperidin-4-yl)acetamido)propanoate (0.100 g, 0.269 mmol) and 3-phenylpropionyl chloride (0.048 μl, 0.323 mmol, 1.2 eq.) using general method D. HPLC: >99% [$t_R$=4.7 min, 70% MeOH, 30% water (with 0.1% TFA), 20 min]. $^1$H NMR (500 MHz, DMSO-$d_6$) δ 8.24 (d, J=8.0 Hz, 1H), 7.32-7.21 (m, 4H), 7.18 (td, J=7.0, 1.8 Hz, 1H), 7.13 (d, J=8.5 Hz, 2H), 6.83 (d, J=8.2 Hz, 2H), 4.45 (ddd, J=12.7, 9.6, 4.7 Hz, 1H), 4.33-4.22 (m, 1H), 3.83-3.70 (m, 1H), 3.72 (s, 1.5H), 3.67 (s, 1.5H), 3.61 (s, 3H), 2.98 (dd, J=13.8, 5.2 Hz, 1H), 2.90-2.73 (m, 4H), 2.57 (td, J=7.5, 3.1 Hz, 2H), 2.48-2.35 (m, 1H), 1.95 (d, J=7.5 Hz, 2H), 1.80-1.65 (m, 1H), 1.51-1.44 (m, 1H), 1.34-1.22 (m, 1H), 0.95-0.71 (m, 2H). HRMS (ESI+): m/z $C_{27}H_{35}N_2O_5$ (M+H)$^+$467.2536; m/z $C_{27}H_{34}N_2O_5Na$ (M+Na)$^+$489.2362; HPLC-MS (ESI+): m/z 467.2 [50% (M+H)$^+$], m/z 489.2 [100%, (M+Na)$^+$].

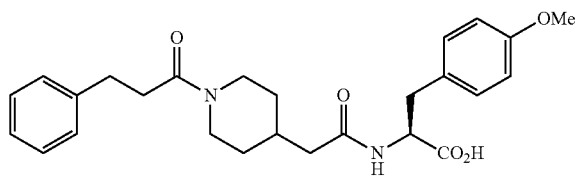 [SMILES: COc1ccc(C[C@H](NC(=O)CC2CCN(C(=O)CCc3ccccc3)CC2)C(=O)O)cc1]

(S)-3-(4-methoxyphenyl)-2-(2-(1-(3-phenylpropanoyl)piperidin-4-yl)acetamido)propanoic acid (SR2-149). The carboxylic acid SR2-149 (0.048 g, 98%) was prepared from the methyl ester SR2-139 (0.050 g, 0.107 mmol) by following the same method used to make SR2-022. HPLC: >99% [$t_R$=3.7 min, 70% MeOH, 30% water (with 0.1% TFA), 20 min]. $^1$H NMR (500 MHz, DMSO-$d_6$) δ 12.42 (bs, 1H), 8.07 (d, J=8.3 Hz, 1H), 7.32-7.20 (m, 4H), 7.17 (m, 1H), 7.13 (d, J=8.6 Hz, 2H), 6.82 (d, J=8.2 Hz, 2H), 4.44-4.34 (m, 1H), 4.25 (m, 1H), 3.79-3.67 (m, 1H), 3.71 (s, 1.5H), 3.66 (s, 1.5H), 3.00 (dd, J=13.8, 4.6 Hz, 1H), 2.88-2.67 (m, 4H), 2.56 (td, J=7.5, 3.0 Hz, 2H), 2.47-2.33 (m, 1H), 1.94 (d, J=7.2 Hz, 2H), 1.78-1.65 (m, 1H), 1.52-1.39 (m, 1H), 1.32-1.19 (m, 1H), 0.94-0.69 (m, 2H). HRMS (ESI+): m/z $C_{26}H_{33}N_2O_5$ (M+H)$^+$453.2383; m/z $C_{26}H_{32}N_2O_5Na$ (M+Na)$^+$475.2207; HPLC-MS (ESI+): m/z 453.2 [50% (M+H)$^+$], m/z 475.2 [100%, (M+Na)$^+$].

Synthesis of Urea Derivarives

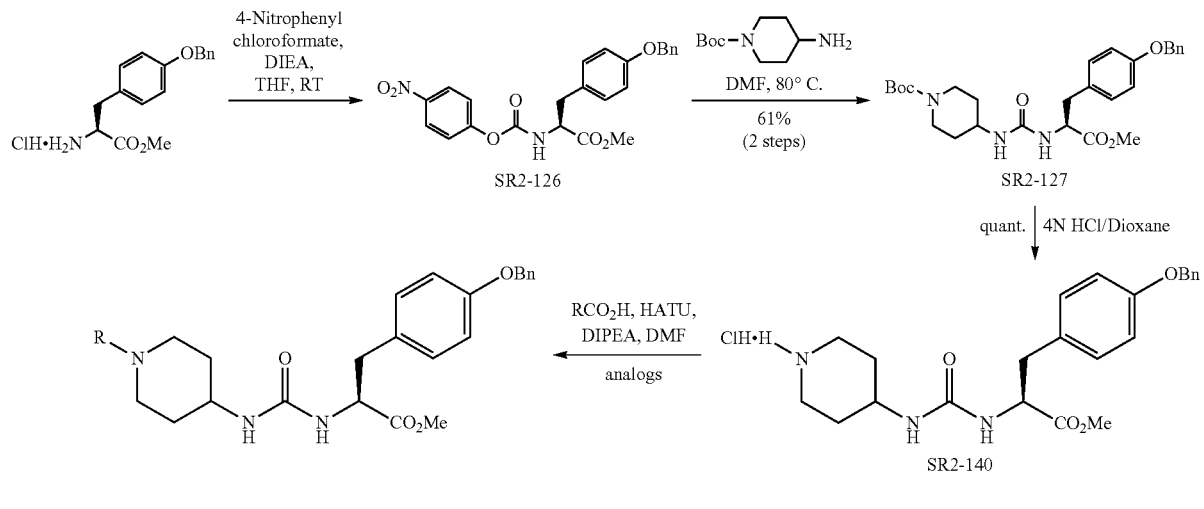

tert-Butyl (S)-4-(3-(3-(4-(benzyloxy)phenyl)-1-methoxy-1-oxopropan-2-yl)ureido)piperidine-1-carboxylate (SR2-127). The amine salt H-Tyr(OBn)OMe.HCl (6.215 mmol, 2.00 g) was dissolved in THF (40 mL). To this solution was added triethylamine (28.645 mmol, 2.60 mL) and 4-nitrophenylchloroformate (9.323 mmol, 1.879 g). The resulting mixture and stirred at room temperature for 5 h. The solvent was removed under reduced pressure and the resulting residue dissolved in DCM (30 mL). The organic layer was washed with water (2×20 mL) and evaporated to afford SR2-126 as a white solid, which was used for the next step directly without further purification. SR2-126 was dissolved in DMF (20 mL) and 1-Boc-4-aminopiperidine (9.322 mmol, 1.867 g) added. The mixture was heated at 80° C. for 16 h and concentrated under reduced pressure. The resulting residue was dissolved in EtOAc (50 mL) and washed with sat. $NH_4C_1$ (3×25 mL). Purification by flash column chromatography using MeOH/DCM (0-10%) as eluent afforded SR2-127 as a white foam (1.953 g, 61%). $^1$H NMR (500 MHz, DMSO-$d_6$) δ 7.44 (m, 2H), 7.40 (m, 2H), 7.33 (m, 1H), 7.06 (d, J=8.6 Hz, 2H), 6.93 (d, J=8.6 Hz, 2H), 6.14 (d, J=7.8 Hz, 1H), 6.02 (d, J=8.2 Hz, 1H), 5.07 (s, 2H), 4.35 (td, J=7.9, 5.6 Hz, 1H), 3.75 (m, 2H), 3.59 (s, 3H), 3.55-3.43 (m, 1H), 2.89 (dd, J=9.8, 4.0 Hz, 1H), 2.89-2.76 (m, 2H), 2.82 (dd, J=13.8, 7.7 Hz, 1H), 1.72-1.63 (m, 2H), 1.39 (s, 9H), 1.21-1.06 (m, 2H). HRMS (ESI+): m/z $C_{28}H_{38}N_3O_6$ (M+H)$^+$512.2745; m/z $C_{28}H_{37}N_3O_6Na$ (M+Na)$^+$534.2567; HPLC-MS (ESI+): m/z 512.3 [60% (M+H)$^+$], m/z 534.3 [100%, (M+Na)$^+$].

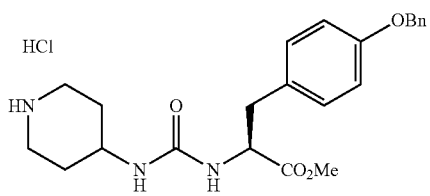 [SMILES: COC(=O)[C@H](Cc1ccc(OCc2ccccc2)cc1)NC(=O)NC1CCNCC1 ; Cl]

Methyl (S)-3-(4-(benzyloxy)phenyl)-2-(3-(piperidin-4-yl)ureido)propanoate hydrochloride (SR2-140). The N-Boc-piperidine SR2-127 (0.603 mmol, 0.309 g) was dissolved in 4N HCl/Dioxane (3.5 mL) and stirred for 2 h at room temperature. The mixture was concentrated under reduced pressure to afford SR2-140 as a white solid (0.267 g, 99%).

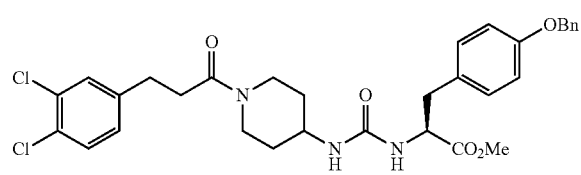 [SMILES: COC(=O)[C@H](Cc1ccc(OCc2ccccc2)cc1)NC(=O)NC1CCN(C(=O)CCc2ccc(Cl)c(Cl)c2)CC1]

Methyl (S)-3-(4-(benzyloxy)phenyl)-2-(3-(1-(3-(3,4-dichlorophenyl)propanoyl)piperidin-4-yl)ureido)propanoate (SR2-141). The amide SR2-141 was obtained as a white foam (0.048 g, 66%) from the amine salt SR2-140 (0.050 g, 0.112 mmol) and 3-(3,4-dichlorophenyl)propionic acid (0.029 g, 0.134 mmol, 1.2 eq.) using the general method D. HPLC: >98% [$t_R$=6.0 min, 70% MeOH, 30% water (with 0.1% TFA), 20 min]. $^1$H NMR (500 MHz, DMSO-$d_6$) δ 7.55 (bs, 1H), 7.52 (d, J=8.2 Hz, 1H), 7.46-7.42 (m, 2H), 7.39 (m, 2H), 7.33 (m, 1H), 7.25 (dd, J=8.4, 2.0 Hz, 1H), 7.06 (d, J=8.6 Hz, 2H), 6.92 (d, J=8.6 Hz, 2H), 6.15 (d, J=7.8 Hz, 1H), 6.04 (dd, J=8.2, 2.7 Hz, 1H), 5.07 (s, 2H), 4.35 (td, J=7.9, 5.6 Hz, 1H), 4.10 (m, 1H), 3.78-3.69 (m, 1H), 3.59 (s, 3H), 3.57-3.49 (m, 1H), 3.12-3.01 (m, 1H), 2.89 (dd, J=13.8, 5.6 Hz, 1H), 2.86-2.72 (m, 4H), 2.68-2.60 (m, 2H), 1.77-1.64 (m, 2H), 1.27-1.04 (m, 2H). HRMS (ESI+): m/z $C_{32}H_{36}Cl_2N_3O_5$ (M+H)$^+$612.2024; m/z $C_{32}H_{35}Cl_2N_3O_5Na$ (M+Na)$^+$634.1849; HPLC-MS (ESI+): m/z 634.2 [80%, (M+Na)$^+$].

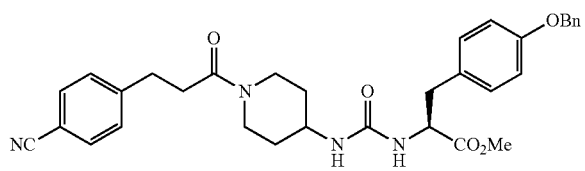 [SMILES: COC(=O)[C@H](Cc1ccc(OCc2ccccc2)cc1)NC(=O)NC1CCN(C(=O)CCc2ccc(C#N)cc2)CC1]

Methyl (S)-3-(4-(benzyloxy)phenyl)-2-(3-(1-(3-(4-cyanophenyl)propanoyl)piperidin-4-yl)ureido)-propanoate (SR2-142). The amide SR2-142 was obtained as a white foam (0.049 g, 77%) from the amine salt SR2-140 (0.050 g, 0.112 mmol) and 3-(4-cyanophenyl)propionic acid (0.029 g, 0.134 mmol, 1.2 eq.) using the general method D. HPLC: >99% [$t_R$=6.4 min, 70% MeOH, 30% water (with 0.1% TFA), 20 min]. $^1$H NMR (500 MHz, DMSO-$d_6$) δ 7.74 (d, J=8.2 Hz, 2H), 7.49-7.42 (m, 4H), 7.39 (td, J=7.5, 1.6 Hz, 2H), 7.35-7.31 (m, 1H), 7.06 (d, J=8.6 Hz, 2H), 6.92 (d, J=8.6 Hz, 2H), 6.15 (d, J=7.7 Hz, 1H), 6.03 (dd, J=8.2, 2.5 Hz, 1H), 5.07 (s, 2H), 4.35 (td, J=7.8, 5.6 Hz, 1H), 4.10 (m, 1H), 3.72 (m, 1H), 3.59 (s, 3H), 3.57-3.49 (m, 1H), 3.06 (td, J=14.6, 3.7 Hz, 1H), 2.94-2.85 (m, 3H), 2.82 (dd, J=13.8, 7.7 Hz, 1H), 2.77 (dt, J=14.0, 7.3 Hz, 1H), 2.71-2.61 (m, 2H), 1.76-1.64 (m, 2H), 1.24-1.02 (m, 2H). HRMS (ESI+): m/z $C_{32}H_{37}N_4O_5$ (M+H)$^+$569.2757; m/z $C_{32}H_{36}N_4O_5Na$ (M+Na)$^+$591.2577; HPLC-MS (ESI+): m/z 569.2 [30%, (M+H)$^+$]; m/z 591.2 [100%, (M+Na)$^+$].

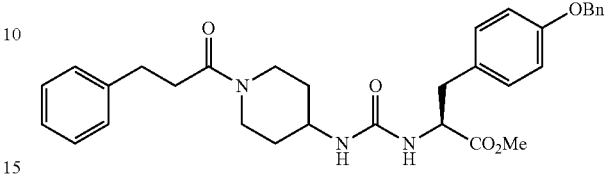

Methyl (S)-3-(4-(benzyloxy)phenyl)-2-(3-(1-(3-phenylpropanoyl)piperidin-4-yl)ureido)-propanoate (SR2-143). The amide SR2-143 was obtained as a white foam (0.048 g, 79%) from the amine salt SR2-140 (0.050 g, 0.112 mmol) and 3-phenylpropionic acid (0.029 g, 0.134 mmol, 1.2 eq.) using by following the general method D. HPLC: >99% [$t_R$=4.7 min, 70% MeOH, 30% water (with 0.1% TFA), 20 min]. $^1$H NMR (500 MHz, DMSO-$d_6$) δ 7.44 (d, J=7.6 Hz, 2H), 7.39 (td, J=7.6, 2.2 Hz, 2H), 7.36-7.30 (m, 1H), 7.31-7.21 (m, 4H), 7.18 (m, 1H), 7.06 (d, J=8.3 Hz, 2H), 6.93 (d, J=8.2 Hz, 2H), 6.13 (d, J=7.7 Hz, 1H), 6.04 (dd, J=7.9, 2.6 Hz, 1H), 5.07 (s, 2H), 4.35 (m, 1H), 4.12 (m, 1H), 3.75-3.66 (m, 1H), 3.59 (s, 3H), 3.53 (m, 1H), 3.05 (dd, J=14.3, 10.8 Hz, 1H), 2.89 (dd, J=13.8, 5.6 Hz, 1H), 2.85-2.71 (m, 4H), 2.65-2.56 (m, 2H), 1.73-1.63 (m, 2H), 1.22-0.97 (m, 2H). HRMS (ESI+): m/z $C_{32}H_{38}N_3O_5$ (M+H)$^+$544.2814; m/z $C_{32}H_{37}N_3O_5Na$ (M+Na)$^+$566.2633; HPLC-MS (ESI+): m/z 544.2 [30%, (M+H)$^+$]; m/z 566.2 [100%, (M+Na)$^+$].

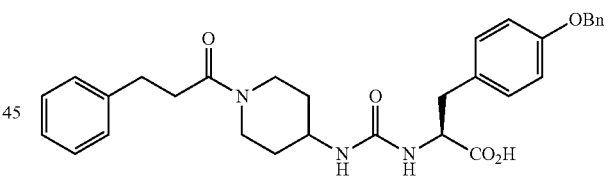

(S)-3-(4-(Benzyloxy)phenyl)-2-(3-(1-(3-phenylpropanoyl)piperidin-4-yl)ureido)propanoic acid (SR2-147). The carboxylic acid SR2-147 was obtained from SR2-143 as a white foam (0.031 g, 80%) by following the method reported for the synthesis of SR2-022. $^1$H NMR (500 MHz, DMSO-$d_6$) δ 12.10 (bs, 1H), 8.20 (d, J=2.2 Hz, 2H), 7.45-7.33 (m, 4H), 7.33-7.21 (m, 5H), 7.20-7.12 (m, 1H), 7.04 (d, J=8.4 Hz, 2H), 6.90 (dd, J=8.3, 4.8 Hz, 2H), 5.06 (d, J=4.5 Hz, 2H), 4.49-4.35 (m, 1H), 4.26 (t, J=4.5 Hz, 1H), 3.89-3.69 (m, 2H), 2.95-2.76 (m, 5H), 2.60 (dd, J=8.8, 6.7 Hz, 2H), 2.49-2.36 (m, 1H), 1.99-1.86 (m, 1H), 1.86-1.69 (m, 1H), 1.25-1.08 (m, 2H). HPLC: >96% [$t_R$=4.9 min, 75% MeOH, 25% water (with 0.1% TFA), 20 min]. HRMS (ESI+): m/z $C_{31}H_{36}N_3O_5$ (M+H)$^+$530.2648; m/z $C_{31}H_{35}N_3O_5Na$ (M+Na)$^+$552.2480; HPLC-MS (ESI+): m/z 530.2 [30%, (M+H)$^+$]; m/z 552.2 [40%, (M+Na)$^+$].

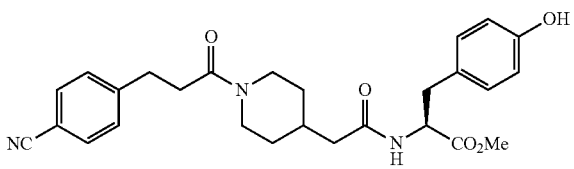 [SMILES: COC(=O)[C@H](Cc1ccc(O)cc1)NC(=O)CC1CCN(C(=O)CCc2ccc(C#N)cc2)CC1]

Methyl (2-(1-(3-(4-cyanophenyl)propanoyl)piperidin-4-yl)acetyl)-L-tyrosinate (SR2-150). The phenol SR2-150 was obtained as a white foam (0.014 g, 87%) from the benzyl ether SR2-142 (0.019 g, 0.033 mmol) by following the method used to make SR2-014. HPLC: >96% [$t_R$=4.6 min, 50% MeOH, 50% water (with 0.1% TFA), 20 min]. $^1$H NMR (500 MHz, DMSO-$d_6$) δ 9.23 (s, 1H), 8.22 (dd, J=7.9, 4.6 Hz, 1H), 7.74 (dd, J=8.2, 1.9 Hz, 2H), 7.46 (d, J=7.4 Hz, 2H), 6.99 (d, J=8.2 Hz, 2H), 6.65 (d, J=8.4 Hz, 2H), 4.45-4.36 (m, 1H), 4.32-4.23 (m, 1H), 3.76 (m, 1H), 3.60 (s, 3H), 2.97-2.81 (m, 4H), 2.79-2.68 (m, 1H), 2.68-2.58 (m, 2H), 2.46-2.36 (m, 1H), 2.00-1.93 (m, 2H), 1.81-1.69 (m, 1H), 1.55-1.44 (m, 1H), 1.37 (m, 1H), 0.98-0.73 (m, 2H). HRMS (ESI+): m/z $C_{27}H_{32}N_3O_5$ (M+H)$^+$478.2343; m/z $C_{27}H_{31}N_3O_5Na$ (M+Na)$^+$500.2161; HPLC-MS (ESI−): m/z 476.2 [100%, (M−H)$^−$]; m/z 500.2 [20%, (M+Na)$^+$].

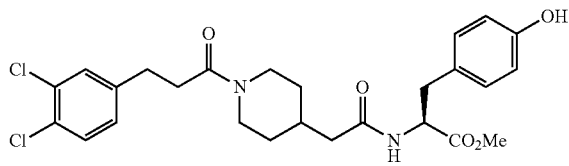 [SMILES: COC(=O)[C@H](Cc1ccc(O)cc1)NC(=O)CC1CCN(C(=O)CCc2ccc(Cl)c(Cl)c2)CC1]

Methyl (2-(1-(3-(3,4-dichlorophenyl)propanoyl)piperidin-4-yl)acetyl)-L-tyrosinate (SR2-151). The phenol SR2-151 was obtained as a white foam (0.011 g, 98%) from the benzyl ether SR2-030 (0.019 g, 0.033 mmol) by following the method used to make SR2-014. HPLC: >97% [$t_R$=9.5 min, 40% MeOH, 60% water (with 0.1% TFA), 20 min]. $^1$H NMR (500 MHz, DMSO-$d_6$) δ 9.23 (s, 1H), 8.22 (dd, J=7.9, 4.6 Hz, 1H), 7.57-7.48 (m, 1H), 7.32-7.20 (m, 1H), 7.18 (m, 1H), 6.99 (d, J=8.0 Hz, 2H), 6.65 (d, J=8.0 Hz, 2H), 4.41 (m, 1H), 4.33-4.24 (m, 1H), 3.76 (m, 1H), 3.60 (s, 3H), 2.97-2.67 (m, 6H), 2.67-2.54 (m, 1H), 2.47-2.35 (m, 1H), 2.04-1.91 (m, 2H), 1.83-1.68 (m, 1H), 1.54-1.44 (m, 1H), 1.42-1.28 (m, 1H), 0.96-0.75 (m, 2H). HRMS (ESI+): m/z $C_{26}H_{31}Cl_2N_2O_5$ (M+H)$^+$521.1612; m/z $C_{26}H_{30}Cl_2N_2O_5Na$ (M+Na)$^+$543.1429; HPLC-MS (ESI+): m/z 521.4 [40%, (M+H)$^−$]; m/z 543.0 [100%, (M+Na)$^+$].

Synthesis of C-Terminal Carboxylic Acid Derivatives

General Method F: Hydrolysis of C-Terminal Methyl Esters:

Selected methyl ester derivative (0.020-0.050 g, 0.045-0.092 mmol) was dissolved in MeOH (1 mL) and aq. 2N NaOH (1.0 mL, 20 mmol) added into the mixture. The reaction was stirred for 1.5 h at room temperature and concentrated under reduced pressure. The resulting aqueous layer was diluted with water (3 mL) and washed with Et$_2$O (2×15 mL). The aqueous layer was acidified with 1N HCl (pH~3.0) and then extracted with EtOAc (2×20 mL). The combined organic layer was dried over anh. (Na$_2$SO$_4$) and evaporated to afford the corresponding carboxylic acid derivatives as white semi-solid or a foam (92-99% yields).

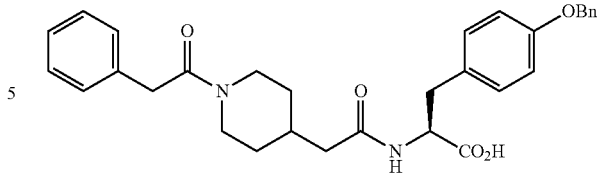

(S)-3-(4-(Benzyloxy)phenyl)-2-(2-(1-(2-phenylacetyl)piperidin-4-yl)acetamido)propanoic acid (SR2-118). The carboxylic acid SR2-118 was obtained from methyl ester SR1-122 (0.024 g, 0.045 mmol) as a white foam (0.023 g, 99%) using general method F. HPLC: >97% [$t_R$=5.3 min, 70% MeOH, 30% water (with 0.1% TFA), 20 min]. $^1$H NMR (500 MHz, DMSO-$d_6$) δ 12.60 (bs, 1H), 8.07 (d, J=8.3 Hz, 1H), 7.41 (dd, J=7.2, 5.4 Hz, 2H), 7.35 (td, J=7.5, 2.3 Hz, 2H), 7.32-7.24 (m, 3H), 7.19 (td, J=7.0, 2.6 Hz, 3H), 7.11 (d, J=7.1 Hz, 1H), 6.88 (d, J=8.6 Hz, 1H), 5.03 (s, 2H), 4.42-4.31 (m, 1H), 4.30-4.19 (m, 1H), 3.87-3.74 (m, 1H), 3.64 (s, 2H), 2.97 (ddd, J=13.9, 4.6, 2.0 Hz, 1H), 2.91-2.80 (m, 1H), 2.71 (dd, J=13.9, 10.3 Hz, 1H), 2.46-2.31 (m, 1H), 1.91 (d, J=7.1 Hz, 2H), 1.78-1.64 (m, 1H), 1.52-1.37 (m, 1H), 1.32-1.19 (m, 1H), 0.90-0.63 (m, 2H). HRMS (ESI+): m/z $C_{31}H_{35}N_2O_5$ (M+H)$^+$515.2533; m/z $C_{31}H_{34}N_2O_5Na$ (M+Na)$^+$537.2349; HPLC-MS (ESI+): m/z 515.2 [80%, (M+H)$^−$]; m/z 537.2 [100%, (M+Na)$^+$].

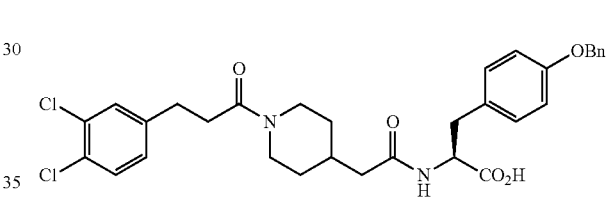

(S)-3-(4-(Benzyloxy)phenyl)-2-(2-(1-(3-(3,4-dichlorophenyl)propanoyl)piperidin-4-yl)acetamido)propanoic acid (SR2-113). The carboxylic acid SR2-113 was obtained from methyl ester SR2-030 (0.030 g, 0.049 mmol) as a white foam (0.028 g, 96%) using general method F. HPLC: >97% [$t_R$=11.3 min, 70% MeOH, 30% water (with 0.1% TFA), 20 min]. $^1$H NMR (500 MHz, DMSO-$d_6$) δ 12.47 (bs, 1H), 8.09 (d, J=8.3 Hz, 1H), 7.54-7.47 (m, 2H), 7.45-7.34 (m, 4H), 7.33-7.28 (m, 1H), 7.23 (td, J=7.9, 2.1 Hz, 1H), 7.13 (d, J=8.6 Hz, 2H), 6.90 (dd, J=8.6, 2.0 Hz, 2H), 5.05 (s, 1H), 5.02 (s, 1H), 4.45-4.36 (m, 1H), 4.31-4.20 (m, 1H), 3.81-3.64 (m, 1H), 3.00 (dd, J=13.9, 4.6 Hz, 1H), 2.89-2.69 (m, 4H), 2.67-2.53 (m, 2H), 2.47-2.34 (m, 1H), 1.95 (d, J=7.2 Hz, 2H), 1.78-1.65 (m, 1H), 1.52-1.43 (m, 1H), 1.37-1.21 (m, 1H), 0.97-0.70 (m, 2H). HRMS (ESI+): m/z $C_{32}H_{35}Cl_2N_2O_5$ (M+H)$^+$597.1909; m/z $C_{32}H_{34}Cl_2N_2O_5Na$ (M+Na)$^+$619.1734; HPLC-MS (ESI+): m/z 619.2 [60%, (M+Na)$^+$].

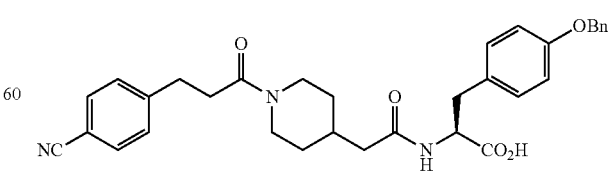

(S)-3-(4-(Benzyloxy)phenyl)-2-(2-(1-(3-(4-cyanophenyl)propanoyl)piperidin-4-yl)acetamido)propanoic acid (SR2-114). The carboxylic acid SR2-114 was obtained from methyl ester SR2-033 (0.023 g, 0.041 mmol) as a white foam (0.022 g, 98%) using general method F. HPLC: >97% [$t_R$=5.9 min, 65% MeOH, 35% water (with 0.1% TFA), 20 min]. $^1$H NMR (500 MHz, DMSO-$d_6$) δ 12.64 (s, 1H), 8.11 (d, J=8.3 Hz, 1H), 7.72 (t, J=8.2 Hz, 2H), 7.50-7.23 (m, 7H), 7.14 (d, J=8.6 Hz, 2H), 6.91 (d, J=7.6 Hz, 2H), 5.05 (s, 1H), 5.03 (s, 1H), 4.46-4.36 (m, 1H), 4.31-4.22 (m, 1H), 3.81-3.65 (m, 1H), 3.01 (dd, J=13.9, 4.6 Hz, 1H), 2.93-2.79 (m, 3H), 2.74 (dd, J=13.8, 10.3 Hz, 1H), 2.69-2.53 (m, 2H), 2.48-2.36 (m, 1H), 1.95 (d, J=7.2 Hz, 2H), 1.78-1.68 (m, 1H), 1.53-1.41 (m, 1H), 1.35-1.24 (m, 1H), 0.98-0.71 (m, 2H). HRMS (ESI+): m/z $C_{33}H_{36}N_3O_5$ (M+H)$^+$554.2648; m/z $C_{33}H_{35}N_3O_5Na$ (M+Na)$^+$576.2463; HPLC-MS (ESI+): m/z 554.2 [50%, (M+H)$^+$]; m/z 576.2 [60%, (M+Na)$^+$].

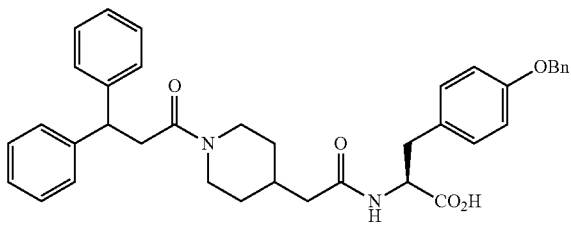 [SMILES: O=C(CC1CCN(C(=O)CC(c2ccccc2)c2ccccc2)CC1)N[C@@H](Cc1ccc(OCc2ccccc2)cc1)C(=O)O]

(S)-3-(4-(Benzyloxy)phenyl)-2-(2-(1-(3,3-diphenylpropanoyl)piperidin-4-yl)acetamido)-propanoic acid (SR2-115). The carboxylic acid SR2-115 was obtained from methyl ester SR2-029 (0.053 g, 0.086 mmol) as a white foam (0.051 g, 98%) using general method F. HPLC: >98% [$t_R$=6.0 min, 75% MeOH, 25% water (with 0.1% TFA), 20 min]. $^1$H NMR (500 MHz, DMSO-$d_6$) δ 12.56 (bs, 1H), 8.02 (dd, J=8.3, 3.3 Hz, 1H), 7.39-7.32 (m, 3H), 7.33-7.25 (m, 2H), 7.27-7.13 (m, 8H), 7.12-7.03 (m, 4H), 6.86-6.79 (m, 2H), 4.97 (s, 2H), 4.41 (td, J=7.4, 3.4 Hz, 1H), 4.37-4.28 (m, 1H), 4.17-4.03 (m, 1H), 3.92-3.76 (m, 1H), 3.11-2.88 (m, 3H), 2.74 (dd, J=20.1, 7.7 Hz, 1H), 2.66 (ddd, J=14.0, 10.2, 4.1 Hz, 1H), 2.35-2.19 (m, 1H), 1.83 (d, J=7.2 Hz, 2H), 1.70-1.51 (m, 1H), 1.45-1.28 (m, 1H), 1.26-1.09 (m, 1H), 0.83-0.52 (m, 2H). HRMS (ESI+): m/z $C_{38}H_{41}N_2O_5$ (M+H)$^+$605.3005; m/z $C_{38}H_{40}N_2O_5Na$ (M+Na)$^+$627.2827; HPLC-MS (ESI+): m/z 605.2 [80%, (M+H)$^+$]; m/z 627.2 [100%, (M+Na)$^+$].

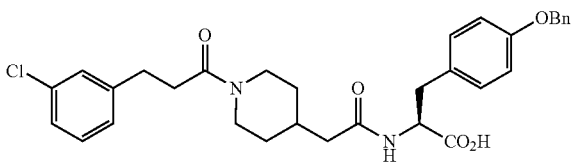 [SMILES: O=C(CC1CCN(C(=O)CCc2cccc(Cl)c2)CC1)N[C@@H](Cc1ccc(OCc2ccccc2)cc1)C(=O)O]

(S)-3-(4-(Benzyloxy)phenyl)-2-(2-(1-(3-(3-chlorophenyl)propanoyl)piperidin-4-yl)acetamido)propanoic acid (SR2-116). The carboxylic acid SR2-116 was obtained from methyl ester SR2-032 (0.030 g, 0.052 mmol) as a white foam (0.027 g, 92%) using general method F. HPLC: >99% [$t_R$=3.1 min, 70% MeOH, 30% water (with 0.1% TFA), 20 min]. $^1$H NMR (500 MHz, DMSO-$d_6$) δ 12.61 (bs, 1H), 8.07 (d, J=8.3 Hz, 1H), 7.45-7.32 (m, 4H), 7.28 (m, 3H), 7.19 (m, 2H), 7.12 (d, J=8.2 Hz, 2H), 6.88 (d, J=8.2 Hz, 2H), 5.03 (s, 1H), 5.01 (s, 1H), 4.44-4.32 (m, 1H), 4.29-4.16 (m, 1H), 3.80-3.64 (m, 1H), 2.98 (dd, J=13.9, 4.6 Hz, 1H), 2.87-2.66 (m, 4H), 2.63-2.52 (m, 1H), 2.44-2.19 (m, 2H), 1.93 (d, J=7.2 Hz, 2H), 1.78-1.63 (m, 1H), 1.51-1.36 (m, 1H), 1.35-1.19 (m, 1H), 0.98-0.64 (m, 2H). HRMS (ESI+): m/z $C_{32}H_{36}ClN_2O_5$ (M+H)$^+$563.2298; m/z $C_{32}H_{35}ClN_2O_5Na$ (M+Na)$^+$585.2135; HPLC-MS (ESI+): m/z 563.2 [40%, (M+H)$^+$]; m/z 585.2 [70%, (M+Na)$^+$].

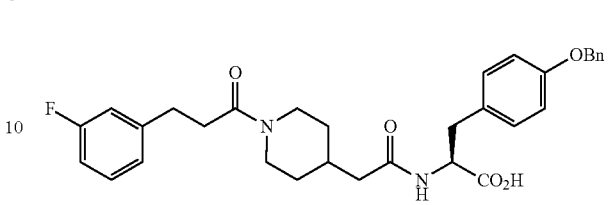

(S)-3-(4-(Benzyloxy)phenyl)-2-(2-(1-(3-(3-fluorophenyl)propanoyl)piperidin-4-yl)acetamido)propanoic acid (SR2-117). The carboxylic acid SR2-117 was obtained from methyl ester SR2-010 (0.051 g, 0.091 mmol) as a white foam (0.049 g, 98%) using general method F. HPLC: >97% [$t_R$=7.8 min, 70% MeOH, 30% water (with 0.1% TFA), 20 min]. $^1$H NMR (500 MHz, DMSO-$d_6$) δ 12.54 (bs, 1H), 8.08 (d, J=8.3 Hz, 1H), 7.45-7.36 (m, 2H), 7.35 (td, J=7.5, 2.2 Hz, 1H), 7.32-7.19 (m, 3H), 7.11 (d, J=8.2 Hz, 2H), 7.10-7.00 (m, 2H), 7.00-6.92 (m, 1H), 6.88 (d, J=8.2 Hz, 2H), 5.03 (s, 1H), 5.01 (s, 1H), 4.39 (td, J=9.3, 4.6 Hz, 1H), 4.30-4.16 (m, 1H), 3.72 (m, 1H), 2.98 (m, 1H), 2.89-2.66 (m, 4H), 2.64-2.50 (m, 2H), 2.46-2.23 (m, 1H), 1.93 (d, J=7.1 Hz, 2H), 1.77-1.62 (m, 1H), 1.50-1.40 (m, 1H), 1.36-1.07 (m, 1H), 0.96-0.63 (m, 2H). NMR (471 MHz, DMSO-$d_6$) δ −113.91 (d, J=8.9 Hz). HRMS (ESI+): m/z $C_{32}H_{35}FN_2O_5$ (M+H)$^+$547.2597; m/z $C_{32}H_{35}FN_2O_5Na$ (M+Na)$^+$569.2421; HPLC MS (ESI+): m/z 547.3 [80%, (M+H)$^+$]; m/z 569.2 [80%, (M+Na)$^+$].

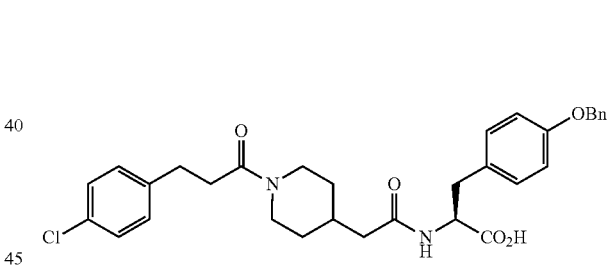

(S)-3-(4-(Benzyloxy)phenyl)-2-(2-(1-(3-(4-chlorophenyl)propanoyl)piperidin-4-yl)acetamido)propanoic acid (SR2-119). The carboxylic acid SR2-119 was obtained from methyl ester SR2-004 (0.020 g, 0.035 mmol) as a white foam (0.019 g, 98%) using general method F. HPLC: >97% [$t_R$=6.6 min, 75% MeOH, 25% water (with 0.1% TFA), 20 min]. $^1$H NMR (500 MHz, DMSO-$d_6$) δ 12.61 (bs, 1H), 8.06 (d, J=8.3 Hz, 1H), 7.40 (dd, J=13.2, 7.1 Hz, 2H), 7.37-7.32 (m, 2H), 7.32-7.26 (m, 3H), 7.23 (m, 2H), 7.11 (d, J=8.6 Hz, 2H), 6.88 (d, J=8.5 Hz, 2H), 5.03 (s, 1H), 5.01 (s, 1H), 4.43-4.34 (m, 2H), 4.28-4.17 (m, 1H), 3.77-3.64 (m, 1H), 2.98 (dd, J=13.9, 4.6 Hz, 1H), 2.86-2.65 (m, 4H), 2.61-2.50 (m, 2H), 2.45-2.32 (m, 1H), 1.93 (d, J=7.2 Hz, 2H), 1.77-1.63 (m, 1H), 1.50-1.39 (m, 1H), 1.31-1.20 (m, 1H), 0.95-0.66 (m, 2H). HRMS (ESI+): m/z $C_{32}H_{36}ClN_2O_5$ (M+H)$^+$ 563.2297; m/z $C_{32}H_{35}ClN_2O_5Na$ (M+Na)$^+$ 585.2125; HPLC-MS (ESI+): m/z 563.2 [80%, (M+H)$^+$]; m/z 585.2 [80%, (M+Na)$^+$].

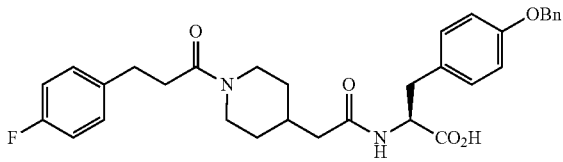 [SMILES: O=C(CC1CCN(C(=O)CCc2ccc(F)cc2)CC1)N[C@@H](Cc1ccc(OCc2ccccc2)cc1)C(=O)O]

(S)-3-(4-(Benzyloxy)phenyl)-2-(2-(1-(3-(4-fluorophenyl)propanoyl)piperidin-4-yl)acetamido)propanoic acid (SR2-120). The carboxylic acid SR2-120 was obtained from methyl ester SR2-008 (0.048 g, 0.085 mmol) as a white foam (0.046 g, 98%) using general method F. HPLC: >99% [$t_R$=8.5 min, 70% MeOH, 30% water (with 0.1% TFA), 20 min]. $^1$H NMR (500 MHz, DMSO-$d_6$) δ 12.62 (bs, 1H), 8.07 (d, J=8.3 Hz, 1H), 7.36 (m, 4H), 7.27-7.19 (m, 3H), 7.11 (d, J=8.6 Hz, 2H), 7.06 (dd, J=9.1, 6.7 Hz, 2H), 6.88 (d, J=8.6 Hz, 2H), 5.03 (s, 1H), 5.01 (s, 1H), 4.39 (m, 1H), 4.31-4.17 (m, 1H), 3.78-3.59 (m, 1H), 2.98 (dd, J=13.9, 4.6 Hz, 1H), 2.87-2.61 (m, 4H), 2.53 (m, 1H), 2.43-2.20 (m, 2H), 1.93 (d, J=7.2 Hz, 2H), 1.76-1.57 (m, 1H), 1.50-1.35 (m, 1H), 1.34-1.11 (m, 1H), 0.95-0.59 (m, 2H). HRMS (ESI+): m/z $C_{32}H_{35}FN_2O_5$ (M+H)$^+$547.2599; m/z $C_{32}H_{35}FN_2O_5Na$ (M+Na)$^+$569.2410; HPLC-MS (ESI+): m/z 547.3 [60%, (M+H)$^+$]; m/z 569.2 [70%, (M+Na)$^+$].

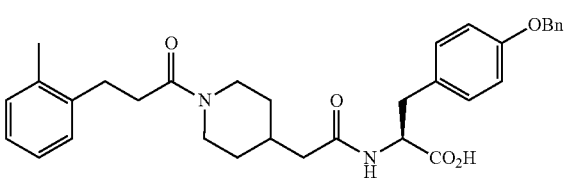 [SMILES: Cc1ccccc1CCC(=O)N1CCC(CC(=O)N[C@@H](Cc2ccc(OCc3ccccc3)cc2)C(=O)O)CC1]

(S)-3-(4-(Benzyloxy)phenyl)-2-(2-(1-(3-(o-tolyl)propanoyl)piperidin-4-yl)acetamido)-propanoic acid (SR2-121). The carboxylic acid SR2-121 was obtained from methyl ester SR2-035 (0.025 g, 0.045 mmol) as a white foam (0.024 g, 99%) using general method F. HPLC: >99% [$t_R$=10.3 min, 70% MeOH, 30% water (with 0.1% TFA), 20 min]. $^1$H NMR (500 MHz, DMSO-$d_6$) δ 12.60 (bs, 1H), 8.08 (d, J=8.2 Hz, 1H), 7.45-7.24 (m, 5H), 7.16-7.00 (m, 6H), 6.88 (d, J=8.3 Hz, 2H), 5.03 (s, 1H), 5.00 (s, 1H), 4.38 (m, 1H), 4.27 (m, 1H), 3.70 (m, 1H), 3.02-2.92 (m, 1H), 2.88-2.58 (m, 4H), 2.58-2.49 (m, 1H), 2.48-2.29 (m, 2H), 2.24 (s, 3H), 1.93 (d, J=7.1 Hz, 2H), 1.71 (m, 1H), 1.51-1.39 (m, 1H), 1.35-1.23 (m, 1H), 0.91-0.69 (m, 2H). HRMS (ESI+): m/z $C_{33}H_{39}N_2O_5$ (M+H)$^+$543.2845; m/z $C_{33}H_{38}N_2O_5Na$ (M+Na)$^+$565.2660; HPLC-MS (ESI+): m/z 543.2 [100%, (M+H)$^+$]; m/z 565.3 [90%, (M+Na)$^+$].

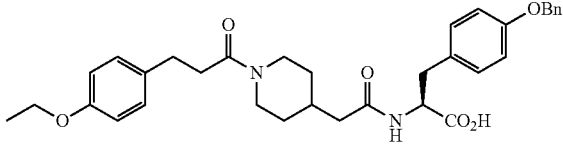 [SMILES: CCOc1ccc(CCC(=O)N2CCC(CC(=O)N[C@@H](Cc3ccc(OCc4ccccc4)cc3)C(=O)O)CC2)cc1]

(S)-3-(4-(Benzyloxy)phenyl)-2-(2-(1-(3-(4-ethoxyphenyl)propanoyl)piperidin-4-yl)acetamido)propanoic acid (SR2-122). The carboxylic acid SR2-122 was obtained as a white foam (0.044 g, 97%) from methyl ester SR2-007 (0.045 g, 0.078 mmol) using general method F. HPLC: >95% [$t_R$=6.5 min, 70% MeOH, 30% water (with 0.1% TFA), 20 min]. $^1$H NMR (500 MHz, DMSO-$d_6$) δ 12.62 (bs, 1H), 8.09 (d, J=8.3 Hz, 1H), 7.48-7.25 (m, 5H), 7.19-7.06 (m, 4H), 6.91 (d, J=8.2 Hz, 2H), 6.80 (dd, J=8.3, 5.0 Hz, 2H), 5.06 (s, 1H), 5.03 (s, 1H), 4.48-4.36 (m, 1H), 4.27 (m, 1H), 3.97 (q, J=6.8 Hz, 2H), 3.83-3.66 (m, 1H), 3.01 (dd, J=13.8, 4.6 Hz, 1H), 2.91-2.79 (m, 1H), 2.78-2.61 (m, 3H), 2.55-2.35 (m, 3H), 1.97-1.92 (m, 2H), 1.81-1.64 (m, 1H), 1.56-1.39 (m, 1H), 1.30 (t, J=7.0, 3H), 1.25 (m, 1H), 1.03-0.71 (m, 2H). HRMS (ESI+): m/z $C_{34}H_{40}N_2O_6$ (M+H)$^+$573.2957; m/z $C_{34}H_{40}N_2O_6Na$ (M+Na)$^+$ 595.2770; HPLC-MS (ESI+): m/z 573.2 [95%, (M+H)$^+$]; m/z 595.2 [100%, (M+Na)$^+$].

Synthesis of C-Terminal Amide Derivatives:

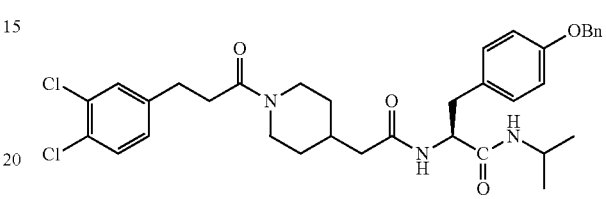

(S)-3-(4-(Benzyloxy)phenyl)-2-(2-(1-(3-(3,4-dichlorophenyl)propanoyl)piperidin-4-yl)acetamido)-N-isopropyl-propanamide (SR2-153). The amide SR2-153 was obtained as a white foam (0.026 g, 63%) from methyl ester SR2-030 (0.040 g, 0.065 mmol) by using the general method B. HPLC: >95% [$t_R$=12.9 min, 75% MeOH, 25% water (with 0.1% TFA), 20 min]. $^1$H NMR (500 MHz, DMSO-$d_6$) δ 7.87 (d, J=8.7 Hz, 1H), 7.71 (dd, J=7.6, 5.1 Hz, 1H), 7.47-7.40 (m, 2H), 7.39-7.20 (m, 5H), 7.16 (td, J=8.3, 2.1 Hz, 1H), 7.06 (d, J=8.2 Hz, 2H), 6.82 (dd, J=8.6, 2.9 Hz, 2H), 4.97 (s, 1H), 4.95 (s, 1H), 4.42-4.32 (m, 1H), 4.23-4.13 (m, 1H), 3.78-3.58 (m, 2H), 2.83-2.66 (m, 4H), 2.53 (m, 3H), 2.38-2.27 (m, 1H), 1.94-1.78 (m, 2H), 1.72-1.54 (m, 1H), 1.49-1.32 (m, 1H), 1.12 (m, 1H), 0.97 (d, J=6.6 Hz, 3H), 0.91 (d, J=6.7, 3H), 0.88-0.48 (m, 2H). HRMS (ESI+): m/z $C_{35}H_{42}Cl_2N_3O_4$ (M+H)$^+$638.2543; m/z $C_{35}H_{41}Cl_2N_3O_4Na$ (M+Na)$^+$660.2363; HPLC-MS (ESI+): m/z 639.2 [30%, (M+H)$^+$].

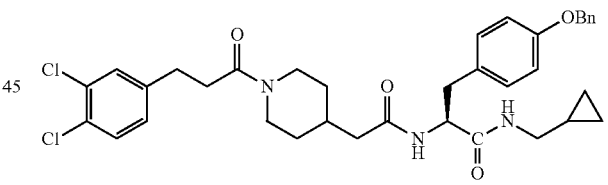

(S)-3-(4-(Benzyloxy)phenyl)-N-(cyclopropylmethyl)-2-(2-(1-(3-(3,4-dichlorophenyl)propanoyl)piperidin-4-yl)acetamido)propanamide (SR2-154). SR2-154 was obtained from methyl ester SR2-030 (0.020 g, 0.032 mmol) as a white foam (0.017 g, 80%) by using the general method B. HPLC: >96% [$t_R$=8.3 min, 75% MeOH, 25% water (with 0.1% TFA), 20 min]. $^1$H NMR (500 MHz, DMSO-$d_6$) δ 8.04-7.94 (m, 2H), 7.50 (m, 2H), 7.45-7.28 (m, 5H), 7.22 (td, J=8.6, 2.0 Hz, 1H), 7.14 (d, J=8.5 Hz, 2H), 6.89 (dd, J=8.6, 3.0 Hz, 2H), 5.04 (s, 1H), 5.01 (s, 1H), 4.47 (m, 1H), 4.28-4.19 (m, 1H), 3.77-3.63 (m, 1H), 2.99-2.92 (m, 2H), 2.89 (dd, J=13.7, 4.6 Hz, 1H), 2.86-2.71 (m, 3H), 2.69-2.51 (m, 3H), 2.45-2.33 (m, 1H), 2.00-1.86 (m, 2H), 1.76-1.59 (m, 1H), 1.42 (m, 1H), 1.27-1.12 (m, 1H), 0.97-0.65 (m, 3H), 0.37 (dd, J=8.0, 1.8 Hz, 2H), 0.16-0.09 (m, 2H). HRMS (ESI+): m/z $C_{36}H_{42}Cl_2N_3O_4$ (M+H)$^+$650.2554; m/z $C_{36}H_{41}Cl_2N_3O_4Na$ (M+Na)$^+$672.2373; HPLC-MS (ESI+): m/z 650.2 [30%, (M+H)$^+$].

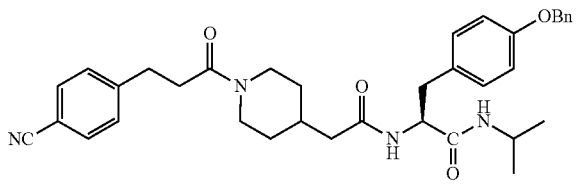 [SMILES: CC(C)NC(=O)[C@H](Cc1ccc(OCc2ccccc2)cc1)NC(=O)CC1CCN(C(=O)CCc2ccc(C#N)cc2)CC1]

(S)-3-(4-(Benzyloxy)phenyl)-2-(2-(1-(3-(4-cyanophenyl) propanoyl)piperidin-4-yl)acetamido)-N-isopropylpropanamide (SR2-155). The amide SR2-155 was obtained from methyl ester SR2-033 (0.040 g, 0.070 mmol) as a white foam (0.021 g, 51%) using the general method B. HPLC: >97% [$t_R$=7.0 min, 70% MeOH, 30% water (with 0.1% TFA), 20 min]. $^1$H NMR (500 MHz, DMSO-$d_6$) δ 7.96 (d, J=8.7 Hz, 1H), 7.79 (dd, J=7.6, 5.3 Hz, 1H), 7.72 (dd, J=10.3, 8.0 Hz, 2H), 7.48-7.34 (m, 6H), 7.34-7.29 (m, 1H), 7.13 (d, J=8.6 Hz, 2H), 6.91-6.87 (m, 2H), 5.05 (s, 1H), 5.01 (s, 1H), 4.44 (m, 1H), 4.32-4.19 (m, 1H), 3.87-3.64 (m, 2H), 2.93-2.77 (m, 4H), 2.71-2.54 (m, 3H), 2.47-2.36 (m, 1H), 2.02-1.85 (m, 2H), 1.79-1.62 (m, 1H), 1.49-1.39 (m, 1H), 1.31-1.14 (m, 1H), 1.04 (d, J=6.7 Hz, 3H), 0.98 (d, J=6.5 Hz, 3H), 0.93-0.67 (m, 2H). HRMS (ESI+): m/z $C_{36}H_{43}N_4O_4$ (M+H)$^+$595.3277; m/z $C_{36}H_{42}N_4O_4Na$ (M+Na)$^+$617.3101; HPLC-MS (ESI+): m/z 595.4 [60%, (M+H)$^+$]; m/z 617.4 [100%, (M+Na)$^+$].

(S)-3-(4-(Benzyloxy)phenyl)-2-(2-(1-(3-(4-cyanophenyl) propanoyl)piperidin-4-yl)acetamido)-N-(cyclopropylmethyl)propanamide (SR2-156). The amide SR2-156 was obtained from methyl ester SR2-033 (0.040 g, 0.070 mmol) as a white foam (0.026 g, 68%) using general method B. HPLC: >97% [$t_R$=4.5 min, 75% MeOH, 25% water (with 0.1% TFA), 20 min]. $^1$H NMR (500 MHz, DMSO-$d_6$) δ 8.05-7.96 (m, 2H), 7.71 (dd, J=10.9, 8.0 Hz, 2H), 7.48-7.27 (m, 7H), 7.14 (d, J=8.5 Hz, 2H), 6.88 (d, J=6.8 Hz, 2H), 5.04 (s, 1H), 5.00 (s, 1H), 4.47 (m, 1H), 4.30-4.18 (m, 1H), 3.77-3.62 (m, 1H), 2.99-2.74 (m, 6H), 2.70-2.53 (m, 3H), 2.47-2.32 (m, 1H), 2.03-1.86 (m, 2H), 1.76-1.62 (m, 1H), 1.42 (m, 1H), 1.28-1.13 (m, 1H), 0.96-0.65 (m, 3H), 0.37 (dd, J=8.1, 1.8 Hz, 2H), 0.15-0.08 (m, 2H). HRMS (ESI+): m/z $C_{37}H_{43}N_4O_4$ (M+H)$^+$607.3286; m/z $C_{37}H_{42}N_4O_4Na$ (M+Na)$^+$629.3106; HPLC-MS (ESI+): m/z 607.2 [70%, (M+H)$^+$]; m/z 629.2 [50%, (M+Na)$^+$].

Synthesis of C-Terminal Oxazole Derivatives

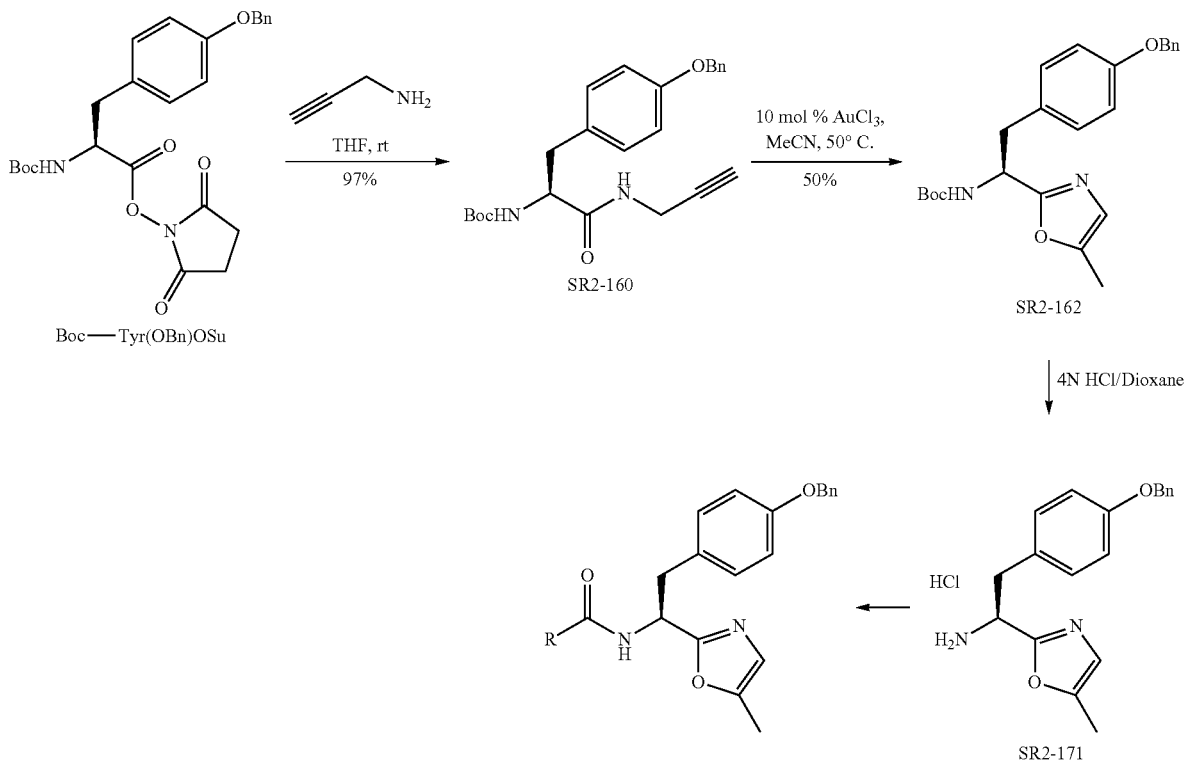

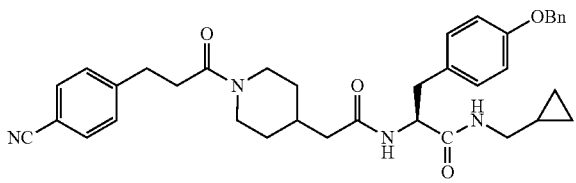 [SMILES: N#Cc1ccc(CCC(=O)N2CCC(CC(=O)N[C@@H](Cc3ccc(OCc4ccccc4)cc3)C(=O)NCC3CC3)CC2)cc1]

A series of C-terminal oxazoles were prepared from oxazoles derived from amino acids. An example is shown in the Figure above. Reaction of Boc-Tyr(OBn))Su with propargylamine gave the propargyl amide SR2-160. Gold(III) catalyzed cyclization (Hashmi, A. S. K., et al., Org Lett. 2004 6(23):4391-4394) of the propargyl amide gave the oxazole SR2-162. The amine SR2-162 serves as an important building block for acylation with the acylpiperidine PPP surrogates as exemplified below.

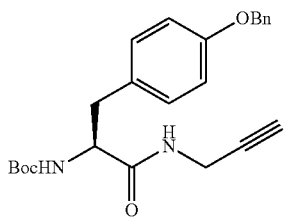 [SMILES: C#CCNC(=O)[C@H](Cc1ccc(OCc2ccccc2)cc1)NC(=O)OC(C)(C)C]

tert-Butyl (S)-(3-(4-(benzyloxy)phenyl)-1-oxo-1-(prop-2-yn-1-ylamino)propan-2-yl)-carbamate (SR2-160). The succinimide ester Boc-Tyr(OBn)OSu (1.00 g, 2.134 mmol) was dissolved in anhydrous THF (20 mL) under argon at room temperature. Propargylamine (0.136 mL, 2.134 mmol) was added to the mixture which was then stirred for 21 h. The reaction mixture was concentrated under reduced pressure and re-dissolved in EtOAc (50 mL). This solution was washed subsequently with 1N HCl (2×25 mL) and sat. NaHCO$_3$ (2×25 mL) and concentrated to afford the propargylamide SR2-160 as a white solid (0.851 g, 97%). $^1$H NMR (500 MHz, DMSO-d$_6$) δ 8.36 (t, J=5.6 Hz, 1H), 7.43 (d, J=7.0 Hz, 2H), 7.39 (t, J=7.4 Hz, 2H), 7.36-7.29 (m, 1H), 7.17 (d, J=8.3 Hz, 2H), 6.91 (d, J=8.2 Hz, 2H), 5.06 (s, 2H), 4.07 (td, J=9.4, 4.4 Hz, 1H), 3.87 (dd, J=5.6, 2.5 Hz, 2H), 3.13 (t, J=2.6 Hz, 1H), 2.85 (dd, J=13.8, 4.5 Hz, 1H), 2.65 (dd, J=13.8, 10.1 Hz, 1H), 1.30 (s, 9H). HRMS (ESI+): m/z C$_{24}$H$_{29}$N$_2$O$_4$ (M+H)$^+$409.2132; m/z C$_{24}$H$_{28}$N$_2$O$_4$Na (M+Na)$^+$431.1953; HPLC-MS (ESI+): m/z 431.2 [100%, (M+Na)$^+$]; m/z 839.2 [30%, (2M+Na)$^+$].

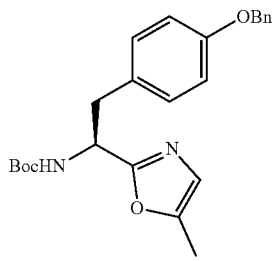 [SMILES: Cc1cnc([C@H](Cc2ccc(OCc3ccccc3)cc2)NC(=O)OC(C)(C)C)o1]

tert-Butyl (S)-(2-(4-(benzyloxy)phenyl)-1-(5-methyloxazol-2-yl)ethyl)carbamate (SR2-162). The propargylamide SR2-160 (0.200 g, 0.489 mmol) was dissolved in acetonitrile (3.5 mL) under argon and gold(III) chloride (0.015 g, 0.049 mmol) added. The mixture was heated at 50° C. for 24 h and filtered through Celite and the filter bed rinsed with EtOAc. The combined filtrate was dried (Na$_2$SO$_4$) and solvent evaporated. Purification by flash column chromatography using EtOAc/hexane (1:9-2:8) as eluent afforded SR2-162 as a white solid (0.096 g, 50%). $^1$H NMR (500 MHz, DMSO-d$_6$) δ 7.49 (dt, J=6.2, 1.5 Hz, 1H), 7.47-7.41 (m, 2H), 7.41-7.35 (m, 1H), 7.17 (d, J=8.4 Hz, 2H), 6.95 (m, 2H), 6.79 (s, 1H), 5.11 (s, 2H), 4.78 (td, J=8.3, 5.8 Hz, 1H), 3.91 (t, J=6.3 Hz, 2H), 3.13 (dd, J=13.8, 6.1 Hz, 1H), 2.97 (dd, J=13.8, 9.4 Hz, 1H), 2.31 (s, 3H), 1.37 (s, 9H). HRMS (ESI+): m/z C$_{24}$H$_{29}$N$_2$O$_4$ (M+H)$^+$409.2134; m/z C$_{24}$H$_{28}$N$_2$O$_4$Na (M+Na)$^+$431.1945; HPLC-MS (ESI+): m/z 409.3 [70%, (M+H)$^+$]; m/z 431.2 [100%, (M+Na)$^+$].

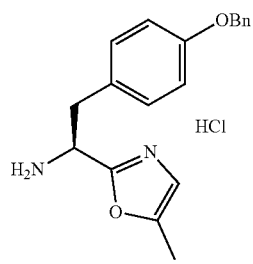 [SMILES: Cc1cnc([C@@H](N)Cc2ccc(OCc3ccccc3)cc2)o1 ; Cl]

(S)-2-(4-(Benzyl oxy)phenyl)-1-(5-methyloxazol-2-yl)ethan-1-amine hydrochloride (SR2-171). The amine salt SR2-171 (70 mg, quantitative yield) was obtained from SR2-162 (0.083 g, 0.203 mmol) as a white semi-solid by the same method used to make SR1-085. The amine salt SR2-171 was used without further purification.

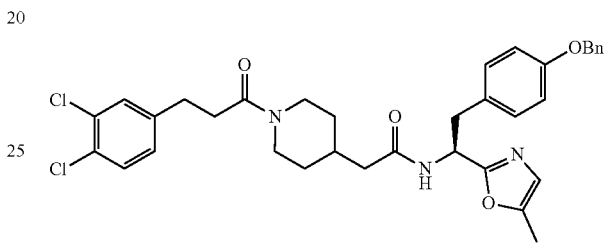

(S)—N-(2-(4-(Benzyloxy)phenyl)-1-(5-methyloxazol-2-yl)ethyl)-2-(1-(3-(3,4-dichlorophenyl)-propanoyl)piperidin-4-yl)acetamide (SR2-176). The oxazole SR2-176 was obtained as white foam (0.024 g, 57%) from SR2-171 (0.023 g, 0.067 mmol) and 3-(3,4-dichlorophenyl)propionic acid (0.028 g, 0.080 mmol, 1.2 eq.) using general method D. HPLC: >94% [t$_R$=7.1 min, 80% MeOH, 20% water (with 0.1% TFA), 20 min]. $^1$H NMR (500 MHz, DMSO-d$_6$) δ 8.39 (d, J=8.7 Hz, 1H), 7.55-7.48 (m, 2H), 7.46-7.34 (m, 4H), 7.34-7.28 (m, 1H), 7.24 (m, 1H), 7.15-7.12 (m, 2H), 6.90 (dd, J=8.7, 2.3 Hz, 2H), 6.76 (d, J=1.4 Hz, 1H), 5.18-5.08 (m, 1H), 5.05 (s, 1H), 5.02 (s, 1H), 4.31-4.22 (m, 1H), 3.78-3.63 (m, 1H), 3.12 (dd, J=13.9, 5.6 Hz, 1H), 2.96-2.86 (m, 1H), 2.79 (m, 3H), 2.68-2.54 (m, 2H), 2.47-2.37 (m, 1H), 2.26 (d, J=1.3 Hz, 3H), 1.94 (dd, J=7.1, 2.2 Hz, 2H), 1.78-1.62 (m, 1H), 1.43 (m, 1H), 1.26 (m, 1H), 0.97-0.67 (m, 2H). HRMS (ESI+): m/z C$_{35}$H$_{38}$C$_{12}$N$_3$O$_4$ (M+H)$^+$; 634.2235; m/z calcd for C$_{35}$H$_{37}$C$_{12}$N$_3$O$_4$Na (M+Na)$^+$ 656.2050; HPLC-MS (ESI+): m/z 634.2 [40%, (M+H)$^+$].

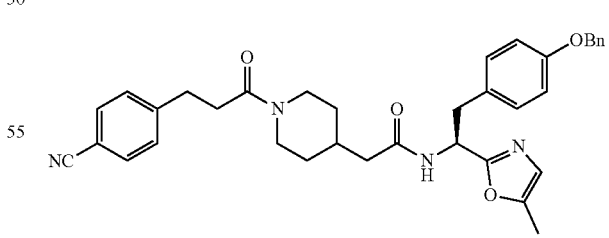

(S)—N-(2-(4-(Benzyloxy)phenyl)-1-(5-methyloxazol-2-yl)ethyl)-2-(1-(3-(4-cyanophenyl)-propanoyl)piperidin-4-yl)acetamide (SR2-177). The oxazole SR2-177 was obtained as white foam (0.023 g, 59%) from SR2-171 (0.023 g, 0.067 mmol) and 3-(4-cyanophenyl)propionic acid (0.024 g, 0.080 mmol, 1.2 eq.) using general method D. HPLC: >95% [t$_R$=4.4 min, 75% MeOH, 25% water (with 0.1%

TFA), 20 min].]. $^1$H NMR (500 MHz, DMSO-d$_6$) δ 8.39 (dd, J=8.9 Hz, 1H), 7.74-7.69 (m, 2H), 7.48-7.34 (m, 6H), 7.32 (dd, J=7.0, 2.2 Hz, 1H), 7.13 (d, J=8.6 Hz, 2H), 6.90 (dd, J=8.6, 1.7 Hz, 2H), 6.76 (d, J=1.4 Hz, 1H), 5.18-5.08 (m, 1H), 5.05 (s, 1H), 5.02 (s, 1H), 4.26 (m, 1H), 3.83-3.62 (m, 1H), 3.12 (dd, J=13.8, 5.6 Hz, 1H), 2.99-2.75 (m, 4H), 2.72-2.54 (m, 2H), 2.47-2.35 (m, 1H), 2.26 (d, J=1.3 Hz, 3H), 1.94 (dd, J=7.4, 3.0 Hz, 2H), 1.77-1.61 (m, 1H), 1.47-1.38 (m, 1H), 1.31-1.15 (m, 1H), 0.97-0.65 (m, 2H). HRMS (ESI+): m/z C$_{36}$H$_{39}$N$_4$O$_4$ (M+H)$^+$; 591.2961; m/z C$_{36}$H$_{38}$N$_4$O$_4$Na (M+Na)$^+$613.2786; HPLC-MS (ESI+): m/z 591.2 [100%, (M+H)$^+$]; m/z 613.2 [30%, (M+Na)$^+$].

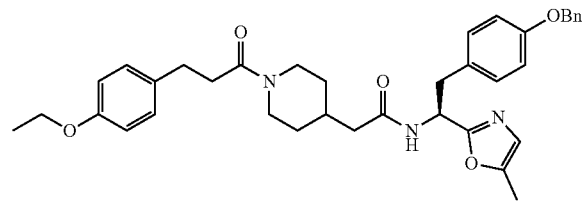 [SMILES: CCOc1ccc(CCC(=O)N2CCC(CC(=O)N[C@@H](Cc3ccc(OCc4ccccc4)cc3)c3ncc(C)o3)CC2)cc1]

(S)—N-(2-(4-(Benzyloxy)phenyl)-1-(5-methyloxazol-2-yl)ethyl)-2-(1-(3-(4-ethoxyphenyl)propanoyl)piperidin-4-yl)acetamide (SR2-178). The oxazole SR2-178 was obtained as white foam (0.028 g, 70%) from SR2-171 (0.023 g, 0.067 mmol) and 3-(4-ethoxyphenyl)propionic acid (0.026 g, 0.080 mmol, 1.2 eq.) using general method D. HPLC: >96% [t$_R$=7.9 min, 75% MeOH, 25% water (with 0.1% TFA), 20 min]. $^1$H NMR (500 MHz, DMSO-d$_6$) δ 8.39 (d, J=8.8 Hz, 1H), 7.47-7.34 (m, 4H), 7.32 (dt, J=8.0, 3.6 Hz, 1H), 7.15-7.09 (m, 4H), 6.89 (d, J=8.2 Hz, 2H), 6.82-6.77 (m, 2H), 6.75 (d, J=1.2 Hz, 1H), 5.17-5.09 (m, 1H), 5.05 (s, 1H), 5.02 (s, 1H), 4.27 (m, 1H), 3.97 (q, J=6.8 Hz, 2H), 3.70 (m, 1H), 3.12 (dd, J=13.8, 5.6 Hz, 1H), 2.95-2.86 (m, 1H), 2.81 (m, 1H), 2.75-2.61 (m, 3H), 2.58-2.51 (m, 1H), 2.49-2.33 (m, 1H), 2.26 (d, J=1.2 Hz, 3H), 1.93 (d, J=7.1 Hz, 2H), 1.78-1.62 (m, 1H), 1.41 (m, 1H), 1.30 (td, J=7.0, 2.2 Hz, 3H), 1.23 (d, J=10.3 Hz, 1H), 0.93-0.67 (m, 2H). HRMS (ESI+): m/z C$_{37}$H$_{44}$N$_3$O$_5$ (M+H)$^+$; 610.3280; m/z C$_{37}$H$_{43}$N$_3$O$_5$Na (M+Na)$^+$632.3096; HPLC-MS (ESI+): m/z 610.2 [90%, (M+H)$^+$]; m/z 632.2 [40%, (M+Na)$^+$].

Synthesis of Tetrazole Analogs

A series of C-terminal tetrazole derivatives were prepared from nitriles from amino acid derivatives, as shown by the examples in the Figure above. The amide SR2-161 was made from Fmoc-Tyr(Bzl)OH by treatment with N-ethoxy-carbonyl-2-ethoxy-1,2-dihydroquinoline (EEDQ) and ammonium bicarbonate (Nozaki, S., *Bull. Chem. Soc. Jpn.*, 1988, 61:2647-2648), followed by triflic anhydride dehydration (Sureshbabu, V. V., *Tetrahedron Lett.*, 2007, 48:7038-7041) to give the nitrile SR2-165. Removal of the Fmoc group gave the amine SR3-018, which was in turn acylated with substituted phenylpropionylpiperidinecetic acid derivatives to provide the PPPY with a C-terminal nitrile group. Tetrazole SR2-173 formation using these nitriles is effected by conditions developed by Sharpless (sodium azide and zinc bromide) (Demko D. P., *Org Lett.*, 2002, μL, 2525-2527) to provide the target PPPY mimics bearing a C-terminal tetrazole group.

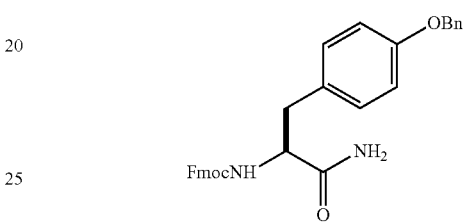

(9H-Fluoren-9-yl)methyl (S)-(1-amino-3-(4-(benzyloxy)phenyl)-1-oxopropan-2-yl)carbamate (SR2-161)*. The amino acid Fmoc-Tyr(Bzl)-OH (1.00 g, 2.026 mmol) was dissolved in CHCl$_3$ (10 mL) under argon at room temperature. To this solution N-ethoxy carbonyl-2-ethoxy-1,2-dihydroquinoline (EEDQ) (0.551 g, 2.228 mmol) and ammonium bicarbonate (0.480 g, 6.078 mmol) were added and the resulting mixture stirred for 20 h. The mixture was concentrated under reduced pressure and the resulting white solid dissolved in EtOAc (50 mL). The solution was washed with water (30 mL) followed by sat. NaHCO$_3$ (30 mL). The separated organic layer was dried (Na$_2$SO$_4$) concentrated to afford SR2-161 as a white solid (0.937 g, 95%). HPLC-MS (ESI+): m/z 493.2 [30%, (M+H)$^+$]; m/z 515.2 [90%, (M+Na)$^+$]. *—reported in the literature: Bull. Chem. Soc., Jpn, 1988, 61, 2647.

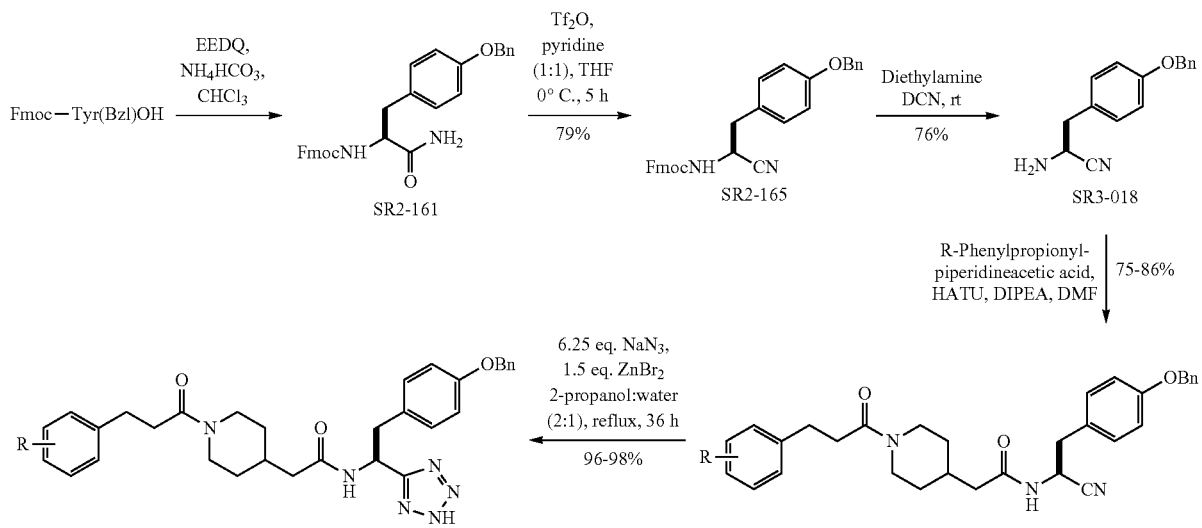

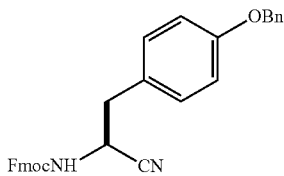

(9H-Fluoren-9-yl)methyl (S)-(2-(4-(benzyloxy)phenyl)-1-cyanoethyl)carbamate (SR2-165). The amide SR2-161 (0.990 g, 2.012 mmol) was dissolved in pyridine (6 mL) under argon and the solution cooled to 0° C. Trifluoromethanesulfonic anhydride (0.508 mL, 3.018 mmol) was added to the mixture dropwise and stirred for 3 h at 0° C. The reaction was quenched with water (1 mL) and the solvents evaporated under vacuum. The residue was diluted with EtOAc (50 mL) and washed with 10% aq. KHSO$_4$ (1×30 mL). The organic layer was dried (Na$_2$SO$_4$) and evaporated under reduced pressure. Purification by flash column chromatography using MeOH/DCM (0:100-10:90) as eluent afforded SR2-165 as a white solid (0.848 g, 89%). $^1$H NMR (500 MHz, DMSO-d$_6$) δ 8.24 (d, J=8.1 Hz, 1H), 7.90 (d, J=7.6 Hz, 2H), 7.64 (dd, J=7.6, 4.8 Hz, 2H), 7.50-7.36 (m, 6H), 7.36-7.29 (m, 3H), 7.21 (d, J=8.1 Hz, 2H), 6.94 (d, J=8.2 Hz, 2H), 5.05 (s, 2H), 4.65 (q, J=8.0 Hz, 1H), 4.41-4.30 (m, 2H), 4.21 (t, J=6.8 Hz, 1H), 3.07-2.93 (m, 2H). HPLC-MS (ESI+): m/z 497.2 [100%, (M+Na)$^+$].

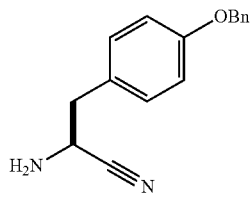

(S)-2-Amino-3-(4-(benzyloxy)phenyl)propanenitrile (SR3-018). Diethylamine (1.0 mL) was added into solution of the nitrile SR2-165 (0.201 g, 0.421 mmol) in DCM (2.5 mL) and stirred for 3 h at room temperature. Volatiles were removed under reduced pressure and the resulting thick oil was purified by flash column chromatography using MeOH/DCM (0:10-10:90) as eluent to afford SR3-018 as a white solid (0.081 g, 76%). $^1$H NMR (500 MHz, DMSO-d$_6$) δ 7.47-7.43 (m, 1H), 7.42-7.37 (m, 1H), 7.36-7.30 (m, OH), 7.20 (d, J=8.6 Hz, 1H), 6.96 (d, J=8.6 Hz, 1H), 5.08 (s, 1H), 3.88 (s, 1H), 2.87 (dd, J=13.5, 6.4 Hz, OH), 2.80 (dd, J=13.5, 8.5 Hz, 1H), 2.38-2.27 (m, 1H). HPLC-MS (ESI+): m/z 253.2 [100%, (M+H)$^+$]; m/z 505.3 [30%, (2M+H)$^+$].

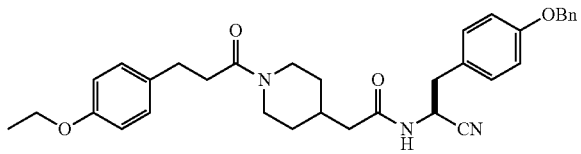 [SMILES: CCOc1ccc(CCC(=O)N2CCC(CC(=O)N[C@H](C#N)Cc3ccc(OCc4ccccc4)cc3)CC2)cc1]

(S)—N-(2-(4-(Benzyloxy)phenyl)-1-cyanoethyl)-2-(1-(3-(4-ethoxyphenyl)propanoyl)piper-idin-4-yl)acetamide (SR3-020). 2-(1-(3-(4-Ethoxyphenyl)propanoyl)piperidin-4-yl)acetic acid (0.059 g, 0.186 mmol) was dissolved in DMF (2 mL) and HATU (0.071 g, 0.185 mmol) and DIEA (0.081 mL, 0.465 mmol) were added. After stirring 5 min, SR3-018 (0.054 g, 0.186 mmol) was added into the mixture and continued stirring for 12 h. The mixture was concentrated under reduced pressure and the resulting thick oil dissolved in EtOAc (30 mL). The organic layer was washed with 1N HCl (2×20 mL) and sat NaHCO$_3$ (2×20 mL) sequentially and evaporated. Purification by flash column chromatography using MeOH/DCM (0:10-9:1) as eluent afforded SR3-020 as a white solid (0.064 g, 75%). $^1$H NMR (500 MHz, DMSO-d$_6$) δ 8.64 (d, J=7.9 Hz, 1H), 7.43 (t, J=8.3 Hz, 2H), 7.38 (t, J=7.4 Hz, 2H), 7.35-7.29 (m, 1H), 7.21 (d, J=8.6 Hz, 2H), 7.11 (dd, J=8.5, 3.5 Hz, 2H), 6.95 (d, J=8.6 Hz, 2H), 6.80 (dd, J=8.5, 3.3 Hz, 2H), 5.07 (s, 1H), 5.05 (s, 1H), 4.91 (dt, J=12.1, 7.9, 7.4 Hz, 1H), 4.30 (m, 1H), 3.97 (q, J=6.9 Hz, 2H), 3.80-3.68 (m, 1H), 3.05 (dd, J=13.6, 6.8 Hz, 1H), 2.94 (dd, J=13.6, 9.0 Hz, 1H), 2.86 (m, 1H), 2.75-2.66 (m, 2H), 2.57-2.52 (m, 2H), 2.48-2.34 (m, 1H), 1.99 (m, 2H), 1.82-1.68 (m, 1H), 1.45 (m, 1H), 1.37-1.20 (m, 1H), 1.30 (t, J=7.0 Hz, 3H), 0.99-0.70 (m, 2H). HPLC-MS (ESI+): m/z 554.3 [100%, (M+H)$^+$]; m/z 576.2 [40%, (M+Na)$^+$]

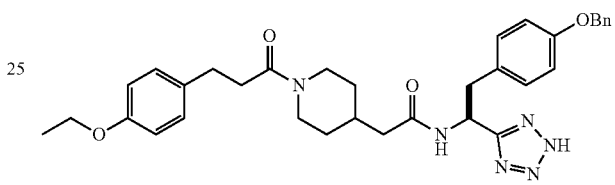

(S)—N-(2-(4-(Benzyloxy)phenyl)-1-(2H-tetrazol-5-yl)ethyl)-2-(1-(3-(4-ethoxyphenyl)propan-oyl)piperidin-4-yl)acetamide (SR3-023). The nitrile SR3-020 (0.058 g, 0.105 mmol) and ZnBr$_2$ (0.035 g, 0.157 mmol) were dissolved in 2:1 mixture of isopropanol:water (2 mL). Sodium azide (0.041 g, 0.630 mmol) was added to the mixture which was then refluxed at 100° C. for 24 h. The reaction mixture was diluted with EtOAc (25 mL) and 3N HCl (15 mL) and the layers were separated. The aqueous layer was extracted with EtOAc (1×25 mL) and the combine organic layer was evaporated. Purification by flash column chromatography using MeOH/DCM (0:10-9:1) as eluent afforded SR3-023 was obtained as a white foam (0.062 g, 98%). HPLC: >97% [t$_R$=6.0 min, 75% MeOH, 25% water (with 0.1% TFA), 20 min]. $^1$H NMR (500 MHz, DMSO-d$_6$) δ 8.52 (s, 1H), 7.47-7.34 (m, 4H), 7.34-7.29 (m, 1H), 7.15 (d, J=8.9 Hz, 2H), 7.11 (dd, J=8.4, 4.7 Hz, 2H), 6.90 (d, J=8.2 Hz, 2H), 6.80 (dd, J=8.4, 5.5 Hz, 2H), 5.47-5.30 (m, 2H), 5.05 (s, 1H), 5.01 (s, 1H), 4.26 (m, 1H), 3.97 (q, J=6.8 Hz, 2H), 3.75-3.62 (m, 1H), 3.21 (dd, J=13.6, 4.9 Hz, 1H), 3.08-2.93 (m, 1H), 2.88-2.74 (m, 1H), 2.71 (td, J=7.7, 2.7 Hz, 2H), 2.62-2.45 (m, 2H), 2.48-2.32 (m, 1H), 1.95 (d, J=7.3 Hz, 2H), 1.76-1.63 (m, 1H), 1.38 (d, J=13.1 Hz, 1H), 1.30 (t, J=6.9 Hz, 3H), 1.26-1.16 (m, 1H), 0.94-0.66 (m, 2H). HRMS (ESI+): m/z C$_{34}$H$_{41}$N$_6$O$_4$ (M+H)$^+$; 597.3190; m/z C$_{34}$H$_{40}$N$_6$O$_4$Na (M+Na)$^+$ 619.2997; HPLC-MS (ESI+): m/z 597.2 [100%, (M+H)$^+$]; m/z 619.2 [30%, (M+Na)$^+$].

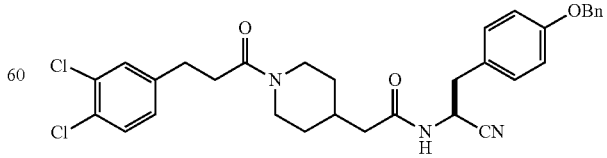

(S)—N-(2-(4-(Benzyloxy)phenyl)-1-cyanoethyl)-2-(1-(3-(3,4-dichlorophenyl)propanoyl)-piperidin-4-yl)acetamide (SR2-019). The nitrile SR2-019 was obtained as a white foam (0.077 g, 86%) from SR3-018 (0.039 g, 0.155 mmol) and 2-(1-(3-(3,4-dichlorophenyl)propanoyl)piperidin-4-yl)acetic acid (0.064 g, 0.186 mmol) following the same method used to make SR3-020. HPLC-MS (ESI+): m/z 578.2 [100%, (M+H)$^+$]. $^1$H NMR (500 MHz, DMSO-d$_6$) δ 8.64 (d, J=8.0 Hz, 1H), 7.56-7.47 (m, 2H), 7.43 (dd, J=10.2, 7.4 Hz, 2H), 7.37 (t, J=7.4 Hz, 2H), 7.32 (t, J=7.5 Hz, 1H), 7.26-7.23 (m, 1H), 7.21 (d, J=8.3 Hz, 2H), 6.95 (d, J=8.2 Hz, 2H), 5.07 (s, 1H), 5.05 (s, 1H), 4.96-4.85 (m, 1H), 4.33-4.25 (m, 1H), 3.85-3.70 (m, 1H), 3.05 (dd, J=13.7, 6.8 Hz, 1H), 2.94 (dd, J=13.6, 9.0 Hz, 1H), 2.90-2.82 (m, 1H), 2.81-2.75 (m, 2H), 2.69-2.53 (m, 2H), 2.48-2.34 (m, 1H), 2.03-1.95 (m, 2H), 1.85-1.69 (m, 1H), 1.46 (d, J=13.1 Hz, 1H), 1.40-1.26 (m, 1H), 1.00-0.72 (m, 2H).

(S)—N-(2-(4-(Benzyloxy)phenyl)-1-(2H-tetrazol-5-yl)ethyl)-2-(1-(3-(3,4-dichlorophenyl)-propanoyl)piperidin-4-yl)acetamide (SR3-034). The tetrazole SR2-034 was obtained as a white foam (0.071 g, 96%) from the nitrile SR2-019 (0.067 g, 0.119 mmol), ZnBr$_2$ (0.035 g, 0.157 mmol), and NaN$_3$ (0.046 g, 0.714 mmol) by the same method used to make SR3-023. HPLC: >97% [t$_R$=9.1 min, 75% MeOH, 25% water (with 0.1% TFA), 20 min]. $^1$H NMR (500 MHz, DMSO-d$_6$) δ 8.53 (d, J=8.3 Hz, 1H), 7.54-7.48 (m, 2H), 7.46-7.29 (m, 5H), 7.23 (td, J=8.0, 2.1 Hz, 1H), 7.14 (d, J=8.2 Hz, 2H), 6.91 (d, J=6.8 Hz, 2H), 5.37 (m, 1H), 5.05 (s, 1H), 5.02 (s, 1H), 4.26 (m, 1H), 3.72 (m, 1H), 3.23 (dd, J=13.8, 5.7 Hz, 1H), 3.01 (dd, J=13.8, 9.9 Hz, 1H), 1.99-1.93 (m, 3H), 1.77-1.61 (m, 1H), 1.45-1.32 (m, 1H), 1.28-1.19 (m, 2H), 0.94-0.61 (m, 3H). HRMS (ESI+): m/z C$_{32}$H$_{35}$Cl$_2$N$_6$O$_3$ (M+H)$^+$; 621.2144; m/z C$_{32}$H$_{34}$Cl$_2$N$_6$O$_3$Na (M+Na)$^+$ 643.1957; HPLC-MS (ESI+): m/z 621.2 [40%, (M+H)$^+$]; m/z 619.0 [30%, (M−Na)$^−$].

Synthesis of SR3-032 on Solid Phase

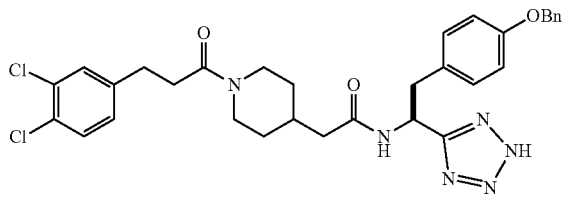 [SMILES: O=C(CC1CCN(C(=O)CCc2ccc(Cl)c(Cl)c2)CC1)N[C@@H](Cc1ccc(OCc2ccccc2)cc1)c1nn[nH]n1]

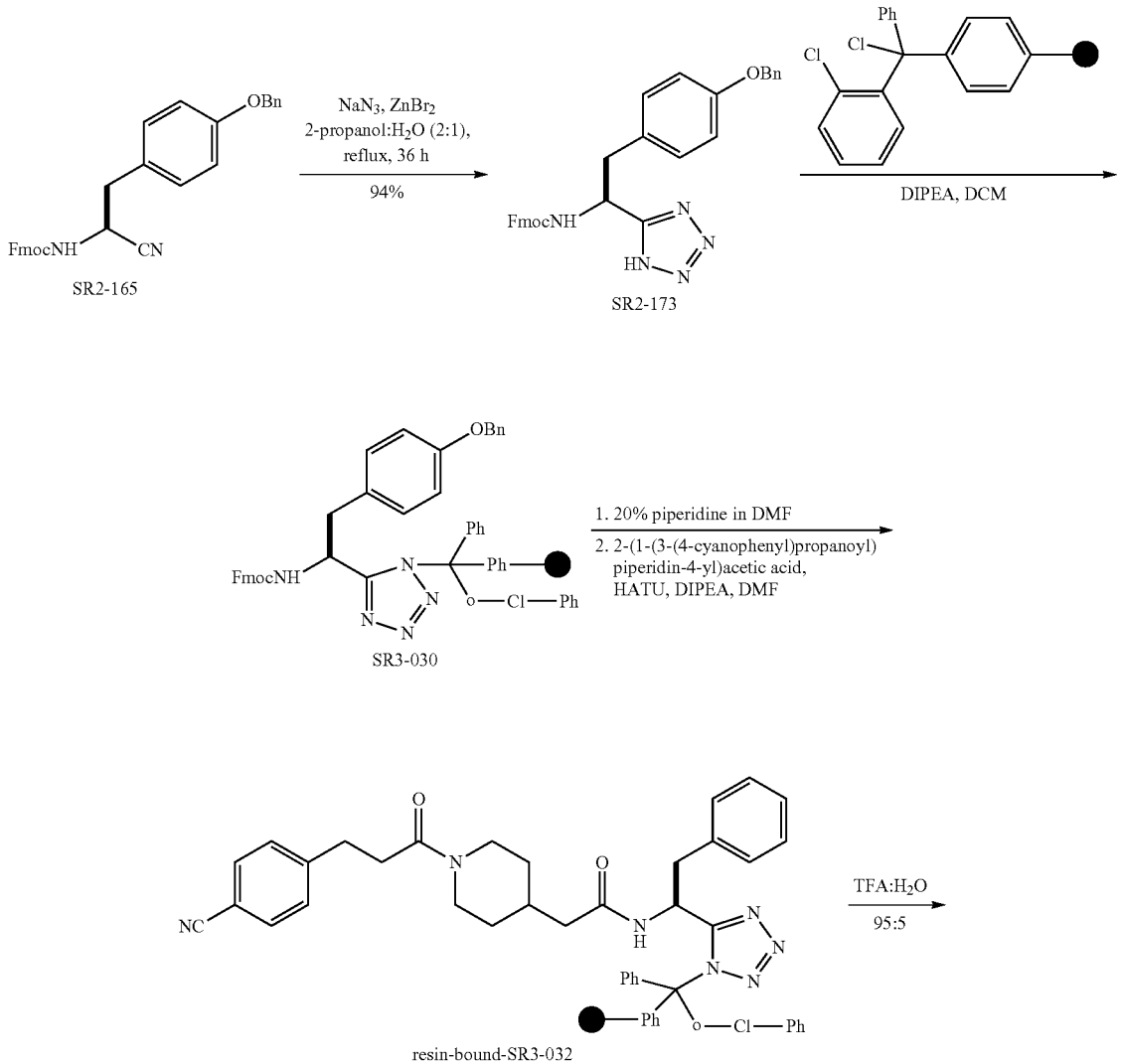

-continued

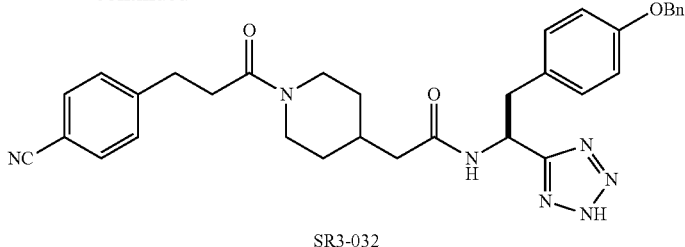

SR3-032

To prepare PPPY mimics containing both a tetrazole and nitrile group, a route shown in the Figure above was adopted. The Fmoc tetrazole SR2-173 was prepared from the nitrile SR2-165. This was then attached to a resin by chloro-trityl protection (Gunn, S. J., et al., Synlett, 2007, 2643-2646) of the tetrazole to provide SR3-030. Removal of the Fmoc group followed by acylation with 2-(1-(3-(4-cyanophenyl)propanoyl)piperidin-4-yl)acetic acid gave resin-bound-SR3-032. The required nitrile-containing PPPY mimic SR3-032 was obtained by treatment of resin-bound-SR3-032 with trifluoroacetic acid.

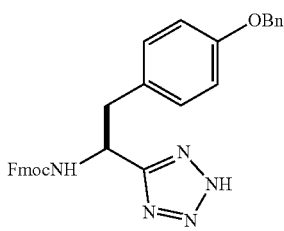

(9H-Fluoren-9-yl)methyl (S)-(2-(4-(benzyloxy)phenyl)-1-(1H-tetrazol-5-yl)ethyl)carbamate (SR2-173). The tetrazole SR2-173 was obtained as a white foam (0.072 g, 94%) from SR2-165 by the same method used to make SR3-023. $^1$H NMR (500 MHz, DMSO-$d_6$) δ 8.12 (bs, 1H), 7.88 (d, J=7.6 Hz, 2H), 7.63 (dd, J=7.6, 3.1 Hz, 2H), 7.44-7.33 (m, 7H), 7.33-7.26 (m, 2H), 7.15 (d, J=8.2 Hz, 2H), 6.86 (d, J=8.2 Hz, 2H), 5.13-5.01 (m, 1H), 4.98 (s, 2H), 4.28-4.06 (m, 1H), 3.26-3.13 (m, 1H), 3.12-3.01 (m, 1H). HPLC-MS (ESI+): m/z 518.2 [100%, (M+H)$^+$]; m/z 540.3 [70%, (M+Na)$^+$]; m/z 516.3 [60%, (M−H)$^−$].

Solid Phase Protocol

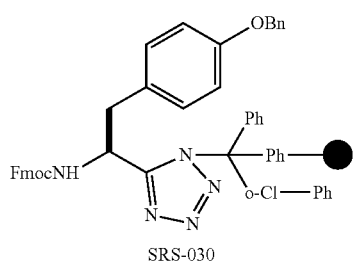

SRS-030

Resin-bound Fmoc-tetrazole SR3-030. A suspension of 2-chlorotrityl chloride resin (0.386 g, 0.744 mmol, 1.1 eq./g loading) in DCM (5 mL) was agitated for 1 h. The solvent was drained and a solution of SR2-173 (0.220 g, 0.425 mmol) and DIEA (0.259 L, 1.487 mmol) in 1:1 DMF/DCM (5 mL) was added to the resin. The mixture was stirred slowly for 6 h at room temperature and the solution drained. The resin was washed successively with DMF (3×3 mL), DCM (3×mL), and hexane (3×3 mL) and dried under high vacuum to afford resin bound product SR3-030 and was used directly in the next step.

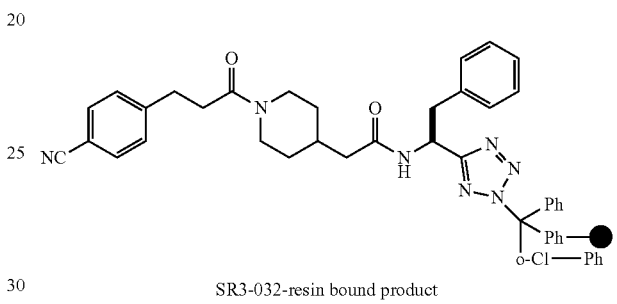

SR3-032-resin bound product

Resin-bound SR3-032. To Fmoc-tetrazole-bound resin SR3-030 was added 20% solution of piperdine in DMF (3 mL) and stirred for 20 min. The solution was drained and the resin washed with DMF (3×3 mL) and DCM (3×3 mL). To the resin HATU (0.323 g, 0.850 mmol), DIEA (0.296 mL, 1.700 mmol), and 2-(1-(3-(4-cyanophenyl)propanoyl)piperidin-4-yl)acetic acid (0.255 g, 0.850 mmol) were added and the resulting mixture stirred slowly for 10 h. The solvent was drained and the resin was sequentially washed with DMF (3×3 mL) and DCM (3×3 mL), and MeOH (1×3 mL) and dried under high vacuum to afford resin bound SR3-032 and was used directly in the next step

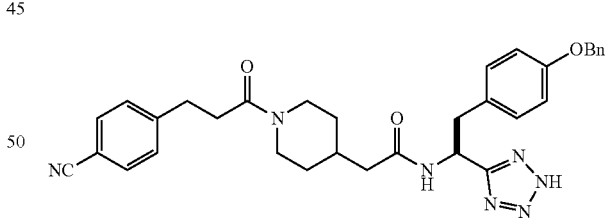

(S)—N-(2-(4-(Benzyloxy)phenyl)-1-(2H-tetrazol-5-yl)ethyl)-2-(1-(3-(4-cyanophenyl)-propanoyl)piperidin-4-yl)acetamide (SR3-032). Cleavage of SR3-032 from resin-bound SR3-032 was affected by stirring with a solution of TFA/H$_2$O (95:5) for 2 h. The suspension was filtered through cotton plug and the residue rinsed with DCM. The combined organic layers were evaporated under reduced pressure to give a gummy residue which then dissolved in EtOAc. This solution was washed with water (1×10 mL) and evaporated to afford an off-white solid. Purification by flash column chromatography using MeOH/DCM (0-15%) as eluent afforded SR3-032 as a white solid (26 mg, 11%). HPLC: >95% [$t_R$=3.9 min, 70% MeOH, 30% water (with 0.1% TFA), 20 min]. $^1$H NMR (500 MHz, DMSO-d$_6$) δ 8.51 (d, J=8.3 Hz, 1H), 7.72 (t, J=8.2 Hz, 2H), 7.51-7.29 (m, 7H), 7.14 (d, J=8.3 Hz, 2H), 6.90 (d, J=8.2 Hz, 2H), 5.42-5.31 (m, 1H), 5.04 (s, 1H), 5.01 (s, 1H), 4.25 (m, 1H), 3.71 (dd, J=23.6, 13.4 Hz, 1H), 3.22 (dd, J=13.8, 5.7 Hz, 1H), 3.00 (dd, J=13.7, 9.9 Hz, 1H), 2.85 (m, 3H), 2.68-2.54 (m, 2H), 2.48-2.33 (m, 1H), 1.96 (d, J=7.3 Hz, 2H), 1.78-1.65 (m, 1H), 1.40 (d, J=13.0 Hz, 1H), 1.27-1.19 (m, 1H), 0.93-0.69 (m, 2H). HRMS (ESI+): m/z C$_{33}$H$_{36}$N$_7$O$_3$ (M+H)$^+$; 578.2872; m/z C$_{33}$H$_{35}$N$_7$O$_3$Na (M+Na)$^+$600.2680; HPLC-MS (ESI+): m/z 576.3 [100%, (M+H)$^+$].

Synthesis of N-Terminal Propionic Amides.

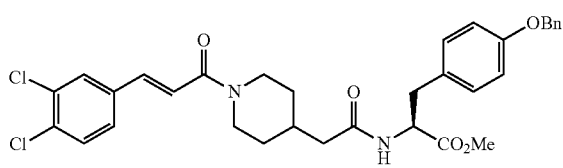 [SMILES: COC(=O)[C@H](Cc1ccc(OCc2ccccc2)cc1)NC(=O)CC1CCN(C(=O)/C=C/c2ccc(Cl)c(Cl)c2)CC1]

Methyl (S,E)-3-(4-(benzyloxy)phenyl)-2-(2-(1-(3-(3,4-dichlorophenyl)acryloyl)piperidin-4-yl)acetamido)propanoate (SR3-001). The amide SR3-001 was obtained as a white foam (0.061 g, 90%) from (E)-(3,4-dichlorophenyl)acrylic acid (0.029 g, 0.134 mmol) and amine salt SR1-085 (0.050 g, 0.112 mmol) using the general method D. HPLC: >99% [t$_R$=7.8 min, 80% MeOH, 20% water (with 0.1% TFA), 20 min]. $^1$H NMR (500 MHz, DMSO-d$_6$) δ 8.27 (d, J=7.9 Hz, 1H), 8.14-8.08 (m, 1H), 7.70 (t, J=9.1 Hz, 1H), 7.64 (dd, J=11.1, 8.3 Hz, 1H), 7.48-7.28 (m, 7H), 7.14 (d, J=8.3 Hz, 2H), 6.92 (d, J=8.7 Hz, 2H), 5.06 (bs, 2H), 4.46 (m, 1H), 4.41-4.29 (m, 1H), 4.29-4.14 (m, 1H), 3.61 (s, 3H), 2.98 (m, 2H), 2.79 (td, J=14.0, 11.7, 5.3 Hz, 1H), 2.67-2.53 (m, 1H), 2.01 (dd, J=7.0, 3.7 Hz, 2H), 1.92-1.74 (m, 1H), 1.66-1.45 (m, 1H), 1.39 (m, 1H), 1.09-0.83 (m, 2H). HRMS (ESI+): m/z C$_{33}$H$_{35}$C$_{12}$N$_2$O$_5$ (M+H)$^+$; 609.1899; m/z C$_{33}$H$_{34}$C$_{12}$N$_2$O$_5$Na (M+Na)$^+$631.1756; HPLC-MS (ESI+): m/z 609.2 [40%, (M+H)$^+$].

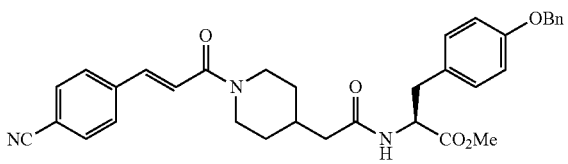

Methyl (S,E)-3-(4-(benzyloxy)phenyl)-2-(2-(1-(3-(4-cyanophenyl)acryloyl)piperidin-4-yl)acetamido)propanoate (SR3-002). The amide SR3-002 was obtained as a white foam (0.059 g, 94%) from trans-4-cyanocinnamic acid (0.023 g, 0.134 mmol) and amine salt SR1-085 (0.050 g, 0.112 mmol) using the general method D. HPLC: >98% [t$_R$=5.2 min, 75% MeOH, 25% water (with 0.1% TFA), 20 min]. $^1$H NMR (500 MHz, DMSO-d$_6$) δ 8.27 (d, J=7.9 Hz, 1H), 7.92 (dd, J=13.6, 8.1 Hz, 2H), 7.85 (dd, J=12.1, 8.1 Hz, 2H), 7.54-7.40 (m, 4H), 7.39-7.34 (m, 2H), 7.31 (t, J=7.2 Hz, 1H), 7.14 (d, J=8.2 Hz, 2H), 6.92 (d, J=8.5 Hz, 2H), 5.06 (bs, 2H), 4.46 (dt, J=8.7, 4.1 Hz, 1H), 4.41-4.32 (m, 1H), 4.28-4.11 (m, 1H), 3.61 (s, 3H), 3.00 (dd, J=19.9, 12.3 Hz, 2H), 2.83-2.74 (m, 1H), 2.68-2.53 (m, 1H), 2.04-1.96 (m, 2H), 1.84-1.74 (m, 1H), 1.64-1.53 (m, 1H), 1.53-1.35 (m, 1H), 1.12-0.81 (m, 2H). HRMS (ESI+): m/z C$_{34}$H$_{36}$N$_3$O$_5$ (M+H)$^+$; 566.2651; m/z C$_{34}$H$_{35}$N$_3$O$_5$Na (M+Na)$^+$588.2472; HPLC-MS (ESI+): m/z 566.2 [70%, (M+H)$^+$].

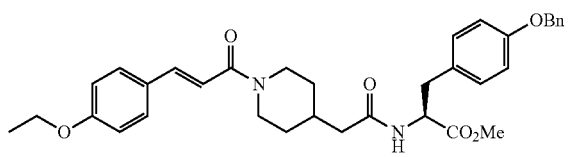 [SMILES: CCOc1ccc(/C=C/C(=O)N2CCC(CC(=O)N[C@@H](Cc3ccc(OCc4ccccc4)cc3)C(=O)OC)CC2)cc1]

Methyl (S,E)-3-(4-(benzyloxy)phenyl)-2-(2-(1-(3-(4-ethoxyphenyl)acryloyl)piperidin-4-yl)acetamido)propanoate (SR3-003). The amide SR3-003 was obtained as a white foam (0.062 g, 95%) from 4-ethoxycinnamic acid (0.026 g, 0.134 mmol) and amine salt SR1-085 (0.050 g, 0.112 mmol) using the general method D. $^1$H NMR (500 MHz, DMSO-d$_6$) δ 8.27 (d, J=8.0 Hz, 1H), 7.68-7.58 (m, 2H), 7.44 (d, J=7.1 Hz, 2H), 7.41-7.35 (m, 3H), 7.32 (m, 1H), 7.14 (d, J=8.6 Hz, 2H), 7.12-7.01 (m, 1H), 6.95-6.89 (m, 4H), 5.07 (s, 2H), 4.46 (dd, J=14.4, 7.2 Hz, 2H), 4.39 (m, 1H), 4.29-4.10 (m, 1H), 4.06 (q, J=6.9 Hz, 2H), 3.61 (s, 3H), 3.03-2.88 (m, 2H), 2.78 (dd, J=13.8, 10.0 Hz, 1H), 2.64-2.53 (m, 1H), 2.00 (d, J=7.2 Hz, 2H), 1.88-1.72 (m, 1H), 1.65-1.51 (m, 1H), 1.45 (m, 1H), 1.33 (t, J=7.0 Hz, 3H), 1.07-0.80 (m, 3H). HPLC: >98% [t$_R$=8.4 min, 75% MeOH, 25% water (with 0.1% TFA), 20 min]. HRMS (ESI+): m/z C$_{35}$H$_{41}$N$_2$O$_6$ (M+H)$^+$; 585.2962; m/z C$_{35}$H$_{40}$N$_2$O$_6$Na (M+Na)$^+$607.2784; HPLC-MS (ESI+): m/z 585.2 [100%, (M+H)$^+$].

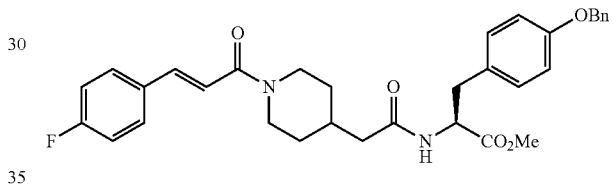

Methyl (S,E)-3-(4-(benzyloxy)phenyl)-2-(2-(1-(3-(4-fluorophenyl)acryloyl)piperidin-4-yl)acetamido)propanoate (SR3-021). The amide SR3-021 was obtained as a white foam (0.077 g, 88%) from 4-fluorocinnamic acid (0.031 g, 0.187 mmol) and amine salt SR1-085 (0.050 g, 0.112 mmol) using the general method D. HPLC: >98% [t$_R$=7.1 min, 75% MeOH, 25% water (with 0.1% TFA), 20 min]. $^1$H NMR (500 MHz, DMSO-d$_6$) δ 8.27 (d, J=8.0 Hz, 1H), 7.78 (m, 2H), 7.50-7.40 (m, 3H), 7.39-7.34 (m, 2H), 7.34-7.28 (m, 1H), 7.27-7.16 (m, 3H), 7.14 (d, J=8.6 Hz, 2H), 6.92 (d, J=8.7 Hz, 2H), 5.06 (s, 2H), 4.53-4.41 (m, 1H), 4.42-4.30 (m, 1H), 4.29-4.11 (m, 1H), 3.61 (s, 3H), 3.07-2.88 (m, 3H), 2.86-2.72 (m, 1H), 2.68-2.53 (m, 1H), 2.00 (d, J=6.9 Hz, 2H), 1.91-1.73 (m, 1H), 1.64-1.52 (m, 1H), 1.51-1.32 (m, 1H), 1.08-0.80 (m, 2H). $^{19}$F NMR (471 MHz, DMSO-d$_6$) δ −111.70. HRMS (ESI+): m/z C$_{33}$H$_{36}$FN$_2$O$_5$ (M+H)$^+$ 559.2598; m/z C$_{33}$H$_{35}$FN$_2$O$_5$Na (M+Na)$^{-1}$ 581.2414; HPLC-MS (ESI+): m/z 559.2 [60%, (M+H)$^+$]; m/z. 581.3 [50% (M+Na)$^+$].

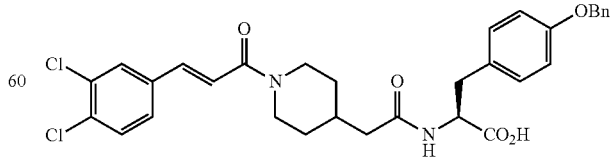

(S,E)-3-(4-(Benzyloxy)phenyl)-2-(2-(1-(3-(3,4-dichlorophenyl)acryloyl)piperidin-4-yl)acetamido)propanoic acid (SR3-010). The carboxylic acid SR3-010 was obtained as a white foam (0.023 g, 90%) from the methyl ester SR3-001 (0.026 g, 0.043 mmol) using general method E. HPLC: >99% [$t_R$=6.6 min, 80% MeOH, 20% water (with 0.1% TFA), 20 min]. $^1$H NMR (500 MHz, DMSO-$d_6$) δ 12.66 (bs, 1H), 8.14-8.08 (m, 2H), 7.73-7.67 (m, 1H), 7.63 (dd, J=12.3, 8.4 Hz, 1H), 7.50-7.26 (m, 6H), 7.15 (d, J=8.3 Hz, 2H), 6.92 (d, J=8.3 Hz, 2H), 5.06 (s, 2H), 4.48-4.30 (m, 2H), 4.27-4.11 (m, 1H), 3.09-2.90 (m, 2H), 2.83-2.68 (m, 1H), 2.65-2.53 (m, 1H), 2.05-1.94 (m, 2H), 1.89-1.74 (m, 1H), 1.64-1.53 (m, 1H), 1.52-1.32 (m, 1H), 1.10-0.70 (m, 2H). HRMS (ESI+): m/z $C_{33}H_{33}Cl_2N_2O_5$ (M+H)$^+$; 595.1757; m/z $C_{33}H_{32}Cl_2N_2O_5Na$ (M+Na)$^{-1}$ 617.1571; HPLC-MS (ESI+): m/z 595.2 [60%, (M+H)$^+$]; HPLC MS (ESI-): m/z. 593.2 [20% (M-H)$^-$].

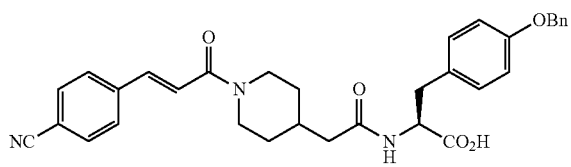 [SMILES: N#Cc1ccc(/C=C/C(=O)N2CCC(CC(=O)N[C@@H](Cc3ccc(OCc4ccccc4)cc3)C(=O)O)CC2)cc1]

(S,E)-3-(4-(Benzyloxy)phenyl)-2-(2-(1-(3-(4-cyanophenyl)acryloyl)piperidin-4-yl)acetamido)propanoic acid (SR3-011). The carboxylic acid SR3-011 was obtained as a white foam (0.019 g, 83%) from the methyl ester SR3-002 (0.024 g, 0.042 mol) using general method E. HPLC: >97% [$t_R$=4.5 min, 75% MeOH, 25% water (with 0.1% TFA), 20 min]. $^1$H NMR (500 MHz, DMSO-$d_6$) δ 12.65 (bs, 1H), 8.12 (d, J=8.2 Hz, 1H), 7.91 (dd, J=14.8, 8.1 Hz, 2H), 7.85 (dd, J=13.4, 8.1 Hz, 2H), 7.53-7.40 (m, 4H), 7.37 (t, J=7.4 Hz, 2H), 7.31 (t, J=7.3 Hz, 1H), 7.15 (d, J=8.3 Hz, 2H), 6.92 (d, J=8.6 Hz, 2H), 5.06 (s, 2H), 4.47-4.30 (m, 2H), 4.26-4.12 (m, 1H), 3.06-2.94 (m, 2H), 2.80-2.68 (m, 1H), 2.66-2.53 (m, 1H), 2.04-1.96 (m, 2H), 1.90-1.72 (m, 1H), 1.68-1.52 (m, 1H), 1.51-1.31 (m, 1H), 1.09-0.72 (m, 2H). HRMS (ESI+): m/z $C_{33}H_{34}N_3O_5$ (M+H)$^+$552.2483; m/z $C_{33}H_{33}N_3O_5Na$ (M+Na)$^+$574.2300; HPLC-MS (ESI+): m/z 552.2 [60%, (M+H)$^+$]; HPLC-MS (ESI-): m/z. 551.0 [20% (M-H)$^-$].

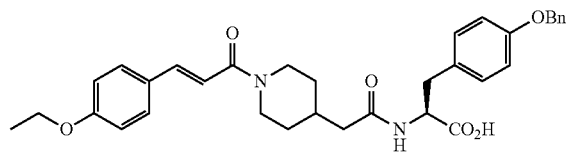 [SMILES: CCOc1ccc(/C=C/C(=O)N2CCC(CC(=O)N[C@@H](Cc3ccc(OCc4ccccc4)cc3)C(=O)O)CC2)cc1]

(S,E)-3-(4-(Benzyloxy)phenyl)-2-(2-(1-(3-(4-ethoxyphenyl)acryloyl)piperidin-4-yl)acetamido)propanoic acid (SR3-012). The carboxylic acid SR3-012 was obtained as a white foam (0.020 g, 83%) from the methyl ester SR3-003 (0.025 g, 0.043 mol) using general method E. HPLC: >97% [$t_R$=6.8 min, 75% MeOH, 25% water (with 0.1% TFA), 20 min]. $^1$H NMR (500 MHz, DMSO-$d_6$) δ 12.65 (bs, 1H), 8.11 (d, J=8.3 Hz, 1H), 7.63 (dt, J=8.3, 4.8 Hz, 2H), 7.49-7.41 (m, 3H), 7.41-7.38 (m, 1H), 7.38-7.34 (m, 1H), 7.32 (m, 1H), 7.15 (d, J=8.7 Hz, 2H), 7.12-7.02 (m, 1H), 6.97-6.97 (m, 2H), 6.92 (d, J=8.7 Hz, 2H), 5.06 (s, 2H), 4.46-4.30 (m, 2H), 4.26-4.06 (m, 1H), 4.06 (q, J=7.8, 7.1 Hz, 2H), 3.01 (dd, J=13.9, 4.6 Hz, 1H), 2.95 (m, 1H), 2.75 (dd, J=13.8, 10.2 Hz, 1H), 2.65-2.53 (m, 1H), 1.99 (d, J=7.2 Hz, 2H), 1.80 (m, 1H), 1.56 (m, 1H), 1.48-1.36 (m, 1H), 1.33 (t, J=7.0 Hz, 3H), 1.10-0.79 (m, 2H). HRMS (ESI+): m/z $C_{34}H_{39}N_2O_6$ (M+H)$^+$571.2810; m/z $C_{34}H_{38}N_2O_6Na$ (M+Na)$^+$593.2618; HPLC-MS (ESI+): m/z 571.2 [60%, (M+H)$^+$]; HPLC-MS (ESI-): m/z. 569.2 [80% (M-H)$^-$].

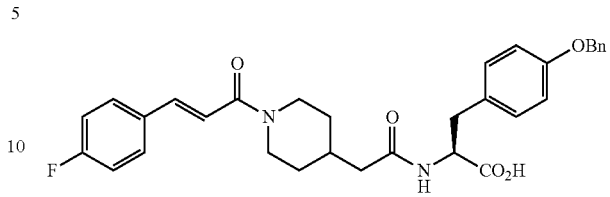

(S,E)-3-(4-(Benzyloxy)phenyl)-2-(2-(1-(3-(4-fluorophenyl)acryloyl)piperidin-4-yl)acetamido)propanoic acid (SR3-027). The carboxylic acid SR3-027 was obtained as a white foam (0.025 g, 87%) %) from the methyl ester SR3-021 (0.030 g, 0.054 mol) using general method E. HPLC: >98% [$t_R$=4.6 min, 75% MeOH, 25% water (with 0.1% TFA), 20 min]. $^1$H NMR (500 MHz, DMSO-$d_6$) δ 12.64 (bs, 1H), 8.11 (d, J=8.3 Hz, 1H), 7.83-7.71 (m, 2H), 7.48-7.41 (m, 3H), 7.39-7.34 (m, 2H), 7.34-7.27 (m, 1H), 7.27-7.18 (m, 3H), 7.15 (d, J=8.6 Hz, 2H), 6.92 (d, J=8.7 Hz, 2H), 5.06 (s, 2H), 4.45-4.30 (m, 2H), 4.25-4.10 (m, 1H), 3.05-2.94 (m, 2H), 2.81-2.68 (m, 1H), 2.67-2.53 (m, 1H), 1.99 (d, J=7.1 Hz, 2H), 1.87-1.74 (m, 1H), 1.65-1.52 (m, 1H), 1.49-1.30 (m, 1H), 1.08-0.76 (m, 2H). HRMS (ESI+): m/z $C_{32}H_{34}FN_2O_5$ (M+H)$^+$545.2460; m/z $C_{32}H_{33}FN_2O_5Na$ (M+Na)$^+$567.2262; HPLC-MS (ESI+): m/z 545.2 [60%, (M+H)$^+$]; HPLC-MS (ESI-): m/z. 543.2 [100% (M-H)$^-$].

Synthesis of NCI 41092 Series

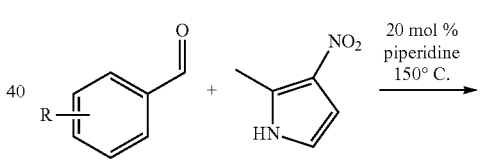

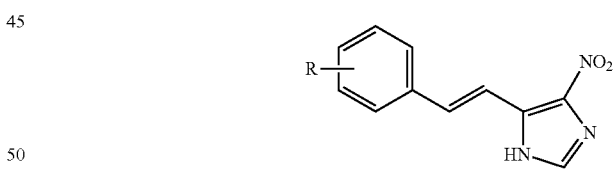

A series of nitroimidazole-substituted alkenes were prepared as OCT4-YAP1 disruptors using the method shown above.

General Procedure for the Condensation Reaction

5-Methyl-4-nitroimidazole (0.200 g, 1.573 mmol) and corresponding aldehyde (3.934 mmol, 2.5 eq.) were mixed in a microwave tube (5 mL). Piperidine (0.031 mL, 0.315 mmol, 0.2 eq.) was added to the mixture under argon and the vial sealed. The mixture was heated at 150° C. for 30 min. The resulting solid mixture was triturated in water (1×5 mL) and ethanol (1×5 mL) or DCM/hexane (1:9 ratio, 3×5 mL)*. The supernatant was decanted and the solid isolated as a pure product. (*Used for the crude products when water/ethanol system did not facilitate precipitation).

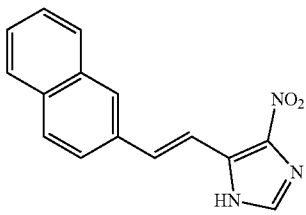 [SMILES: O=[N+]([O-])c1nc[nH]c1/C=C/c1ccc2ccccc2c1]

(E)-5-(2-(Naphthalen-2-yl)vinyl)-4-nitro-1H-imidazole (SR2-048). The alkene SR2-048 was obtained as a bright yellow solid (0.186 g, 45%) using 2-naphthaldehyde (0.614 g, 3.934 mmol) by following the above general procedure. HPLC: >99% [$t_R$=5.6 min, 70% MeOH, 30% water (with 0.1% TFA), 20 min]. $^1$H NMR (400 MHz, DMSO-$d_6$) δ 13.68 (bs, 1H), 8.05-8.02 (bs, 1H), 8.00 (m, 1H), 7.98 (bs, 0.5H), 7.96 (bs, 0.5H), 7.94 (m, 1.5H), 7.92 (m, 0.5H), 7.82 (d, J=1.8 Hz, 0.5H), 7.80 (s, 0.5H), 7.80 (s, 0.3H), 7.76 (s, 0.7H), 7.65 (s, 0.6H), 7.61 (s, 0.4H), 7.54 (m, 2H). HRMS (ESI+): m/z $C_{15}H_{12}N_3O_2$ (M+H)$^+$266.0922; m/z $C_{15}H_{11}N_3O_2$Na 288.0738. HPLC-MS (ESI+): m/z 266.2 [40%, (M+H)$^+$], 553.2 [100%, (2M+Na)$^+$].

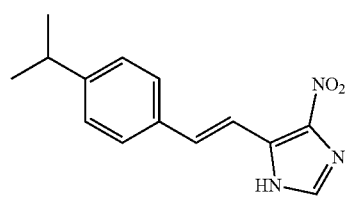 [SMILES: CC(C)c1ccc(/C=C/c2[nH]cnc2[N+](=O)[O-])cc1]

(E)-5-(4-Isopropylstyryl)-4-nitro-1H-imidazole (SR2-054). The alkene SR2-054 was obtained as a bright yellow solid (0.296 g, 73%) using 4-isopropylbenzaldehyde (0.607 mL, 3.934 mmol) by following the above general procedure. HPLC: >99% [$t_R$=8.5 min, 70% MeOH, 30% water (with 0.1% TFA), 20 min]. $^1$H NMR (400 MHz, DMSO-$d_6$) δ 13.57 (bs, 1H), 7.89 (m, 1H), 7.61 (s, 0.4H), 7.57 (s, 0.6H), 7.52 (s, 1H), 7.50 (s, 1H), 7.46 (s, 0.6H), 7.41 (s, 0.4H), 7.32 (1, 1H), 7.30 (s, 1H), 2.90 (h, J=6.9 Hz, 1H), 1.21 (s, 3H), 1.19 (s, 3H). HRMS (ESI+): m/z $C_{14}H_{16}N_3O_2$ (M+H)$^+$ 258.1242; m/z $C_{14}H_{15}N_3O_2$Na (M+Na)$^+$280.1052. HPLC-MS (ESI+): m/z 258.2 [40%, (M+H)$^+$], 537.3 [100%, (2M+Na)$^+$].

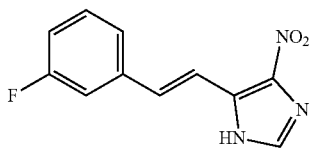 [SMILES: O=[N+]([O-])c1nc[nH]c1/C=C/c1cccc(F)c1]

(E)-5-(3-Fluorostyryl)-4-nitro-1H-imidazole SR2-055). The alkene SR2-055 was obtained as a bright yellow solid (0.220 g, 60%) using 3-fluorobenzaldehyde (0.413 mL, 3.934 mmol) by following the above general procedure. HPLC: >99% [$t_R$=7.2 min, 60% MeOH, 40% water (with 0.1% TFA), 20 min]. $^1$H NMR (400 MHz, DMSO-$d_6$) δ 13.66 (bs, 1H), 7.93 (s, 1H), 7.69 (s, 0.5H), 7.65 (s, 0.5H), 7.54-7.39 (m, 4H), 7.21 (td, J=8.7, 2.5 Hz, 1H). $^{19}$F NMR (376 MHz, DMSO-$d_6$) δ -112.71 (td, J=9.3, 6.1 Hz). HRMS (ESI+): m/z $C_{11}H_9FN_3O_2$ (M+H)$^+$234.0676; m/z $C_{11}H_8FN_3O_2$Na (M+Na)$^+$256.0488. HPLC-MS (ESI+): m/z 234.1 [40%, (M+H)$^+$], 489.1 [100%, (2M+Na)$^+$].

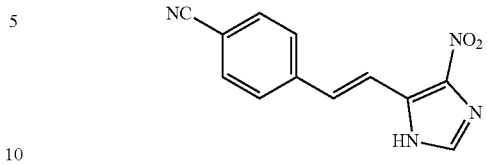

(E)-4-(2-(4-Nitro-1H-imidazol-5-yl)vinyl)benzonitrile (SR2-067). The alkene SR2-067 was obtained as an orange color solid (0.134 g, 36%) using 4-cyanobenzaldehyde (0.517 g, 3.934 mmol) by following the above general procedure. HPLC: >99% [$t_R$=6.9 min, 50% MeOH, 50% water (with 0.1% TFA), 20 min]. $^1$H NMR (400 MHz, DMSO-$d_6$) δ 13.69 (bs, 1H), 7.94 (s, 1H), 7.88 (s, 1H), 7.86 (s, 1H), 7.82-7.73 (m, 3H), 7.49 (d, J=16.7 Hz, 1H). HRMS (ESI+): m/z $C_{12}H_9N_4O_2$ (M+H)$^+$241.0718; m/z $C_{12}H_8N_4O_2$Na (M+Na)$^+$263.0532. HPLC-MS (ESI+): m/z 241.2 [100%, (M+H)$^+$], 503.2 [80%, (2M+Na)$^+$].

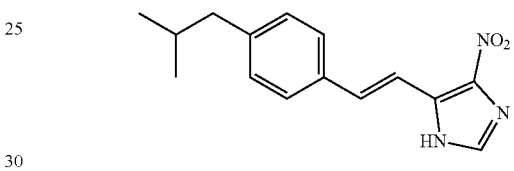

(E)-5-(4-Isobutylstyryl)-4-nitro-1H-imidazole SR2-068). The alkene SR2-068 was obtained as a yellow solid (0.223 g, 52%) using 4-isobutylbenzaldehyde (0.638 g, 3.934 mmol) by following the above general procedure. HPLC: >99% [$t_R$=4.9 min, 20% MeOH, 80% water (with 0.1% formic acid), 20 min]. $^1$H NMR (400 MHz, DMSO-$d_6$) δ 13.55 (bs, 1H), 7.90 (b, 1H), 7.61 (d, J=16.7 Hz, 1H), 7.51 (d, J=8.2 Hz, 2H), 7.45 (d, J=16.8 Hz, 1H), 7.24 (d, J=8.2 Hz, 2H), 2.53 (s, 1H), 2.47 (s, 1H), 1.85 (h, J=7.1 Hz, 1H), 0.88 (s, 3H), 0.86 (s, 3H). HRMS (ESI+): m/z $C_{15}H_{18}N_3O_2$ (M+H)$^+$272.1397; m/z $C_{15}H_{17}N_3O_2$Na (M+Na)$^+$294.2109. HPLC-MS (ESI+): m/z 272.2 [30%, (M+H)$^+$], 565.3 [100%, (2M+Na)$^+$].

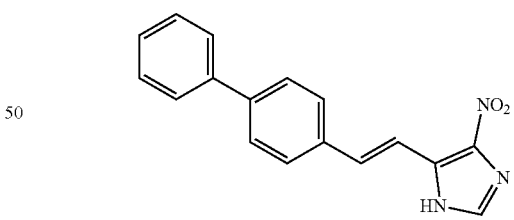

(E)-5-(2-([1,1'-Biphenyl]-4-yl)vinyl)-4-nitro-1H-imidazole (SR2-069). The alkene SR2-069 was obtained as a yellow solid (0.381 g, 83%) using 4-biphenylcarboxaldehyde (0.717 g, 3.934 mmol) by following the above general procedure. HPLC: >99% [$t_R$=9.1 min, 70% MeOH, 30% water (with 0.1% TFA), 20 min]. $^1$H NMR (400 MHz, DMSO-$d_6$) δ 13.63 (bs, 1H), 7.92 (b, 1H), 7.75 (d, J=8.4 Hz, 2H), 7.73-7.69 (m, 3H), 7.67 (d, J=10.5 Hz, 2H), 7.51 (d, J=10.5 Hz, 1H), 7.47 (m, 2H), 7.38 (m, 1H). HRMS (ESI+): m/z $C_{17}H_{14}N_3O_2$ (M+H)+292.1080; m/z $C_{17}H_{13}N_3O_2$Na (M+Na)$^+$314.0893. HPLC-MS (ESI+): m/z 605.2 [100%, (2M+Na)$^+$]; (ESI-): m/z 290.1 [100%, (M-H)$^-$].

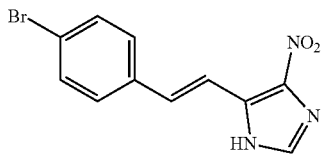 [SMILES: O=[N+]([O-])c1nc[nH]c1/C=C/c1ccc(Br)cc1]

(E)-5-(4-Bromostyryl)-4-nitro-1H-imidazole (SR2-071). The alkene SR2-071 was obtained as a brick red solid (0.322 g, 70%) using 4-bromobenzaldehyde (0.437 g, 2.360 mmol, 1.5 eq.) by following the above general procedure. HPLC: >99% [$t_R$=5.3 min, 70% MeOH, 30% water (with 0.1% TFA), 20 min]. $^1$H NMR (400 MHz, DMSO-$d_6$) δ 13.62 (bs, 1H), 7.92 (s, 1H), 7.65 (d, J=15.9 Hz, 1H), 7.62 (d, J=8.6 Hz, 2H), 7.54 (d, J=8.5 Hz, 2H), 7.40 (d, J=16.7 Hz, 1H). HRMS (ESI+): m/z $C_{11}H_9BrN_3O_2$ (M+H)$^+$293.9869; m/z $C_{11}H_8BrN_3O_2Na$ (M+Na)$^+$315.9690. HPLC-MS (ESI+): m/z 294.0 [40%, (M+H)$^+$], 611.0 [100%, (2M+Na)$^+$]; (ESI−): m/z 292.0 [100%, (M−H)$^-$].

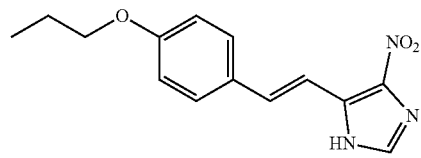 [SMILES: CCCOc1ccc(/C=C/c2[nH]cnc2[N+](=O)[O-])cc1]

(E)-4-Nitro-5-(4-propoxystyryl)-1H-imidazole (SR2-072). The alkene SR2-072 was obtained as a bright yellow solid (0.353 g, 82%) using 4-propoxybenzaldehyde (0.373 mL, 2.360 mmol, 1.5 eq.) by following the above general procedure. HPLC: >99% [$t_R$=14.2 min, 60% MeOH, 40% water (with 0.1% formic acid), 20 min]. $^1$H NMR (400 MHz, DMSO-$d_6$) δ 13.50 (bs, 1H), 7.86 (s, 1H), 7.52 (d, J=8.8 Hz, 2H), 7.50 (d, J=16.7 Hz, 1H), 7.40 (d, J=16.8 Hz, 1H), 6.98 (d, J=8.8 Hz, 2H), 3.95 (t, J=6.5 Hz, 2H), 1.72 (qt, J=7.1 Hz, 2H), 0.97 (t, J=7.4 Hz, 3H). HRMS (ESI+): m/z $C_{14}H_{16}N_3O_3$ (M+H)$^+$274.1190; m/z $C_{14}H_{15}N_3O_3Na$ (M+Na)$^+$296.1003. HPLC-MS (ESI+): m/z 274.2 [30%, (M+H)$^+$], 569.2 [100%, (2M+Na)$^+$]; (ESI−): m/z 272.2 [100%, (M−H)$^-$].

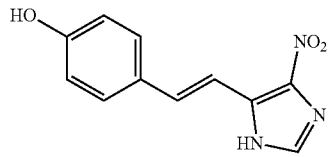

(E)-4-(2-(4-Nitro-1H-imidazol-5-yl)vinyl)phenol (SR2-073). The alkene SR2-073 was obtained as a brick red solid (0.352 g, 96%) using 4-hydroxybenzaldehyde (0.288 g, 2.360 mmol, 1.5 eq.) by following the above general procedure. HPLC: >99% [$t_R$=9.2 min, 40% MeOH, 60% water (with 0.1% formic acid), 20 min]. $^1$H NMR (400 MHz, DMSO-$d_6$) δ 13.14 (bs, 1H), 9.89 (bs, 1H), 7.81 (s, 1H), 7.45 (d, J=15.8 Hz, 1H), 7.42 (d, J=8.7 Hz, 2H), 7.36 (d, J=16.7 HZ, 1H), 6.81 (D, J=8.6 HZ, 2H). HRMS (ESI+): M/Z $C_{11}H_{10}N_3O_3$ (M+H)$^+$232.0723; m/z $C_{11}H_9N_3O_3Na$ (M+Na)$^+$254.0536. HPLC-MS (ESI+): m/z 232.2 [80%, (M+H)$^+$], 485.1 [100%, (2M+Na)$^+$]; (ESI−): m/z 230.2 [90%, (M−H)$^-$].

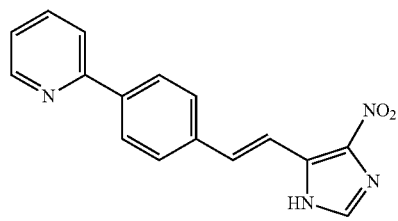 [SMILES: O=[N+]([O-])c1nc[nH]c1/C=C/c1ccc(-c2ccccn2)cc1]

(E)-2-(4-(2-(4-Nitro-1H-imidazol-5-yl)vinyl)phenyl)pyridine (SR2-074). The alkene SR2-074 was obtained as a bright yellow solid (0.331 g, 72%) using 4-(2-pyridyl)benzaldehyde (0.432 g, 2.360 mmol, 1.5 eq.) by following the above general procedure. HPLC: >97% [$t_R$=5.8 min, 55% MeOH, 45% water (with 0.1% formic acid), 20 min]. $^1$H NMR (400 MHz, DMSO-$d_6$) δ 13.63 (bs, 1H), 8.67 (ddd, J=4.8, 1.9, 0.9 Hz, 1H), 8.17 (d, J=8.4 Hz, 2H), 8.01 (d, J=8.1 Hz, 1H), 7.92 (s, 1H), 7.89 (td, J=7.7, 1.9 Hz, 1H), 7.72 (d, J=16.7 Hz, 1H), 7.71 (d, J=8.4 Hz, 2H), 7.51 (d, J=16.7 Hz, 1H), 7.36 (ddd, J=7.4, 4.7, 1.1 Hz, 1H). HRMS (ESI+): m/z $C_{16}H_{13}N_4O_2$ (M+H)$^+$293.1041; m/z $C_{16}H_{12}N_4O_2Na$ (M+Na)$^+$315.0851. HPLC-MS (ESI+): m/z 293.1 [100%, (M+H)$^+$], 485.1 [20%, (2M+Na)$^+$]; (ESI−): m/z 291.2 [100%, (M−H)$^-$].

Synthesis of NCI 111847 Series

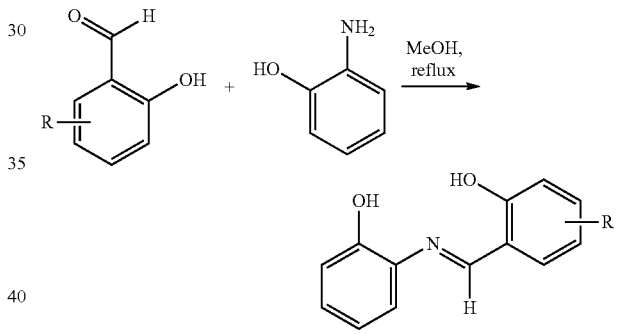

A series of substituted imines were prepared from substituted o-hydroxyarylamines and substituted aryladehydes as OCT4-YAP1 disruptors using the method shown above.

General Procedure for the Imine Derivatives.

2-Aminophenol (0.156 g, 1.427 mmol, 1 eq.) and corresponding aldehyde (200 mg, 1.427 mmol, 1 eq.) were dissolved in MeOH (3 mL). The mixture was refluxed at 82° C. for 3.5 h and allowed to cool to room temperature. To the resulting solid mixture, DCM (1-2 mL) was added until solids were totally dissolved. The mixture was triturated with hexane (10-15 mL, added with sonication until precipitation completed) to afford pure imine product.

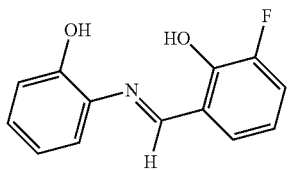 [SMILES: Oc1ccccc1/N=C/c1cccc(F)c1O]

(E)-2-Fluoro-6-(((2-hydroxyphenyl)imino)methyl)phenol (SR2-059). The imine SR2-059 was obtained as a bright orange solid (0.282 g, 86%) using 3-fluoro-2-hydroxybenzaldehyde (0.200 g, 1.427 mmol, 1.0 eq.) by following the above general procedure for imine derivatives. HPLC: >99% [$t_R$=5.8 min, 40% MeOH, 60% water (with 0.1% formic acid), 20 min]. $^1$H NMR (400 MHz, DMSO-$d_6$) δ 9.96 (s, 1H), 9.05 (d, J=1.1 Hz, 1H), 7.45 (dd, J=7.9, 1.6 Hz, 1H), 7.40 (dt, J=7.9, 1.2 Hz, 1H), 7.32 (ddd, J=11.7, 8.0, 1.5 Hz, 1H), 7.14 (ddd, J=8.7, 7.3, 1.6 Hz, 1H), 6.97 (dd, J=8.2, 1.3 Hz, 1H), 6.89 (dd, J=7.5, 1.4 Hz, 1H), 6.88-6.81 (m, 1H). $^{19}$F NMR (376 MHz, DMSO-$d_6$) δ −138.07 (dd, J=11.5, 4.6 Hz). HRMS (ESI+): m/z $C_{13}H_{11}FNO_2$ (M+H)$^+$232.0769; m/z $C_{13}H_{10}FNO_2Na$ (M+Na)$^+$254.0579. HPLC-MS (ESI+): m/z 232.2 [30%, (M+H)$^+$], 487.1 [20%, (2M+Na)$^+$]; (ESI−): m/z 230.1 [30%, (M−H)$^−$].

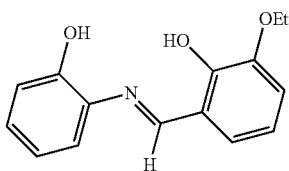 [SMILES: CCOc1cccc(/C=N/c2ccccc2O)c1O]

(E)-2-Ethoxy-6-(((2-hydroxyphenyl)imino)methyl)phenol (SR2-060). The imine SR2-060 was obtained as a bright red solid (0.208 g, 67%) using 3-ethoxysalicyladehyde (0.200 g, 1.205 mmol, 1.0 eq.) by following the above general procedure for imine derivatives. HPLC: >99% [$t_R$=7.4 min, 40% MeOH, 60% water (with 0.1% formic acid), 20 min]. $^1$H NMR (400 MHz, DMSO-$d_6$) δ 9.80 (s, 1H), 8.96 (s, 1H), 7.38 (dd, J=7.9, 1.6 Hz, 1H), 7.18 (dd, J=7.9, 1.5 Hz, 1H), 7.13 (ddd, J=8.1, 7.3, 1.6 Hz, 1H), 7.06 (dd, J=8.0, 1.5 Hz, 1H), 6.96 (dd, J=8.1, 1.4 Hz, 1H), 6.88 (td, J=7.6, 1.4 Hz, 1H), 6.83 (t, J=7.9 Hz, 1H), 4.06 (q, J=7.0 Hz, 2H), 1.35 (t, J=6.9 Hz, 3H). HRMS (ESI+): m/z $C_{15}H_{16}NO_3$ (M+H)$^+$258.1128; m/z $C_{15}H_5NO_3Na$ (M+Na)$^+$ 280.0945. HPLC-MS (ESI−): m/z 257.1 [40%, (M−H)$^−$].

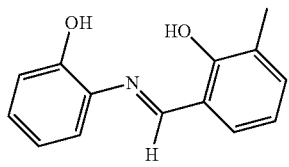 [SMILES: Cc1cccc(/C=N/c2ccccc2O)c1O]

(E)-2-(((2-Hydroxyphenyl)imino)methyl)-6-methylphenol (SR2-061). The imine SR2-061 was obtained as a bright orange solid (isolated 0.136 g, 41%) using 2-hydroxy-3-methyl benzaldehyde (0.200 g, 1.469 mmol, 1.0 eq.) by following the above general procedure for imine derivatives. HPLC: >99% [$t_R$=6.4 min, 55% MeOH, 45% water (with 0.1% formic acid), 20 min]. $^1$H NMR (400 MHz, DMSO-$d_6$) δ 9.76 (s, 1H), 8.94 (s, 1H), 7.40 (dd, J=7.7, 1.7 Hz, 1H), 7.36 (dd, J=7.9, 1.6 Hz, 1H), 7.26 (ddd, J=7.4, 1.7, 0.9 Hz, 1H), 7.14-7.08 (m, 1H), 6.95 (dd, J=8.1, 1.4 Hz, 1H), 6.90-6.80 (m, 2H), 2.19 (s, 3H). HRMS (ESI+): m/z $C_{14}H_{14}NO_2$ (M+H)$^+$228.1021; m/z $C_{14}H_{13}NO_2Na$ (M+Na)$^+$ 250.0851.

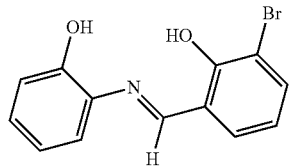 [SMILES: Oc1ccccc1/N=C/c1cccc(Br)c1O]

(E)-2-Bromo-6-(((2-hydroxyphenyl)imino)methyl)phenol (SR2-062). The imine SR2-062 was obtained as a bright red solid (0.183 g, 63%) using 3-bromo-2-hydroxybenzaldehyde (0.200 g, 0.995 mmol, 1.0 eq.) by following the above general procedure for imine derivatives. HPLC: >99% [$t_R$=6.9 min, 50% MeOH, 50% water (with 0.1% formic acid), 20 min]. $^1$H NMR (400 MHz, DMSO-$d_6$) δ 10.06 (s, 1H), 9.05 (s, 1H), 7.68 (dd, J=7.8, 1.6 Hz, 1H), 7.56 (dd, J=7.8, 1.6 Hz, 1H), 7.49 (dd, J=8.0, 1.6 Hz, 1H), 7.18-7.12 (m, 1H), 6.98 (dd, J=8.2, 1.3 Hz, 1H), 6.93-6.87 (m, 1H), 6.80 (t, J=7.8 Hz, 1H). HRMS (ESI+): m/z $C_{13}H_{11}BrNO_2$ (M+H)$^+$291.9972; m/z $C_{13}H_{10}BrNO_2Na$ (M+Na)$^+$313.9777.

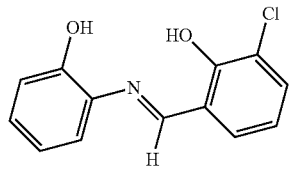 [SMILES: Oc1ccccc1/N=C/c1cccc(Cl)c1O]

(E)-2-Chloro-6-(((2-hydroxyphenyl)imino)methyl)phenol (SR2-063). The imine SR2-063 was obtained as a bright orange solid (0.251 g, 80%) using 3-chloro-2-hydroxybenzaldehyde (0.200 g, 1.227 mmol, 1.0 eq.) by following the above general procedure for imine derivatives. HPLC: >99% [$t_R$=4.2 min, 50% MeOH, 50% water (with 0.1% formic acid), 20 min]. $^1$H NMR (400 MHz, DMSO-$d_6$) δ 10.06 (s, 1H), 9.07 (s, 1H), 7.54 (s, 1H), 7.52 (s, 1H), 7.49 (dd, J=8.0, 1.6 Hz, 1H), 7.15 (ddd, J=8.5, 7.3, 1.6 Hz, 1H), 6.98 (dd, J=8.2, 1.4 Hz, 1H), 6.94-6.82 (m, 2H). HRMS (ESI+): m/z $C_{13}H_{11}ClNO_2$ (M+H)$^+$248.0476; m/z $C_{13}H_{10}ClNO_2Na$ (M+Na)$^+$270.0273.

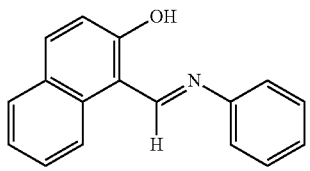 [SMILES: Oc1ccc2ccccc2c1/C=N/c1ccccc1]

(E)-1-((Phenylimino)methyl)naphthalen-2-61 (SR2-076). The imine SR2-076 was obtained as a yellow solid (0.182 g, 63%) using 2-hydroxy-1-naphthaldehyde (0.200 g, 1.162 mmol, 1.0 eq.) and aniline (0.106 g, 1.162 mmol, 1.0 eq.) by following the above general procedure for imine derivatives. HPLC: >99% [$t_R$=8.0 min, 70% MeOH, 30% water (with 0.1% formic acid), 20 min]. $^1$H NMR (400 MHz, DMSO-$d_6$) δ 9.64 (s, 1H), 8.48 (d, J=8.4 Hz, 1H), 7.91 (d, J=9.2 Hz, 1H), 7.77 (dd, J=7.9, 1.3 Hz, 1H), 7.63 (dd, J=8.5, 1.2 Hz, 2H), 7.55-7.45 (m, 3H), 7.36-7.26 (m, 2H), 6.97 (d, J=9.2 Hz, 1H). HRMS (ESI+): m/z $C_{17}H_{14}NO$ (M+H)$^+$248.1076; m/z $C_{17}H_{13}NONa$ (M+Na)$^+$270.0912. HPLC-MS (ESI+): m/z 248.2 [100%, (M+H)$^+$], 517.2 [70%, (2M+Na)$^+$].

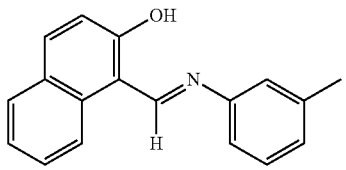 [SMILES: Cc1cccc(/N=C/c2c(O)ccc3ccccc23)c1]

(E)-1-((m-Tolylimino)methyl)naphthalen-2-ol (SR2-077). The imine SR2-077 was obtained as a yellow solid (0.147 g, 49%) using 2-hydroxy-1-naphthaldehyde (0.200 g, 1.162 mmol, 1.0 eq.) and m-toluene (0.126 mL, 1.162 mmol, 1.0 eq.) by following the above general procedure for imine derivatives. HPLC: >99% [$t_R$=11.2 min, 70% MeOH, 30% water (with 0.1% formic acid), 20 min]. $^1$H NMR (400 MHz, DMSO-$d_6$) δ 9.61 (s, 1H), 8.46 (d, J=8.5 Hz, 1H), 7.89 (d, J=9.3 Hz, 1H), 7.76 (d, J=7.8 Hz, 1H), 7.55-7.49 (m, 1H), 7.47 (s, 1H), 7.42-7.29 (m, 3H), 7.11 (d, J=7.2 Hz, 1H), 6.95 (d, J=9.2 Hz, 1H), 2.38 (s, 3H). HRMS (ESI+): m/z $C_{17}H_{14}NO$ (M+H)$^+$248.1076; m/z $C_{17}H_{13}NONa$ (M+Na)$^+$ 270.0912. HRMS (ESI+): m/z $C_{18}H_{16}NO$ (M+H)$^+$262.1232; m/z $C_{18}H_{15}NONa$ (M+Na)$^+$284.1052. HPLC-MS (ESI+): m/z 262.2 [100%, (M+H)$^+$], 545.3 [90%, (2M+Na)$^+$].

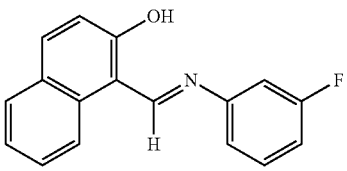 [SMILES: Oc1ccc2ccccc2c1/C=N/c1cccc(F)c1]

(E)-1-(((3-Fluorophenyl)imino)methyl)naphthalen-2-ol (SR2-080). The imine SR2-080 was obtained as a yellow solid (0.217 g, 70%) using 2-hydroxy-1-naphthaldehyde (0.200 g, 1.162 mmol, 1.0 eq.) and 3-fluoroaniline (0.112 mL, 1.162 mmol, 1.0 eq.) by following the above general procedure for imine derivatives. HPLC: >99% [$t_R$=9.6 min, 70% MeOH, 30% water (with 0.1% formic acid), 20 min]. $^1$H NMR (400 MHz, DMSO-$d_6$) δ 9.65 (s, 1H), 8.51 (d, J=8.4 Hz, 1H), 7.94 (d, J=9.2 Hz, 1H), 7.79 (d, J=7.8 Hz, 1H), 7.65 (dt, J=10.8, 2.3 Hz, 1H), 7.54 (t, J=7.5 Hz, 1H), 7.49 (dd, J=8.2, 6.7 Hz, 1H), 7.44-7.31 (m, 2H), 7.12 (td, J=8.3, 2.0 Hz, 1H), 7.01 (d, J=9.2 Hz, 1H). HRMS (ESI+): m/z $C_{17}H_{14}NO$ (M+H)$^+$248.1076; m/z $C_{17}H_{13}NONa$ (M+Na)$^+$270.0912. HRMS (ESI+): m/z $C_{17}H_{13}FNO$ (M+H)$^+$266.0982; m/z $C_{17}H_{12}FNONa$ (M+Na)$^+$288.0797. HPLC-MS (ESI+): m/z 262.2 [90%, (M+H)$^+$], 545.3 [20%, (2M+Na)$^+$].

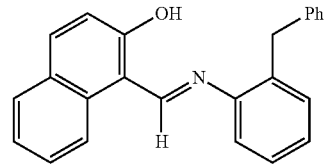 [SMILES: Oc1ccc2ccccc2c1/C=N/c1ccccc1Cc1ccccc1]

(E)-1-(((2-Benzylphenyl)imino)methyl)naphthalen-2-ol (SR2-084). The imine SR2-084 was obtained as a yellow solid (0.371 g, 95%) using 2-hydroxy-1-naphthaldehyde (0.200 g, 1.162 mmol, 1.0 eq.) and 2-benzylamine (0.213 g, 1.162 mmol, 1.0 eq.) by following the above general procedure for imine derivatives. HPLC: >99% [$t_R$=8.4 min, 80% MeOH, 20% water (with 0.1% formic acid), 20 min]. $^1$H NMR (500 MHz, DMSO-$d_6$) δ 9.60 (d, J=2.6 Hz, 1H), 8.47 (d, J=8.4 Hz, 1H), 7.94 (d, J=9.2 Hz, 1H), 7.80 (dd, J=8.0, 1.3 Hz, 1H), 7.73 (dd, J=8.1, 1.1 Hz, 1H), 7.53 (ddd, J=8.4, 6.9, 1.4 Hz, 1H), 7.39 (td, J=7.6, 1.7 Hz, 1H), 7.37-7.30 (m, 2H), 7.29-7.25 (m, 2H), 7.25-7.19 (m, 3H), 7.17-7.11 (m, 1H), 7.05 (d, J=9.1 Hz, 1H), 4.14 (s, 2H). HRMS (ESI+): m/z $C_{24}H_{20}N_0$ (M+H)$^+$338.1544; m/z $C_{24}H_{19}NONa$ (M+Na)$^+$360.1350. HPLC-MS (ESI+): m/z 338.2 [80%, (M+H)$^+$], 360.2 [60%, (M+Na)$^+$], 697.3 [50%, (2M+Na)$^+$].

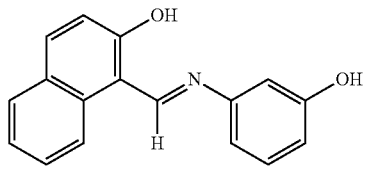 [SMILES: Oc1cccc(/N=C/c2c(O)ccc3ccccc23)c1]

(E)-1-(((3-Hydroxyphenyl)imino)methyl)naphthalen-2-ol (SR2-085). The imine SR2-085 was obtained as a yellow solid (0.288 g, 94%) using 2-hydroxy-1-naphthaldehyde (0.200 g, 1.162 mmol, 1.0 eq.) and 3-aminophenol (0.127 g, 1.162 mmol, 1.0 eq.) by following the above general procedure for imine derivatives. HPLC: >99% [$t_R$=3.9 min, 70% MeOH, 30% water (with 0.1% formic acid), 20 min]. $^1$H NMR (400 MHz, DMSO-$d_6$) δ 9.69 (s, 1H), 9.54-9.49 (m, 1H), 8.42 (d, J=8.5 Hz, 1H), 7.86 (d, J=9.2 Hz, 1H), 7.73 (dd, J=8.0, 1.3 Hz, 1H), 7.48 (ddd, J=8.3, 6.9, 1.5 Hz, 1H), 7.29 (t, J=7.4 Hz, 1H), 7.24 (t, J=8.0 Hz, 1H), 7.02 (dd, J=7.9, 2.0 Hz, 1H), 6.94 (t, J=2.2 Hz, 1H), 6.92 (d, J=9.2 Hz, 1H), 6.69 (dd, J=8.1, 2.3 Hz, 1H). HRMS (ESI+): m/z $C_{17}H_{14}NO_2$ (M+H)$^+$264.1023; m/z $C_{17}H_{13}NO_2Na$ (M+Na)$^+$ 286.0831. HPLC-MS (ESI+): m/z 264.2 [100%, (M+H)$^+$], 549.2 [50%, (2M+Na)$^+$]; (ESI−): m/z 262.1 [80%, (M−H)$^-$].

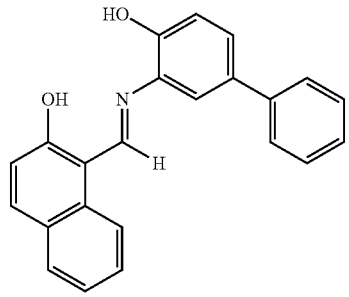 [SMILES: Oc1ccc(-c2ccccc2)cc1/N=C/c1c(O)ccc2ccccc12]

(E)-1-(((4-Hydroxy-[1,1'-biphenyl]-3-yl)imino)methyl)naphthalen-2-ol (SR2-086). The imine SR2-086 was obtained as a yellow solid (0.373 g, 95%) using 2-hydroxy-1-naphthaldehyde (0.200 g, 1.162 mmol, 1.0 eq.) and 2-amino-3-phenylphenol (0.215 g, 1.162 mmol, 1.0 eq.) by following the above general procedure for imine derivatives. HPLC: >99% [$t_R$=5.1 min, 80% MeOH, 20% water (with 0.1% formic acid), 20 min]. $^1$H NMR (400 MHz, DMSO-$d_6$) δ 10.43 (s, 1H), 9.60 (d, J=9.4 Hz, 1H), 8.43 (d, J=8.4 Hz, 1H), 8.16 (d, J=2.1 Hz, 1H), 7.78 (d, J=9.5 Hz, 1H), 7.73 (m, 2H), 7.65 (dd, J=7.9, 1.4 Hz, 1H), 7.44 (m, 3H), 7.38 (dd, J=8.4, 2.1 Hz, 1H), 7.34-7.27 (m, 1H), 7.24 (t, J=7.4 Hz, 1H), 7.04 (d, J=8.4 Hz, 1H), 6.76 (d, J=9.4 Hz, 1H). HRMS (ESI+): m/z $C_{23}H_{18}NO_2$ (M+H)$^+$340.1332; m/z $C_{23}H_{17}NO_2Na$ (M+Na)$^+$462.1146. HPLC-MS (ESI+): m/z 340.2 [100%, (M+H)$^+$], 701.3 [10%, (2M+Na)$^+$]; (ESI−): m/z 338.2 [50%, (M−H)$^-$].

Activities of Compounds in the In Vitro YAP1:OCT4 ELISA Binding Assay

Selected compounds were assayed in a YAP1:OCT4 binding assay. The results are provided in Table 1.

TABLE 1

| ID | IC$_{50}$ binding assay |
|---|---|
| SR1-083 | ++ |
| SR1-090 | + |
| SR1-094 | + |
| SR1-117 | + |
| SR1-118 | ++ |
| SR1-119 | ++ |
| SR1-122 | ++ |
| SR1-152 | ++ |
| SR1-167 | ++ |
| SR2-004 | +++ |
| SR2-006 | ++ |
| SR2-007 | ++ |
| SR2-008 | ++ |
| SR2-009 | ++ |
| SR2-010 | +++ |
| SR2-015 | ++ |
| SR2-016 | ++ |
| SR2-019 | ++ |
| SR2-022 | +++ |
| SR2-029 | +++ |
| SR2-030 | +++ |
| SR2-032 | +++ |
| SR2-033 | +++ |
| SR2-036 | ++ |
| SR2-046 | +++ |
| SR2-051 | +++ |
| SR2-052 | +++ |
| SR2-106 | +++ |
| SR2-107 | +++ |
| SR2-113 | +++ |
| SR2-114 | +++ |
| SR2-117 | +++ |
| SR2-120 | +++ |
| SR2-122 | +++ |

+: IC$_{50}$ (YAP1:OCT4 disruption) > 10 μM;
++: IC$_{50}$ (YAP1:OCT4 disruption) 1 to 10 μM
+++: IC$_{50}$ (YAP1:OCT4 disruption) < 10 μM Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

And replace it with:
--with--
Column 114, Line 63, Claim 16 delete:
"The"
And replace it with:
--A--
Column 115, Line 4, Claim 17 delete:
"The method of claim 16, wherein cancer is lunc cancer."
And replace it with:
--The method of claim 16, wherein the cancer is lung cancer.--
Column 117, Line 18-25, Claim 19 the structure reading:
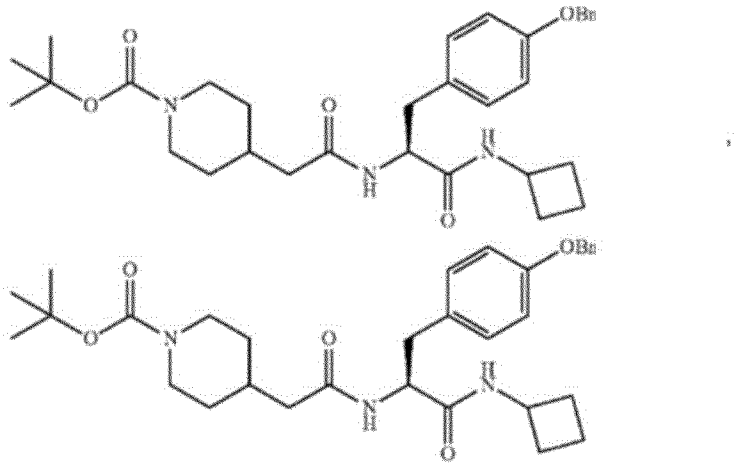
Should read:
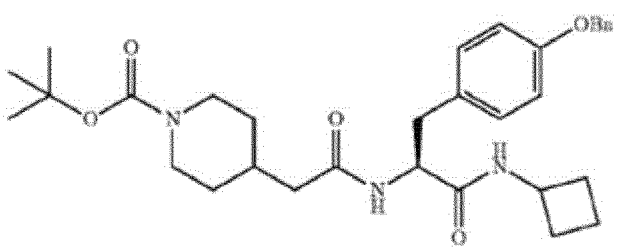
Column 117, Line 42, Claim 19 the structure reading:
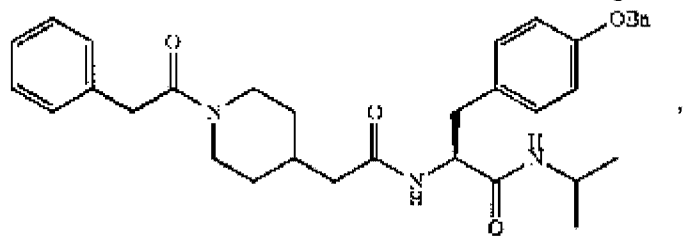

Should read:
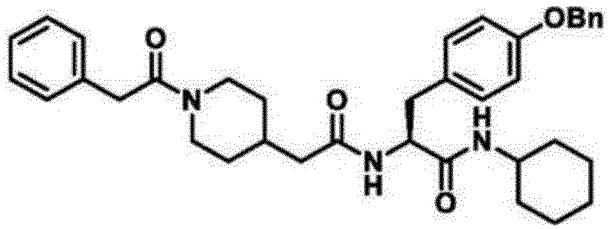
Column 119, Line 1-7, Claim 19 the structure reading:
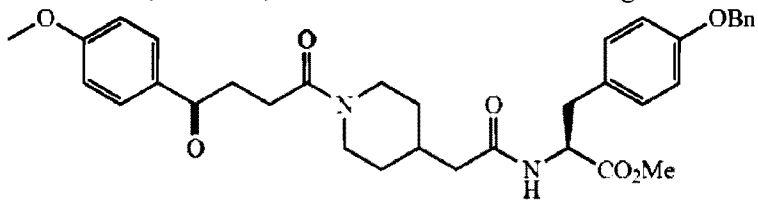
Should read:
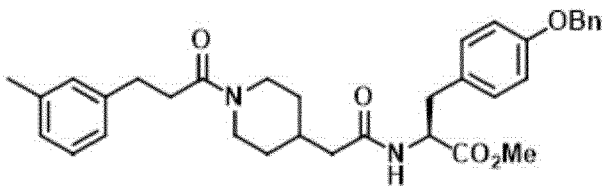
Column 120, Line 15-22, Claim 19 the structure reading:
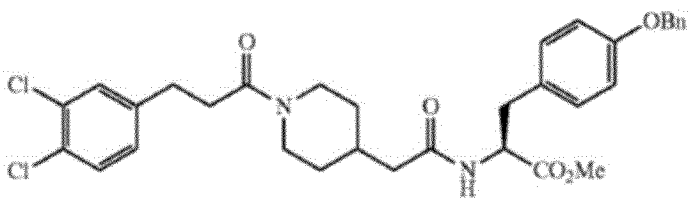
Should read:
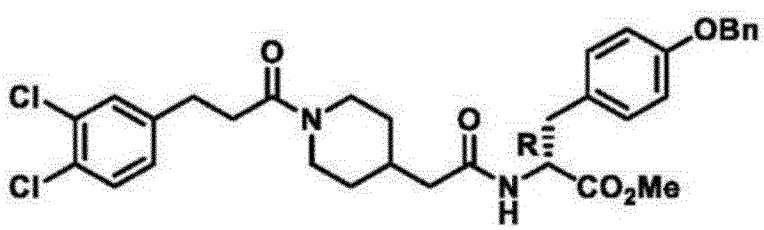
Column 120, Line 61-66, Claim 19 the structure reading:
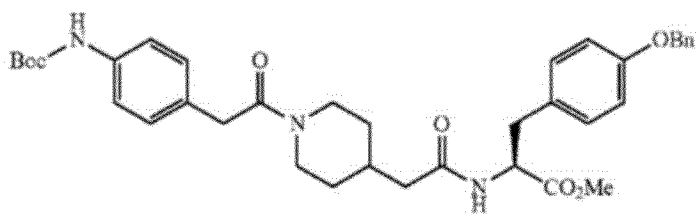

Should read:
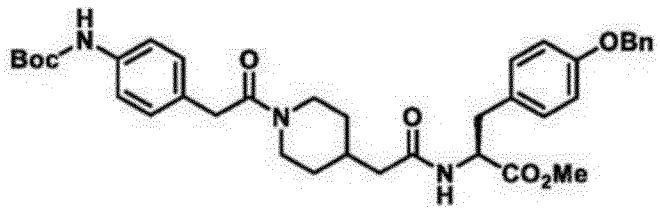
Column 121, Line 1-7, Claim 19 the structure reading:
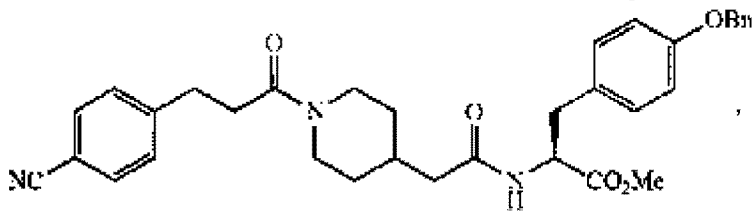
Should read:
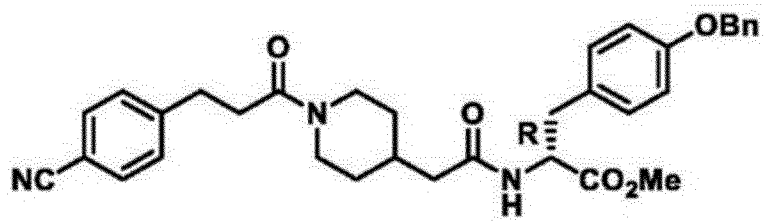
Column 121, Line 21-26, Claim 19 the structure reading:
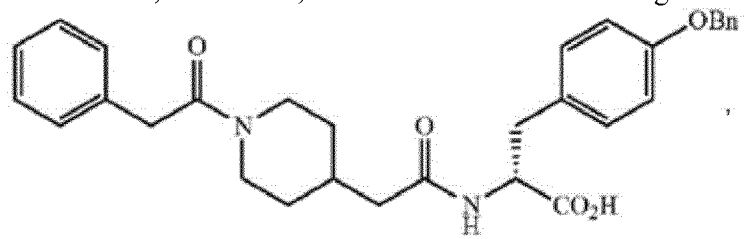
Should read:
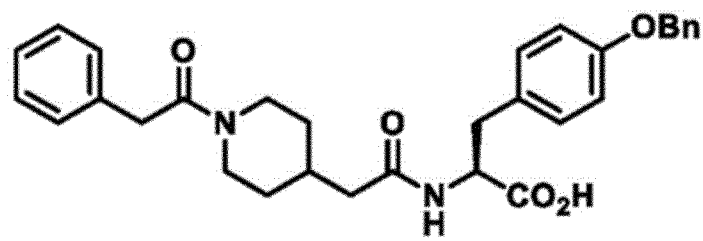
Column 122, Line 19, Claim 19 the structure reading:
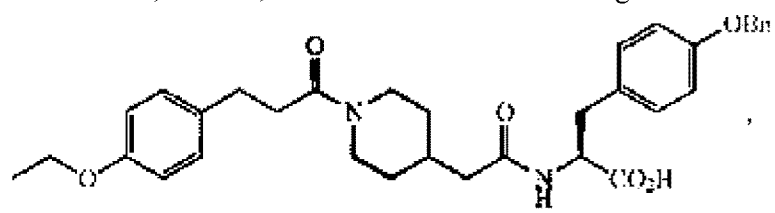

Should read:
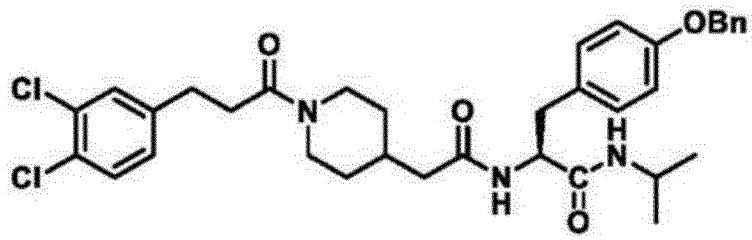
Column 122, Line 60, Claim 19 the structure reading:
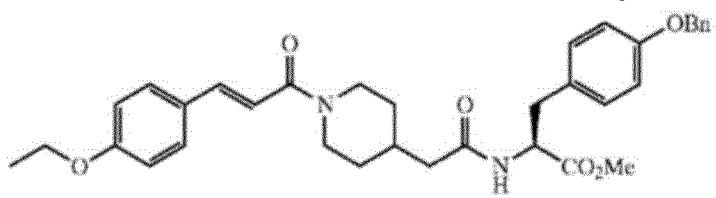
Should read:
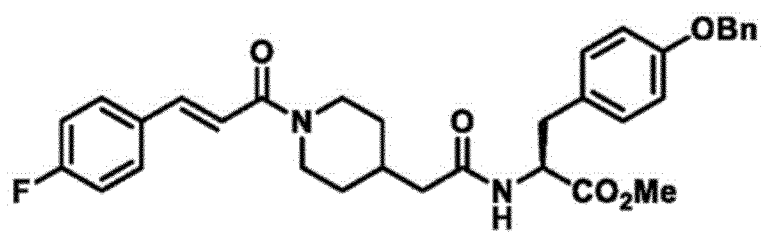

What is claimed is:

1. A compound having Formula I

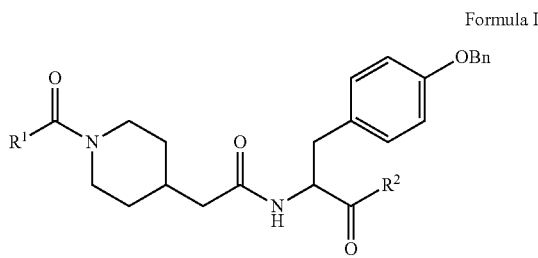

Formula I wherein,

R$^1$ is C$_1$-C$_8$ alkyl, C$_1$-C$_8$ alkenyl, C$_1$-C$_8$ alkynyl, C$_1$-C$_8$ alkoxyl, C$_1$-C$_8$ heteroalkyl, C$_3$-C$_6$ cycloalkyl, or phenyl, any of which is optionally substituted with one or more carbonyl (C=O), C$_1$-C$_6$ alkyl, C$_1$-C$_6$ haloalkyl, C$_1$-C$_6$ alkoxyl, amino, —NR$^6$R$^7$, —C(O)NR$^6$R$^7$, C$_1$-C$_6$ alkylhydroxy, C$_3$-C$_6$ cycloalkyl, C$_3$-C$_6$ heterocycloalkyl, phenyl, halo, hydroxyl, thiol, cyano, nitro, or radiolabeled isotope;

R$^2$ is amino, hydroxyl, C$_1$-C$_8$ alkyl, or C$_1$-C$_8$ alkoxyl, where the amino is optionally substituted with one or more C$_1$-C$_6$ alkyl, C$_1$-C$_6$ alkoxyl, C$_1$-C$_6$ alkylC$_{3-6}$cycloalkyl, C$_3$-C$_6$ cycloalkyl, C$_3$-C$_6$ heterocycloalkyl, phenyl; and R$^6$ and R$^7$ are independently selected from hydrogen, C$_1$-C$_8$ alkyl, C$_1$-C$_8$ alkenyl, C$_1$-C$_8$ alkynyl, C$_1$-C$_8$ alkoxide, C$_1$-C$_8$ carboxylate, C$_1$-C$_8$ haloalkyl, C$_1$-C$_8$ haloalkenyl, C$_1$-C$_8$ haloalkynyl, C$_3$-C$_6$ cycloalkyl, C$_3$-C$_6$ heterocycloalkyl, phenyl, or C$_1$-C$_3$ alkylheteroaryl, ; any of which is optionally substituted with a halogen; and n is 1-5.

2. The compound of claim 1, wherein Z is CH$_2$.

3. The compound of claim 1, wherein R$^1$ is C$_1$-C$_8$ alkoxyl.

4. The compound of claim 1, wherein R$^1$ is phenyl.

5. The compound of claim 1, wherein R$^1$ is C$_{1-3}$ alkyl substituted with phenyl, wherein the phenyl is optionally substituted with one or more C$_1$-C$_6$ alkyl, C$_1$-C$_6$ haloalkyl, C$_1$-C$_6$ alkoxyl, amino, halo, hydroxyl, thiol, cyano, nitro, or radiolabeled isotope.

6. The compound of claim 1, wherein R$^1$ is CH$_2$CH$_2$Ph, CH$_2$CH$_2$CH$_2$Ph, CH(CH$_2$)Ph, C(CH$_3$)$_2$Ph, or CH$_2$CH(Ph)$_2$.

7. The compound of claim 1, wherein R$^1$ is CH$_2$CH$_2$Ph, where the phenyl is substituted with one or more C$_1$-C$_6$ alkyl, C$_1$-C$_6$ haloalkyl, C$_1$-C$_6$ alkoxyl, amino, halo, hydroxyl, thiol, cyano, nitro, or radiolabeled isotope.

8. The compound of claim 1, wherein R$^1$ is a C$_{1-3}$ alkyl substituted with a phenyl substituted with one or more halogen, methoxyl, ethoxyl, propoxyl, cyano, and CF$_3$, or R$^1$ is a C$_{1-3}$ alkyl substituted with a phenyl substituted with a dioxole.

9. The compound of claim 1, wherein R$^1$ is C$_{1-3}$ alkenyl substituted with phenyl, wherein the phenyl is optionally substituted with one or more C$_1$-C$_6$ alkyl, C$_1$-C$_6$ haloalkyl, C$_1$-C$_6$ alkoxyl, amino, halo, hydroxyl, thiol, cyano, nitro, or radiolabeled isotope.

10. The compound of claim 1, wherein R$^1$ is CH=CHPh, where the phenyl is substituted with one or more C$_1$-C$_6$ alkyl, C$_1$-C$_6$ haloalkyl, C$_1$-C$_6$ alkoxyl, amino, halo, hydroxyl, thiol, cyano, nitro, or radiolabeled isotope.

11. The compound of claim 1, wherein R$^1$ is C$_1$-C$_8$ heteroalkyl, C$_3$-C$_6$ heterocycloalkyl, which is optionally substituted with one or more C=O, C$_{1-6}$ alkyl, and phenyl.

12. The compound of claim 1, wherein R$^1$ is pyrrolidine substituted with C(O)CH$_3$.

13. The compound of claim 1, wherein R$^2$ is OMe or OH.

14. The compound of claim 1, wherein R$^2$ is unsubstituted amino, amino substituted with C$_1$-C$_6$ alkyl, amino substituted with with C$_3$-C$_6$ cycloalkyl, or amino substituted with C$_1$-C$_6$ alkyl C$_{3-6}$cycloalkyl.

15. A pharmaceutical composition comprising a therapeutically effective amount of a compound of claim 1 and a pharmaceutical carrier and optional anticancer or anti-inflammatory agent.

16. The method of treating cancer in a subject in need thereof, comprising: administering to the subject the compound of claim 1, wherein the cancer is selected from lung cancer, bladder cancer, brain cancer, breast cancer, colorectal cancer, cervical cancer, gastrointestinal cancer, genitourinary cancer, head and neck cancer, ovarian cancer, pancreatic cancer, prostate cancer, renal cancer, skin cancer, melanoma, and testicular cancer.

17. The method of claim 16, wherein cancer is lung cancer.

18. A method of killing a tumor cell in a subject, comprising contacting the cell with the compound of claim 1, wherein the tumor cell is from a cancer selected from lung cancer, bladder cancer, brain cancer, breast cancer, colorectal cancer, cervical cancer, gastrointestinal cancer, genitourinary cancer, head and neck cancer, ovarian cancer, pancreatic cancer, prostate cancer, renal cancer, skin cancer, melanoma, and testicular cancer.

19. A compound chosen from the following:

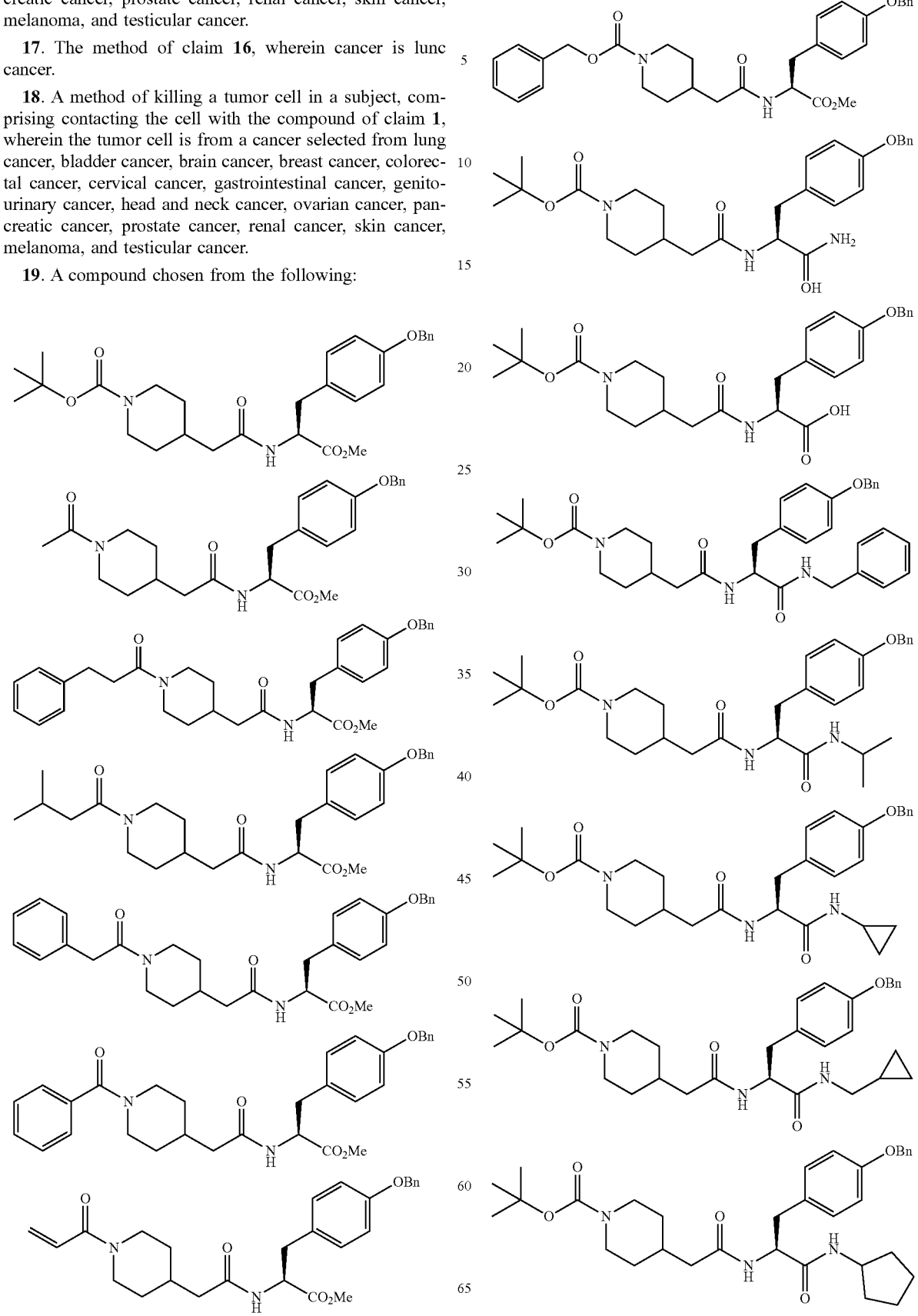

117
-continued
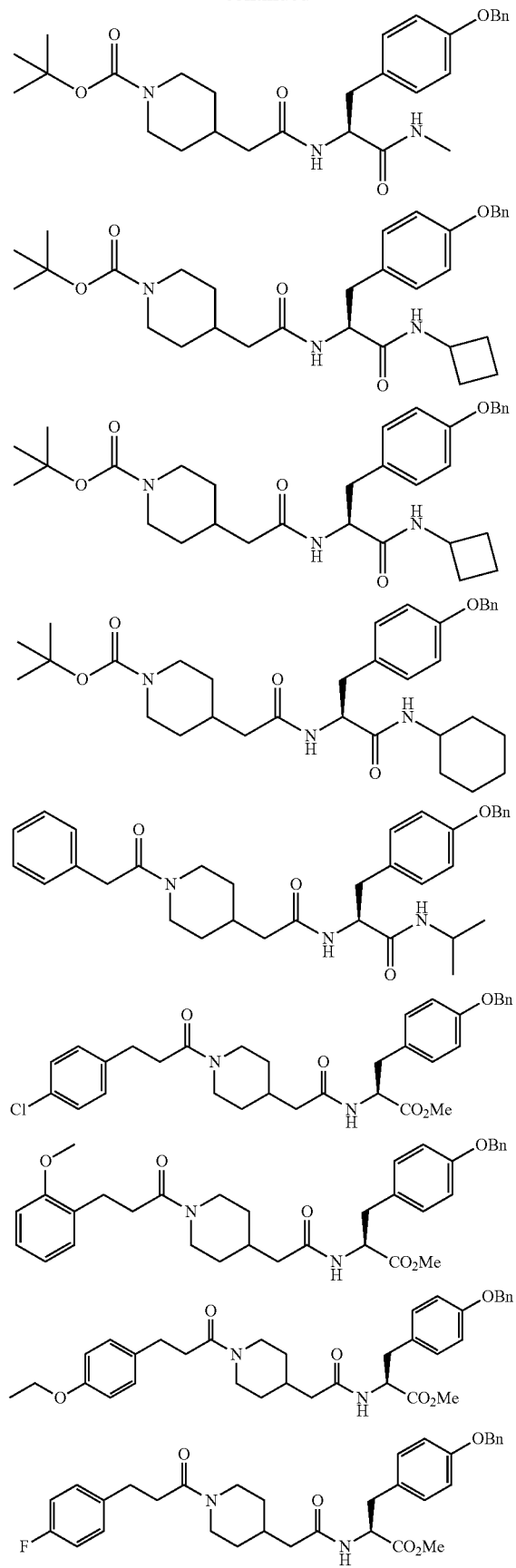
118
-continued
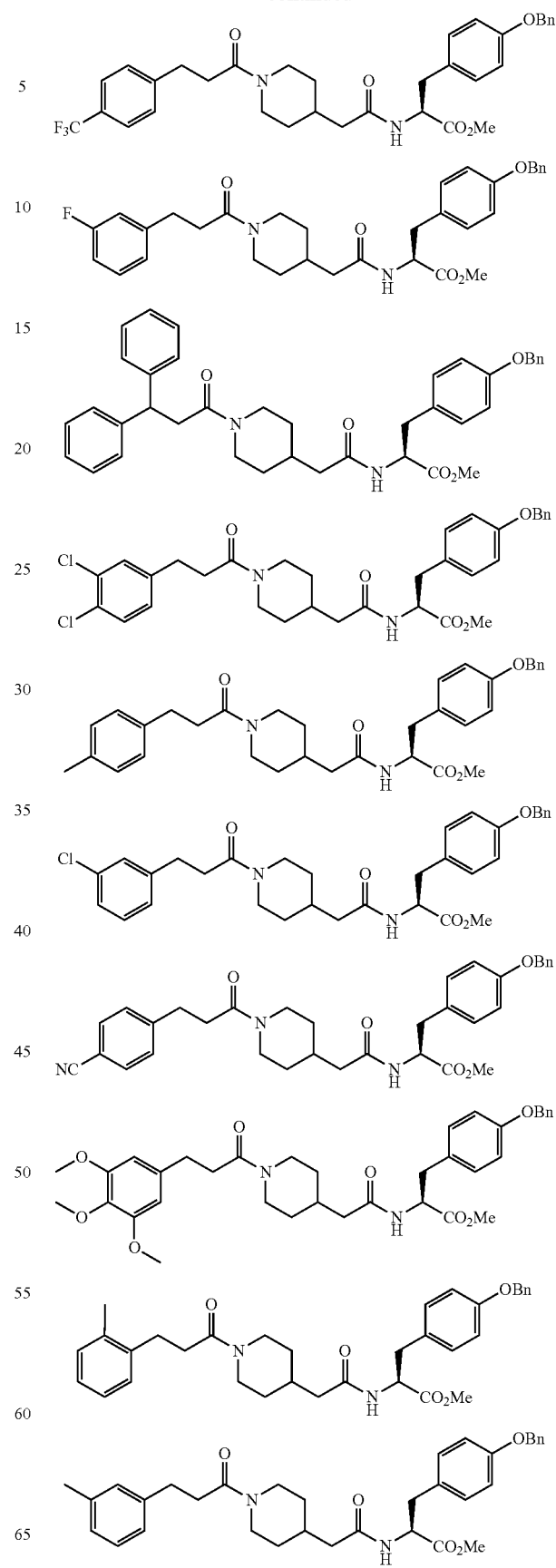

119
-continued
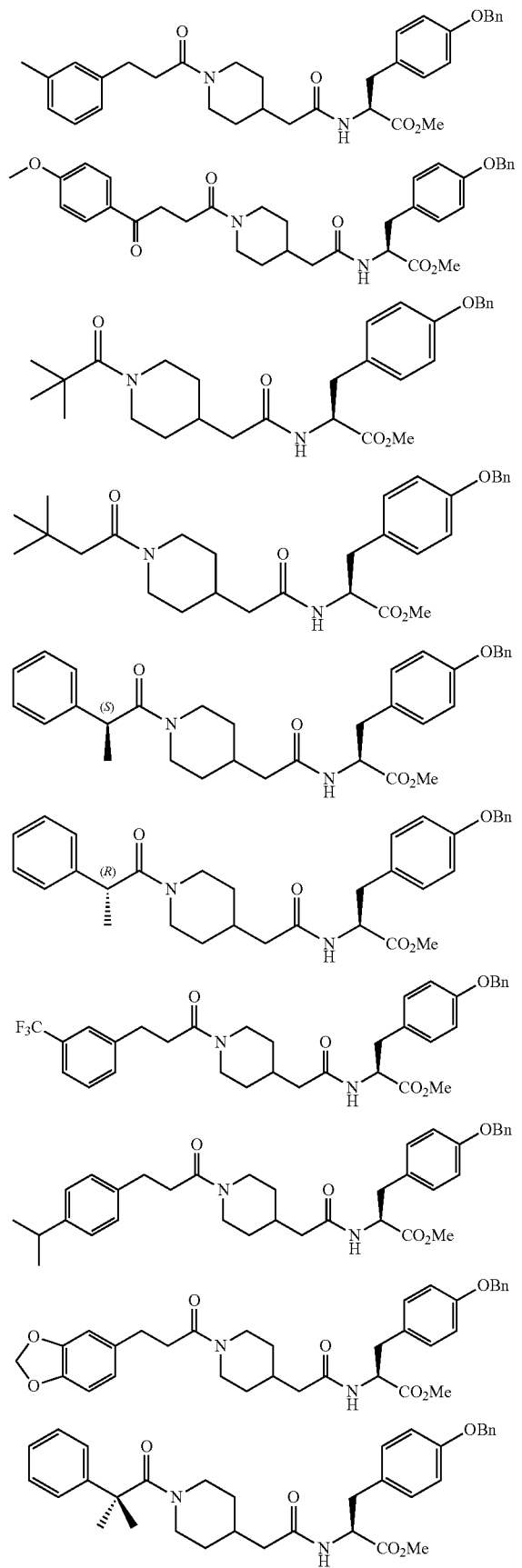
120
-continued
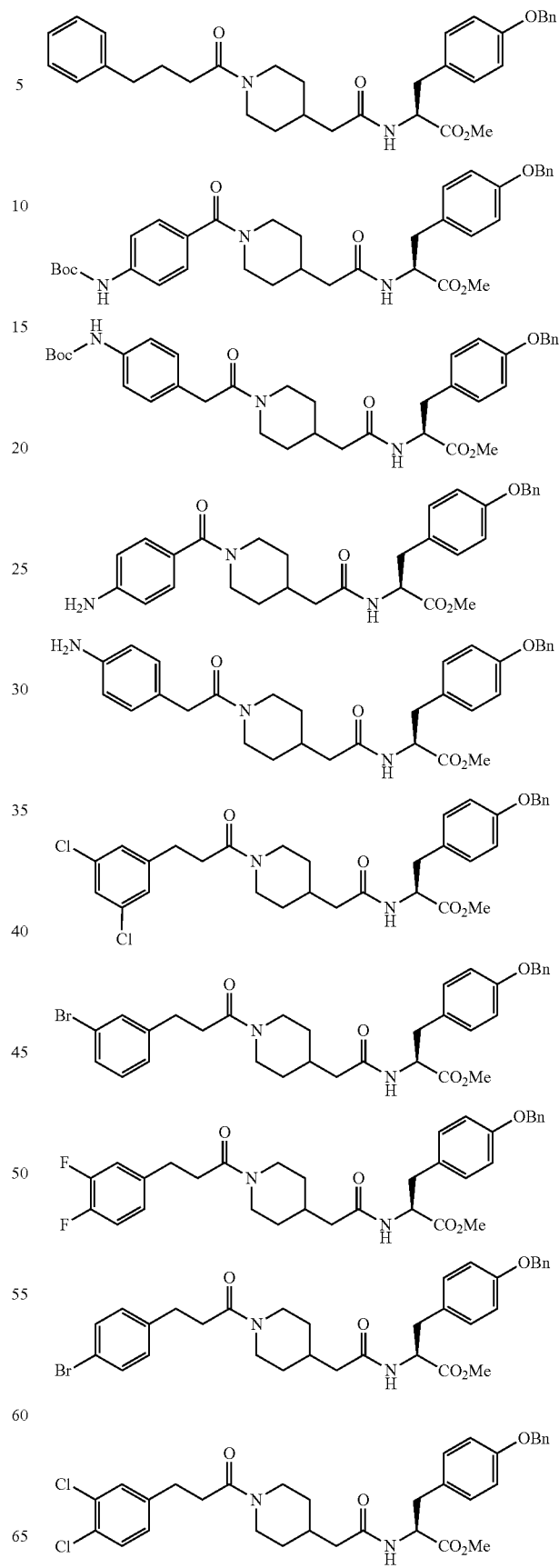

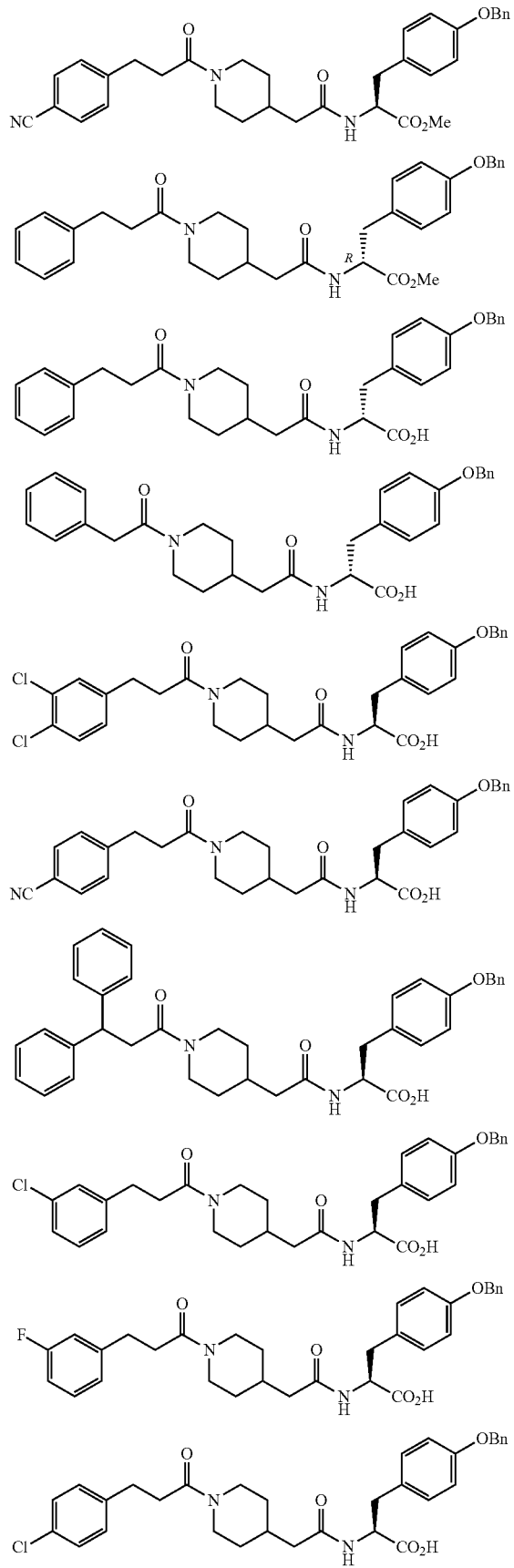
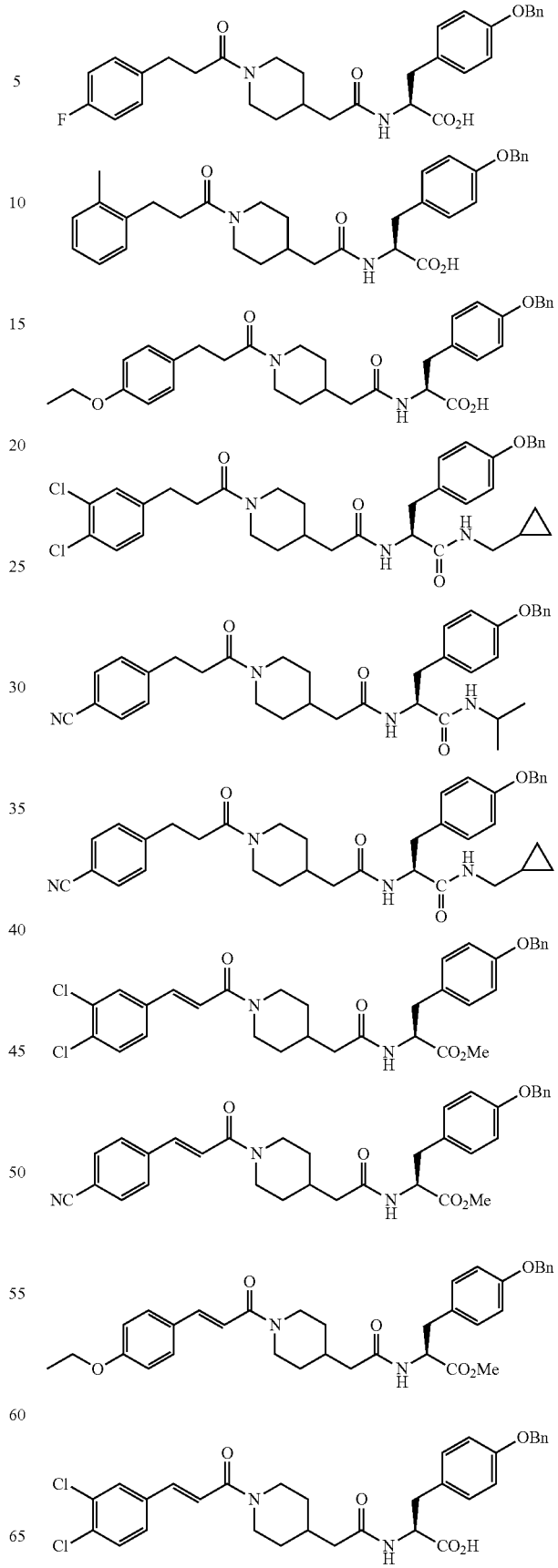

123
-continued
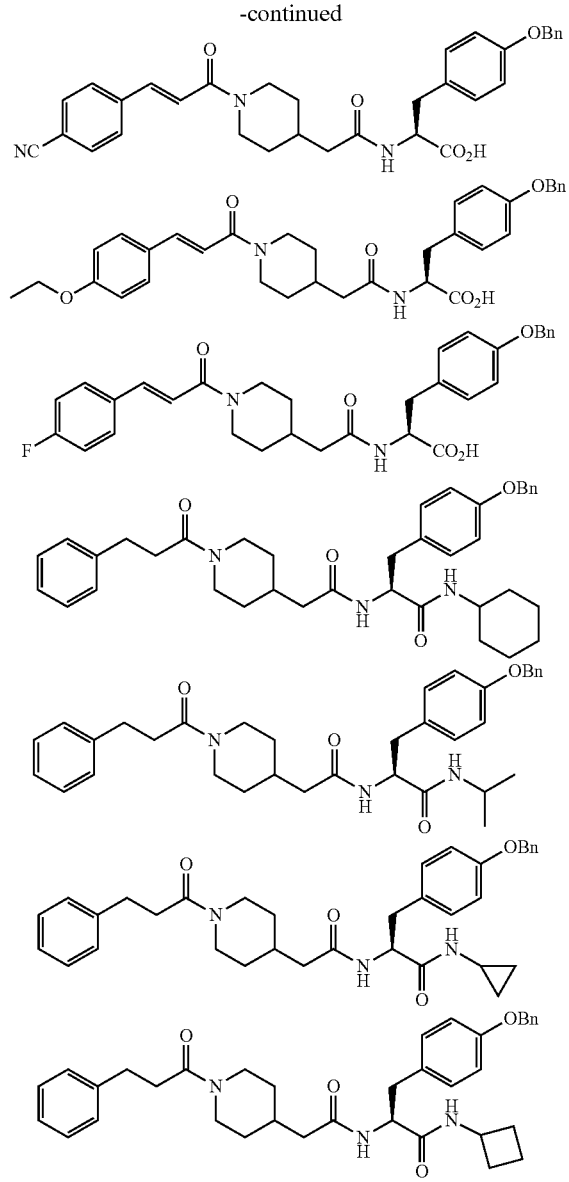
124
-continued
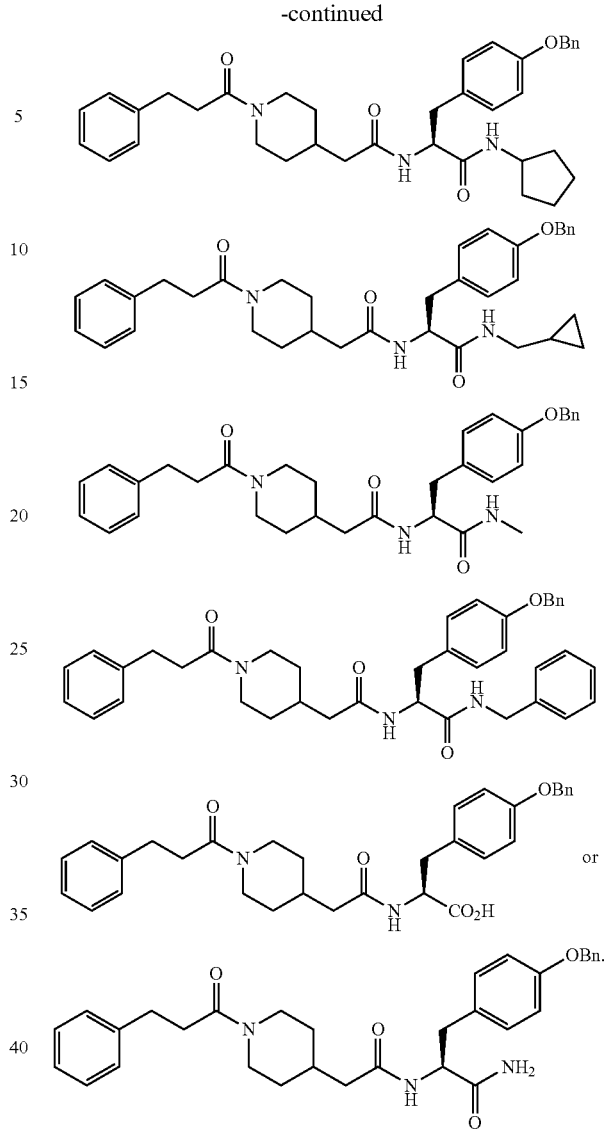
* * * * *

UNITED STATES PATENT AND TRADEMARK OFFICE
CERTIFICATE OF CORRECTION

PATENT NO. : 10,906,874 B2
APPLICATION NO. : 16/334087
DATED : February 2, 2021
INVENTOR(S) : Srikumar Chellappan, Nicholas J. Lawrence and Sujeewa Ranatunga Mahanthe Mudiyanselage It is certified that error appears in the above-identified patent and that said Letters Patent is hereby corrected as shown below:

On the Title Page

Item [57], Line 6, delete:
"Delivering a peptide corresponding to the WAV domain"
And replace it with:
--Delivering a peptide corresponding to the WW domain--

In the Specification

Column 1, Line 7, delete:
"This application claims the benefit of priority to U.S. Provisional Applications 62/396,190, filed Sep. 18, 2016, and 62/396,383, filed Sep. 19, 2016, which are both incorporated by reference herein in their entirities"
And replace it with:
--This application claims the benefit of priority to U.S. Provisional Application Numbers 62/396,190, filed Sep. 18, 2016, and 62/396,383, filed Sep. 19, 2016, which are both incorporated by reference herein in their entireties--

In the Claims

Column 114, Line 13, Claim 1:
After "cycloalkyl," insert --or--

Column 114, Line 18, Claim 1 delete:
"alkylheteroaryl, ;"
And replace it with:
--alkylheteroaryl;--

Column 114, Line 57, Claim 14 delete:
"with with"

Signed and Sealed this
Second Day of November, 2021

Drew Hirshfeld
*Performing the Functions and Duties of the
Under Secretary of Commerce for Intellectual Property and
Director of the United States Patent and Trademark Office*